(12) United States Patent
Bix

(10) Patent No.: US 9,072,713 B2
(45) Date of Patent: *Jul. 7, 2015

(54) PERLECAN DOMAIN V PROTECTS, REPAIRS AND RESTORES ISCHEMIC BRAIN STROKE INJURY AND MOTOR FUNCTION

(75) Inventor: Gregory J. Bix, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 464 days.

This patent is subject to a terminal disclaimer.

(21) Appl. No.: 13/175,518

(22) Filed: Jul. 1, 2011

(65) Prior Publication Data
US 2012/0003180 A1   Jan. 5, 2012

Related U.S. Application Data

(60) Provisional application No. 61/360,739, filed on Jul. 1, 2010.

(51) Int. Cl.
| | | |
|---|---|---|
| *C07K 1/00* | (2006.01) | |
| *A61K 38/02* | (2006.01) | |
| *A61K 31/727* | (2006.01) | |
| *A61K 38/20* | (2006.01) | |
| *A61K 38/17* | (2006.01) | |
| *A61K 45/06* | (2006.01) | |
| *C07K 16/28* | (2006.01) | |

(52) U.S. Cl.
CPC ........... *A61K 38/2006* (2013.01); *A61K 31/727* (2013.01); *A61K 38/177* (2013.01); *A61K 45/06* (2013.01); *A61K 2300/00* (2013.01); *C07K 16/2842* (2013.01); *C07K 2317/75* (2013.01); *C07K 2317/76* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 6,821,947 B2 | 11/2004 | Iozzo | |
| 7,081,345 B1 * | 7/2006 | Roecklin et al. | 435/7.1 |
| 7,141,551 B1 | 11/2006 | DeCarlo et al. | |
| 7,510,843 B2 * | 3/2009 | Roecklin et al. | 435/7.1 |
| 2003/0104999 A1 | 6/2003 | Iozzo | |
| 2003/0233669 A1 | 12/2003 | Snow et al. | |
| 2006/0223121 A1 | 10/2006 | Roecklin et al. | |
| 2007/0072821 A1 * | 3/2007 | Iakoubova et al. | 514/44 |
| 2010/0092469 A1 | 4/2010 | Simard et al. | |
| 2010/0168025 A1 | 7/2010 | Bix et al. | |

FOREIGN PATENT DOCUMENTS

| | | | | |
|---|---|---|---|---|
| ES | WO2010015659 | * | 2/2010 | G01N 33/574 |
| FR | WO01/05422 | * | 1/2001 | A61K 38/17 |
| KR | 20080028642 | * | 4/2008 | C07K 14/47 |
| WO | WO 03/048333 | | 6/2003 | |
| WO | WO2004058052 | * | 7/2004 | |
| WO | WO2004058990 | * | 7/2004 | |

OTHER PUBLICATIONS

Wright et al., Neurobiology of Aging 2012; 33: 1379-1388.*
Tokuriki and Tawflik, Current Opinion in Structural Biology 2009, 19: 596-604.*
Murdoch et al., J. Biol. Chem. 1992; 267: 8544-8557.*
Kallunki, J. Cell Biol, 1992; 116: 559-571.*
Hutchison et al., J Neurotrauma. 2007; 24: 1545-1557.*
Greenhalgh et al., Disease Models & Mechanisms, 2012; 5: 823-833.*
Dumont et al., BioDrugs. 2006; 20: 151-60.*
Hesse, Current Opinion in Neurology 2003, 16: 705-710.*
Hacke et al., Neurology. 1999; 53 (7 Suppl 4): S3-14.*
Ducker, Spine, 1994; 19: 2281-2287.*
Aronowski, J. et al. "Neurofilament Proteolysis After Focal Ischemia; When Do Cells Die After Experimental Stroke?" *Journal of Cerebral Blood Flow & Metabolism*, 1999, pp. 652-660, vol. 19.
Asou, H. et al. "Cell Adhesion molecule L1 guides cell migration in primary reaggregation cultures of mouse cerebellar cells" *Neuroscience Letters*, 1992, pp. 221-224, vol. 144.
Auerbach, R. et al. "Angiogenesis Assays: A Critical Overview" *Clinical Chemistry*, 2003, pp. 32-40, vol. 49, No. 1.
Bix, G. J. et al. "Platelet-Activating Factor Receptor Stimulation Disrupts Neuronal Migration In Vitro" *The Journal of Neuroscience*, Jan. 1, 1998, pp. 307-318, vol. 18, No. 1.
Bix, G. et al. "Matrix revolutions: 'tails' of basement-membrane components with angiostatic functions" *TRENDS in Cell Biology*, Jan. 2005, pp. 52-60, vol. 15, No. 1.
Bix, G. et al. "Endorepellin, the C-terminal angiostatic module of perlecan, enhances collagen-platelet response via the α2β1-intergrin receptor" *Blood*, May 1, 2007, pp. 3745-3748, vol. 109, No. 9.
Bix, G. et al. "Endorepellin In Vivo: Targeting the Tumor Vasculature and Retarding Cancer Growth and Metabolism" *Journal of the National Cancer Institute*, Nov. 15, 2006, pp. 1634-1646, vol. 98, No. 22.
Bix, G. et al. "Endorepellin causes endothelial cell disassembly of actin cytoskeleton and focal adhesions through α2β1 integrin " *The Journal of Cell Biology*, Jul. 5, 2004, pp. 97-109, vol. 166, No. 1.
Brittingham, R. et al. "Single Amino Acid Substitutions in Procollagen VII Affect Early Stages of Assembly of Anchoring Fibrils" *The Journal of Biological Chemistry*, Jan. 7, 2005, pp. 191-198, vol. 280, No. 1.

(Continued)

*Primary Examiner* — Christina Borgeest
(74) *Attorney, Agent, or Firm* — Saliwanchik Lloyd & Eisenschenk

(57) ABSTRACT

The disclosed invention relates to the use of perlecan domain V (DV) for the treatment of stroke, traumatic brain injury (TBI) or spinal cord injuries (SCI). In certain embodiments, fusion proteins of DV can be used for the treatment of stroke, TBI or SCI. DV is also referred to as endorepellin in the art. This application also provides compositions and combination therapies for the treatment of stroke, TCI and/or SCI. Another aspect of the invention provides methods of restoring motor function in subjects having neurological damage arising from a stroke, TBI or SCI.

34 Claims, 51 Drawing Sheets
(30 of 51 Drawing Sheet(s) Filed in Color)

(56) References Cited

OTHER PUBLICATIONS

Clarke, D. et al. "Endorepellin and Endostatin Affect the Neurovascular Unit In Vitro" *J. Neurochem.*, 2008, p. 1, vol. 104, Suppl. 1.

Hirotsune, S. et al. "Graded reduction of *Pafah1b1* (*Lis1*) activity results in neuronal migrating defects and early embryonic lethality" *Nature Genetics*, Aug. 1998, pp. 333-339, vol. 19.

Milner, R. et al. "Responses of Endothelial Cell and Astrocyte Matrix-Integrin Receptors to Ischemia Mimic Those Observed in the Neurovascular Unit" *Stroke*, 2008, pp. 191-197, vol. 39.

Mongiat, M. "Endorepellin, a Novel Inhibitor of Angiogenesis Derived from the C Terminus of Perlecan" *The Journal of Biological Chemistry*, Feb. 7, 2003, pp. 4238-4249, vol. 278, No. 6, XP-002547225.

Mundel, T. M. "Type IV collagen-derived angiogenesis inhibitors" *Microvascular Research*, 2007, pp. 85-89, vol. 74.

Myszka, D. G. et al. "CLAMP: a biosensor kinetic data analysis program" *TIBS*, Apr. 1998, pp. 1-2, vol. 23.

Ohab, J. J. et al. "A Neurovascular Niche for Neurogenesis after Stroke" *The Journal of Neuroscience*, Dec. 13, 2006, pp. 13007-13016, vol. 26, No. 50.

Ohwaki, K. et al. "Blood Pressure Management in Acute Intracerebral Hemorrhage Relationship between Elevated Blood Pressure and Hematoma Enlargement" *Stroke*, 2004, pp. 1364-1367, vol. 35.

O'Reilly, M. S. et al. "Endostatin: An Endogenous Inhibitor of Angiogenesis and Tumor Growth" *Cell*, Jan. 24, 1997, pp. 277-285, vol. 88.

O'Regan, C. et al. "Statin Therapy in Stroke Prevention: A Meta-analysis Involving 121,000 Patients" *The American Journal of Medicine*, 2008, pp. 24-33, vol. 121.

Hankey, G. J. "Statins after transient ischaemic attack and ischaemic stroke" *Neurology*, Oct. 2006, pp. 810-812, vol. 5.

Sapatino, B. V. et al. "Cloned Mouse Cerebrovascular Endothelial Cells That Maintain Their Differentiation Markers for Factor VIII, Low Density Lipoprotein, and Angiotensin-Converting Enzyme" *In Vitro Cellular & Developmental Biology*, Dec. 1993, pp. 923-928, vol. 29A, No. 12.

Schallert, T. et al. "Use-Dependent Structural Events in Recovery of Function" *Brain Plasticity, Advances in Neurology*, 1997, pp. 229-238, vol. 73.

Bix, G. et al. "Novel Interactions of Perlecan: Unraveling Perlecan's Role in Angiogenesis" *Microscopy Research and Technique*, 2008, pp. 339-348, vol. 71.

Arai, K. et al. "Brain angiogenesis in developmental and pathological processes: neurovascular injury and angiogenic recovery after stroke" *FEBS Journal*, 2009, pp. 4644-4652, vol. 276.

Brown, J. C. et al. "The C-terminal domain V of perlecan promotes β1 integrin-mediated cell adhesion, binds heparin, nidogen and fibulin-2 and can be modified by glycosaminoglycans" *Eur. J. Biochem.*, 1997, pp. 39-46, vol. 250.

García De Yébenes, E. et al. "Regulation of the Heparan Sulfate proteoglycan, Perlecan, by Injury and Interleukin-1α" *Journal of Neurochemistry*, 1999, pp. 812-820, vol. 73.

Giros, A. et al. "Perlecan controls neurogenesis in the developing telencephalon" *BMC Developmental Biology*, 2007, pp. 1-17, vol. 7.

Iozzo, R. V. "Basement membrane Proteoglycans: From Cellar to Ceiling" *Nature Reviews Mol. Cell Biol.*, Aug. 2005, pp. 646-656, vol. 6.

Kaji, T. et al. "The vascular endothelial growth factor VEGF165 induces perlecan synthesis via VEGF receptor-2 in cultured human brain microvascular endothelial cells" *Biochimica et Biophysica Acta*, 2006, pp. 1465-1474, vol. 1760.

Laplante, P. et al. "Perlecan Proteolysis Induces an α2β1 Integrin- and Src Family Kinase-dependent Anti-apoptotic Pathway in Fibroblasts in the Absence of Focal Adhesion Kinase Activation" *Journal of Biological Chemistry*, Oct. 13, 2006, pp. 30383-30392, vol. 281, No. 41.

Woodall, B. P. et al. "Integrin α2β1 is the Required Receptor for Endorepellin Angiostatic Activity" *Journal of Biological Chemistry*, Jan. 25, 2008, pp. 2335-2343, vol. 283, No. 4.

Written Opinion in International Application No. PCT/US2011/042808, Feb. 29, 2012, pp. 1-5.

Office Action dated Apr. 10, 2012 in U.S. Appl. No. 12/655,503.

Lee, B. et al. "Perlecan domain V is neuroprotective and proangiogenic following ischemic stroke in rodents" *Journal of Clinical Investigation*, Aug. 2011, pp. 3005-3023, vol. 121, No. 8.

Tokuriki, N. et al. "Stability effects of mutations and protein evolvability" *Current Opinion in Structural Biology*, 2009, pp. 596-604, vol. 19.

Zheng, Z. et al. "Cellular and molecular events underlying ischemia induced neuronal apoptosis" *Drug News Perspect*, 2003, pp. 497-503, vol. 16, abstract only.

"MD Conference Express: Perlecan Domain V is a Novel Stroke Treatment", Mar. 2010, retrieved from the internet: URL: http://www.nxtbook.com/nxtbooks/mdconferencexpress/isc2010/index.php?startid=20#/20, p. 20, XP-002715653.

Bix, G.J. et al. "Perlecan Domain V Inhibits Alpha 2 Integrin Mediated Abeta Neurotoxicity" *Alzheimer's & Dementia: The Journal of the Alzheimer's Association*, Jul. 1, 2010, p. S591, vol. 6, No. 4.

Clarke, D. et al. "Perlecan domain V improves stroke outcome" *Journal of Cerebral Blood Flow & Metabolism*, Brain oral session: experimental stroke and cerebral ischemia 1, Oct. 1, 2009, pp. S37-S41 (see pp. S39-S40), vol. 29.

Clarke, D.N. et al. "Proteolytic Extracellular Matrix Fragments Following Ischemic Stroke: New Insights to Potential Therapeutic Targets" *The Open Drug Discovery Journal*, Jan. 1, 2010, pp. 168-173, vol. 2.

\* cited by examiner

Anterior

Stroke tissue

Posterior

Stroke PBS    Stroke DV

Nestin +
CD31+
DAPI

FIG. 3A
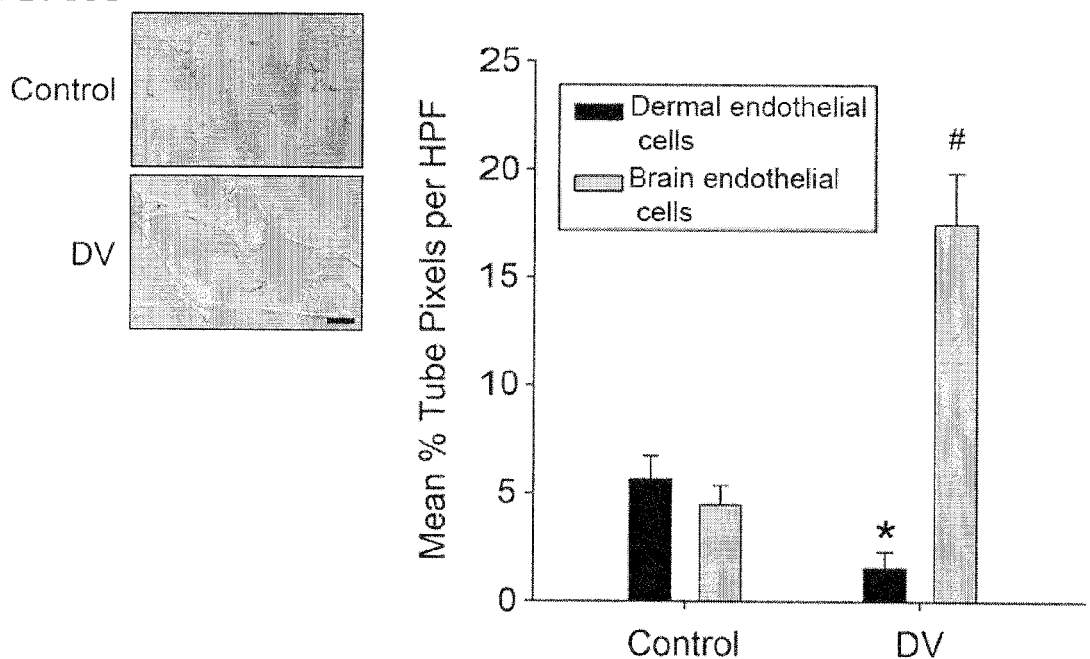
FIG. 3B
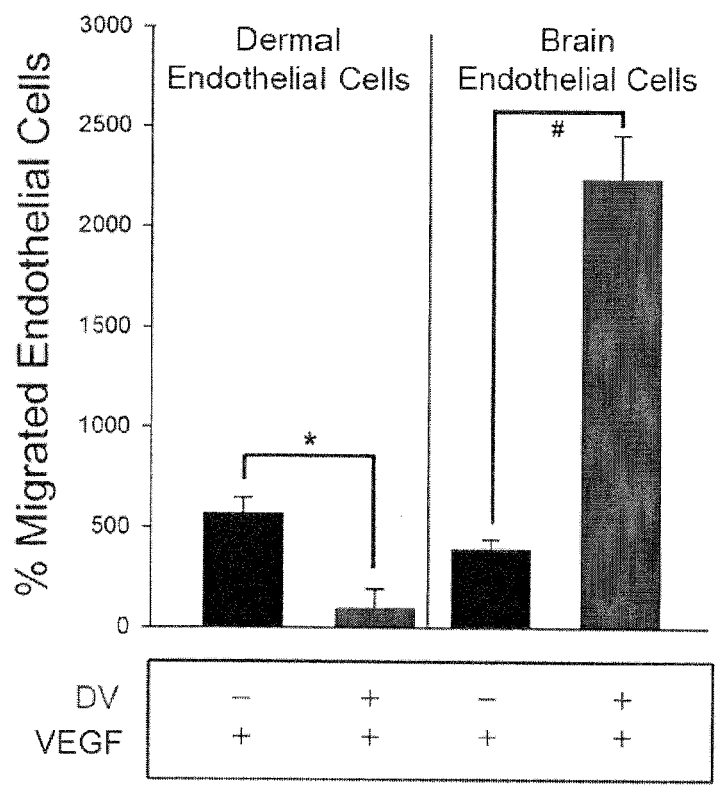
FIG. 3C

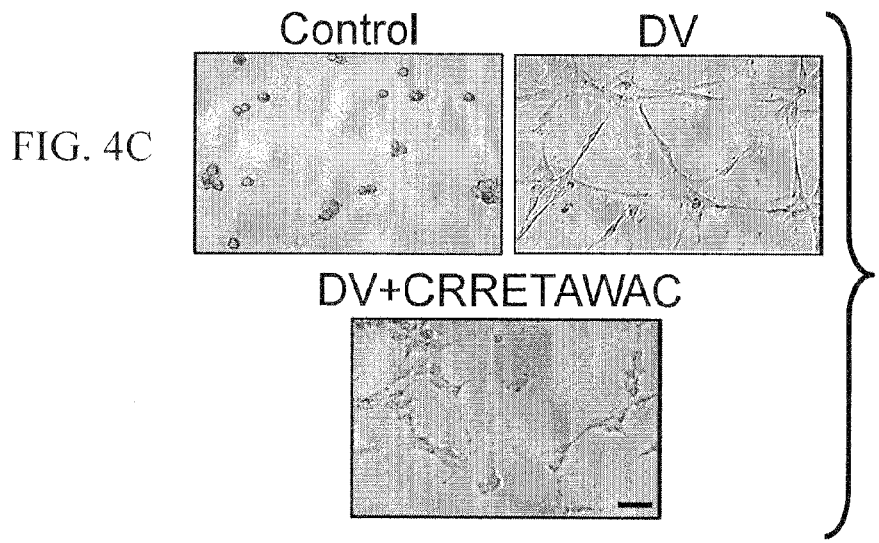
FIG. 4C
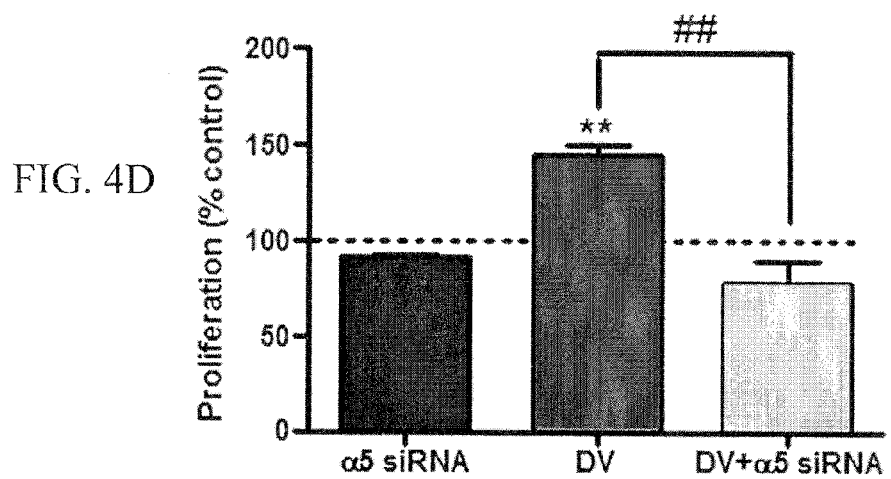
FIG. 4D
FIG. 4E
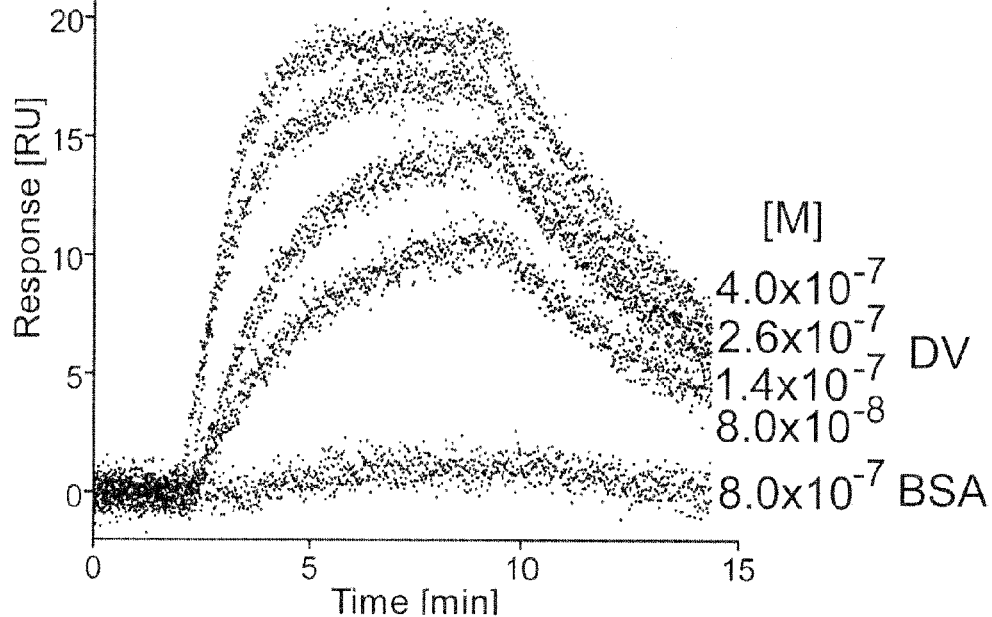

FIG. 5E
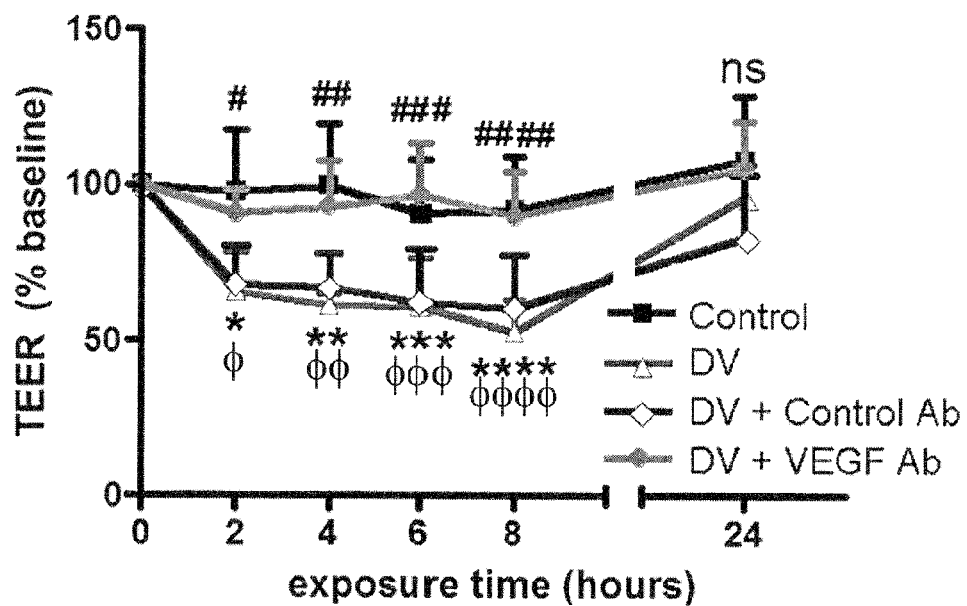
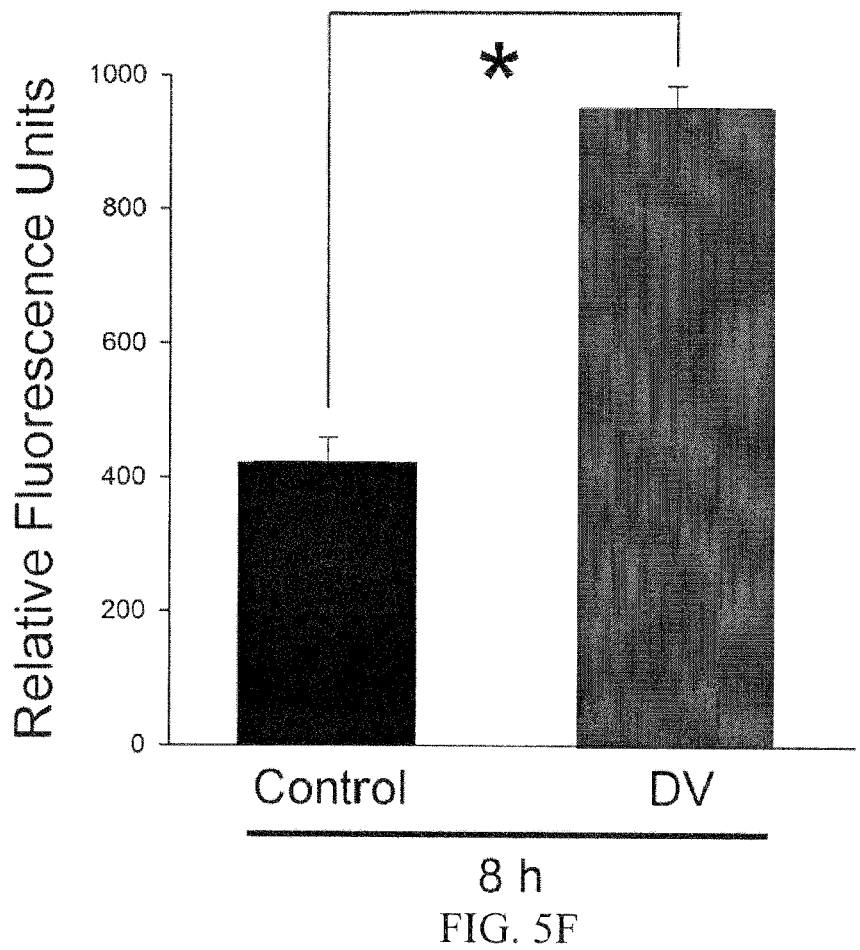
FIG. 5F

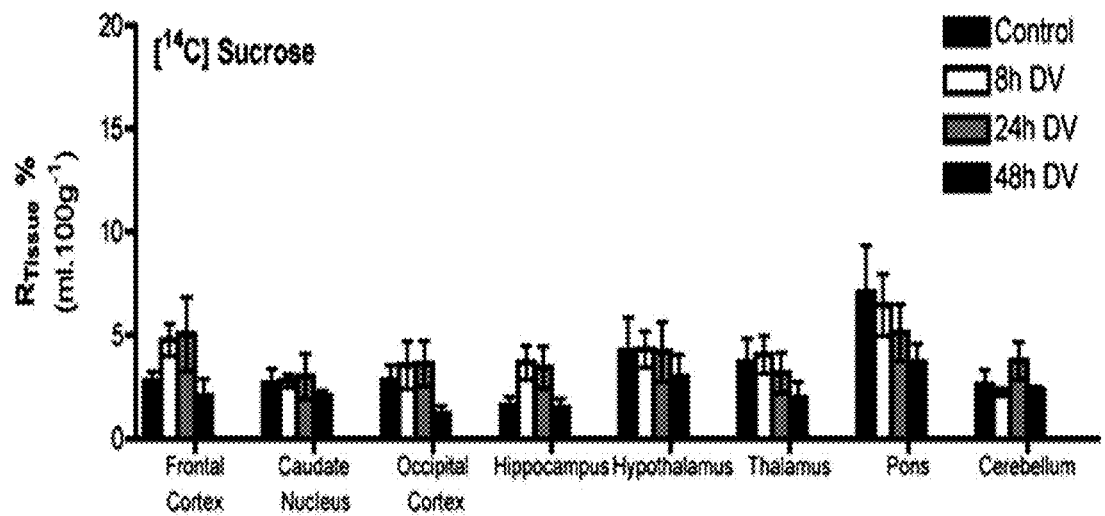
FIG. 5I
FIG. 5J
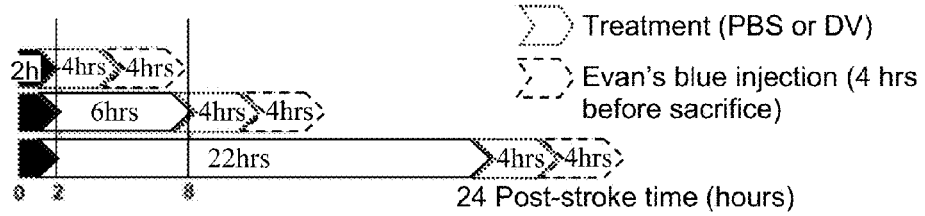
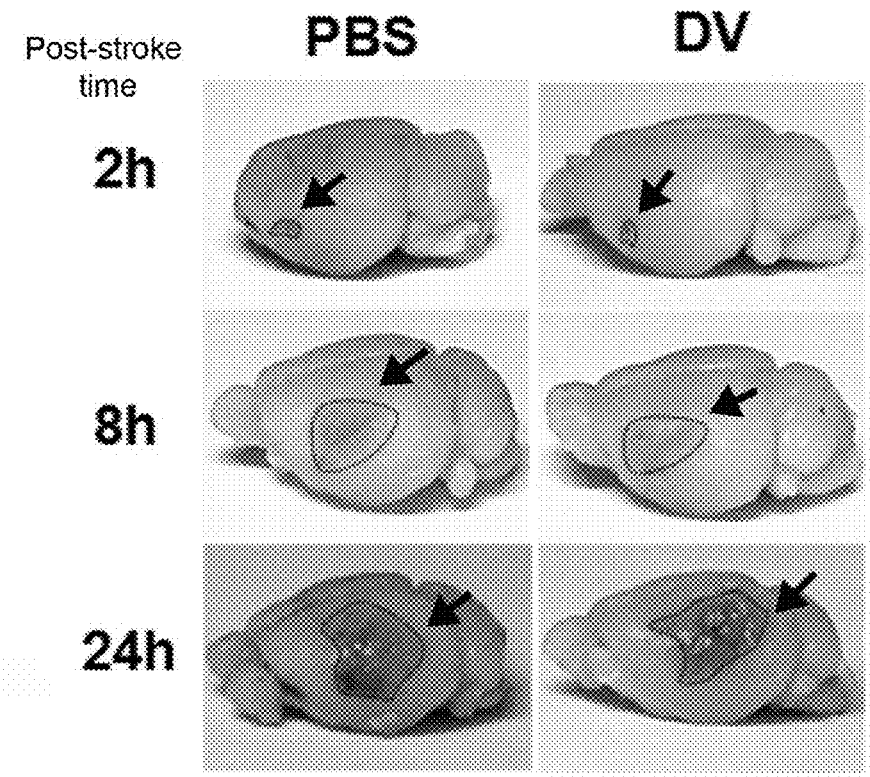

FIG. 5S
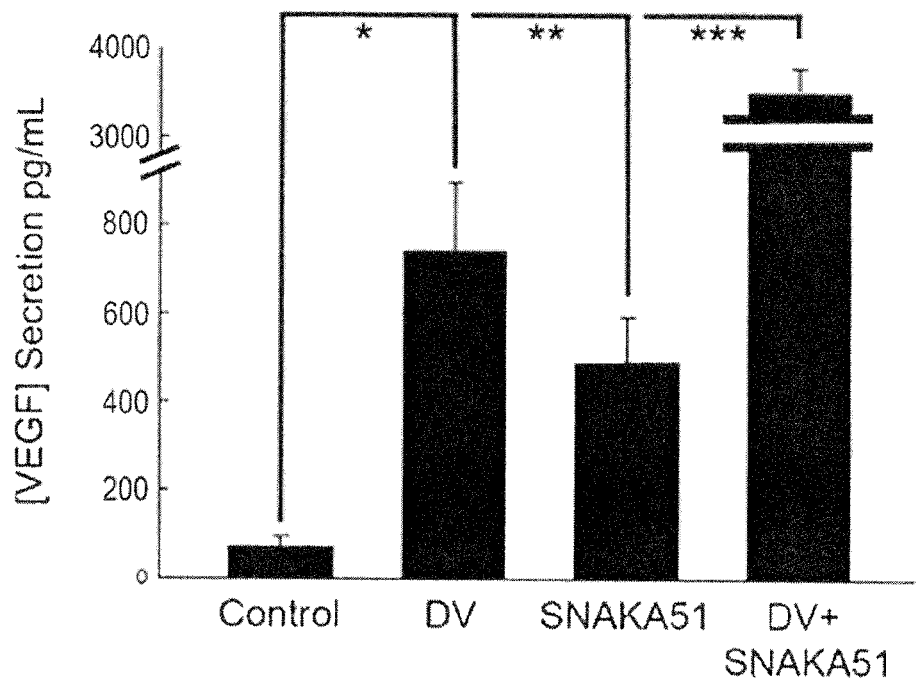
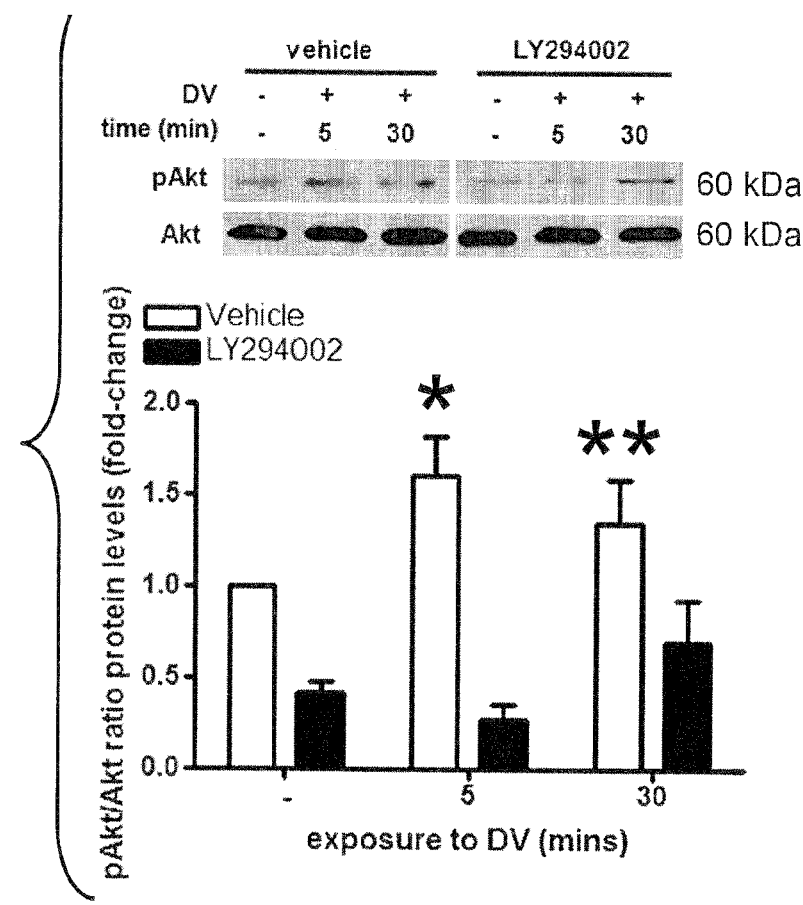
FIG. 5T

FIG. 5U
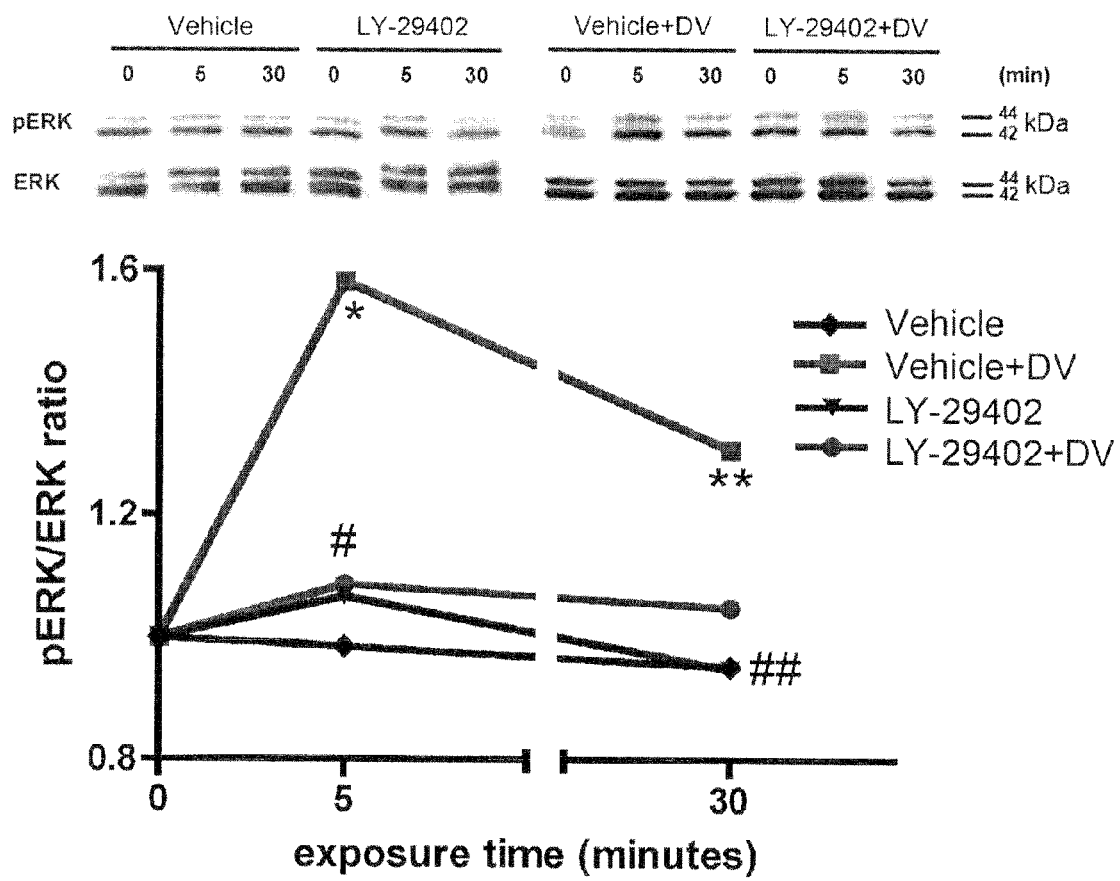
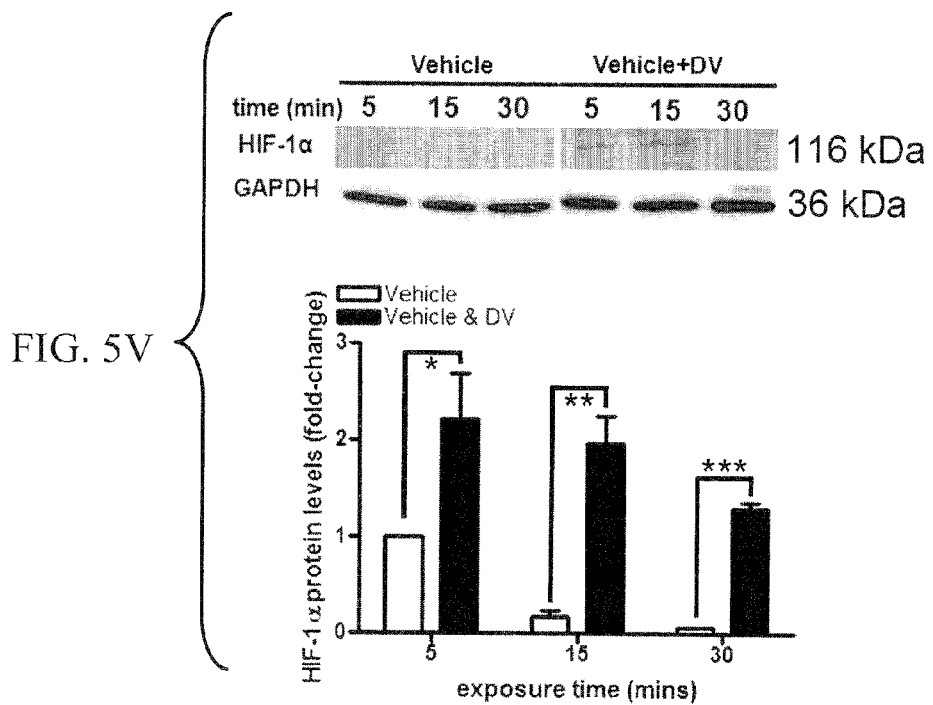
FIG. 5V

FIG. 16A
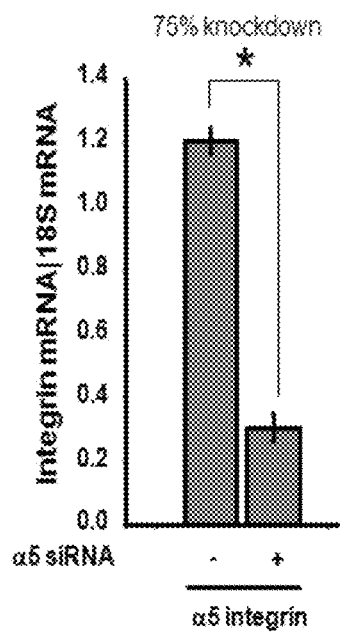
FIG. 16B
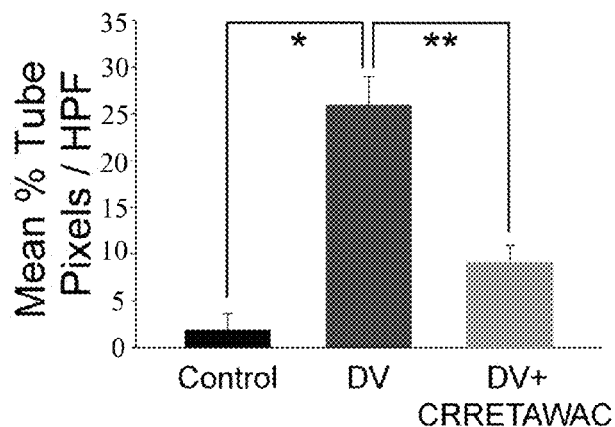
FIG. 17
FIG. 18A
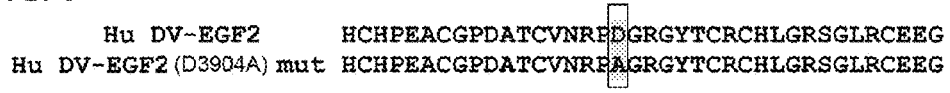
Hu DV-EGF2            HCHPEACGPDATCVNREDGRGYTCRCHLGRSGLRCEEG
Hu DV-EGF2 (D3904A) mut  HCHPEACGPDATCVNREAGRGYTCRCHLGRSGLRCEEG
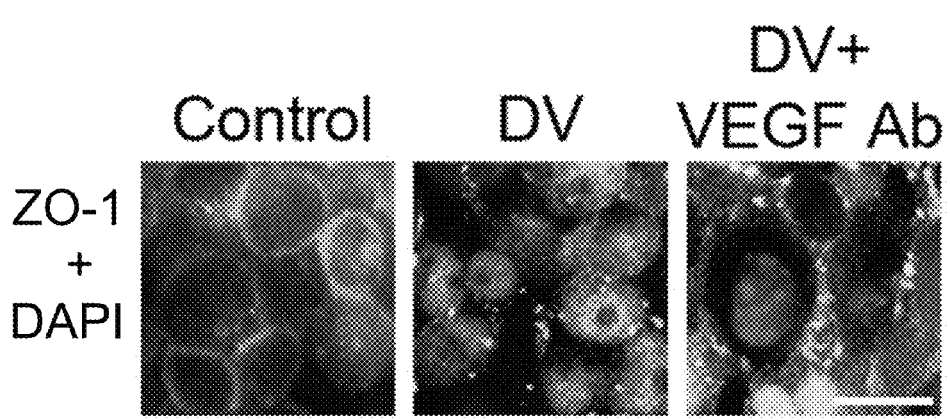
FIG. 19

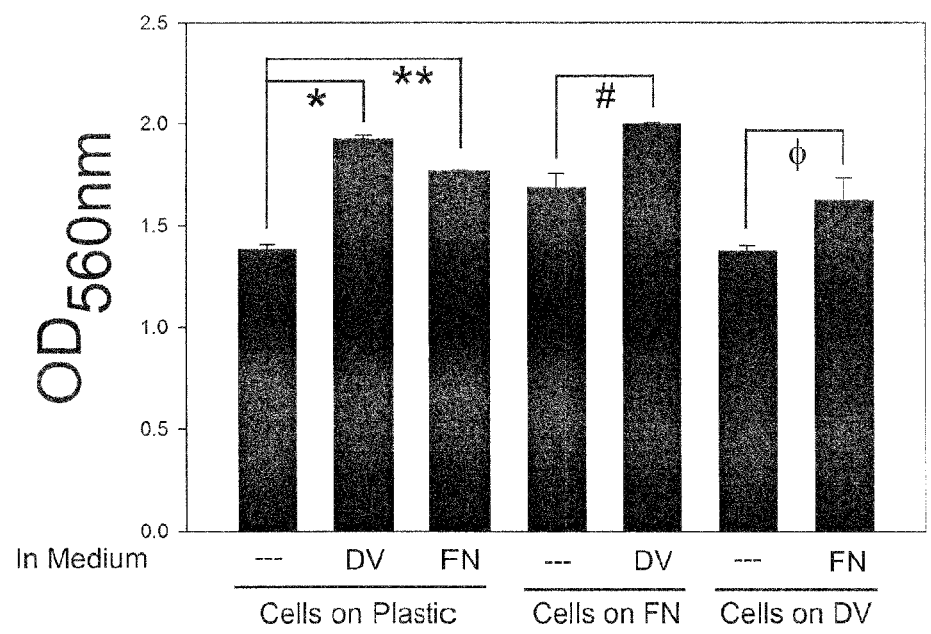
FIG. 21A
FIG. 21B
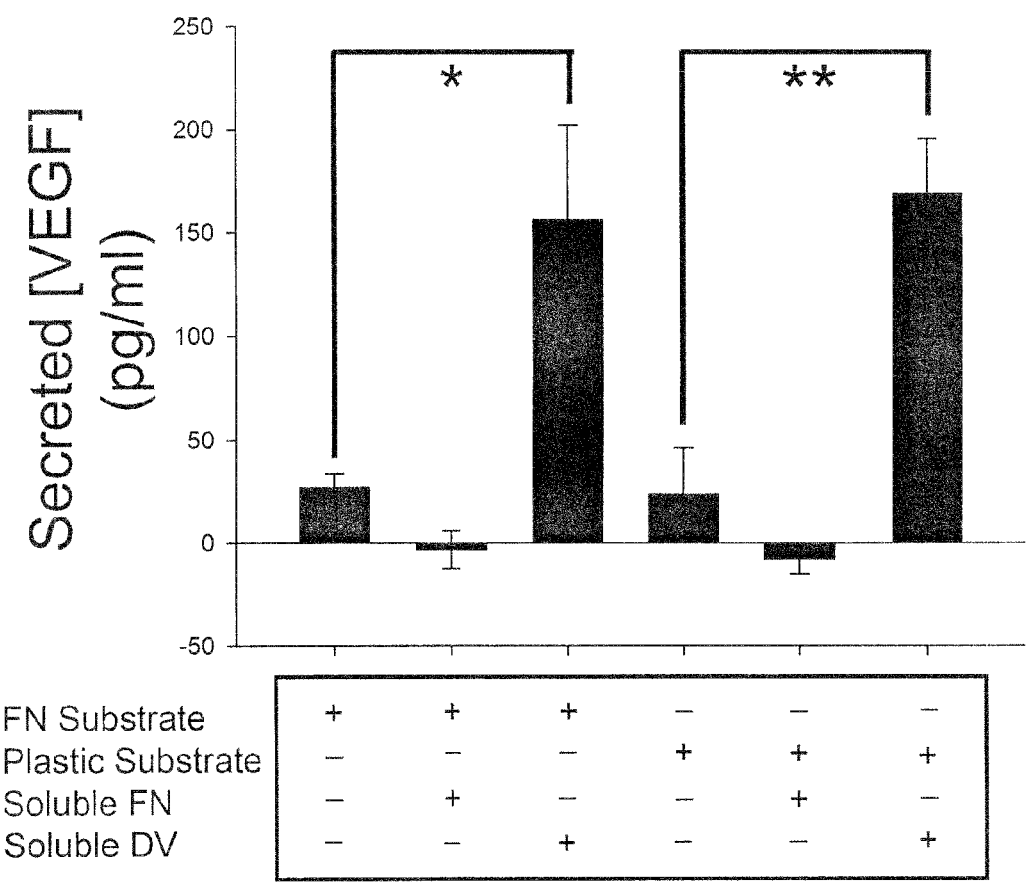

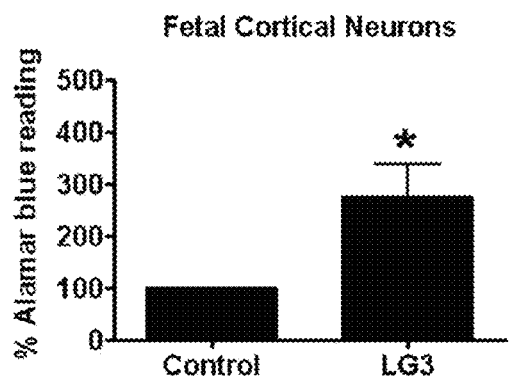
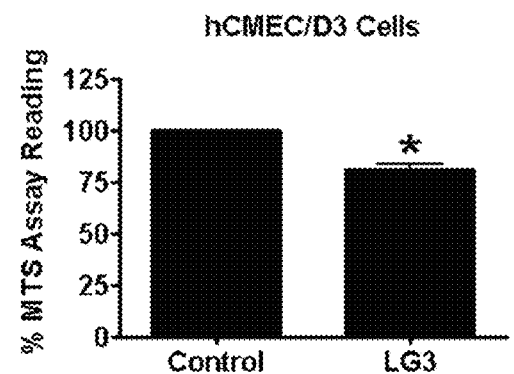
FIG. 27A          FIG. 27B
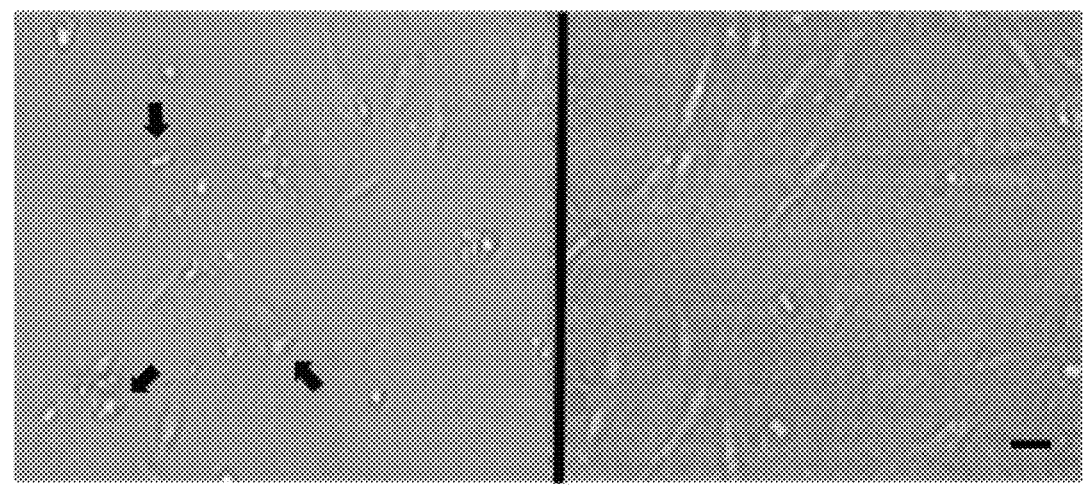
FIG. 27C

SEQUENCE LISTING

```
<160> NUMBER OF SEQ ID NOS: 14

<210> SEQ ID NO 1
<211> LENGTH: 705
<212> TYPE: PRT
<213> ORGANISM: Homo sapiens

<400> SEQUENCE: 1

Glu Ile Lys Ile Thr Phe Arg Pro Asp Ser Ala Asp Gly Met Leu Leu
1               5                   10                  15

Tyr Asn Gly Gln Lys Arg Val Pro Gly Ser Pro Thr Asn Leu Ala Asn
            20                  25                  30

Arg Gln Pro Asp Phe Ile Ser Phe Gly Leu Val Gly Gly Arg Pro Glu
        35                  40                  45

Phe Arg Phe Asp Ala Gly Ser Gly Met Ala Thr Ile Arg His Pro Thr
    50                  55                  60

Pro Leu Ala Leu Gly His Phe His Thr Val Thr Leu Leu Arg Ser Leu
65                  70                  75                  80

Thr Gln Gly Ser Leu Ile Val Gly Asp Leu Ala Pro Val Asn Gly Thr
                85                  90                  95

Ser Gln Gly Lys Phe Gln Gly Leu Asp Leu Asn Glu Glu Leu Tyr Leu
            100                 105                 110
```

```
Gly Gly Tyr Pro Asp Tyr Gly Ala Ile Pro Lys Ala Gly Leu Ser Ser
            115                 120                 125
Gly Phe Ile Gly Cys Val Arg Glu Leu Arg Ile Gln Gly Glu Ile
    130                 135                 140
Val Phe His Asp Leu Asn Leu Thr Ala His Gly Ile Ser His Cys Pro
145                 150                 155                 160
Thr Cys Arg Asp Arg Pro Cys Gln Asn Gly Gly Gln Cys His Asp Ser
                165                 170                 175
Glu Ser Ser Ser Tyr Val Cys Val Cys Pro Ala Gly Phe Thr Gly Ser
            180                 185                 190
Arg Cys Glu His Ser Gln Ala Leu His Cys His Pro Glu Ala Cys Gly
    195                 200                 205
Pro Asp Ala Thr Cys Val Asn Arg Pro Asp Gly Arg Gly Tyr Thr Cys
210                 215                 220
Arg Cys His Leu Gly Arg Ser Gly Leu Arg Cys Glu Glu Gly Val Thr
225                 230                 235                 240
Val Thr Thr Pro Ser Leu Ser Gly Ala Gly Ser Tyr Leu Ala Leu Pro
                245                 250                 255
Ala Leu Thr Asn Thr His His Glu Leu Arg Leu Asp Val Glu Phe Lys
            260                 265                 270
Pro Leu Ala Pro Asp Gly Val Leu Leu Phe Ser Gly Gly Lys Ser Gly
    275                 280                 285
Pro Val Glu Asp Phe Val Ser Leu Ala Met Val Gly Gly His Leu Glu
    290                 295                 300
Phe Arg Tyr Glu Leu Gly Ser Gly Leu Ala Val Leu Arg Ser Ala Glu
305                 310                 315                 320
Pro Leu Ala Leu Gly Arg Trp His Arg Val Ser Ala Glu Arg Leu Asn
                325                 330                 335
Lys Asp Gly Ser Leu Arg Val Asn Gly Gly Arg Pro Val Leu Arg Ser
            340                 345                 350
Ser Pro Gly Lys Ser Gln Gly Leu Asn Leu His Thr Leu Leu Tyr Leu
    355                 360                 365
Gly Gly Val Glu Pro Ser Val Pro Leu Ser Pro Ala Thr Asn Met Ser
370                 375                 380
Ala His Phe Arg Gly Cys Val Gly Glu Val Ser Val Asn Gly Lys Arg
385                 390                 395                 400
Leu Asp Leu Thr Tyr Ser Phe Leu Gly Ser Gln Gly Ile Gly Gln Cys
                405                 410                 415
Tyr Asp Ser Ser Pro Cys Glu Arg Gln Pro Cys Gln His Gly Ala Thr
            420                 425                 430
Cys Met Pro Ala Gly Glu Tyr Glu Phe Gln Cys Leu Cys Arg Asp Gly
    435                 440                 445
Phe Lys Gly Asp Leu Cys Glu His Glu Glu Asn Pro Cys Gln Leu Arg
    450                 455                 460
Glu Pro Cys Leu His Gly Gly Thr Cys Gln Gly Thr Arg Cys Leu Cys
465                 470                 475                 480
Leu Pro Gly Phe Ser Gly Pro Arg Cys Gln Gln Gly Ser Gly His Gly
                485                 490                 495
Ile Ala Glu Ser Asp Trp His Leu Glu Gly Ser Gly Gly Asn Asp Ala
            500                 505                 510
Pro Gly Gln Tyr Gly Ala Tyr Phe His Asp Asp Gly Phe Leu Ala Phe
    515                 520                 525
Pro Gly His Val Phe Ser Arg Ser Leu Pro Glu Val Pro Glu Thr Ile
```

```
                    530                 535                 540
Glu Leu Glu Val Arg Thr Ser Thr Ala Ser Gly Leu Leu Trp Gln
545                 550                 555                 560

Gly Val Glu Val Gly Glu Ala Gly Gln Gly Lys Asp Phe Ile Ser Leu
                    565                 570                 575

Gly Leu Gln Asp Gly His Leu Val Phe Arg Tyr Gln Leu Gly Ser Gly
                580                 585                 590

Glu Ala Arg Leu Val Ser Glu Asp Pro Ile Asn Asp Gly Glu Trp His
                595                 600                 605

Arg Val Thr Ala Leu Arg Glu Gly Arg Gly Ser Ile Gln Val Asp
            610                 615                 620

Gly Glu Glu Leu Val Ser Gly Arg Ser Pro Gly Pro Asn Val Ala Val
625                 630                 635                 640

Asn Ala Lys Gly Ser Val Tyr Ile Gly Gly Ala Pro Asp Val Ala Thr
                    645                 650                 655

Leu Thr Gly Gly Arg Phe Ser Ser Gly Ile Thr Gly Cys Val Lys Asn
                660                 665                 670

Leu Val Leu His Ser Ala Arg Pro Gly Ala Pro Pro Gln Pro Leu
            675                 680                 685

Asp Leu Gln His Arg Ala Gln Ala Gly Ala Asn Thr Arg Pro Cys Pro
                690                 695                 700

Ser
705

<210> SEQ ID NO 2
<211> LENGTH: 195
<212> TYPE: PRT
<213> ORGANISM: Homo sapiens

<400> SEQUENCE: 2

Asp Ala Pro Gly Gln Tyr Gly Ala Tyr Phe His Asp Asp Gly Phe Leu
1               5                   10                  15

Ala Phe Pro Gly His Val Phe Ser Arg Ser Leu Pro Glu Val Pro Glu
                20                  25                  30

Thr Ile Glu Leu Glu Val Arg Thr Ser Thr Ala Ser Gly Leu Leu Leu
            35                  40                  45

Trp Gln Gly Val Glu Val Gly Glu Ala Gly Gln Gly Lys Asp Phe Ile
    50                  55                  60

Ser Leu Gly Leu Gln Asp Gly His Leu Val Phe Arg Tyr Gln Leu Gly
65                  70                  75                  80

Ser Gly Glu Ala Arg Leu Val Ser Glu Asp Pro Ile Asn Asp Gly Glu
                85                  90                  95

Trp His Arg Val Thr Ala Leu Arg Glu Gly Arg Gly Ser Ile Gln
                100                 105                 110

Val Asp Gly Glu Glu Leu Val Ser Gly Arg Ser Pro Gly Pro Asn Val
            115                 120                 125

Ala Val Asn Ala Lys Gly Ser Val Tyr Ile Gly Gly Ala Pro Asp Val
    130                 135                 140

Ala Thr Leu Thr Gly Gly Arg Phe Ser Ser Gly Ile Thr Gly Cys Val
145                 150                 155                 160

Lys Asn Leu Val Leu His Ser Ala Arg Pro Gly Ala Pro Pro Gln
                165                 170                 175

Pro Leu Asp Leu Gln His Arg Ala Gln Ala Gly Ala Asn Thr Arg Pro
            180                 185                 190
```

Cys Pro Ser
        195

<210> SEQ ID NO 3
<211> LENGTH: 29
<212> TYPE: DNA
<213> ORGANISM: Artificial sequence
<220> FEATURE:
<223> OTHER INFORMATION: DV Asci pSecTag 2A primer

<400> SEQUENCE: 3
agggcgcgcc atcaagatca ccttccggc                              29

<210> SEQ ID NO 4
<211> LENGTH: 31
<212> TYPE: DNA
<213> ORGANISM: Artificial sequence
<220> FEATURE:
<223> OTHER INFORMATION: DV Xho1 pSEc Tag 2A primer

<400> SEQUENCE: 4
agctcgagcc gaggggcagg ggcgtgtgtt g                            31

<210> SEQ ID NO 5
<211> LENGTH: 28
<212> TYPE: DNA
<213> ORGANISM: Artificial sequence
<220> FEATURE:
<223> OTHER INFORMATION: NHEI whole DV Forward primer

<400> SEQUENCE: 5
aggctagcga tcaagatcac cttccggc                               28

<210> SEQ ID NO 6
<211> LENGTH: 32
<212> TYPE: DNA
<213> ORGANISM: Artificial sequence
<220> FEATURE:
<223> OTHER INFORMATION: Xho1 HIS DV Reverse primer

<400> SEQUENCE: 6
agctcgagca tgatgatgat gatgatgcga gg                          32

<210> SEQ ID NO 7
<211> LENGTH: 32
<212> TYPE: DNA
<213> ORGANISM: Artificial sequence
<220> FEATURE:
<223> OTHER INFORMATION: NHEI primer

<400> SEQUENCE: 7
aggcatacgc atggcatagc aatagcagag tc                          32

<210> SEQ ID NO 8
<211> LENGTH: 32
<212> TYPE: DNA
<213> ORGANISM: Artificial sequence
<220> FEATURE:
<223> OTHER INFORMATION: Xho1 primer

<400> SEQUENCE: 8
agctcgagca tgatgatgat gatgatgcga gg                          32

<210> SEQ ID NO 9
<211> LENGTH: 27
<212> TYPE: DNA

```
<213> ORGANISM: Artificial sequence
<220> FEATURE:
<223> OTHER INFORMATION: Primer

<400> SEQUENCE: 9
gtgaaccggc ctgccggtcg aggctac                                          27

<210> SEQ ID NO 10
<211> LENGTH: 27
<212> TYPE: DNA
<213> ORGANISM: Artificial sequence
<220> FEATURE:
<223> OTHER INFORMATION: Primer

<400> SEQUENCE: 10
gtagcctcga ccggcaggcc ggttcac                                          27

<210> SEQ ID NO 11
<211> LENGTH: 9
<212> TYPE: PRT
<213> ORGANISM: Artificial Sequence
<220> FEATURE:
<223> OTHER INFORMATION: binding peptide

<400> SEQUENCE: 11

Cys Arg Arg Glu Thr Ala Trp Ala Cys
1               5

<210> SEQ ID NO 12
<211> LENGTH: 38
<212> TYPE: PRT
<213> ORGANISM: Homo sapiens

<400> SEQUENCE: 12

His Cys His Pro Glu Ala Cys Gly Pro Asp Ala Thr Cys Val Asn Arg
1               5                   10                  15

Pro Asp Gly Arg Gly Tyr Thr Cys Arg Cys His Leu Gly Arg Ser Gly
            20                  25                  30

Leu Arg Cys Glu Glu Gly
        35

<210> SEQ ID NO 13
<211> LENGTH: 38
<212> TYPE: PRT
<213> ORGANISM: Artificial Sequence
<220> FEATURE:
<223> OTHER INFORMATION: mutated Human DV-EGF2

<400> SEQUENCE: 13

His Cys His Pro Glu Ala Cys Gly Pro Asp Ala Thr Cys Val Asn Arg
1               5                   10                  15

Pro Ala Gly Arg Gly Tyr Thr Cys Arg Cys His Leu Gly Arg Ser Gly
            20                  25                  30

Leu Arg Cys Glu Glu Gly
        35

<210> SEQ ID NO 14
<211> LENGTH: 9
<212> TYPE: PRT
<213> ORGANISM: Artificial Sequence
<220> FEATURE:
<223> OTHER INFORMATION: binding peptide
```

```
<400> SEQUENCE: 14

Cys Arg Arg Glu Thr Ala Asp Ala Cys
1               5
```

PERLECAN DOMAIN V PROTECTS, REPAIRS AND RESTORES ISCHEMIC BRAIN STROKE INJURY AND MOTOR FUNCTION

CROSS-REFERENCE TO RELATED APPLICATION

This application claims the benefit of U.S. Provisional Application Ser. No. 61/360,739, filed Jul. 1, 2010, the disclosure of which is hereby incorporated by reference in its entirety, including all figures, tables and amino acid or nucleic acid sequences.

The Sequence Listing for this application is labeled "Seq-List-replace.txt" which was created on Apr. 16, 2014 and is 11 KB. The entire contents of the sequence listing is incorporated herein by reference in its entirety.

BACKGROUND OF THE INVENTION

Stroke is the leading cause of long-term disability and third leading cause of death. While most research has focused on acute stroke treatment and neuroprotection, exploiting brain self-repair may provide better therapies. Unfortunately, current experimental therapies including pharmaceuticals, and stem cells may engender significant and unacceptable risks. Here we describe a distinct type of stroke therapy, a naturally occurring extracellular matrix fragment of perlecan, domain V, which functions by being neuroprotective and enhancing the brain's own response to injury. Domain V is well tolerated, specifically targets stroked and peri-infarct brain tissue, can be administered 24 hours after stroke, restores stroke-affected motor function to baseline pre-stroke levels, and exerts its beneficial effect via a previously unreported mechanism of upregulation of and interaction with the α5β1 integrin and subsequent release of vascular endothelial growth factor.

Ischemic stroke, a condition resulting from occlusion of brain vasculature[1], manifests as an energy deprived ischemic core of rapid cell death, surrounded by vulnerable regions with less severe energy deprivation (i.e. penumbra)[2-4]. Within these regions, reparative revascularization (angiogenesis) and neuronal repopulation (neurogenesis) occur in close proximity[5-7] affording mutually supportive growth factor-mediated neuron-endothelial cell cross-talk[8-11]. Additionally, angiogenic blood vessels serve as a physical scaffold for neurons to migrate towards the ischemic core[5]. Collectively, neurovascular coupling appears to represent an important means of post-stroke brain repair that could be therapeutically exploited[12]. Indeed, recent experimental stroke therapies, including pharmaceuticals, stem cell replacement therapies, and growth factors have attempted to capitalize on our understanding of emerging neurovascular concepts to promote functional stroke recovery[13-17]. However, drug and growth factor therapies raise questions of potentially serious systemic side effects, drug interactions, and contra-indications. Similarly, cell-based therapies raise important safety issues of "where do the cells go?" once injected and whether injected cells become undesirable tumors or other abnormal ectopic tissue. Furthermore, growth factors can have vastly different positive or negative consequences for stroke depending on when they are administered relative to the stroke injury. For example, vascular endothelial growth factor (VEGF) may worsen already disrupted blood brain barrier permeability (a hallmark of early stroke pathology) and promote brain edema, as well as enhance hemorrhagic transformation and brain infarct size[18] if administered early after stroke onset. However, if the same VEGF is given more chronically post-stroke, it is neuroprotective, enhances angiogenesis and neurogenesis[19-21].

Perlecan is required for both angiogenesis and neurogenesis[24], and may be neuroprotective due to the sequestration and release of various growth factors. Interestingly, perlecan is also known to harbor an anti-angiogenic C-terminal protein Domain V (DV, also known as endorepellin[25]) that is activated by proteolysis from full length perlecan[22]. However, the presence and brain activity of DV have not been characterized due in part to the absence of DV's previously identified anti-angiogenic α5β1 integrin receptor from angiogenic brain endothelial cells[25-27].

Using two different stroke models (the rat endothelin-1-induced cerebral ischemia and the mouse middle cerebral artery occlusion MCAo models), a stable and long-lasting increase in brain DV levels following stroke injury has been demonstrated. In addition, post-stroke administered DV is well-tolerated, targets stroke and peri-infarct vasculature, is neuroprotective, unexpectedly enhances brain angiogenesis and significantly improves post-stroke functional motor recovery to pre-stroke baseline function via a previously unidentified receptor and signal transduction pathway. Collectively, the results reveal unexpected differences between brain and nonbrain angiogenesis and demonstrate that DV is a putative, distinct, well tolerated, neurovascular-targeting experimental stroke therapy.

BRIEF SUMMARY OF THE INVENTION

The disclosed invention relates to the use of perlecan domain V (DV) for the treatment of stroke, traumatic brain injury (TBI) or spinal cord injuries (SCI). In certain embodiments, fusion proteins of DV can be used for the treatment of stroke, TBI or SCI. DV is also referred to as endorepellin in the art. This application also provides compositions and combination therapies for the treatment of stroke, TCI and/or SCI. Another aspect of the invention provides methods of restoring motor function in subjects having neurological damage arising from a stroke, TBI or SCI.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

(FIG. 1A) TTC stain of a representative rat brain, sectioned from anterior to posterior, 24 hours after stroke with stereotactic injection of endothelin-1 to transiently occlude the middle cerebral artery, demonstrating stroked brain tissue (white tissue as indicated by label). (FIG. 1B) representative anti-DV western blot analysis on post-stroke rat brain homogenates. GAPDH was used as an internal loading control. DV levels were assessed in both ipsilateral (stroked) and contralateral hemispheres at post-stroke day (PSD) 1, 3, 5 and 7 (upper panel), sham-operated animals showed no detectable DV. (FIG. 1C) Densitometry analysis of DV Western-blot showed in 1 b. DV band densities intensities were normalized to their respective GAPDH bands. *p=0.0001, **p=0.0007, #p=0.007, and ##p=0.005 denotes significant differences between ipsi- and contralateral hemispheres at 1, 3, 5 and 7 days respectively. (FIG. 1D) DV levels are up-regulated in human stroke tissue. Representative DV western blot obtained from human cerebral tissue samples. C1 and C2 denote two independent nonstroked human brain tissue samples, S1 and S2 denote sample from two hemorrhagic stroke patients (middle cerebral artery rupture, surgery performed within 24 h). 40 μg samples were loaded, whereas 100 ng of purified recombinant human DV (rhDV) was loaded as positive control. Note the complete absence of DV band in control tissues, whereas DV is strongly detected in stroked samples. (FIG. 1E) Representative DV and CD31 co-immunohistochemistry of rat stroked brain tissue on post-stroke day 3 and 7 demonstrating that post-stroke DV is generated in close association with blood vessels. This was expected as perlecan brain expression is predominantly in the vascular basement membrane. Scale bar=50 μM. (FIG. 1F) Representative Domain IV (DIV<red) and DV (green) double immunohistochemistry of PSD3 and PSD7 stroked rat brain tissue. Note the distinction between perlecan-bound DV (arrowheads) from perlecan-cleaved DV (arrows). Scale bar=20 μm.

(FIG. 2A) Representative mouse brain TTC staining at post-stroke day 3 (tandem ipsilateral common carotid/middle cerebral artery occlusion (CCA/MCAo). Sections are presented from rostral to caudal positions. TTC staining was performed on wild-type animals (WT) or perlecan hypomorph mice (Pln−/−). Mice received intraperitoneal DV injection (1 mg/kg) at post-stroke day 1 and 2. Yellow asterisks indicate ischemic lesions (TIC negative). (FIG. 2B) DV treatment decreases stroke infarct volume in WT and Pln−/− animals on post-stroke day 3. Hemispheric lesion volume (HLV) was calculated from the total hemisphere volume. Note the significant HLV decrease in WT and Pln−/− mice treated with DV, n=10 per treatment group. *$p=0.00003$ and #$p=0.00007$ respectively). Conversely, Pln−/− mice showed the highest HLV values (**$p=0.0006$), likely due to low endogenous levels of cleaved DV. (FIG. 2C) Representative cresyl violet stain, cleaved caspase-3, and TUNEL stain at the peri-infarct area in wt treated with PBS or with DV. Propidium iodide (PI) was used as nuclear counterstaining in the TUNEL assay. Note the decreased number of shrunken and misshapen cells present in the Cresyl violet staining in DV-treated versus PBS-treated animals. Note the anti-apoptotic effect of DV on neurons, as seen as decreased cleaved caspase-3 staining, as well as decreased of TUNEL-positive nuclei. Scale bars=5 μm (Cresyl violet) and 10 μm (caspase-3 and TUNEL) (FIG. 2D) Representative von-Willebrand factor staining (green) micrograph pictures obtained on post-stroke day 5 to analyze peri-infarct vasculature in WT and pln−/−±PBS or DV treatment as labeled. Bar is 10 μm. (FIG. 2E) Quantification of von Willebrand-positive vessels per high power field (hpf) for each treatment group on post-stroke days 3, 5 and 7 (n=20 images analyzed per animal, 10 animals per experimental condition). DV treatment resulted in a significant increases in stroke peri-infarct vasculature on post-stroke days 3 (*$p=0.001$), 5 ($p=0.000008$) and 7 (*$p=0.00000004$) as compared to WT. Pln−/− mice experienced significantly reduced peri-infarct vasculature on post-stroke days 3 (*$p=0.0002$) and 7 (**$p=0.0001$) while DV treatment of pln−/− mice increased peri-infarct vasculature above WT levels on post-stroke days 5 (#$p=0.0006$) and 7 (##$p=0.0001$). (FIG. 2F) von Willebrand (green) and HIS (red, to detect administered DV) immunohistochemistry revealed an abundance of DV in stroked tissue and stroke peri-infarct brain tissue (here DV deposited in a perivascular distribution). In contrast, no DV was detected in the corresponding unstroked contralateral brain tissue. Bar is 10 μm. (FIG. 2G) Post-stroke day 5 rat brain immunostained with anti-His antibody (red, to detect administered DV) and DAPI nuclear counterstain demonstrating that the HIS signal is almost completely contained within the stroke core and peri-infarct region. (FIG. 2H) Nestin and CD31 immunohistochemistry (with DAPI nuclear counterstain) of peri-infarct post-stroke day 7 brain±DV treatment demonstrating increased nestin positive cells in close proximity to blood vessels. Bar is 5 p.m. (FIG. 2I) Quantification of mean percent doublecortin positive pixels per HPF on PBS or DV treated animals measured as in FIG. 2E. DV resulted in significantly more doublecortin positive pixels on all 3 days measured (*$p=0.00001$, $p=0.000008$, *$p=0.000009$, respectively). (FIG. 2J) CD45 immunohistochemistry of peri-infarct post-stroke day 5 PBS and DV treated brain tissue demonstrating no significant CD4+ cells in either condition. Bar is 5 μm. (FIG. 2K) Cylinder test of post-stroke motor function in stroked rats±DV treatment and sham surgery control rats. On post-stroke days 3-7, contralateral paw use was significantly increased (*$p=0.03$, **$p=0.009$) in the stroked, DV treated group (0.5 mg/kg given via I.P. injection on post-stroke days 1, 3, 5, 7) as compared to the stroked, PBS treated group. Also on post-stroke days 3-7, there was no significant difference between the stroked, DV treated group and the sham surgery control group. (Figure L) Vibrissae-elicited forelimb placement test on WT and pln−/− stroked mice±DV (0.5 or 1.0 mg/kg) or PBS treatment demonstrating that all stroked mice groups placed the contralateral forelimb significantly less on post-stroke day 1 than prior to stroke (p=0.0003 for WT DV (1 mg/kg), p=0.0001 for WT DV (0.5 mg/kg), p=0.0002 for WT PBS, p=0.0001 for pin−/− DV (1 mg/kg) and p=0.0001 for pln−/− PBS). However, by post-stroke day 3 and 5, the WT DV 1 mg/kg, WI DV 0.5 mg/kg and pln−/− DV 1 mg/kg groups, respectively, significantly improved their use of the stroke-affected forelimb while the PBS-treated mice remained significantly impaired (p=0.001, p=0.0008, p=0.006, p=0.005 for PBS treated group on post-stroke days 1, 3, 5, and 7, respectively, as compared to day 0). The WT DV 1 mg/kg treated and the pln−/− DV 1 mg/kg groups were indistinguishable from the sham surgery control group (100% use of contralateral paw at all times measured, data not shown) by post-stroke day 5 (p=0.6, p=0.7 respectively). Furthermore, each WT DV treated group was significantly different from each other and the WT PBS-treated group (p=0.01 between WT DV treated groups, p=0.006 between WT DV (1 mg/kg) and WT PBS-treated group, and p=0.009 between WT DV (0.5 mg/kg) and WT PBS-treated group). The pln−/− PBS treated group was not significantly different from the WT PBS treated group (p=0.3). Finally, the pln−/− DV 1 mg/kg treated group was significantly different than the pln−/− PBS treated group (p=0.009), the WT DV 0.5 mg/kg treated group (p=0.03) but not significantly different from the WT DV 1 mg/kg treated group (p=0.8).

FIGS. 3A-3D. DV enhances brain angiogenesis in vitro (FIG. 3A) P0 mouse brain microvascular endothelial cells were added to Matrigel±DV for 12 hours followed by fixation and photography. Representative photomicrographs demonstrate that endothelial cells exposed to DV form interconnected tube-like structures while untreated controls have not. Bar is 10 (FIG. 3B) Quantification of Matrigel capillary tube assays for mouse dermal and brain endothelial cells demonstrating significant enhancement of brain endothelial cell tube formation and inhibition of dermal endothelial cell tube formation (n=15, #$p=0.0009$, n=15, *$p=0.001$, as compared to corresponding control, HPF=high power field, error bars=standard deviation). (FIG. 3C) Quantification of migration of dermal and brain endothelial cells towards VEGF (20 ng/ml) in a modified Boyden chamber migration assay±direct exposure to DV (mean normalized values for n=15±standard deviation plotted), as normalized to random migration across the membrane in the absence of VEGF. DV significantly inhibited dermal endothelial cell migration (*p=0.0008 as compared to VEGF alone) but significantly enhanced brain endothelial cell migration (n=15, # indicates significance, p=0.000001 for DV). (FIG. 3D) Quantification of proliferation of dermal and brain endothelial cells±addition of the α2 integrin plasmid after hours±DV in serum free media as measured via MTS assay. Values shown (n=15, mean±standard deviation normalized to control proliferation arbitrarily set to 100%) demonstrate significant inhibition of dermal endothelial cell proliferation (#p=0.00005) and brain endothelial cells expressing α2β1 integrin (**p=0.00009) and significant enhancement of brain endothelial cell proliferation (*p=0.002).

FIGS. 4A-4L. Identification of α5β1 integrin as a pro-angiogenic DV receptor in vitro and in vivo. (FIG. 4A) Quantification of representative brain endothelial cell adhesion assay to immobilized BSA (negative control) or DV±α5β1 function blocking antibody (10 μg/ml) demonstrating that DV supports significantly more cell adhesion as compared to BSA (#p=0.00005) which could be significantly inhibited by α5β1 function blocking antibody (*p=0.0007) or knockdown of α5β1 integrin with α5 siRNA (##p=0.000009). (FIG. 4B) Quantification of mean number cells (±standard deviation) migrating towards 3% fetal bovine serum (control) or DV±α5β1-GST or α5 knockdown with α5 siRNA (as normalized to negative control (no chemotractant) demonstrating that DV was as powerful a chemotractant as 3% serum which could be significantly inhibited by α5β1-GST (*p=0.02) or α5 knockdown (p=0.009) (FIG. 4C) Representative images of brain endothelial cells on Matrigel after 12 hours, ±DV± the α5β1 specific binding peptide CRRETAWAC (SEQ ID NO: 11) demonstrating that CRRETAWAC inhibits DV's enhancement of tube-like structure formation. Bar is 10 vim. (FIG. 4D) Quantification of proliferation of brain endothelial cells±addition of the α5 integrin plasmid after 48 hours±DV in serum free media as measured via MTS assay. Values shown (n=15, mean±standard deviation normalized to control proliferation arbitrarily set to 100%) demonstrate that α5 siRNA did not significantly inhibit brain endothelial cell proliferation (p=0.6), but did inhibit the positive (p=0.002) proliferative effect of DV (##p=0.0001). (FIG. 4E) optical biosensor traces showing the association and dissociation of DV and BSA (control) with immobilized α5 integrin at the concentrations listed (RU=relative units). (FIG. 4F) α51(red) and DV (anti-HIS, green) co-immunocytochemistry of brain endothelial cells (±DV treatment for 30 minutes) demonstrating DV and α5β1 co-localization (yellow/orange color in merged field and as magnified in 3 boxes). Bar is 2 μm. (FIG. 4G) Quantified mean (±standard deviation) fold change in α5/VLA5 mRNA in brain endothelial cells after 1.5 or 3 h of DV treatment (*p=0.0001, **p=0.006). (FIG. 4H) Representative α5β1 immunohistochemistry in mouse post-stroke day 3 brain sections±DV treatment. Bar is 10 μM. (FIG. 4I) post-stroke day 3 brain tissue from PBS and DV treated animals (with corresponding GAPDH loading control) demonstrating a significant increase in total stroked brain α5β1 levels with DV treatment. (FIG. 4J) Representative images of von-Willebrand immunohistochemistry (green) on post-stroke day 5 to analyze peri-infarct vasculature in WT mice±PBS±α5β1 function blocking antibody (Ab)±DV treatment as labeled. Bar is 10 μm. (FIG. 4K) Quantification of mean von Willebrand pixels per high power field (HPF)±standard deviation as seen in FIG. 4J for each treatment group on post-stroke days 3, 5 and 7 (n=20 images analyzed per animal, 10 animals per experimental condition). Treatment with α5β1 function blocking antibody alone resulted in significantly less von Willebrand positive pixels per HPF on post-stroke days 5 (*p=0.001) and 7 (**p=0.0008) that was not improved with DV treatment (#p=0.001, ## p=0.0007 on post-stroke day 5 and 7 respectively). Control IgG had no effect. (FIG. 4L) α5β1-function blocking antibody prevented DV neuroprotection resulting in visibly more apoptotic appearing neurons in the peri-infarct region compared to PBS treated controls as detected by cresyl violet caspase-3 and TUNEL staining (control IgG had no visible effect on neuronal apoptosis, data not shown). Scale bars=5 μm (Cresyl violet) and 10 μm (caspase-3 and TUNEL).

(FIG. 5A) qPCR from mouse brain endothelial cells+DV exposure for 1.5 or 3 h demonstrates a significant fold increase in VEGF mRNA (*p=0.0001, **p=0.003) and VEGFR2 mRNA (#p=0.02, ##p=0.007) as compared to control. n=3 for each condition. values are mean±standard error. (FIG. 5E) TEER measurements over 24 hours of a confluent mouse brain endothelial cell monolayer±DV±VEGF neutralizing antibody or ±control antibody (rabbit IgG) treatment demonstrates that DV from 2 to 8 h, significantly decreases TEER (*p=0.003, p=0.002, *p=0.001, ****p=0.0009) that was unaffected by control antibody (Φp=0.002, ΦΦp=0.004, ΦΦΦp=0.001, ΦΦΦΦp=0.002) but was inhibited by VEGF neutralizing antibody (10 μg/ml, #p=0.9, ##p=0.7, ###p=0.6, ####p=0.8) n=3 for each point, ±standard deviation, normalized to mean TEER at 0 h (142.40±31.58 Ohms/cm2). No conditions were significantly different from control TEER at 24 h. (FIG. 5F) Representative permeability assay across a confluent mouse brain endothelial monolayer after 8 hours+DV with 40 kDa FITC dextran further demonstrating a significant (*p=0.0005) increase in monolayer permeability. (FIG. 5I) In vivo non-stroked WT mouse blood brain permeability experiment showing percent extent (mean of n=3, +/− standard deviation) of $^{14}C$ Sucrose taken up into various brain regions across the blood brain barrier prior to (Control) and 8, 24 and 48 h after intraperitoneal injection of DV. Although there is a trend of increased permeability with DV treatment in the frontal cortex and hippocampus, none of the values are significantly different than the corresponding control value. (FIG. 5J) Schematic of Evan's Blue dye extravasation post-stroke in vivo blood brain permeability paradigm where mice were stroked and treated with PBS or DV 2, 8 or 24 h after stroke followed by I.V. injection of Evan's Blue dye (4 h later) and animal sacrifice 4 h later. Images of representative brains from animals treated with PBS or DV 2, 8 or 24 h after stroke showing the brain surface spread of Evan's blue dye as circled by the dashed black line and indicated by the black arrow in each image. (FIG. 5S) Representative VEGF ELISA demonstrating that as in addition to DV ($*p=0.0002$), the α5β1 specific activating antibody SNAKA51 significantly increases VEGF levels ($p=0.0003$) and the combination of DV and SNAKA51 further increase VEGF secreted levels ($*p=0.000001$ compared to control, p=0.002 compared to DV alone). N=3, mean values+/−standard deviation shown. (FIG. 5T) DV phosphorylates/activates brain endothelial cell Akt after 5 minutes ($*p=0.005$ versus control) and 30 minutes ($**p=0.02$ versus control) as demonstrated with representative western blot and plot (mean fold-change+/−standard deviation plotted) as normalized to total Akt signal. This activation is inhibited with LY294002. (FIG. 5U) DV phosphorylates/activates ERK in brain microvascular endothelial cells after 5 minutes ($*p=0.001$, which persists to at least 30 minutes, $**p=0.02$) as demonstrated with representative western blot and plot as normalized to total ERK signal. This transient phosphorylation could be inhibited with the PI3K inhibitor LY-294002 ($\#p=0.003, \#\#p=0.009$ as compared to DV changes). The inhibitor by itself had no significant effect on ERK phosphorylation. (FIG. 5V) DV treatment results in a sustained (from 5 to 30 min) increased in brain endothelial cell HIF-1α levels as demonstrated with representative western blot and plot (mean fold change as normalized to GAPDH loading control+/−standard deviation, $*p=0.04, p=0.01, *p=0.001$). (FIG. 5Z) Hypothetical schematic for DV induced VEGF release in brain microvascular endothelial cells via the α5β1 integrin. Signal transduction components that have been demonstrated in this manuscript are colored green. Various inhibitors and activators used in this study are indicated with red and green lines, respectively. The various proposed effects of VEGF (i.e. stimulation of angiogenesis and neuroprotection) are also schematically illustrated.

(FIG. 8B) Fibronectin western blot with varying amounts of loaded fibronectin as indicated demonstrating that the anti-fibronectin antibody (ab80923, Abcam) can readily detect 100 ng or more of fibronectin. (FIG. 8C) Fibronectin western blot (with anti-fibronectin antibody used in FIG. 8B) of 500 ng of fibronectin control and 100 μg of three separate preparations of DV demonstrates a fibronectin band at the appropriate size in the control lane but no fibronectin signal in the DV preparations. Based on the determined sensitivity of the anti-fibronectin antibody in FIG. 8B, this blot demonstrates that any fibronectin contamination of these 3, 100 μg DV samples must be less than 100 ng. (FIG. 8D) Quantification of brain endothelial cell proliferation±addition of DV (250 nM) or fibronectin (1 mg/ml) fibronectin neutralizing antibody at different concentrations shown after 48 hours±DV in serum free media as measured via MTS assay. Values shown (n=15, mean±standard deviation normalized to control proliferation arbitrarily set to 100%) demonstrate that the fibronectin antibodies had no effect on DV enhancement of proliferation but did significantly inhibit FN enhanced proliferation (*p=0.002, **p=0.001). (FIG. 8E) Representative images of mouse brain microvascular endothelial cells added to Matrigel±DV±anti-fibronectin antibody (20 μg/ml) for 12 hours followed by fixation and photography. Representative photomicrographs demonstrate that endothelial cells exposed to DV form interconnected tube-like structures that are unaffected by the fibronectin antibody. Bar is 10 μm. (FIG. 8F) Quantification of the capillary tube-like structures as shown in (FIG. 8E) demonstrating that anti-fibronectin antibody has no effect on DV-induced increases in tube formation, but that this same antibody significantly inhibits fibronectin-induced effects (*p=0.0002).

(FIG. 9A) The middle cerebral arteries (MCA) in perlecan hypomorph mice (pln−/−) and wild type littermate control C57B16 mice, indicated by the labeled arrows in each, appear identical in gross appearance. (FIG. 9B) Western Blot analysis of post-stroke administered DV. Lysate of the stroked ipsilateral (I) brain tissue or corresponding contralateral (C) nonstroked tissue from a representative PBS or DV treated animal was analyzed by western immunoblot with antibodies to DV (detects both endogenous and administered DV), HIS (detects only administered DV) and GAPDH protein loading control. Significantly more DV was detected in the stroked tissue as compared to the contralateral tissue (when normalized to GAPDH loading control) in both the PBS (p=0.0001) and DV (p=0.000001) treated animals, the latter even more so due to the extra administered DV. Administered DV as detected by anti-HIS antibody could only be detected in the lysate from the stroked brain hemisphere of the animal treated with DV.

(FIG. 13A) Representative MTS proliferation assay of primary rat brain microvascular endothelial cells after 48 hours in serum free media containing VEGF 20 ng/ml±DV (250 nM). Mean OD at 490 nm±standard deviation shown from n=3 per treatment condition. DV significantly increased rat brain endothelial cells (*p=0.009). (FIG. 13B) Representative migration assay of human brain microvascular endothelial cells±DV (250 nM) migrating towards a lower chamber±the chemo-attractant VEGF (20 ng/ml) over 6 h. The mean number of migrated cells±standard deviation from n=3 wells (10,000 per well) per treatment condition is shown. DV significantly increased human brain microvascular cell migration towards VEGF (*p=0.0001).

(FIG. 15A) Brain endothelial cells on type I collagen were treated with DV for 10 minutes followed by fixation with 4% paraformaldehyde and immunocytochemistry for vinculin (a focal adhesion component and marker) and stained for F-actin with rhodamine conjugated phalloidin. Unlike in non-brain endothelial cells[25], prominent actin stress fibers were unchanged despite the presence of DV. Images are representative. Bar is 2 μm. (FIG. 15B) Brain endothelial cells on plastic±DV were allowed to adhere to the plastic for 2 hours. The mean percent of the total adherent brain endothelial cells that were no longer rounded was assessed and plotted. DV exposure resulted in significantly more cell spreading (**p=0.0001), unlike what has been reported in brain endothelial cells[25].

FIGS. 16A-16B. Representative α5 integrin (GAPDH loading control also shown) western blot (FIG. 16A) and (FIG. 16B) qPCR of wild type and α5 siRNA treated brain endothelial cells demonstrating a 75% knockdown of α5 protein, and mRNA, respectively. *p=0.000061.

FIG. 17. DV-enhanced brain endothelial cell capillary tube-like structure formation is inhibited by the alpha5beta1 integrin specific peptide CRRETAWAC (SEQ ID NO: 11). Quantification of Matrigel tube experiments in FIG. 4c demonstrating that DV significantly enhanced of tube-like structure formation (* p=0.0003) was significantly inhibited (** p=0.001) by CRRETAWAC (SEQ ID NO: 11).

FIGS. 18A-18E. DV binds to α5β1 integrin, in part, via its DGR amino acid sequence. (FIG. 18A) Sequence schematic of the second EGF repeat within DV demonstrating the exact location (SEQ ID NO: 12), in box, where D3904A was mutated (SEQ ID NO: 13). (FIG. 18B) Western blots (with an anti-HIS antibody recognizing the C-terminal 6XHIS tag added to each cloned and purified protein) of cloned and purified D3904A and the C-terminal fragment of DV, LG3 demonstrating that as expected, D3904A yields a single 85 kDa band as does normal DV (FIG. 8a), and LG3 yields a single 25 kDa band. (FIG. 18C) optical biosensor traces showing the association and dissociation of DV D3904A with immobilized α5 integrin at the concentrations listed (RU=relative units). (FIG. 18D) Quantification of proliferation of brain endothelial cells after 24 hours±DV, D3904A or LG3 at 100 nM or 300 nM concentrations in serum starved media as measured via MTS assay. Values shown (n=3, mean±standard deviation normalized to control proliferation arbitrarily set to 100%) demonstrate that at 100 nM, DV D3904 is significantly less effective in increasing brain endothelial cell proliferation than is DV at 100 nM (* p=0.02), while LG3 has no effect on proliferation at 100 or 300 nM concentrations. At 300 nM concentrations, DV D3904A still stimulates brain endothelial cell proliferation less than unmutated DV, but this difference is not quite significant, p=0.06. (FIG. 18E) optical biosensor traces showing the association and dissociation of LG3 with immobilized α5 integrin at the concentrations listed (RU=relative units).

FIG. 19. DV induces ZO-1 delocalization by VEGF secretion. Under control conditions, ZO-1 (green) is homogenously located the cell periphery. Addition of DV for 8 h significantly induced loss of ZO-1 localization. Addition of VEGF blocking antibody (DV±VEGF Ab), partially restored ZO-1 localization at the cell periphery. Cells were counterstained with nuclear DAPI stain (blue). Bar is 5 µm.

FIGS. 21A-21B. DV activity on brain endothelial cells in the presence of fibronectin. (FIG. 21A) Mouse brain microvascular brain endothelial cells were grown on plastic or wells coated with DV (20 µg/ml) or fibronectin (FN, 20 µg/ml) for 24 hours±DV (250 nM) or FN (20 µg/ml) in suspension, followed by MTS proliferation assay. Bars are mean $OD_{560nm}$±standard error, n=6 per condition. In suspension, DV significantly increased proliferation of cells grown on plastic (*p=0.001) and grown on fibronectin (#p=0.02). However, DV had no effect on proliferation when cells were directly grown on DV coated wells (as compared to cells on plastic). In contrast, soluble fibronectin significantly enhanced brain endothelial cell proliferation in cells grown on plastic (**p=0.005), DV (φp=0.04) or when cells were grown directly on fibronectin (as compared to cells grown on plastic, p=0.04). (FIG. 21B) Mouse brain microvascular brain endothelial cells were grown to confluency on plastic or wells coated with fibronectin (FN, 20 µg/ml). The cells were then serum starved overnight and treated with soluble FN, 20 ug/mL or DV 20 ug/mL for 4 hrs. Following incubation, the conditioned media was analyzed on the Ray Biotech VEGF 165 Mouse ELISA assay. Bars are mean secreted [VEGF]+/− standard deviation (n=3 for each condition). DV significantly increased VEGF secretion on cells growing on fibronectin (*p=0.008) and cells growing on plastic (*p=0.007). There was no significant difference in the DV-induced VEGF release between cells growing on fibronectin and plastic (p=1.0). The addition of soluble FN significantly inhibited VEGF secretion (#p=0.01) from cells growing on fibronectin, but this inhibition was not significant for cells growing on plastic (p=0.09).

FIG. 22A) or LPS (1 ug/ml; FIG. 22B) was added and incubated for 24 h. Levels of CINC-1 in supernatants and cell lysates were analysed by ELISA. These graphs demonstrate that while DV by itself had no effect on astrocyte production or release of CINC-1, it very much potentiated the release of CINC-1 induced by IL-β and LPS.

FIGS. 27A-27C. LG3 is neuroprotective in nature and is anti-proliferative for brain endothelial cells. a) Fetal cortical neurons were treated with 2 hours of OGD and then treated with 150 nM LG3 or left untreated (control). Alamar blue readings were taken 72 hours later and the elevation in Alamar blue readings obtained after LG3 treatment is shown as a percentage of the Alamar blue readings obtained for control cultures. Data was analyzed by student's t-test and is significant at *p<0.05 when compared to control. b) hCMEC/D3 brain endothelial cells were treated with 150 nM LG3 and their proliferation was analyzed 48 hours later using MTS assay. The mean MTS reading of LG3 treated cells is shown as a percentage of mean MTS reading of untreated cells. Data was analyzed by student's t-test and is significant at *p<0.05. c) LG3 causes hCMEC/D3 cells to express a 'shrivelled' morphology (arrows). Cells were treated with LG3 and images were taken after 48 hours of LG3 treatment using a light microscope. Scale bar=10 μm.

BRIEF DESCRIPTION OF THE SEQUENCE

Figure 1A:
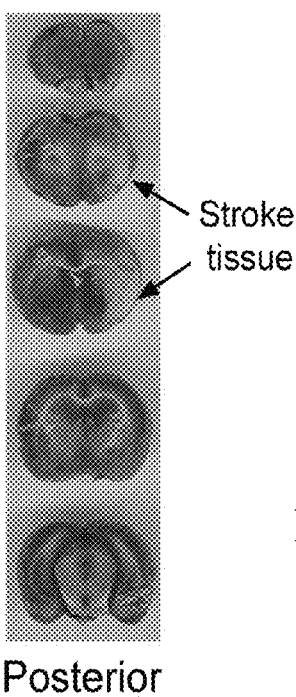
FIGS. 1A-1F. Perlecan Domain V (DV) is up-regulated after stroke in rodent and human brains.

SEQ ID NO: 1 is the sequence for perlecan domain V (DV).
SEQ ID NO: 2 is the sequence for the LG3 fragment of perlecan domain V (DV).
SEQ ID NOs: 3-10 are primer sequences.

DETAILED DISCLOSURE OF THE INVENTION

The disclosed invention relates to the use of perlecan domain V (DV) for the treatment of stroke, traumatic brain injury (TBI) or spinal cord injuries (SCI). In certain embodiments, fusion proteins of DV can be used for the treatment of stroke, TBI or SCI. DV is also referred to as endorepellin in the art.

Thus, one embodiment of the disclosed invention relates to a method of treating TBI, SCI or stroke comprising optionally identifying a subject suffering from a stroke, traumatic brain injury or spinal cord injury by identifying the presence of stroke, TBI or SCI symptoms, and administering a therapeutically effective amount of a composition comprising a pharmaceutically acceptable excipient and DV, a polypeptide comprising DV, fragments of DV, or a fragment of DV consisting of (or consisting essentially of) SEQ ID NO: 2 or a fusion protein comprising a DV fragment to the subject. The composition can be administered to the subject within 168, 144, 120, 96, 72, 48, 24, 12, 6, 2, or 1 hour of a stroke, TBI or SCI. In various embodiments of this aspect of the invention, the composition administered to the subject can cause an improvement in motor function to pre-injury (or near pre-injury) levels. Alternatively, the composition can also be administered within 15 minutes of a stroke, TBI or SCI. Certain aspects of the invention contemplate the administration of the disclosed compositions in amounts that are neuroprotective, enhance angiogenesis in neural tissue damaged by a stroke, TBI or SCI or improve motor function in a subject having had a stroke, TBI or SCI.

Another embodiment provides methods of enhancing brain angiogenesis and improving post-stroke functional motor recovery comprising the administration of a therapeutically effective amount of a composition comprising a pharmaceutically acceptable excipient and DV, a polypeptide comprising DV, fragments of DV, or a fragment of DV consisting of (or consisting essentially of) SEQ ID NO: 2 or a fusion protein comprising a DV fragment to the subject. In this embodiment, the administration of a therapeutically effective amount of a composition comprising a pharmaceutically acceptable excipient and a polypeptide comprising DV to a subject can result in the subject regaining functional motor recovery to near pre-stroke baseline function or to pre-stroke baseline function. The composition can be administered to the subject within 168, 144, 120, 96, 72, 48, 24, 12, 6, 2, or 1 hour of a stroke, TBI or SCI. Alternatively, the composition can also be administered within 15 minutes of a stroke, TBI or SCI.

As used herein, a subject is a mammal. In various embodiments, the subject is a human, mouse or rat.

Stroke is a general term for acute brain damage resulting from disease or injury of blood vessels. Stroke can be classified into at least two main categories: hemorrhagic stroke (resulting from leakage of blood outside of the normal blood vessels) and ischemic stroke (cerebral ischemia due to lack of blood supply). Some events that can cause ischemic stroke include thrombosis, embolism, and systemic hypoperfusion (with resultant ischemia and hypoxia).

Stroke generally causes neuronal death and injury in the brain by oxygen deprivation and secondary events. The area of the brain that dies as a result of the lack of blood supply or other damage is called an infarct. In some cases, the treatments described herein can be used to reduce or minimize the size of an infarct, e.g., by reducing neuronal death.

Obstruction of a cerebral artery resulting from a thrombus which has built up on the wall of a brain artery is generally called cerebral thrombosis. In cerebral embolism, the occlusive material blocking the cerebral artery arises downstream in the circulation (e.g., an embolus is carried to the cerebral artery from the heart). Because it is difficult to discern whether a stroke is caused by thrombosis or embolism, the term thromboembolism is used to describe both these types of stroke.

In the various aspects disclosed herein, the DV polypeptide has (or consists of) the sequence:

(SEQ ID NO: 1)
```
EIKITFRPDS ADGMLLYNGQ KRVPGSPTNL ANRQPDFISF GLVGGRPEFR FDAGSGMATI

RHPTPLALGH FHTVTLLRSL TQGSLIVGDL APVNGTSQGK FQGLDLNEEL YLGGYPDYGA

IPKAGLSSGF IGCVRELRIQ GEEIVFHDLN LTAHGISHCP TCRDRPCQNG GQCHDSESSS

YVCVCPAGFT GSRCEHSQAL HCHPEACGPD ATCVNRPDGR GYTCRCHLGR SGLRCEEGVT

VTTPSLSGAG SYLALPALTN THHELRLDVE FKPLAPDGVL LFSGGKSGPV EDFVSLAMVG

GHLEFRYELG SGLAVLRSAE PLALGRWHRV SAERLNKDGS LRVNGGRPVL RSSPGKSQGL

NLHTLLYLGG VEPSVPLSPA TNMSAHFRGC VGEVSVNGKR LDLTYSFLGS QGIGQCYDSS

PCERQPCQHG ATCMPAGEYE FQCLCRDGFK GDLCEHEENP CQLREPCLHG GTCQGTRCLC

LPGFSGPRCQ QGSGHGIAES DWHLEGSGGN DAPGQYGAYF HDDGFLAFPG HVFSRSLPEV

PETIELEVRT STASGLLLWQ GVEVGEAGQG KDFISLGLQD GHLVFRYQLG SGEARLVSED

PINDGEWHRV TALREGRRGS IQVDGEELVS GRSPGPNVAV NAKGSVYIGG APDVATLTGG

RFSSGITGCV KNLVLHSARP GAPPPQPLDL QHRAQAGANT RPCPS.
```

Other aspects of the invention can utilize a composition that is a polypeptide comprising the DV polypeptide. In these aspects of the invention, the such a polypeptide is a fusion protein comprising a heterologous sequence fused to the DV polypeptide. The additional amino acid domain may be located upstream (N-terminal) or downstream (C-terminal) from the sequence of the DV polypeptide. The heterologous sequence may comprise any functional region, providing for instance an increased stability, targeting or bioavailability of the fusion protein; facilitating purification or production, or conferring on the fusion protein additional biological activity. Specific, non-limiting examples of such additional amino acid sequences include a GST sequence, a His tag sequence, a multimerization domain, or the constant region of an immunoglobulin (Ig) molecule. The term "operably linked" indicates that the polypeptide and additional amino acid domain are associated through peptide linkage, either directly or via spacer residues. In this manner, the fusion protein can be produced recombinantly, by direct expression in a host cell. Also, if needed, the additional amino acid sequence included in the fusion proteins may be eliminated, either at the end of the production/purification process or in vivo, e.g., by means of an appropriate endo-/exopeptidase. For example, a spacer sequence included in the fusion protein may comprise a recognition site for an endopeptidase (such as a caspase) that can be used to separate by enzymatic cleavage the desired polypeptide variant from the additional amino acid domain, either in vivo or in vitro.

In a particular embodiment, the additional amino acid residues in the fusion protein comprises the constant region of an immunoglobulin, particularly the Fc portion of a human immunoglobulin. The sequence of the Fc portion may be derived for instance from an IgG, preferably from a human IgG. The Ig sequence may also be modified to reduce effector function or to increase the stability of a resulting dimer. The amino acid sequence derived from the constant region of an immunoglobulin may be linked to the C-terminus or to the N-terminus of the DV, preferably to the C-terminus.

In a further embodiment, the additional amino acid residues in the fusion protein comprise a multimerization domain, allowing complexes to be formed between two or more fusion proteins of this invention, or between one or more fusion proteins of this invention and a distinct protein. An example of such multimerization domains include a leucine zipper. The multimerization domain may be linked to the C-terminus or to the N-terminus of the DV polypeptide, preferably to the C-terminus.

Various other aspects of the invention contemplate the use of a polypeptide fragment of DV for treating stroke, TBI, SCI or enhancing brain angiogenesis and improving post-stroke functional motor recovery. In these aspects of the invention, a fragment of DV consists of at least 10 contiguous amino acids of SEQ ID NO: 1 and contains the sequence DGR. Thus, a DGR containing fragment of SEQ ID NO: 1 can span 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 105, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 704 or 704 consecutive amino acids of SEQ ID NO: 1. As used herein, the phrase "consisting of at least 10 contiguous amino acids of SEQ ID NO: 1 and containing the amino acid sequence DGR" is to be construed as any polypeptide between 10 and 704 consecutive amino acids of SEQ ID NO: 1 that also contains the DGR motif. Other embodiments provide for the use of a fragment of DV consisting of (or consisting essentially of) SEQ ID NO:2 for the treatment of stroke, TBI, SCI or enhancing brain angiogenesis and improving post-stroke functional motor recovery. Where the phrase "consisting essentially of" is used in connection with SEQ ID NO: 2, this phrase allows for the addition of C-terminal or N-terminal amino acids that do not affect the ability of the polypeptide to provide a neuroprotective effect in the treatment of stroke, TBI, SCI, enhancing brain angiogenesis or improving post-stroke functional motor recovery in a subject. In some embodiments, the use of the phase "consisting essentially of SEQ ID NO: 2" can expressly exclude full length perlecan, the full length DV polypeptide and/or fragments of SEQ ID NO: 1 that include the DGR motif. Further, any such fragments can be operably linked to heterologous sequences as disclosed herein.

A variety of agents, such as tissue plasminogen activator (t-PA), have been used in the treatment of thromboembolic stroke and are believed to be most useful if administered as soon as possible after acute stroke (preferably within 3 hours) in order to at least partially restore cerebral blood flow in the ischemic region and to sustain neuronal viability. DV and/or polypeptides comprising DV can be used alone or in combination with such agents to achieve a therapeutic benefit in a subject who has experienced a thromboembolic stroke. The agents can be administered at the same time as DV or polypeptides comprising DV or at separate times, e.g., at separate times that are within a specified interval, e.g., within 168, 144, 120, 96, 72, 48, 24, 12, 6, 2, 1 hour or 15 minutes of an stroke.

Non-limiting examples of agents that can be administered in combination with DV or a polypeptide comprising DV include: thrombolytic agents such as streptokinase, acylated plasminogen-streptokinase activator complex (APSAC), urokinase and single-chain urokinase-plasminogen activator (scu-PA); anti-inflammatory agents, thrombin-like enzymes from snake venoms such as ancrod, thrombin inhibitors, tissue plasminogen activator (t-PA) and biologically active variants of each of the above); an anticoagulant such as warfarin or heparin; anti-platelet drugs (e.g., aspirin); a glycoprotein IIb/IIIa inhibitor; a glycosaminoglycan; coumarin; GCSF; melatonin; a caspase inhibitor; an anti-oxidants (e.g., NXY-059, see Lees et al., (2006) N. Engl., J. Med 354, 588-600), additional neuroprotectants (e.g., an NMDA receptor antagonist and a cannabinoid antagonist, or Niaspan, a neuroprotective extended-release formulation of niacin (vitamin B3), Shehadah et al., (2010) Neurobiol. Dis., in press), an anti-CD 18 antibody; IL-1α; an anti-CD11a antibody; an anti-ICAM-1 antibody; an anti-VLA-4 antibody, an anti-TWEAK antibody, or an anti-TWEAK-R antibody. Particular examples of combination treatments include administering DV, a fragment of DV, a fragment of DV consisting of (or consisting essentially of) SEQ ID NO: 2, or a polypeptide comprising DV to a subject who has experienced a stroke shortly after the onset of stroke symptoms and/or at the same time as another treatment, such as t-PA. The following day, the subject can further commence daily treatments with an anti-platelet drug to protect against a future stroke and later receive additional doses of DV or a polypeptide comprising DV.

DV or a polypeptide comprising DV can also be used to treat traumatic brain injury. Damage to the brain by a physical force is broadly termed traumatic brain injury (TBI). Traumatic brain injury (TBI) is damage to the brain resulting from external mechanical force, such as rapid acceleration or deceleration, impact, blast waves, or penetration by a projectile. Brain function is temporarily or permanently impaired and structural damage may or may not be detectable with current technology. TBI is one of two subsets of acquired brain injury (brain damage that occurs after birth); the other subset is non-traumatic brain injury, which does not involve external mechanical force (examples include stroke and infection). All traumatic brain injuries are head injuries, but the latter term may also refer to injury to other parts of the head. However, the terms head injury and brain injury can be used interchangeably.

TBI is usually classified based on severity, anatomical features of the injury, and the mechanism (the causative forces). Mechanism-related classification divides TBI into closed and penetrating head injury. A closed (also called non-penetrating, or blunt) injury occurs when the brain is not exposed. A penetrating, or open, head injury occurs when an object pierces the skull and breaches the dura mater, the outermost membrane surrounding the brain.

The Glasgow Coma Scale (GCS), a universal system for classifying TBI severity, grades a person's level of consciousness on a scale of 3-15 based on verbal, motor, and eye-opening reactions to stimuli, wherein a TBI with a GCS of 13 or above is mild, 9-12 is moderate, and 8 or below is severe. Other classification systems determine severity based on the GCS after resuscitation, the duration of post-traumatic amnesia, loss of consciousness, or combinations thereof.

Damage from TBI can be focal or diffuse, confined to specific areas or distributed in a more general manner, respectively. Diffuse injury manifests with little apparent damage in neuroimaging studies, but lesions can be seen with microscopy techniques post-mortem. Types of injuries considered diffuse include concussion and diffuse axonal injury, widespread damage to axons in areas including white matter and the cerebral hemispheres. Focal injuries often produce symptoms related to the functions of the damaged area, manifesting in symptoms like hemiparesis or aphasia when motor or language areas are respectively damaged.

The resulting effect of TBI causes alteration of normal brain processes attributable to changes in brain structure and/or function, typically via neuronal death. Depending on the type of force impacting the head, varying injuries can result: jarring of the brain within the skull, concussion, skull fracture, contusion, subdural hematoma, or diffuse axonal injury. Though each person's experience is different, there are common problems that many people with TBI face. Possibilities documented include difficulty in concentrating, ineffective problem solving, short and long-term memory problems, and impaired motor or sensory skills; to the point of an inability to perform daily living skills independently such as eating, dressing or bathing. The most widely accepted concept of brain injury divides the process into primary and secondary events. Primary brain injury is considered to be more or less complete at the time of impact, while secondary injury evolves over a period of hours to days following trauma.

Primary injuries are those commonly associated with emergency situations such as auto accidents, or anything causing temporary loss of consciousness or fracturing of the skull. Contusions, or bruise-like injuries, often occur under the location of a particular impact. The shifting and rotating of the brain inside the skull after a closed brain injury results in shearing injury to the brain's long connecting nerve fibers or axons, which is referred to as diffuse axonal injury. Lacerations are defined as the tearing of frontal and temporal lobes or blood vessels caused by the brain rotating across ridges inside the skull. Hematomas, or blood clots, result when small vessels are broken by the injury. They can occur between the skull and the brain (epidural or subdural hematoma), or inside the substance of the brain itself (intracerebral hematoma).

Delayed secondary injury at the cellular level has come to be recognized as a major contributor to the ultimate tissue loss that occurs after brain injury. A cascade of physiologic, vascular, and biochemical events is set in motion in injured tissue. This process involves a multitude of systems, including possible changes in neuropeptides, electrolytes such as calcium and magnesium, excitatory amino acids, arachidonic acid metabolites such as the prostagladins and leukotrienes, and the formation of oxygen free radicals. This secondary tissue damage is at the root of most of the severe, long-term adverse effects a person with brain injury may experience. Procedures that minimize this damage can be the difference between recovery to a normal or near-normal condition, or permanent disability.

Diffuse blood vessel damage has been increasingly implicated as a major component of brain injury. The vascular response seems to be biphasic. Depending on the severity of the trauma, early changes include an initial rise in blood pressure, an early loss of the automatic regulation of cerebral blood vessels, and a transient breakdown of the blood-brain barrier (BBB). Vascular changes peak at approximately six hours post-injury but can persist for as long as six days.

Secondary systemic insults (outside the brain) may consequently lead to further damage to the brain. This is extremely common after brain injuries of all grades of severity, particularly if they are associated with multiple injuries. Thus, people with brain injury may experience combinations of low blood oxygen, blood pressure, heart and lung changes, fever, blood coagulation disorders, and other adverse changes at recurrent intervals in the days following brain injury. These occur at a time when the normal regulatory mechanism, by which the cerebrovascular vessels can relax to maintain an adequate supply of oxygen and blood during such adverse events, is impaired as a result of the original trauma.

The protocols for immediate assessment of TBI are limited in their efficiency and reliability and are often invasive. Computer-assisted tomographic (CT) scanning is currently accepted as the standard diagnostic procedure for evaluating TBI, as it can identify many abnormalities associated with primary brain injury, is widely available, and can be performed at a relatively low cost.

Immediate treatment for TBI typically involves surgery to control bleeding in and around the brain, monitoring and controlling intracranial pressure, insuring adequate blood flow to the brain, and treating the body for other injuries and infection. Those with mild brain injuries often experience subtle symptoms and may defer treatment for days or even weeks. Once a patient chooses to seek medical attention, observation, neurological testing, magnetic resonance imaging (MRI), positron emission tomography (PET) scan, single-photon emission CT (SPECT) scan, monitoring the level of a neurotransmitter in spinal fluid, computed tomography (CT) scans, and X-rays may be used to determine the extent of the patient's injury. The type and severity of the injury determine further care.

Spinal cord injury (SCI) is an insult to the spinal cord resulting in a change, either temporary or permanent, in its normal motor, sensory, or autonomic function. Both clinical and experimental studies evidence that the spinal cord suffers from primary and secondary damage after acute SCI. Primary SCI arises from mechanical disruption, transection, extradural pathology, or distraction of neural elements. This injury usually occurs with fracture and/or dislocation of the spine. However, primary SCI may occur in the absence of spinal fracture or dislocation. Penetrating injuries due to bullets or other weapons may also cause primary SCI.

SCI are classified as complete or incomplete, based on the extent of injury, according to the American Spinal Injury Association (ASIA) Impairment Scale. In complete SCI, there is no sensory and motor function preserved in the lowest sacral segments. In incomplete SCI, sensory or motor function is preserved below the level of injury including the lowest sacral segments. Incomplete cord lesions may evolve into more complete lesions. More commonly, the injury level rises one or two spinal levels during the hours to days after the initial event.

Glucocorticoids such as methylprednisolone are thought to reduce the secondary effects of acute SCI, and the use of high-dose methylprednisolone in nonpenetrating acute SCI has become the standard of care in North America. Thus, another aspect of the invention provides methods of treating SCI comprising the administration of a polypeptide comprising DV alone, or in combination with glucocorticoids or IL-1α.

Multiple sclerosis (MS) is a slowly progressive CNS disease characterized by disseminated patches of demyelination in the brain and spinal cord, resulting in multiple and varied neurological symptoms and signs, usually with remissions and exacerbation (see The Merck Manual Home Edition, worldwide web site: merck.com).

The cause is unknown but an immunological abnormality is suspected, with few clues presently indicating a specific mechanism. Postulated causes include infection by a slow or latent virus, and myelinolysis by enzymes. IgG is usually elevated in the CSF, and elevated titers have been associated with a variety of viruses, including measles. The significance of these findings and of reported associations with HLA allotypes and altered number of T cells is unclear, and the evidence somewhat conflicting. An increased family incidence suggests genetic susceptibility; women are somewhat more often affected than men. Environmental factors seem to be present.

Plaques or islands of demyelination with destruction of oligodendroglia and perivascular inflammation are disseminated through the CNS, primarily in the white matter, with a predilection for the lateral ad posterior columns (especially in the cervical and dorsal regions), the optic nerves, and periventricular areas. Tracts in the midbrain, pons, and cerebellum also are affected, and gray matter in both cerebrum and cord may be affected. Cell bodies and axons are usually preserved, especially in early lesions. Later, axons may be destroyed, especially in the long tracts, and a fibrous gliosis gives the tracts their "sclerotic" appearance. Both early and late lesions may be found simultaneously. Chemical changes in lipid and protein constituents of myelin have been demonstrated in and around the plaques. Interestingly, early and active plaques may be populated with oligodendrocytes undertaking the task of remyelinating the lesion. This may be due in part to their expression of the CINC1 chemokine receptor CXCR2 (Omari et al., CXCR2 and CXCL1 on glia in multiple sclerosis. *Glia*, 53:24-31 (2006)).

MS is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized.

Diagnosis of MS is indirect, by deduction from clinical and laboratory features. MRI, the most sensitive diagnostic imaging technique, may show plaques. Gadolinium-contrast enhancement can distinguish areas of active inflammation from older brain plaques. MS lesions may also be visible on contrast-enhanced CT scans, in which sensitivity may be increased by giving twice the iodine dose and delaying scanning (double-dose delayed CT scan).

CSF is abnormal in the majority of patients. IgG may be >13%, and lymphocytes and protein content may be slightly increased. Oligoclonal bands, which indicate IgG synthesis within the blood-brain barrier, may be detected by agarose electrophoresis of CSF in up to 90% of patients with MS, but absence of these bands does not rule out MS. IgG levels correlate with disease severity. Myelin basic protein may be elevated during active demyelination.

Corticosteroids are the main form of MS therapy and may shorten the symptomatic period during attacks, although they may not affect eventual long-term disability. Patients presenting with acute severe optic neuritis may delay the onset of MS by using high-dose IV corticosteroids. Other immunosuppressive drugs can also be used for treatment of MS and drugs such as methotrexate, azathioprine, cyclophosphamide and/or cladribine are generally used for more severe progressive forms. Immunomodulatory therapy with interferon-β reduces the frequency of relapses in MS. Other promising treatments still under investigation include other interferons, oral myelin, and glatiramer to help keep the body from attacking its own myelin.

DV or fragments thereof, or a fragment of DV consisting of (or consisting essentially of) SEQ ID NO: 2 and polypeptides comprising DV can be formulated as a pharmaceutical composition, e.g., for administration to a subject to treat MS, stroke, TBI or SCI. Typically, a pharmaceutical composition includes a pharmaceutically acceptable carrier. As used herein, pharmaceutically acceptable carrier includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19). In various embodiments of the invention, additional therapeutic agents for the treatment of stroke, MS, TBI and/or SCI are combined with polypeptides comprising DV.

Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000). Such compositions can be administered by a parenteral mode (e.g., intravenous, subcutaneous, intraperitoneal, or intramuscular injection). The phrases parenteral administration and administered parenterally as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

A polypeptide comprising DV can be modified, e.g., with a moiety that improves its stabilization and/or retention in circulation, e.g., in blood, serum, or other tissues, e.g., by at least 1.5, 2, 5, 10, or 50 fold. The modified antagonist can be evaluated to assess whether it can reach sites of damage after a stroke, TBI or SCI (e.g., by using a labeled form of the modified DV polypeptide). For example, the polypeptide can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When a polypeptide comprising DV is used in combination with a second agent, the two agents can be formulated separately or together. For example, the respective pharmaceutical compositions can be mixed, e.g., just prior to administration, and administered together or can be administered separately, e.g., at the same or different times.

The composition comprising DV or a polypeptide comprising DV may be administered at least once between about 10 minutes to about 168 hours of a stroke, TBI or SCI. Thus, the composition can be administered to the subject within 168, 144, 120, 96, 72, 48, 24, 12, 6, 2, or 1 hour of a stroke, TBI or SCI. In certain embodiments, the composition is administered within 48 hours, more preferably between about 10 minutes and 24 hours, more preferably within 3 hours, after the onset of stroke, TBI or SCI symptoms or manifestation. Single or multiple dosages may be given. Alternatively, or in addition, the polypeptide may be administered via continuous infusion. The treatment can continue for days, weeks, months or longer so as to minimize damage from the stroke, restore motor function to the subject, minimize damage from post-stroke inflammatory events, prevent another stroke, minimize damage that might result from a subsequent stroke, treat primary or secondary TBI or symptoms, or to treat primary or secondary SCI or symptoms.

Pharmaceutical compositions that include DV or a polypeptide comprising DV can be administered with a medical device. The device can designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include the polypeptide, and can be configured to deliver one or more unit doses. For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or U.S. Pat. No. 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

The polypeptide comprising DV can also be provided in a kit. In one embodiment, the kit includes (a) a container that contains a composition that includes a polypeptide comprising DV, and optionally (b) informational material. The informational material can be descriptive, instructional, marketing or other material that relates to the methods described herein and/or the use of the agents for therapeutic benefit. In an embodiment, the kit includes also includes a second agent for treating stroke, TBI or SCI. For example, the kit includes a first container that contains a composition that includes the polypeptide, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the DV polypeptide, e.g., in a suitable dose, dosage form, or mode of administration (e.g., a dose, dosage form, or mode of administration described herein), to treat a subject who has had a stroke, TBI or SCI). The information can be provided in a variety of formats, include printed text, computer readable material, video recording, or audio recording, or a information that provides a link or address to substantive material.

In addition to the DV polypeptide, the composition in the kit can include other ingredients, such as a solvent or buffer, a stabilizer, or a preservative. The antagonist can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the polypeptide comprising DV and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight. The kit optionally includes a device suitable for administration of the composition, e.g., a syringe or other suitable delivery device. The device can be provided pre-loaded with one or both of the agents or can be empty, but suitable for loading.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 1

Materials and Methods

Cell Culture

Figure 12:
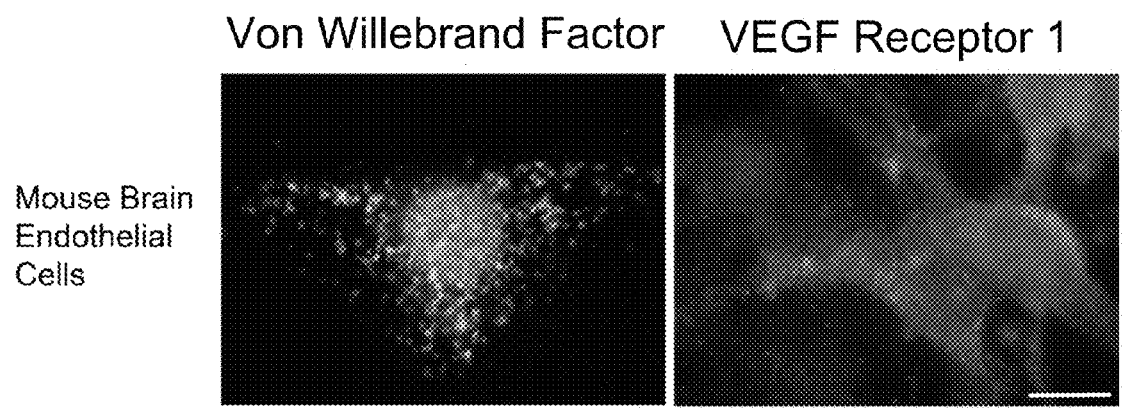
FIG. 12. Immunological characterization of C57BL6 mouse brain endothelial cells. Brain endothelial cells isolated from C57BL6 mice were both von Willebrand factor and VEGF receptor 1 positive.

Human brain microvascular endothelial cells were purchased from Lonza (Basel, Switzerland) and Cell Systems (Kirkland, Wash.), and passaged as per the supplier's instructions. Mouse and rat brain microvascular endothelial cells were kindly provided by Jane Welsh, Texas A&M University, and passaged as previously described[25]. Primary mouse dermal endothelial cells were purchased from Celprogen, Inc. (San Pedro, Calif.) and maintained initially as recommended by the manufacturer. After the second passage, cells were passaged to flasks precoated with 1 mg/ml gelatin and fed with culture medium prepared as described[98]. Briefly, 500 ml M199 was supplemented with 15% FBS (Invitrogen), 200 mg bovine hypothalamic extract, 50 mg heparin (Sigma-Aldrich), 5 ml antibiotics (Invitrogen) and 0.5 ml gentamycin (Invitrogen). In all endothelial cells, the presence of endothelial cell markers von Willebrand Factor and VEGF receptor was confirmed via immunohistochemistry and western blot (FIG. 12).

Domain V and Other Protein Production

Human Domain V (DV) was cloned into the vector pSecTag2A (Invitrogen) using the following primers: 5'DV Asci pSecTag 2A: 5'AGG GCG CGC CAT CAA GAT CAC CTT CCG GC 3' (SEQ ID NO: 3); 3'DV XhoI pSEc Tag 2A: 5' AGC TCG AGC CGA GGG GCA GGG GCG TGT GTT G 3' (SEQ ID NO: 4). To further verify that DV effects were not due to any single clone specific irregularities, we also cloned DV into the vector pCepPu (kindly provided by Maurizio Mongiat, Aviano, Italy) using the following primers: NHEI whole DV Forward 5'AGG CTA GCG ATC AAG ATC ACC TTC CGG C3' XHOI HIS DV REVERSE (SEQ ID NO: 5) and 5'AGCTCGAGCATGATGATGATGATGATGC-GAGG3' (SEQ ID NO: 6). The DV cDNA was amplified from HUVEC cDNA utilizing a GC-rich PCR system and dNT-Pack (Roche Applied Science, Indianapolis, Ind.) and used the restriction enzymes XhoI, Asci (NEB Corp., Ipswich, Mass.) Maxi-preps of DV DNA were transfected into 293FT (for pSecTag2A vector, ATCC, Manassas, Va.) or 293 ENBA (for pCepPu vector, kindly provided by Maurizio Mongiat) cells via lipofectamine (Invitrogen). After transfection, the 293 cells were put into a CELLine adhere 1000 bioreactor (Argos Technologies, Elgin, Ill.) and grown for 7 days in complete media containing 10% FBS, 1×Antibiotic/Antimycotic, 1% G418 Sulfate, and 0.05 ug Puromycin. After 7 days the complete media was removed, the cells were washed 5 times with CD293 media containing 4 mM L-glutamine, 1× Antibotic/Antimycotic, 1% G418 Sulfate, and 0.05 ug Puromycin to remove any serum, and then fresh CD293 media was added to the cells. The cells were incubated for 7 days followed by collection of the DV-containing conditioned media and DV purification via its C-terminal 6×His tag and Ni-ATA agarose bead (Qiagen, Valencia, Calif.) as per the company's instructions. Eluted fractions that contained DV were combined and dialyzed against 1×PBS and the purity of the resultant DV was confirmed via SDS-PAGE stained with Brilliant Blue G-colloidal, silver stain (FASTsilver Gel Staining Kit, Calbiochem) following the instructions of the manufacturer, western blot analysis using commercially available anti-DV antibody (R&D systems, Minneapolis, Minn.), anti-His antibody (EMD Chemicals, Gibbstown, N.J.) (FIG. 8) and anti-fibronectin antibody (Abeam) to check for fibronectin contamination of DV preparations. Previously demonstrated anti-angiogenic concentrations of DV (250 nM)[25] and heat inactivated controls (100° C. for 30 min) were used for all experiments unless otherwise stated. The 26 kDa LG3 C-terminal domain of DV was cloned and ligated using the pCep-Pu vector using the following primers: 5'AGGCATACG-CATGGCATAGCAAATAGCAGAGTC-NHEI 3' (SEQ ID NO: 7); 5'AGC TCG AGC ATGATG ATGATGATGATGC-GAGG-XHO1 3' (SEQ ID NO: 8). LG3 was expressed in 293FT cells and purified via an added C-terminal 6×His tag in an identical fashion to DV.

To produce DV with an aspartic acid (D, amino acid position 3904 in DV) mutated to alanine (A), hereafter referred to as D3904A, to change the potential α5β1 integrin DGR binding motif to AGR, the single amino acid mutation was done using the QuikChange II XL Site-Directed Mutagenesis Kit (Agilent Technologies) according to manufacturer's protocol. The codon GAC was changed to GCC using the following primer sequences: 5-GTGAACCGGCCTGCCGGTCGAG-GCTAC-3 (SEQ ID NO: 9) and 5-GTAGCCTCGACCG-GCAGGCCGGTTCAC-3 (SEQ ID NO: 10) (Integrated DNA Technologies). The result was confirmed by sequencing. The mutated DV protein was then produced, purified and assessed for purity as above for the unmutated DV.

Liquid Chromatography Tandem Mass Spectrometry (LC-MSMS)

DV preparations were analyzed by Liquid Chromatography Tandem Mass Spectrometry (LCMSMS) by the Texas A&M Protein Chemistry Laboratory. After digestion in situ with trypsin (Promega), the digests were analyzed by HPLC-ESI-tandem MS on a Thermo Fisher LTQ fitted with a New Objective PicoView 550 nanospray interface. On-line HPLC separation of the digests was accomplished with an Eksigent NanoLC micro-HPLC system: column, Pico-Frit™ (New Objective; 75-um inner diameter) packed to 11 cm with C18 adsorbent (Vydac 218MS; 5 um, 300 Å); mobile phase A, 0.5% acetic acid (HAc), 0.005% TFA; mobile phase B, 90% acetonitrile, 0.5% HAc, 0.005% TFA; gradient, 2-42% B in 30 min; flow rate, 0.4 ul/min. MS conditions were as follows: ESI voltage, 2.9 kV; isolation window for MS/MS, 3; relative collision energy, 35%; scan strategy, survey scan followed by acquisition of data-dependent CID spectra of the seven most intense ions in the survey scan above a set threshold. Dynamic exclusion was used with a repeat count of 3 and a duration of 30 s. Mascot (Matrix Science, London, UK) was used to search the uninterpreted CID spectra against a locally generated 201_2-1 protein database that had been concatenated with the Swiss-Prot (version 51.6) database, totaling 216,849 sequences. Methionine was considered as a variable modification, and alkylation with iodoacetamide was selected as a fixed modification. Mass tolerances for the Mascot searches were 1.0 Da for precursor ions and 0.8 Da for fragment ions. Peak lists were generated using Extract_msn.exe (ThermoFisher). Determination of probabilities of protein identifications and cross-correlation of the Mascot results with X! Tandem were accomplished by Scaffold (Proteome Software, Inc., Portland Oreg.). Unless otherwise noted, a 95% confidence limit was used for assignment of peptides.

In Vivo Stroke Models

Human hemorrhagic stroke brain tissue and control non-stroked human brain tissue for anti-DV western immunoblot was kindly provided by Dr. Kunlin Jin (Buck Institute, Calif.)[31, 32]. The samples from the two intracerebral hemorrhage patients (due to a ruptured middle cerebral artery aneurysm) were obtained within 24 hours after onset of symptoms of the bleed based on interviews with the patients, family or other witnesses. The control normal human brain tissue, cortex and striatum, were obtained at autopsy from patients who died from acute myocardial infarction. Harlan Sprague Dawley rats or C57B16 mice, wild type or hypomorphic for perlecan pln−/− (kindly provided by Kathryn Rodgers[39] were subject to middle cerebral artery occlusion by stereotaxic injection with endothelin-1 (American Peptide Company, Sunnyvale, Calif.) or by tandem common carotid artery and middle cerebral artery occlusion[28, 33, 34], respectively, in accordance with Texas A&M College of Medicine guidelines. Diminished blood flow was confirmed via laser doppler measurements with the laser Doppler flowmeter (model LDF; PF5010, Perimed, Dickinson, Tex.)[99] and only those animals that displayed a cerebral perfusion reading<10 (approximately 12% to 15% of the initial value) on the LDF scale (expressing relative values of cerebral perfusion) were included in subsequent experimentation. Animal physiologic measurements such as pulse rate (beats per minute, BPM), and respiratory rate (breaths per minute, BrPM) before and after DV injection (1 mg/kg) were made with the Starr Mouse Oximeter (STARR Life Sciences Corp., Oakmont, Pa.). With some animals, on post stroke day 1, blood was collected from the animals before and 2 hours after the DV injection (1 mg/kg) for blood gas and ion analysis (Irma True Point blood analysis system) done within 30 mins after the samples were collected.

The animals were terminated up to 7 days post surgery and removed brain tissue was divided into stroked and contralateral (nonstroked) hemispheres and lysate processed for DV (R&D systems, Minneapolis, Minn.), HIS (GeneTex, Inc, Irvine, Calif.), α5β1 (Millipore, Billerica, Mass.), CD31 (BD Biosciences, San Jose, Calif.) and GAPDH (Abcam, Cambridge, Mass.) western immunoblot analysis or frozen in liquid nitrogen followed by sectioning via cryostat, fixation with acetone, and immunohistochemically stained with antibodies directed to doublecortin (Abcam), von Willebrand factor (Dako, Glostrup, Denmark), CD31, or HIS (Calbiochem, San Diego, Calif.), nestin (Abcam), α5β1 (Millipore). For immunohistochemistry, the site of ischemic injury was identified morphologically. The peri-infarct region of focus was defined as a 500 μm boundary extending from the edge of the infarct core, medial and lateral to the infarct[5]. To detect the post-stroke distribution of administered DV, anti-HIS immunohistochemistry was performed with the appropriate Texas Red conjugated secondary antibody and whole brain section images were obtained with an Olympus MVX10 microscope outfitted with a 2× objective (NA, 0.5) and an optical zoom of 0.63-6.3×. Excitation and emission filters were 350±50 nm and 460±50 nm for DAPI and 560±55 nm and 645±75 nm. For other immunohistochemistry, images were obtained with a BD Biosystems Cary II spinning disk confocal mounted on a Zeiss Axioplan. The images were captured and analyzed using an attached Apple Macintosh computer and iVision-Mac™ Image Acquisition and Analysis Software. To confirm stroke size and location, several animals' brains were sectioned and analyzed by 2,3 triphenyltetrazolium chloride (TIC) stain[100] on post-stroke day 1 and on post-stroke day 3. In some experiments, 24 h after stroke and then on either post-stroke days 1 and 2 or post-stroke days 3, 5 and 7, animals were treated with intraperitoneal injections of sterile filtered DV (0.5-1 mg/kg), heat inactivated DV control or PBS vehicle control. Additionally, in some experiments, perlecan hypomorph mice were stroked[39]. In some experiments, mice were treated with I.V. injections of α5 integrin function blocking antibody (mg/kg) prior to each DV treatment. In other experiments, in addition to I.P. PBS or DV treatment, mice were also treated with the VEGFR inhibitor PTK787/ZK 222584 (2 mg/kg, Selleck Chemicals, Houston, Tex.) or PBS vehicle control by oral gavage, starting on one day prior to the stroke daily through post stroke day 7. PTK/ZK is a known potent, selective, orally active inhibitor of the VEGF receptor kinases[63]. The mean % hemispheric lesion volume (HLV) for stroked animals was calculated using the equation: % HLV={[Total infarct volume−(Left Hemisphere Volume−Right Hemisphere Volume)]/Right hemisphere volume}× 100%[101]. Edema was calculated by determining the difference between left hemisphere volume and right hemisphere volume. In all cases, volume measurements of 2 millimeter sectioned brains (5 sections per brain) were made with Invision software for Apple Macintosh computers.

Pre- and Post Stroke Motor Function Assays

Stroked or sham surgery control rats were placed in a 20 cm diameter×35 cm high transparent cylinder for 3 min to test limb preference and their ability to support weight on either forelimb[42]. As the animal rears to explore the environment the number of bilateral paw placements, placements of the paw ipsilateral to the lesion (left), and placements of the paw contralateral to lesion (right) were counted. Paw contacts were videotaped and analyzed later by a blinded investigator. The percent of contralateral limb use was calculated using the equation=contralateral contacts/(ipsilateral+contralateral)× 100. Stroked or sham surgery control mice were tested with the vibrissae-elicited forelimb placement test (stimulation of the vibrissae triggers reflex extension of the ipsilateral paw in neurologically intact animals)[43] to measure post-stroke motor function. Briefly, with the experimenter blinded to the different treatment groups, the animals were held by their torsos with the forelimbs hanging freely, and the forelimb placement was induced by gently touching the respective vibrissae against the edge of a plexi glass plate (size: 4×6 inches, 3 inches raised from the bottom). Contralateral (the right "affected" forelimb) and ipsilateral forelimb placing responses were counted with 10 trials for each side. Placement of each paw on the glass plate in response to the respective vibrissae stimulation was given a score of 1. The proportion of successful placements with the affected forelimb was calculated and converted to a percent usage.

In Vitro Angiogenesis Assays

Matrigel experiments were performed as previously described[102]. After 12-18 hrs, cells were imaged and tube formation was quantified (tube pixels/high power field, 10 areas per condition) with Adobe Photoshop CS. Cell migration was assessed with a modified Boyden Chamber (NeuroProbe, Gaithersburg, Md.) following the instructions of the manufacturer. Migration across a type I collagen-coated polycarbonate membrane (PVD-free 8 micron pore) towards VEGF (20 ng/ml) was assessed after 6-8 hours. In some experiments, migration towards DV (300 nM) was assessed. Proliferation was assessed after 48 hours in serum free media containing VEGF 20 ng/ml with MTS solution (Promega, Madison, Wis.) following the manufacturer's instructions. In some experiments, cells were pre-treated with α5β1 specific peptide CRRETAWAC (SEQ ID NO: 11) or CRRETADAC (SEQ ID NO: 14) control peptide (10 mg/ml, kindly provided by Martin Humphries, U. Manchester, Manchester, England)[52].

α5β1 Integrin Knockdown

Brain microvascular endothelial cells at 50% confluency were transferred from normal growth media to Optimem (Gibco) for 20 minutes. Lipofectamine 2000 (Invitrogen) and siRNA oligos targeted against the human alpha5 integrin (Mission siRNA; Sigma) were diluted in Optimem media individually for 5 minutes. Tubes were combined and incubated at room temperature for 20 minutes. α5 SiRNA-containing media was then added to the brain endothelial cells dropwise and incubated for 2 hours. After 2 hours, Optimem was replaced with antibiotic free growth media (M199, 10% FBS, 150 mg/ml bovine brain extract, 60 mg/ml heparin), and cells were allowed to recover overnight. After 24 hours, the media was changed to normal growth media containing antibiotics. α5 integrin knockdown was confirmed by α5 QT-PCR and α5 western blot.

α2 Integrin Expression

Brain microvascular cells were transfected with a plasmid vector (pEGFP-N2, Clontech) containing a sequence encoding the α2-subunit integrin with a C-terminal RFP fusion protein (Texas A&M University Biomedical Engineering), empty vector was used as a control. Cells were allowed to recover during 24 h in medium containing no antibiotics. Transfection efficiency was appreciated after 24 h using an inverted fluorescent microscope.

VEGF ELISA Analysis

Confluent microvascular brain endothelial cells were serum-starved for 12 hours prior to treatment with DV±20 minute pretreatment with α5β1 function blocking antibody. After 24 hours, VEGF ELISAs (Insight Genomics, Santa Barbara) were performed on the endothelial cell conditioned media following the instructions of the manufacturer. In some conditions, cells were pretreated with α5β1 function blocking antibody or the α5β1 integrin activating antibody SNAKA51 (kindly provided by Martin Humphries)[64].

qPCR

A 12 well plate of C57BL6 cells was grown to confluency. Prior to the experiment cells were serum starved overnight in 1% FBS IMDM media. The cells were then washed with PBS and fresh 1% IMDM+/−DV was added back to the wells and allowed to grow at various time points. At the end of the experiment, the media was aspirated, cells were rinsed with PBS and the protocol from RNEASY MiniKit was followed. (Cat. #74104). Samples were quantified using a spectrophotometer and qualitative analysis was performed by running samples on a 1% agarose gel. First-strand cDNA synthesis used cloned AMV RT for RT-PCR. cDNA from each sample was prepared following the Invitrogen cloned AMV Reverse Transcriptase protocol (Cat. No. 12328-019). Briefly, the following components were mixed in a RNASE-Free eppendorf tube: 1 uL oligo(dT)$_{20}$ (500 ug/mL), 1 ug total RNA, 2 uL 10 mM dNTP Mix. Samples were incubated at 65 C for 5 min collected by centrifugation and the following components were added:4 uL 5× cDNA Synthesis buffer, 1 uL 0.1M DTT, 1 uL Cloned AMV RT (15 units/uL) Final volume was adjusted to 20 uL and the samples were mixed and incubated at room temp for 10 min. The samples were then incubated at 45 C for 1 hr. the reaction was terminated by heating the samples at 85 C for 5 min. The samples were then adjusted to 200 uL with RNA-FREE H$_2$O. QPCR products included TaqMan® Fast Universal PCR Master Mix (2×), No AmpErase® UNG Cat. No. 4352042, MicroAmP® Fast 96-Well Reaction Plate, 0.1 mL Cat. No. 4346907 (AppliedBiosystems). Vascular Endothelial Growth factor A. Assay ID Mm00437304_ml, Glyceraldehyde-3-phosphate dehydrogenase. Assay ID Mm99999915_gl and Integrin alpha-5. Assay ID Mm00439797 ml primers were used. The following were mixed to a final volume of 25 uL and added to TaqMan® Fast 96-well Reaction Plate: Fast Universal PCR Master Mix, gene expression assay mix, cDNA and H$_2$0. The amount of cDNA to add for each gene expression was optimized so that the dCT was around 18 cycles. Once the reaction plate was complete it was analyzed using an Applied Biosystems 7500 Fast Reverse transcriptase PCR system.

Transendothelial Electrical Resistance

Transendothelial electrical resistance (TEER) measurements were performed on Transwells™ (Corning, Schiphol, The Netherlands) coated with rat tail collagen. These inserts allow proper cellular polarization with formation of an apical (upper compartment) and basolateral face (lower compartment) mimicking luminal and abluminal faces. Primary isolated mouse brain microvascular cells were seeded on the upper side of the insert at a density of $0.5 \times 10^6$ cells/insert. Monolayers were cultivated for 8 days[103] and then exposed to DV (300 nM). TEER was measured using an EVOM chopstick (World Precision Instruments, Fla., USA) after 2, 4, 8 and 24 h. All resistance measurements were compared to collagen-coated blank filters. In some experiments, endothelial cell monolayers were analyzed via beta catenin (Cell Signaling Technology, Danvers, Mass.) immunocytochemistry. Inhibition of DV-induced barrier opening was performed by incubation of DV with the presence of 0.15 µg/mL anti-VEGF antibody (clone YU13, R&D Systems, Minneapolis, Minn.) or with 10 µM LY294002 (PI3Kinase inhibitor, Cell Signaling Technologies) or with 10 µM PD98059 (ERK1/2 inhibitor, Cell Signaling Technologies). In some experiments, primary mouse astrocytes, kindly provided by Dr. Jianrong Li and Dr. Evelyn Castiglioni (Texas A&M University) were grown to confluence on the underside of the coverslip[62].

Immunocytochemistry

In order to correlate the presence of alteration of the barrier function following DV exposure, confluent C57 cells were grown on collagen-coated glass coverslip chambers (LabTek™, Thermo-Fisher Scientific, Rochester, N.Y.) fixed with 4% paraformaldehyde, permeabilized with 0.2% Triton X-100 and stained Cells were stained against ZO-1 (1:100, rabbit, Invitrogen) and detected using an Alexa-488 conjugated antibody (1:500, goat, Invitrogen). Nuclei were counterstained with DAPI. Potential effects on the actin cytoskeleton and focal adhesions were assessed with rhodamine conjugated phalloidin (Sigma) and antibody against vinculin (Cell Signaling), with appropriate secondary antibody (Cell Signaling) respectively. α5β1 co-localization with administered DV was examined with antibodies directed to α5β1 (Millipore) and the 6×HIS tag on the human recombinant DV (Calbiochem) with appropriate secondary antibodies.

In Vitro Permeability Assays

Permeability assays were performed on Transwells. Fresh medium containing 40 kDa fluorescein isothiocyanate conjugated-dextran (1 mg/mL, Sigma-Aldrich, Switzerland) was added to the upper compartment. At 0 and 24 hours aliquots were taken from the bottom compartment. Sample radioactivity was determined using a liquid scintillation β-counter (Tricarb 1600TR, Can berra Packard, Austria) whereas fluorescence was determined with a fluorescence plate reader (FLx800, Biotek Instruments, Winooski, Vt., USA).

In Vivo Permeability Assays

[$^{14}$C]sucrose (412 mCi/mmol) were purchased from Moravek Biochemicals (USA). The remaining chemicals were purchased from Sigma Chemical Company (UK). Mice were purchased from Harlan, UK. All experiments were performed within the guidelines of the Animals Scientific Procedures Act (1986, UK). Adult male mice (27.3±0.3 g) were anaesthetised (i.p. medetomidine hydrochloride (2 mg/kg) and ketamine (150 mg/kg)) and heparinised (100 U, i.p.) and the in situ brain perfusion technique performed by cannulation of the left ventricle of the heart and sectioning of the right atria as described by Sanderson et al., 2007[104]. The artificial plasma contained [$^{14}$C]sucrose (1.1 µM; 342 Da; radius 4.6 Å) and perfusion was for 10 minutes. After which the animal was decapitated and brain regions (frontal cortex, occipital cortex, caudate nucleus, hippocampus, hypothalamus, thalamus, cerebellum, pons) taken for liquid scintillation counting. The amount of tissue radioactivity was expressed as a percentage of that in the artificial plasma and termed $R_{Tissue}\%$ (ml. $100$ $g^{-1}$). Separate groups of mice were given DV (1 mg/kg) via I.P. injection dissolved in PBS vehicle and the in situ brain perfusion procedure performed at 8, 24 and 48 hours post-injection. These experimental groups were compared to animals which had received vehicle only. The effect of DV on brain (anterior central gyms) water content was also examined at the time points studied. The results were analyzed via Two Way ANOVA or One Way ANOVA using GraphPad Prism 5.0 software package (GraphPad Software Inc.).

Evans Blue (EB) permeability assays were performed following previously published protocols[105-107]. Briefly, anesthetized animals were stroked as described above. After 2 hours of injury, animal were reperfused and immediately treated (2 h post-stroke timepoint) or allowed to recover for 6 hours or 22 hours (8 h and 24 h timepoints respectively) prior treatment. Treatment consisted of I.P. injection of PBS or recombinant human DV (1 mg/kg, same dose than before) for 4 hours. Following DV treatment, intravenous injection of 2% Evans Blue was performed in the tail vein and allowed to circulate for an additional 4 hours. Animals were sacrificed by cardiac perfusion with saline solution. Brains were rapidly removed. 2-mm thickness sections were used to calculate extravasated EB volume in infract hemispheres. Percent Blood brain barrier disruption was determined by following the formula: ((EB extravasated volume−(Ipsilateral volume−Contralateral volume))/Ipsilateral volume)×100[105]. Extravasated EB was calculated by the following formula: Extravasated EB=µg extravasated EB/mg wet tissue. In addition to the quantification of barrier disruption, the total amount of EB present in hemispheres homogenates was quantified by treatment with 300 µl of formamide solution (Fluka Chemicals, Sigma Aldrich) and incubation at 55° C. for 3 days. Homogenates were centrifuged at 14000 rpm for 10 min. Supernatants were used to quantify extracted EB by measuring absorbance at 620 nm. Total amount of EB was quantified using standard curves and normalized against hemisphere-wet weight. Data are Mean±SD from 3 different animals.

In vitro Oxygen and Glucose Deprivation (OGD) Neuroprotection Assays

Primary mouse cortical neurons were dissected from embryonic day 15 C57B16 mice. Neurons were plated in Poly-D-lysine coated 24 well plates. In some wells, C57BL6 brain endothelial cells were plated in Transwell inserts placed above the neurons but not in direct contact with the neurons. The various experimental conditions are illustrated in FIG. 5Q. Cells were treated with various conditioned media and exposed to OGD (oxygen glucose deprivation; 1% glucose, 90% N2, 5% H2, 5% CO2, 37° C.) for 4 hours in a hypoxia chamber (Billups-Rothenberg) and returned to normal oxygen conditioned incubator (5% CO2, 37° C.) for reoxygenation. The cells were then incubated cells for another 18 hours under normoxic conditions. Cell survival rate was measured using MTS assay. Data was normalized to cells treated as above under normoxic conditions.

Cell Adhesion Assays

Brain endothelial cells±pre-incubation with α5β1 function blocking antibody were added to wells coated with 1% BSA or 10 µg/ml DV, followed by fixation, staining with 0.1% crystal violet, solubilization of the stain with acetic acid, and OD560 spectrophotometry as described previously[25].

DV α5 integrin binding assays

Binding assays were carried out using an optical biosensor (IAsys; Affinity Sensors, UK) as described[108]. In brief, to covalently bind the α5β1 protein, designated as an acceptor, onto the surfaces of a sensor, carboxylate groups present on the surface were activated by injection of a 1:1 mixture of 0.1 M N-hydroxysuccinimide and 0.4 M N-Ethyl-3-(3-dimethylaminopropyl) carbodiimide (Pierce). The acceptor dissolved in phosphate buffered saline (PBS) was then allowed to bind to the activated surface until a response plateau was reached. The residual active groups were blocked by an injection of 100 µL of 1 M Tris-HCl (pH 8.5).

A cuvette with immobilized α5 was primed with the binding buffer (150 mM NaCl, 25 mM Tris-HCl, pH=7.4, and 1 mM $MnCl_2$) at 25° C. for 10 min. A 100-4 sample containing free DV, free D3904A DV, or free LG3 interactant dissolved in the binding buffer was added to the cuvette, and then the association phase was recorded. Subsequently, the sample was removed, analyte-free buffer was added to the cuvette, and the dissociation phase was recorded. After each assay, the surface of the cuvette was regenerated by a brief wash with 100 mM glycine, pH=4, followed by equilibration with the binding buffer. During regeneration cycles attention was paid to complete removal of the surface-bound analyte, and the washing continued until a response equal to a baseline value was reached.

For binding assays, free DV or free D3904A DV were added at concentrations ranging from $8.0 \times 10^{-8}$ M to $4.0 \times 10^{-7}$ M, while LG3 was added at concentrations ranging from $3.1 \times 10^{-8}$ M to $3.1 \times 10^{-7}$ M. Data from the biosensor were analyzed by the global fitting method described by Myszka and Morton[109]. For each assay, the association rate constants ($K_{on}$) and the dissociation rate constants ($K_{off}$) were obtained, and the equilibrium dissociation constants (KO values were calculated from a ratio of $K_{off}/K_{on}$. In addition, control binding of bovine serum albumin (BSA) at the molar concentration of $8.0 \times 10^{-7}$ (double of the highest concentration for DV) was also performed.

Cell Signaling Western Immunoblot

Confluent mouse brain microvascular endothelial cells or the same cells treated with α5β1 integrin siRNA were serum-starved for 24 h prior their exposure to 20 µg/mL DV. In experiments involving inhibitors, drug were diluted in DMSO and incubated for 1 h at 37° C. prior DV addition. In all cases, the DMSO maximum concentration reached was not over 0.1% PI3Kinase, MEK1 and ERK inhibition experiments were performed by incubating cells in the presence of 10 µM LY294002, 10 µM U0126 (Cell Signaling) or 10 µM PD98059, respectively 1 h prior to DV exposure. Following DV exposure, cells were washed with ice-cold PBS and homogenized in RIPA buffer complemented with protease inhibitor cocktail (Calbiochem, EMD Chemicals, San Diego, Calif.). Protein concentration was determined using a Bradford assay (Bio-Rad, Hercules, Calif.), samples containing 20 µg protein/well were loaded in 10% SDS-PAGE and transferred on PVDF membranes. Membranes were incubating in blocking buffer (5% non-fat dry milk/TBS) for 1 h at room temperature followed by an overnight incubation in the presence of antibodies directed against phosphorylated ERK (1:1000, rabbit, Cell signaling), ERK (Cell Signaling), phosphorylated-AKT (Cell Signaling), AKT (Cell Signaling), phospho-eIF4E (Cell Signaling), eIF4E (Cell Signaling), HIF-1 alpha (Novus Biologicals). All antibodies were used at the manufacture's recommended concentrations. Band detection was performed using an HRP-conjugated antibody (GeneTex, Irvine, Calif.) and chemiluminescent-based HRP activity detection (PicoWest Signal, Thermo-Fisher Scientific). Quantification was performed using ImageJ software (ImageJ, NIH, Bethesda, Md.). Signal transduction western blots were performed n=3.

Statistical Analysis

For all described experiments unless otherwise stated, N=15 (5 separate experiments, each condition performed in triplicate). Data are presented as Mean+/−standard deviation (unless otherwise stated). Statistical significance (p<0.05) was determined for all experiments by Student's unpaired t-test with the Sigmastat software package. For comparison between various treatment groups such as in motor function between stroked or sham surgery control animals±DV administration, and in in vivo permeability assays, variance was analyzed via One or Two Way ANOVA using Prism statistical package (Prism 4.0, Graphpad Software, La Jolla, Calif.).

Results

Perlecan Domain V is Upregulated after Stroke

Figure 1B:
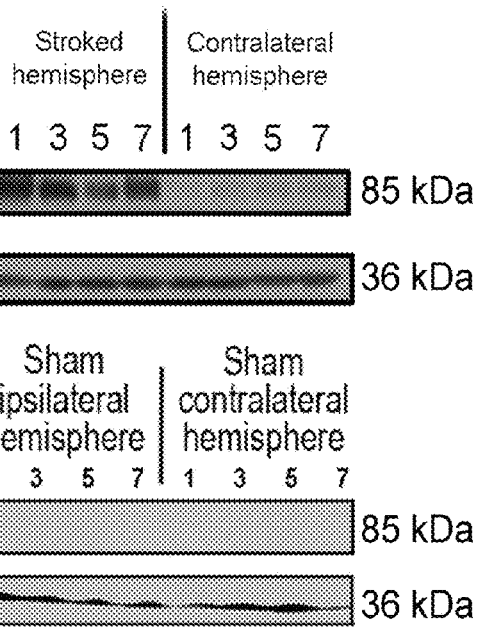
Figure 1C:
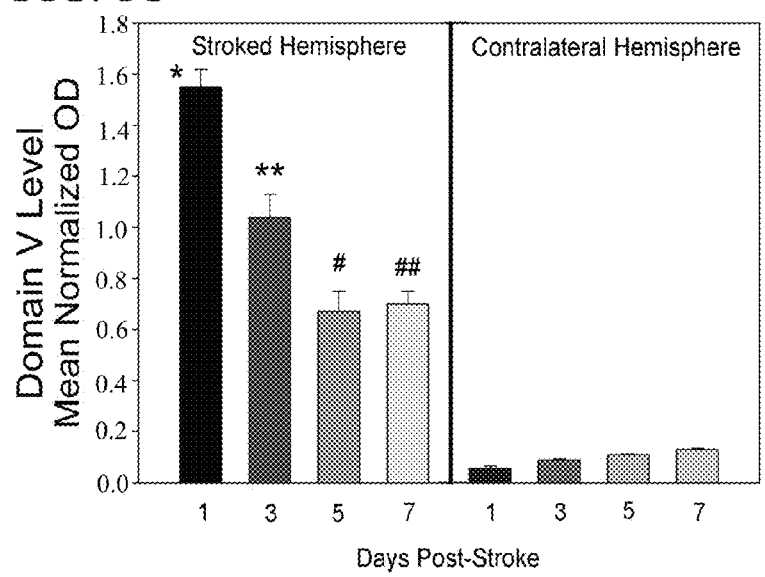
Figure 1D:
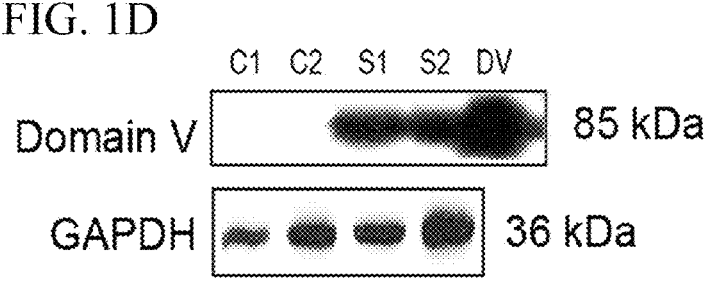

In the rat, stereotactic injection of endothelin-1, a stroke model first developed by Sharkey et al.[28] to induce focal cerebral ischemia (FIG. 1A) by transiently occluding the middle cerebral artery (MCAo)[29] was used. The endothelin-1 stroke model produces reduced cerebral blood flow from 2-4 hours after endothelin-1 injection, which returns to normal after 16-22 h[30]. Thus, the endothelin model mimics aspects of human stroke. Following MCAo, brain samples were harvested at 1, 3, 5, and 7 days post-stroke for western immunoblot analysis (FIG. 1B). Compared to sham surgical controls, which demonstrated no western blot detectable DV in the ipsi- or contralateral hemispheres on post-surgery days 1, 3, 5, 7 (FIG. 1B, 40 µg of total protein loaded per well for all wells), and corresponding contralateral hemisphere DV levels, stroked hemisphere DV levels were elevated at post-stroke day 1 (*p=0.0001, 40 µg of total protein loaded per well for all wells), slightly diminished at post-stroke day 3 (**p=0.0007) and reduced to a plateau at post-stroke days 5 and 7 (#p=0.007, ##p=0.005). A nominal increase was observed in the contralateral hemisphere (FIG. 1B, 1C). To further demonstrate whether DV is produced after human stroke, we performed DV western blot analysis on hemorrhagic stroke brain tissue from two patients who had brain surgery within 24 hours of middle cerebral artery (MCA) rupture (S1 and S2, both stroked cortical brain samples), and 2 normal control brains obtained at autopsy (C1 and C2, control human cortex and striatum, respectively, kindly provided by Dr. Kunlin Kim, Buck Institute, Calif., FIG. 1D, 40 µg total protein loaded per well in all wells, 100 ng of purified human DV control also loaded as labeled)[31, 32]. While DV was not detected in the non-stroked human brain tissue samples, DV was clearly detectable in both hemorrhagic stroke patients' brain samples thereby demonstrating that DV is generated post-stroke in humans.

Figure 2A:
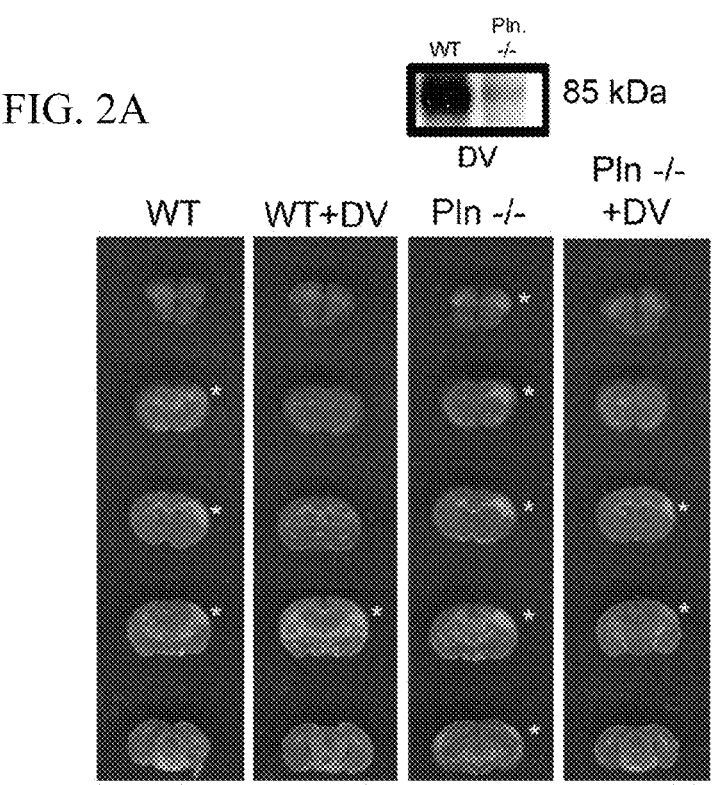
FIGS. 2A-2L. DV reduces ischemic lesion and improves motor function by neuroprotection and enhanced angiogenesis and neurogenesis.
Figure 6:
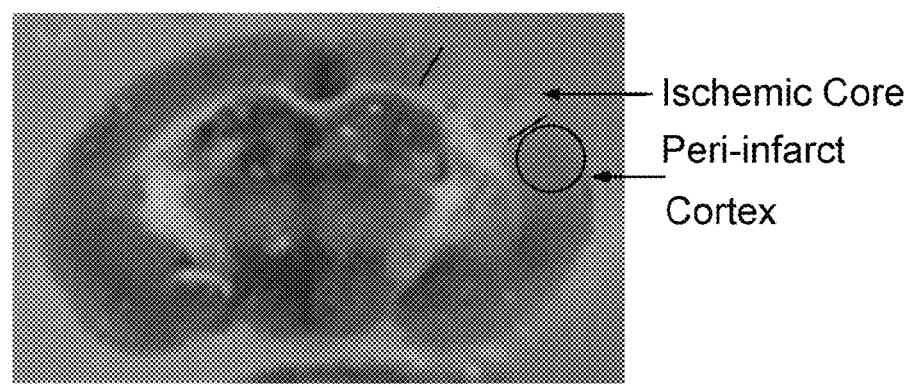
FIG. 6. Representative TTC stained mouse brain section 24 h after a tandem common carotid artery and middle cerebral artery stroke. The white ischemic/stroke core and peri-infarct cortex are designated with arrows, boundary lines and a circle, respectively.

To further confirm that these observations were not species or stroke model-specific, the tandem ipsilateral common carotid artery (CCA) and MCA occlusion stroke model in C57B16 mice[33, 34] was employed. This stroke model mimics human distal MCA occlusion and generates reproducibly similar cortical strokes, both in infarct volume and motor deficit. FIG. 6 and FIG. 2A show a typical injury from this stroke model. Using this focal ischemia model, identical increased and chronically sustained levels of DV in brain tissue (data not shown) was observed, supporting the observation in the endothelin-1 stroked brain.

Figure 1E:
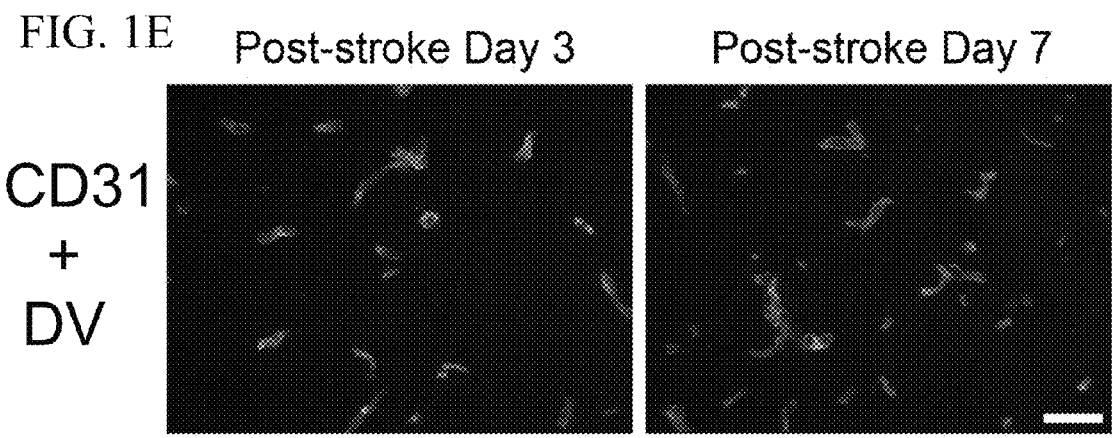
Figure 1F:
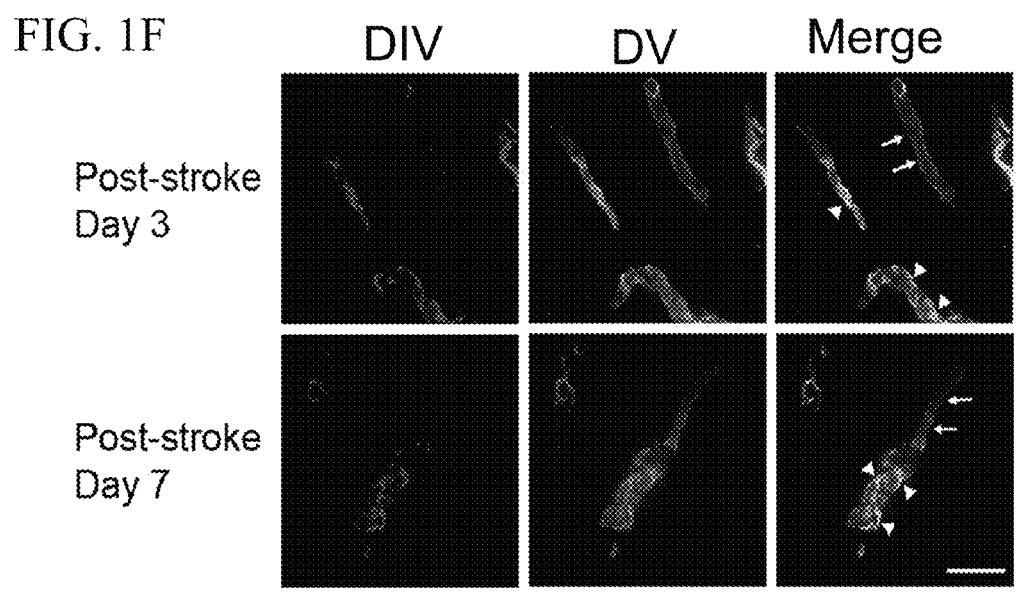

It was expected that post-stroke DV generated would be generated in close proximity to blood vessels since perlecan brain expression is predominantly in the vascular basement membrane[35]. Indeed, DV and CD31 (to label the endothelial cell component of blood vessels) co-immunohistochemistry of stroked brain tissue on post-stroke day 3 and 7 demonstrated that DV was generated in very close association with blood vessels (FIG. 1E). However, because immunohistochemistry antibodies are unable to distinguish perlecan-detached DV (i.e. proteolytically cleaved or free DV) from perlecan-attached DV, we performed perlecan Domain IV (DIV, the perlecan domain immediately adjacent to DV in non-proteolyzed perlecan)[36] and DV co-immunohistochemistry (FIG. 1F) of post-stroke day 3 and 7 brain tissue to better visualize the post-stroke generation of free DV. This method clearly displayed DV that was distinct from/did not co-localize with DIV (arrows, free DV) from DV that did co-localize with DIV (arrowheads, perlecan-attached DV). Collectively, these results demonstrate that post-stroke perlecan processing results in a rapid peri-vascular increase in stroked brain DV levels that diminishes to a persistently elevated level up to post-stroke day 7.

Figure 7:
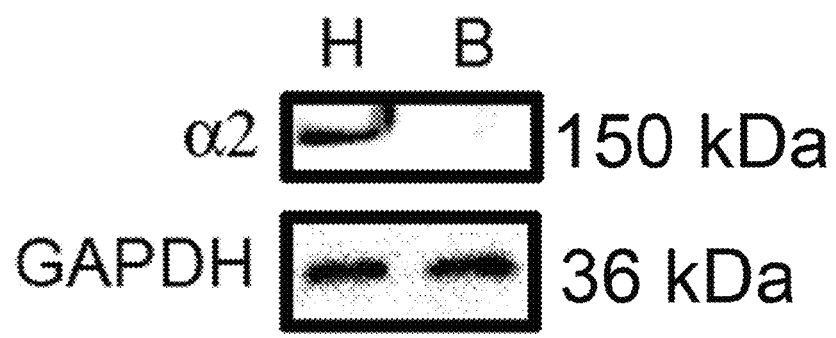
FIG. 7. Representative α2 integrin western blot analysis of HUVEC (H) and mouse brain microvascular endothelial cells (B) from C57BL6 mice with GAPDH loading control demonstrating that no α2 integrin could be detected in these brain microvascular endothelial cells.
Figure 5Z:
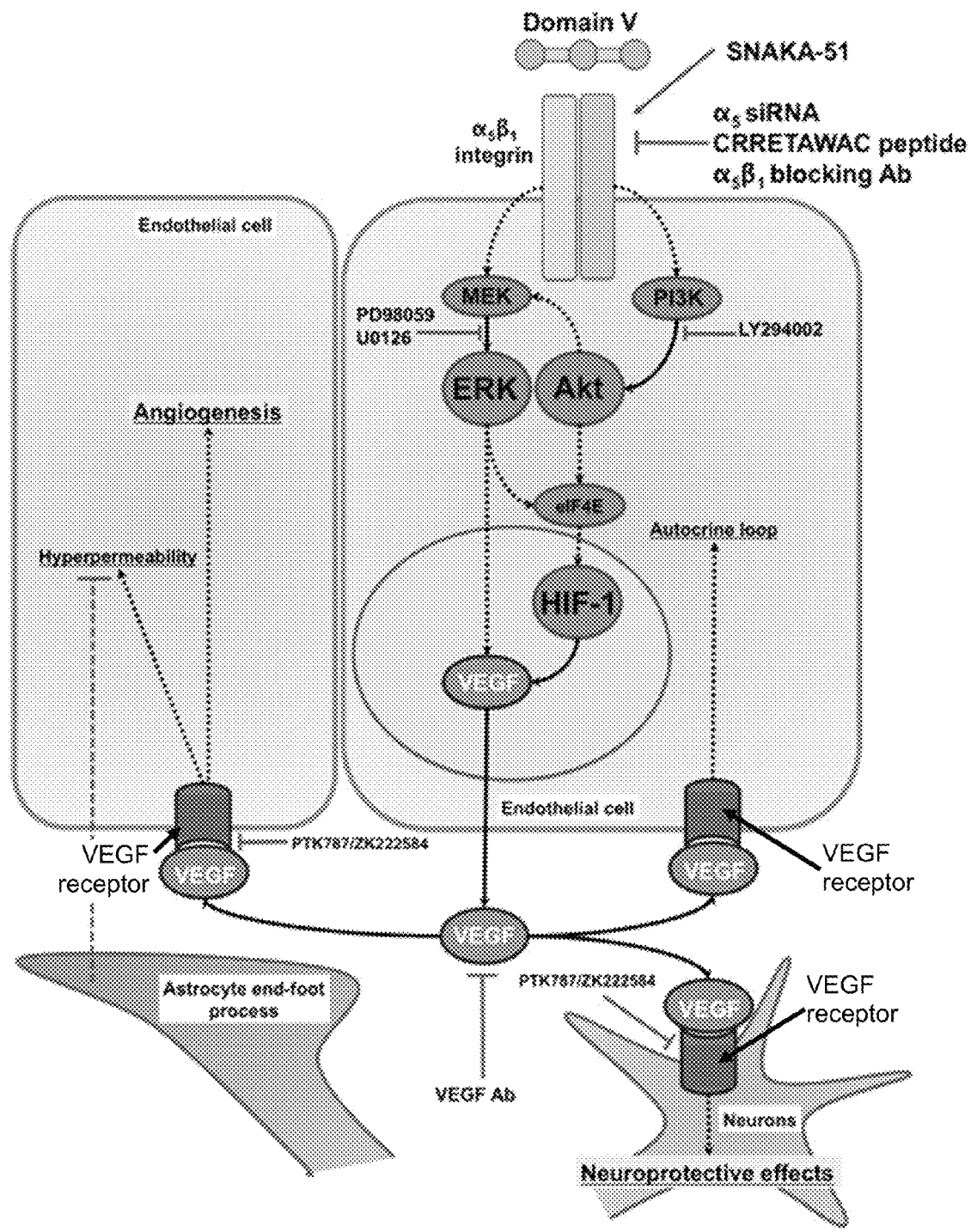
Figure 8A:
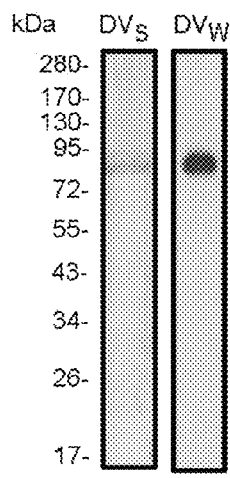
FIGS. 8A-8F. DV cloning, purification and purity assessment. DV was cloned into the pSecTag2A vector (Invitrogen) which added a 6×His tag to the C-terminus of DV. Plasmids were transfected into 293FT (ATCC, Manassas, Va.) cells via Lipofectamine (Invitrogen). After transfection, serum-free conditioned media (containing cell secreted DV) was collected and DV was purified via Ni-ATA agarose bead column chromatography at 4° C. The eluted DV was dialyzed against 1×PBS and assessed for purity via (FIG. 8A) SDS-PAGE silver stained ($DV_S$, FASTsilver Gel Staining Kit, Calbiochem), and western blot ($DV_W$) analysis with anti-DV antibody (R&D systems, shown), and anti-HIS antibody. 100 micrograms of DV used for each.
Figure 8B:
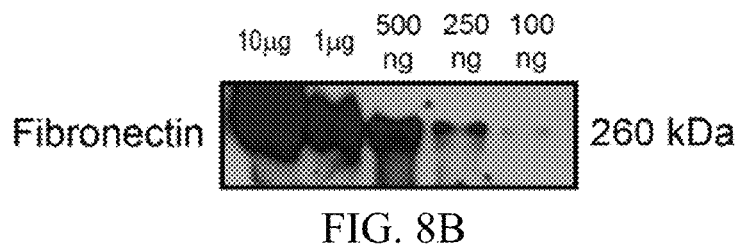
Figure 8C:
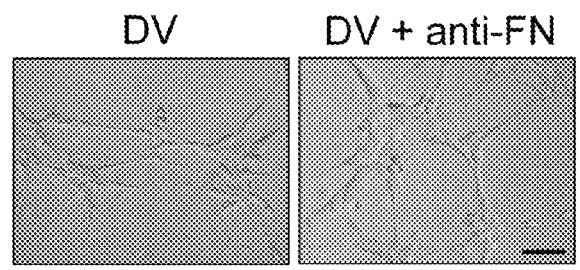
Figure 8C:
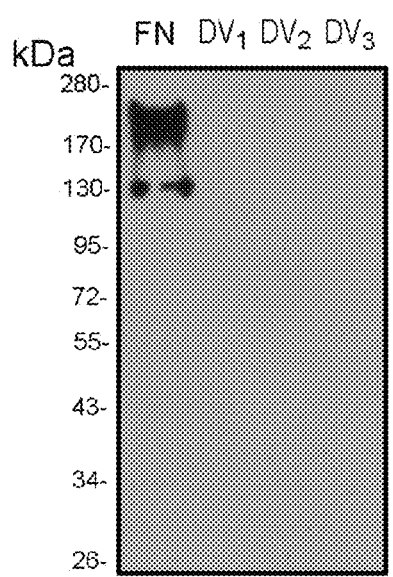
Figure 8E:
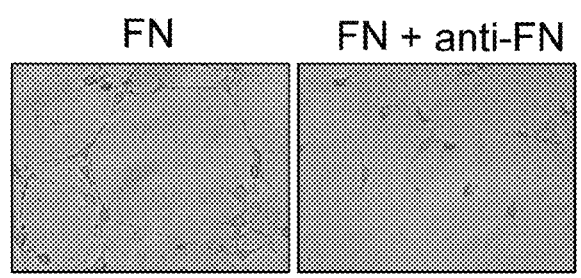
Figure 8F:
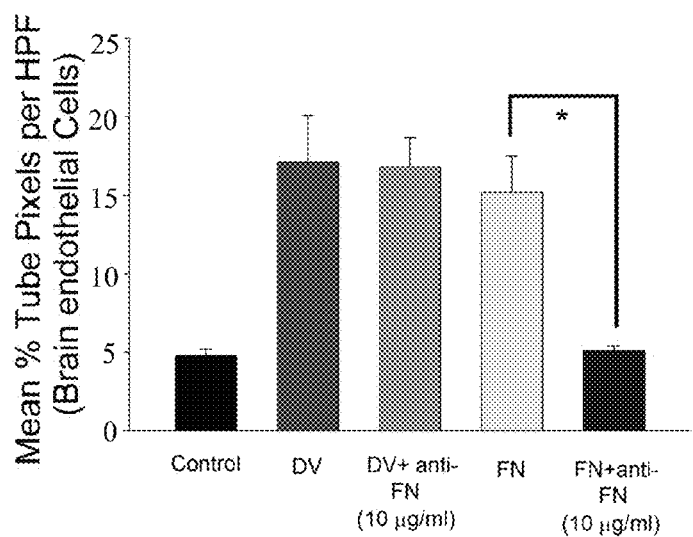

Domain V Homes to Stroke Tissue and Peri-Infarct Vasculature, is Neuroprotective, and Unexpectedly Enhances Post-Stroke Angiogenesis and the Neurovascular Niche As DV, a known inhibitor of angiogenesis[25], is produced in the post-stroke brain in very close association with endothelial cells, we hypothesized that it could play a role in regulating post-stroke angiogenesis. However, as brain microvascular endothelial cells do not express the previously identified DV receptor $\alpha 2\beta 1$ integrin[27, 37] (FIG. 7), DV's exact target in the brain was unknown. We first purified human recombinant DV and demonstrated that these preparations were free of contamination with fibronectin, an abundant serum component that has been shown to reduce brain injury following transient cerebral ischemia (FIG. 8)[38]. Specifically, silver stain of DV preps, a sensitive procedure that can detect sub-nanogram levels of protein, did not demonstrate bands in the 260 kDa range of fibronectin, or any other contaminating bands (FIG. 8). Furthermore, Liquid Chromatography Tandem Mass Spectrometry (LCMSMS) analysis of the purified DV protein did not detect fibronectin or any other protein contaminant from *E. coli*, serum, or the 293 cells used to produce the DV. Finally, fibronectin western blot (which could readily detect as little as 100 ng of fibronectin, FIG. 8B) of 3 separate DV preparations (100 µg DV protein loaded per well) failed to yield any fibronectin bands (FIG. 8C). DV (0.5-1.0 mg/kg), heat inactivated DV control, or PBS vehicle control was administered via intraperitoneal injection[26] to stroked rats and wild type mice on post-stroke days 1, 2, and 3. In some of these experiments, mutant mice engineered to express only 10% (hypomorph) of normal total perlecan levels[39] were used to further determine whether reduced endogenous perlecan (perlecan hypomorph mice, pln−/−) and DV levels might affect stroke severity and the post-stroke angiogenesis response[39]. Perlecan null mice were not used as they are embryonic lethal[40], while perlecan hypomorph mice are viable, fertile, and have no reported defects in the CNS[39, 41]. Prior to use in our stroke model, the gross neurovascular anatomy (i.e. the size, location and branching patterns of the major cerebral arteries with particular focus on the middle cerebral artery) of several pln−/− mice was investigated and appeared identical to wild type (WT) littermate controls as can be seen in representative brains in FIG. 9A.

Figure 2B:
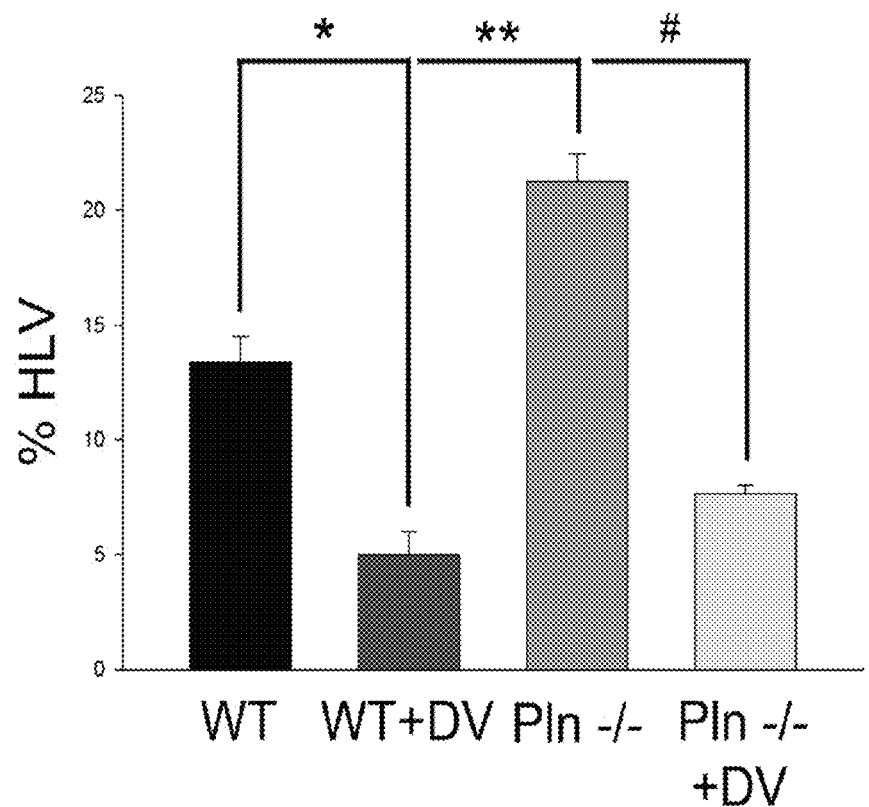

When DV was administered post-stroke, it was well tolerated in all cases as previously reported[26], with no animal sickness, weight loss, or death noted. Furthermore, no changes were noted in animal systolic blood pressure, heart rate, breath rate, arterial partial pressure of $O_2$ or $CO_2$, serum sodium, potassium, ionized calcium, or blood pH with 24 hour post-stroke DV or PBS treatment in rats or mice (Table 1, mice parameters 2 hours after PBS or DV treatment, administered 24 hours after stroke, shown). Additionally, 24 hours after stroke, wild type (WT) mice had a mean+/−standard deviation cerebral blood flow of 123.00+/−20.00 PU (perfusion units) which was not significantly affected by subsequent DV treatment (122.83+/−11.92) measured two hours after I.P. DV administration, given 24 hours after stroke. Furthermore FIG. 2A. demonstrates representative TTC stained brain sections from WT or pln−/− mice±DV treatment on post-stroke day 3 with the white ischemic lesions bulleted with yellow asterisk. Surprisingly, DV treated control animals exhibited a significantly smaller % hemispheric lesion volume (% HLV) than their wild type littermate controls (FIG. 2B, *p=0.00003). Furthermore, pln−/− hypomorph mice suffered an even larger % HLV than wild type controls (**p=0.0006), which was reversed by DV administration (#p=0.00007). Such a discrepancy between WT and pln−/− mice is likely due to the relative absence of endogenously cleaved DV in pln−/− following stroke injury rather than due to differences in post-MCA occlusion blood flow. Indeed, 24 hours after stroke the mean cerebral blood flow was not significantly different (130.1667+/−25.19 PU) between pln−/− and WT mice, and the flow was significantly affected by DV administration (132.66+/−22.16 PU, DV given 24 hours post-stroke, measurement made 2 hours after DV administered). Finally, cerebral blood flow was restored to pre-occlusion levels after MCA reperfusion at similar rates for both WT and pln−/− mice (data not shown). Thus, any differences in stroke outcomes between WT and pln−/− mice, or between PBS and DV treated mice, are unlikely due to any DV induced changes in vascular tone or direct vascular responses.

Figure 2C:
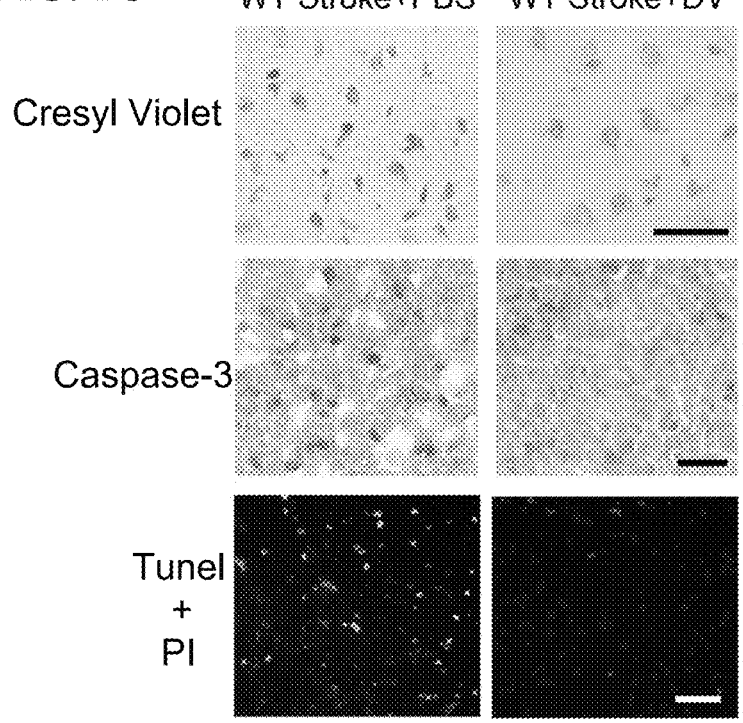

Surprisingly, further analysis of post-stroke brain tissue peri-infarct regions, (defined as a 500 µm boundary extending from the edge of the infarct core, medial and lateral to the infarct[5]) from wild-type and DV treated animals demonstrated that DV treatment resulted in more neurons with normal morphology, fewer shrunken and misshapen cells, decreased staining of the 17 to 20-kDa Caspase-3 cleavage product, and decreased TUNEL-positive cells (FIG. 2C) collectively demonstrating that DV administered 24 and 48 after stroke is neuroprotective.

Stroke experiments were repeated in rats, WT and pln−/− mice out to post-stroke day 7 to determine if DV could stimulate angiogenesis. By post-stroke day 3, significant (*p=0.001) increase in angiogenesis (as recognized by von Willebrand factor immunohistochemistry) was detected in the brain region immediately surrounding the stroke area (i.e. peri-infarct brain, as defined above) (FIGS. 2D, 2E) in WT mice treated with DV. This increase in peri-infarct vasculature became even more prominent by post-stroke days 5 (p=0.000008) (FIG. 2E) and 7 (*p=0.00000004). Additionally, the post-stroke angiogenic response in pln−/− mice was stunted by post-stroke day 5 (φp=0.0002) and 7 (φφp=0.0001), but could be rescued and increased beyond wild type levels on post-stroke days 5 and 7 (#p=0.0006, ##p=0.0001 respectively) with DV treatment. Similar results were obtained with CD31 immunohistochemistry and in rats (data not shown). Likewise, heat-inactivated DV had no effect on post-stroke angiogenesis as expected (data not shown)[26]. These results suggest that DV could be an unexpected pro-angiogenic protein in the post-stroke brain.

Figure 9A:
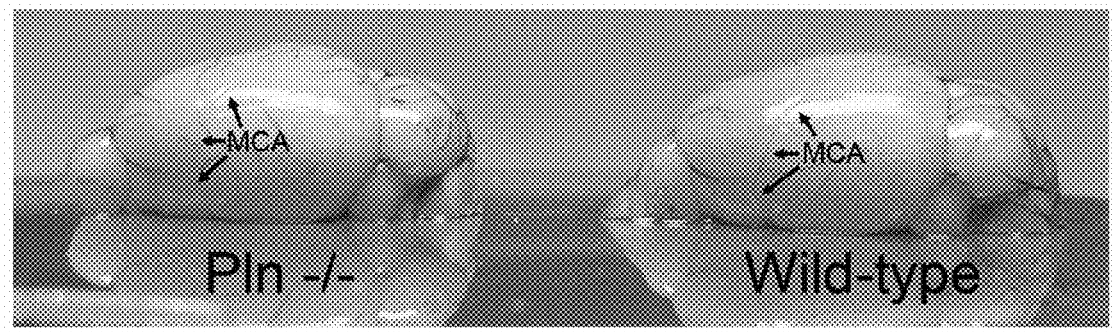
FIGS. 9A-9B.
Figure 9B:
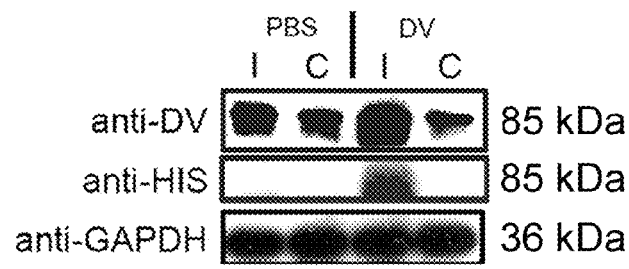
Figure 10:
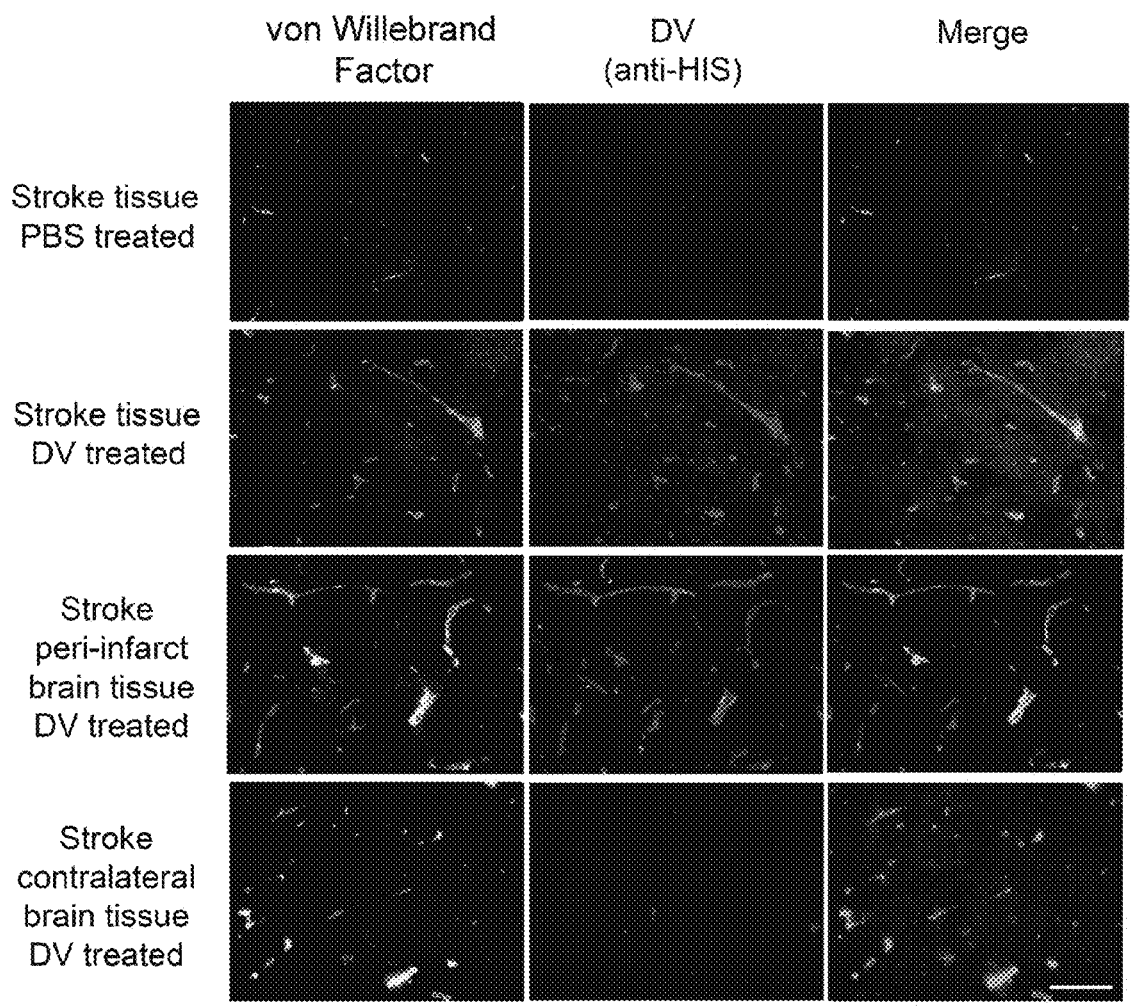
FIG. 10. DV localizes to stroke and peri-infarct tissue. Frozen tissue sections from stroked C57BL6 mice treated with DV or PBS vehicle control were processed via immunohistochemistry with antibodies directed against von Willebrand factor (green) and the HIS epitope (red) to visualize blood vessels and administered DV, respectively. We noted an abundance of DV in stroked tissue and the stroke peri-infarct brain tissue (here DV deposited in a perivascular distribution). In contrast, no DV was detected in the corresponding unstroked contralateral brain tissue of the same DV treated animal suggesting that DV specifically homes to stroked and peri-infarct brain tissue. Bar is 10 μm.

The above results suggest that administered DV (via intraperitoneal injection) was likely to reach the site of stroke brain injury. Recombinant DV was followed by means of a HIS epitope tag placed at its C-terminus and immunohistochemistry for the HIS tag (FIGS. 2F, 2G) revealed that administered DV could be found in abundance in rat stroked brain tissue (identified morphologically by cresyl violet stain of the immediately preceding 8 µm thick brain section) and to a lesser extent in the peri-infarct brain, but not to any significant extent in the contralateral unstroked hemisphere of the same animal. Furthermore, virtually all of the administered DV deposited in a perivascular (distribution in the peri-infarct brain and to a lesser extent in the stroked tissue), consistent with its brain blood-vessel promoting effects and its ability to target activated solid tumor perivasculature in vivo[26]. Western blot analysis further confirmed that administered DV was found in the stroked brain hemisphere but not the contralateral unstroked brain hemisphere in stroked rat (FIG. 9B). Similar results were seen in stroked mouse brain (FIG. 10). Finally, administered heat inactivated DV could not be detected in stroked brain tissue (data not shown).

DV Enhances Neurogenesis Following Stroke Injury

Figure 11:
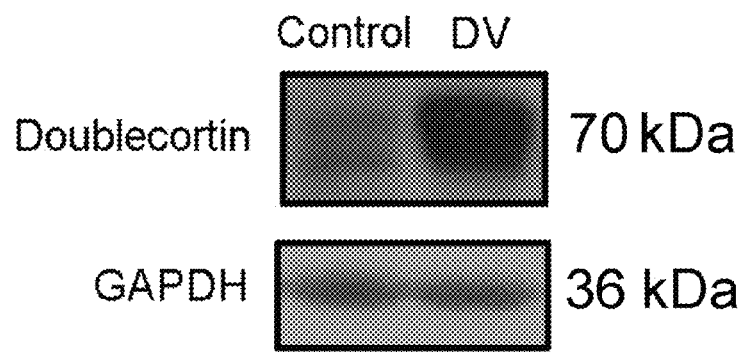
FIG. 11. Post-stroke doublecortin western blot analysis. Representative doublecortin western blot (with GAPDH loading control) of stroke brain tissue (post-stroke day 7) from control and DV treated animals demonstrating significantly (quantification not shown) increased doublecortin immunoreactivity with DV treatment.

As peri-infarct blood angiogenic blood vessels have been shown to serve as a physical scaffold for neurons to migrate towards the ischemic core[5], DV administration was investigated to determine if it could also affect the extent of neuroblasts migrating into the peri-infarct brain tissue, and thereby potentially influence the repopulation of stroked brain tissue with new neurons. Using doublecortin and nestin, two cytoskeletal markers of immature neurons[5], we investigated the presence of immature neurons around peri-infarct vasculature in immunohistochemistry (FIGS. 2H, 2I) of brain sections from PBS and DV treated (post-stroke days 1, 3, 5 and 7) stroked animals. Quantification of doublecortin immunohistochemistry (FIG. 2I) (n=20 images per animal, n=10 animals per post-stroke day, per experimental condition) in the respective stroke peri-infarct tissue revealed a significant increase in doublecortin signal on post-stroke days 3, 5 and 7 (*$p=0.00001$, $p=0.000008$, *$p=0.000009$, respectively) with DV treatment. Likewise, total doublecortin signal per stroked and contralateral brain hemispheres was determined by western blot (FIG. 11). Here, a significant increase in doublecortin positive signal in the DV treated animals was noted compared to controls (western blot quantification not shown). Furthermore, in agreement with the hypothesis that DV fosters formation of the peri-infarct neurovascular niche, a significantly ($p=0.0006$) greater percentage of doublecortin positive cells directly adjacent (defined as directly visible neuroblast-blood vessel contact or a neuroblast cell body within 10 microns of a blood vessel) to blood vessels (as identified by antibodies directed to CD31 antibody or the HIS epitope in the DV treated animal (90%±5%, n=20 images per animal) as compared to the PBS control treated animal (60%±3%) in the peri-infarct brain tissue on post-stroke day 3) was noted. Similar results were seen in rat stroked brain (data not shown). Lastly, DV did not influence the infiltration of immune cells into the post-stroke brain inasmuch as few CD45 (a neutrophil marker) positive cells in or around the ischemic lesion in either the control or DV treated animals on post-stroke day 3, 5 or 7 (post-stroke day 5 shown, FIG. 2J) could be detected.

Domain V Improves Post-Stroke Function

Figure 2D:
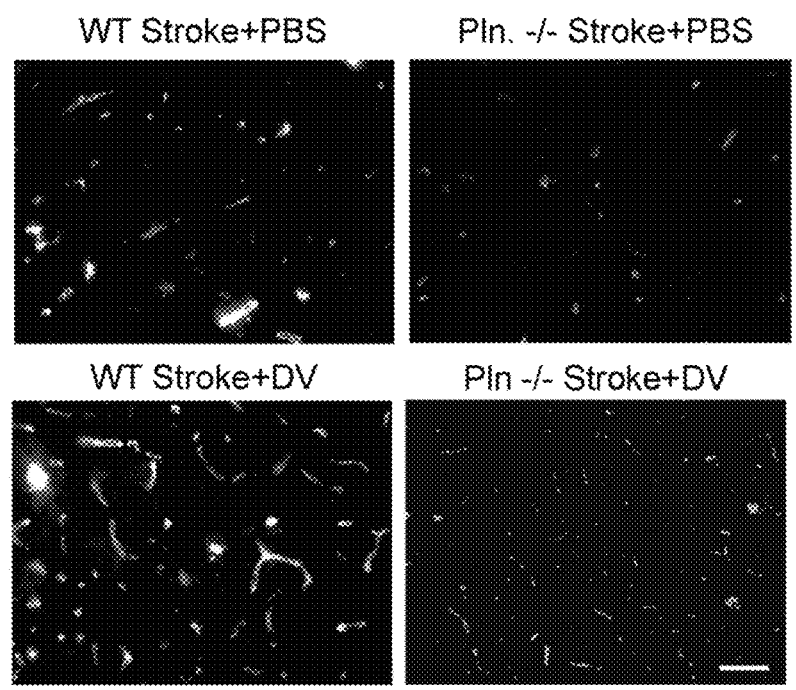
Figure 2E:
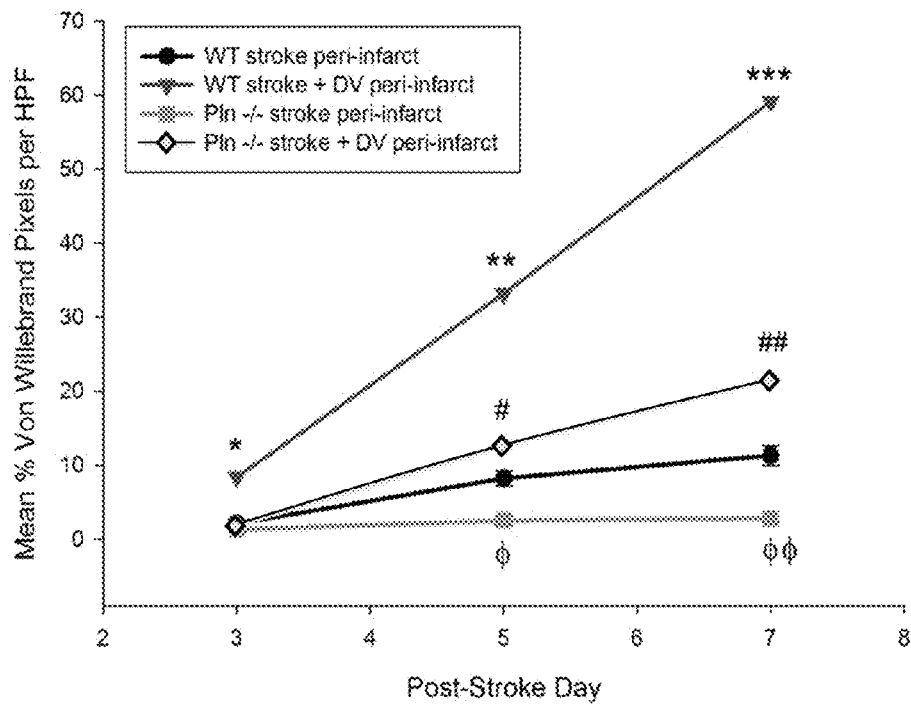
Figure 2F:
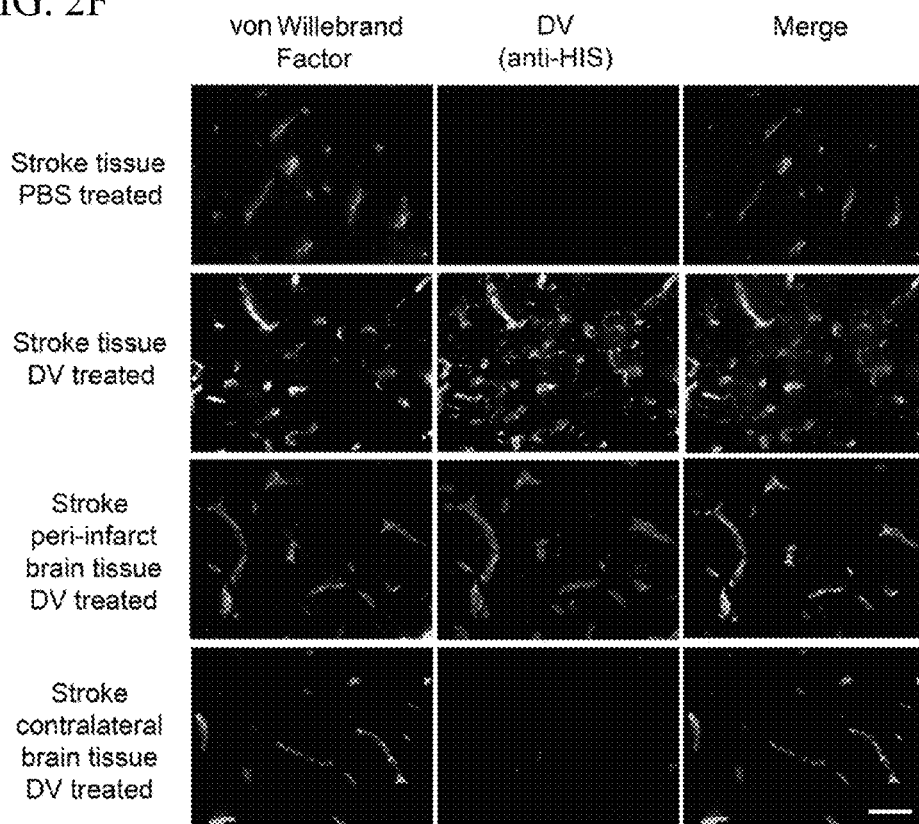
Figure 2G:
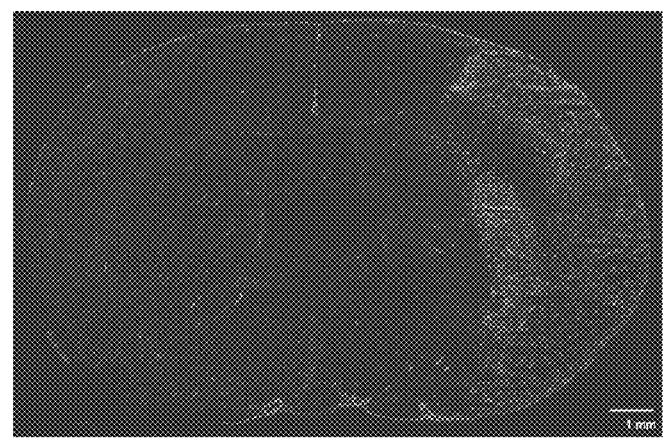
Figure 2H:
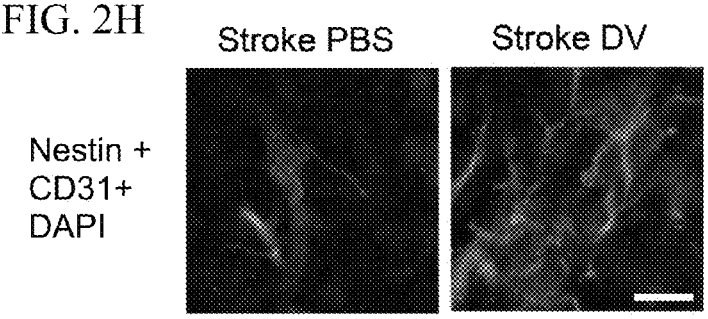
Figure 2I:
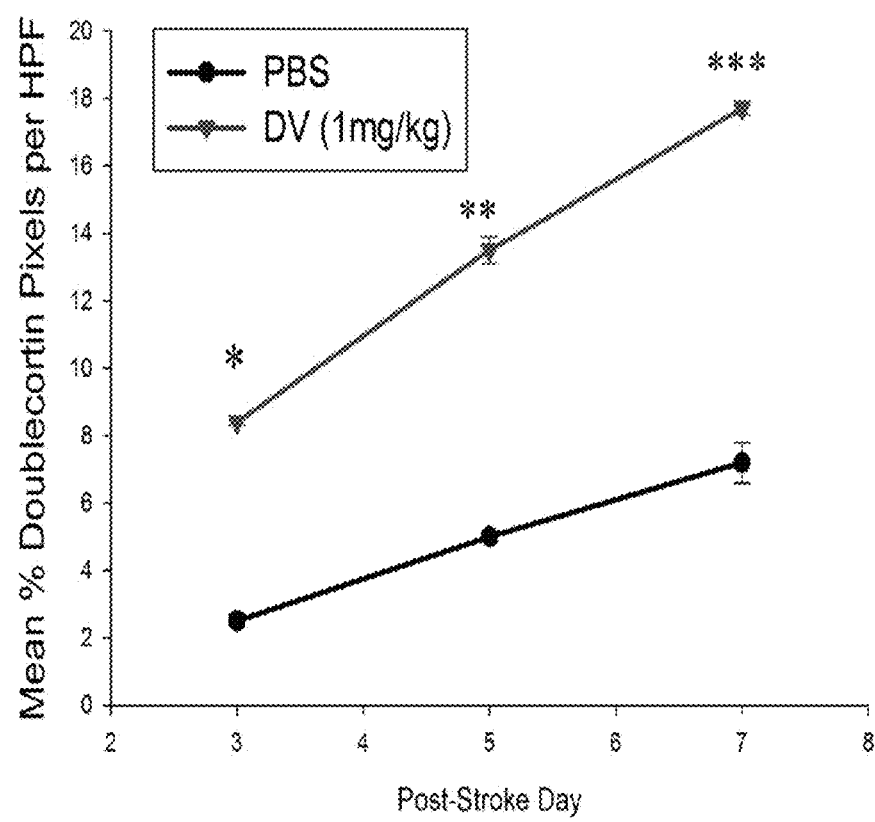
Figure 2J:
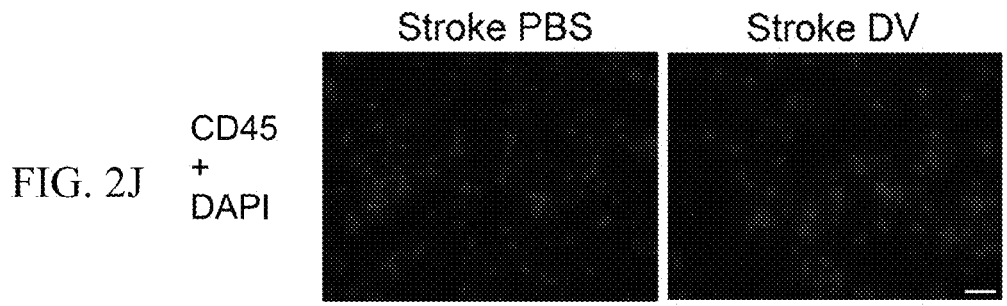
Figure 2K:
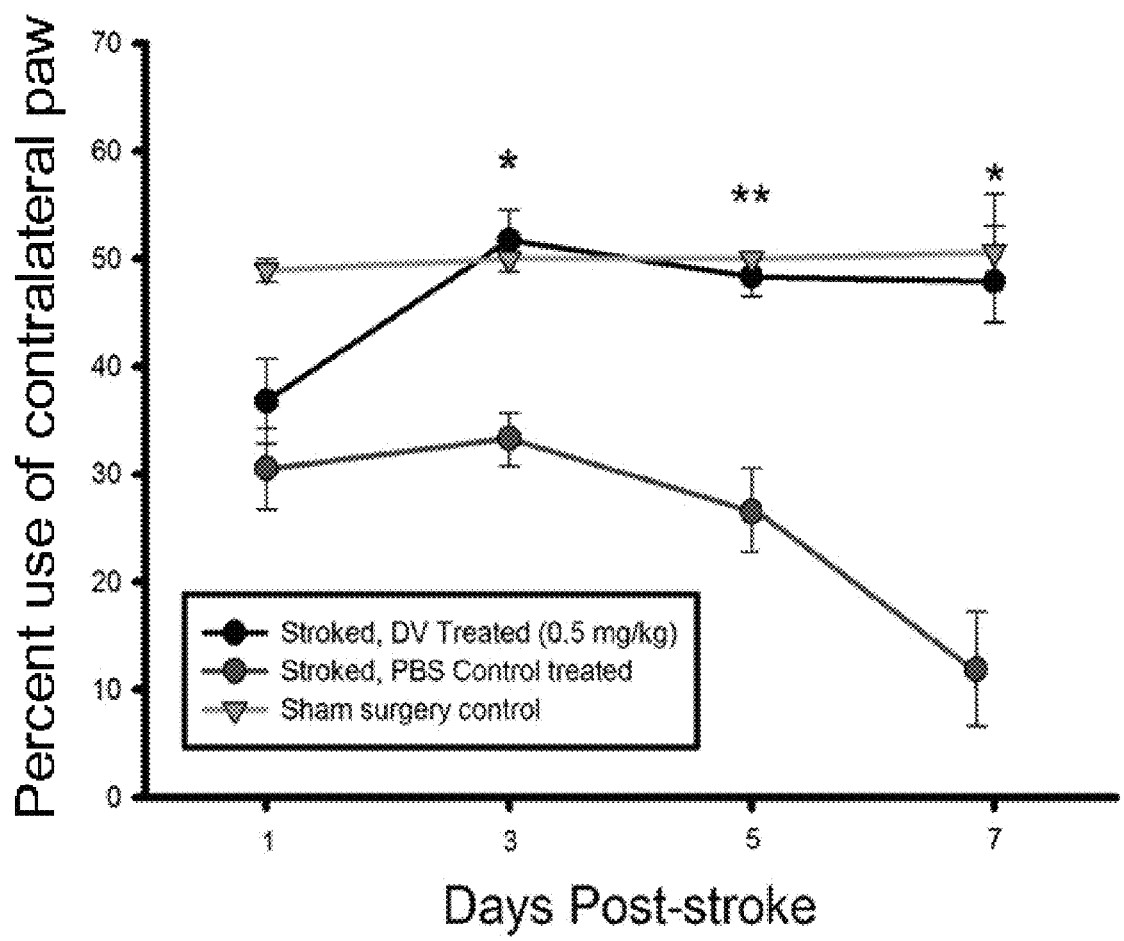
Figure 2L:
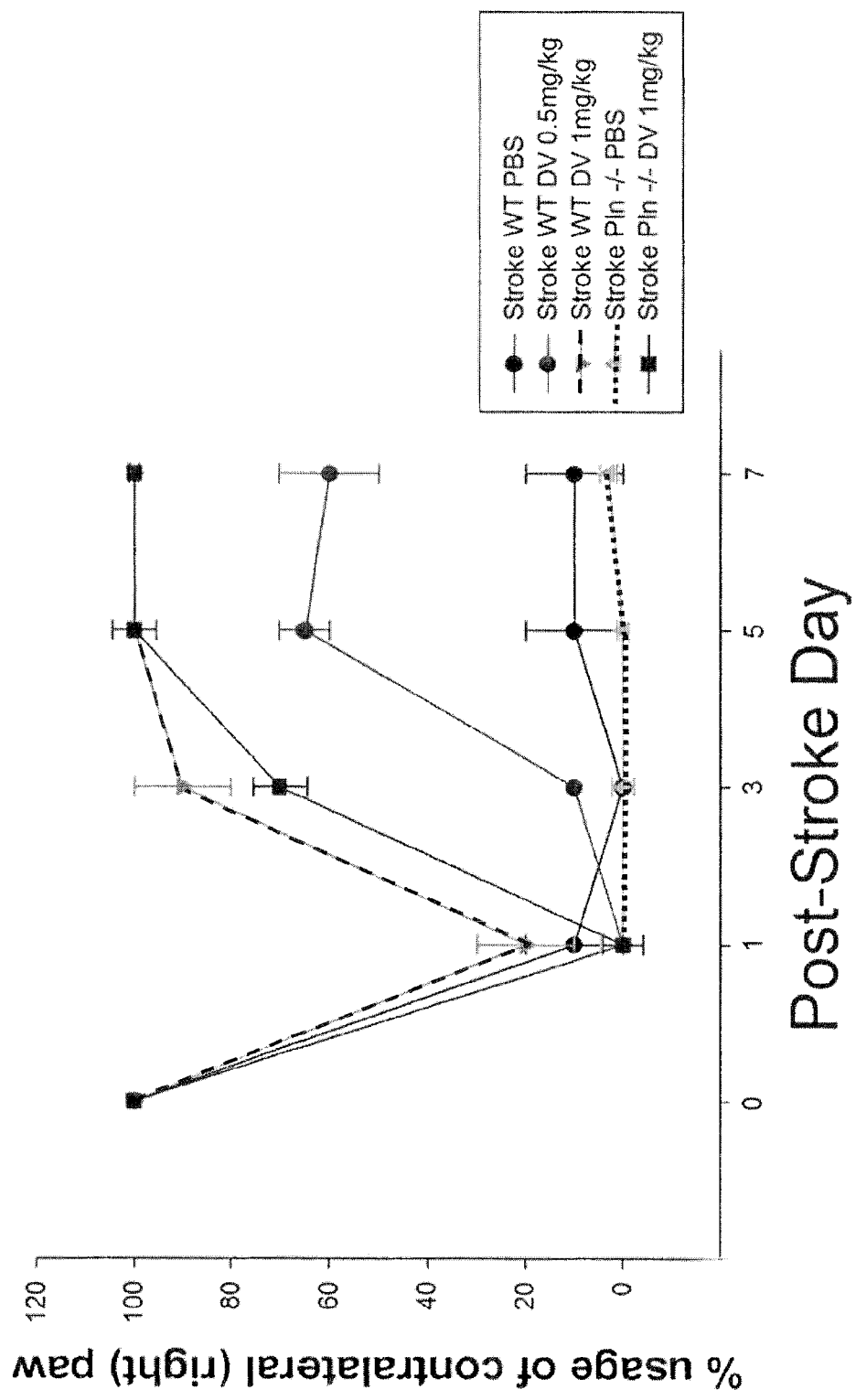

Because DV was unexpectedly neuroprotective, pro-angiogenic, and had beneficial effects on stroke infarct volume and neuronal migration, DV treatment was investigated to determine if it could also improve functional motor outcome after stroke in rats and mice. Using the cylinder test to test rats[42], DV treatment significantly increased ($p=0.03$) spontaneous use of the stroke affected forelimb by post-stroke day 3 ($p=0.03$) that persisted to post-stroke day 7 ($p=0.004$) (FIG. 2K). Overall, the DV-treated stroked group significantly differed from the PBS-treated stroked group ($p=0.015$), but not from the sham surgery control group ($p=0.3$), demonstrating that administered DV improved post-stroke function to baseline pre-stroke levels. In the vibrissae-elicited forelimb placement test[43], used to test WT and pln–/– mice, all stroked mice groups placed the contralateral forelimb significantly less on post-stroke day 1 than prior to stroke ($p=0.0003$ for WT DV (1 mg/kg), $p=0.0001$ for WT DV (0.5 mg/kg), $p=0.0002$ for WT PBS, $p=0.0001$ for pln–/– DV (1 mg/kg) and $p=0.0001$ for pln–/– PBS) (FIG. 2L). However, by post-stroke days 3 and 5, the WT DV 1 mg/kg, WT DV 0.5 mg/kg and pln–/– DV 1 mg/kg groups significantly improved their use of the stroke-affected forelimb while the PBS-treated mice remained significantly impaired ($p=0.001$, $p=0.0008$, $p=0.006$, $p=0.005$ for PBS treated group on post-stroke days 1, 3, 5, and 7, respectively, as compared to day 0). The WT DV 1 mg/kg treated and the pln–/– DV 1 mg/kg groups were indistinguishable from the sham surgery control group (100% use of contralateral paw at all times measured, data not shown) by post-stroke day 5 ($p=0.6$, $p=0.7$ respectively). Furthermore, each WT DV treated group was significantly different from each other and the WT PBS-treated group ($p=0.01$ between WT DV treated groups, $p=0.006$ between WT DV (1 mg/kg) and WT PBS-treated group, and $p=0.009$ between WT DV (0.5 mg/kg) and WT PBS-treated group). The pln–/– PBS treated group was not significantly different from the WT PBS treated group ($p=0.3$). Finally, the pln–/– DV 1 mg/kg treated group was significantly different than the pln–/– PBS treated group ($p=0.009$), the WT DV 0.5 mg/kg treated group ($p=0.03$) but not significantly different from the WT DV 1 mg/kg treated group ($p=0.8$). Therefore, in two distinct in vivo stroke models and in two separate species, including a perlecan deficient animal, DV treatment restored post-stroke motor function to baseline pre-stroke function by post-stroke day 3.

Domain V Increases Angiogenesis In Vitro

Figure 3D:
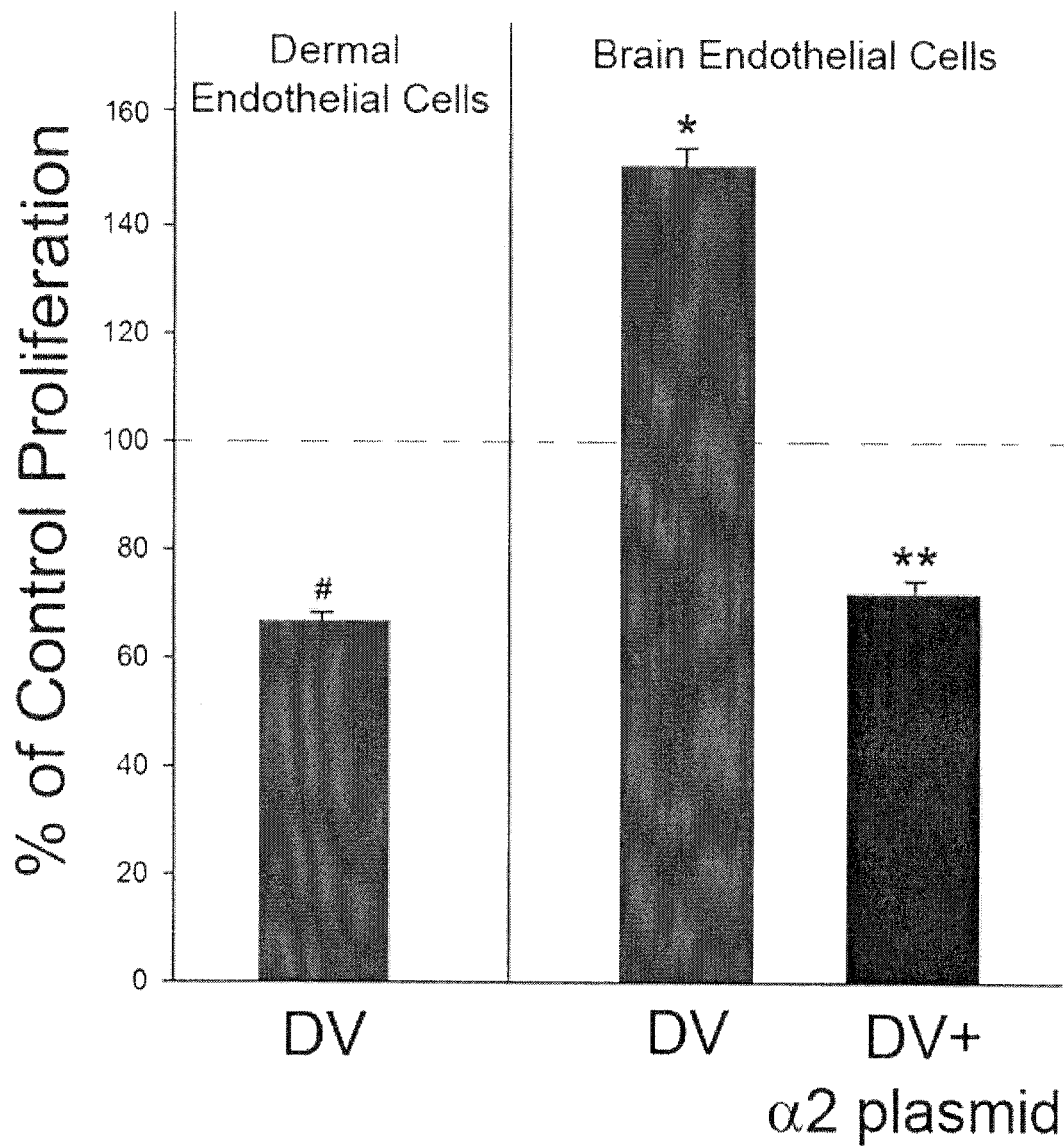
Figure 8D:
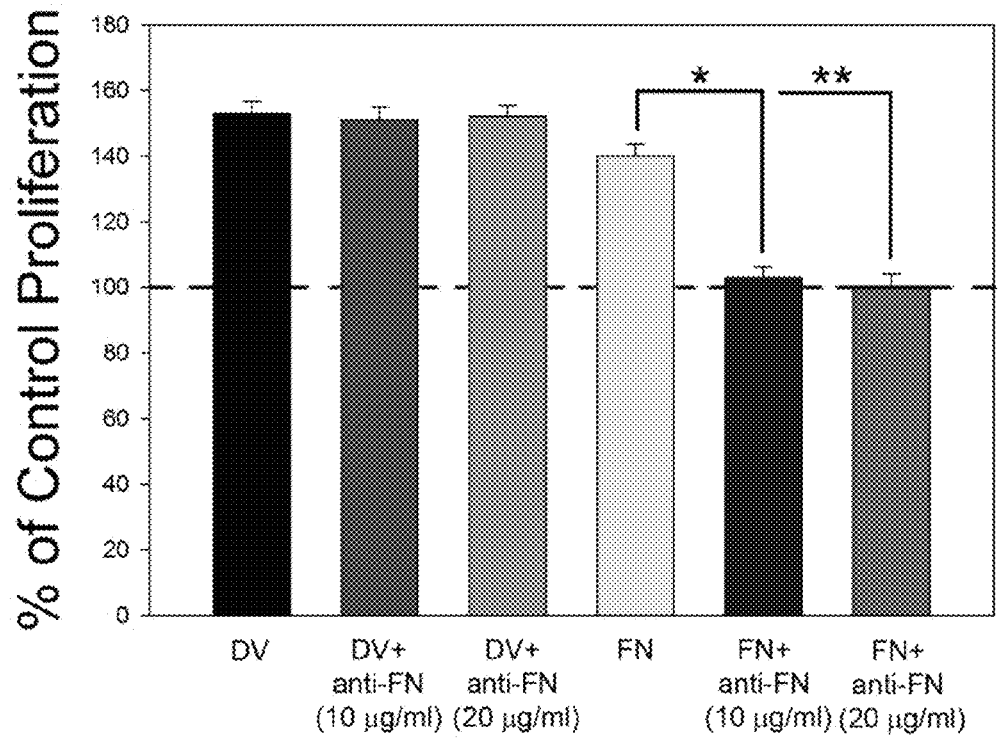
Figure 14:
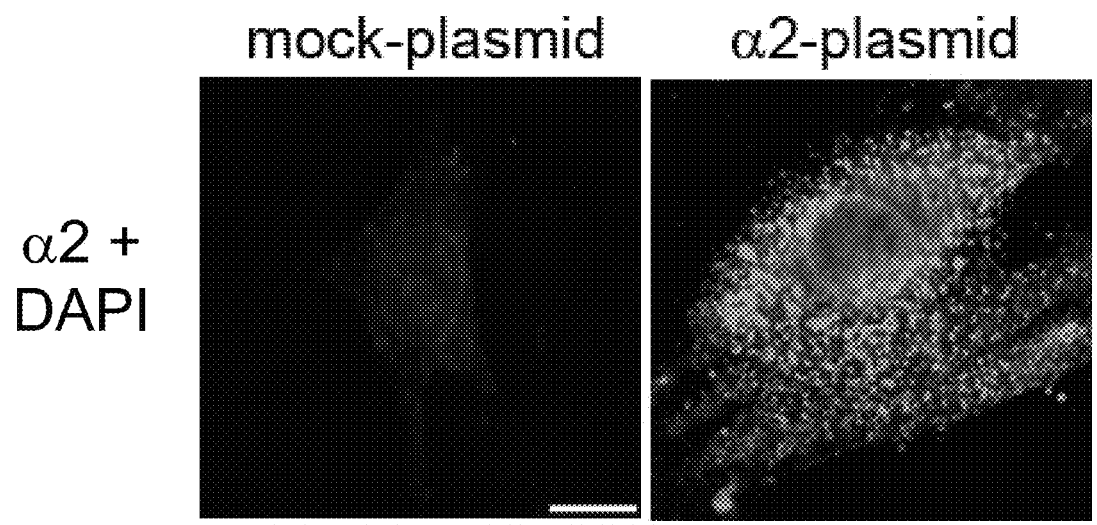
FIG. 14. α2 integrin transfection into mouse brain microvascular endothelial cells. Representative images (taken with the same exposure times) of α2 integrin immunocytochemistry of mouse brain endothelial cells transfected with an empty mock plasmid (control) demonstrating faint background fluorescence or with an α2 integrin plasmid demonstrating significant α2 integrin expression. Bar is 2 μm.
Figure 13A:
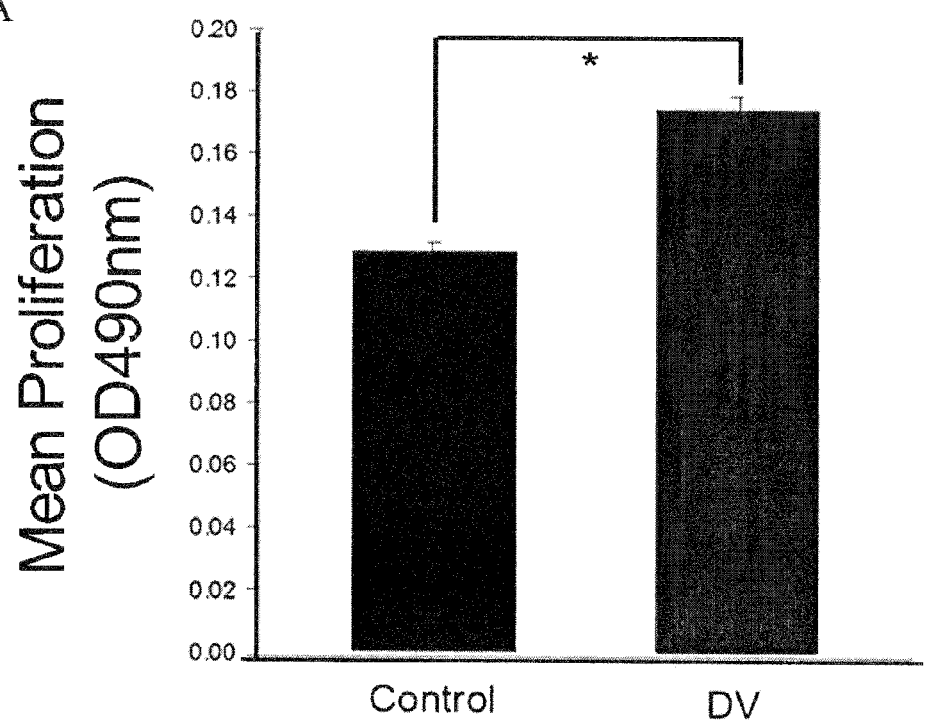
FIGS. 13A-13B.
Figure 13B:
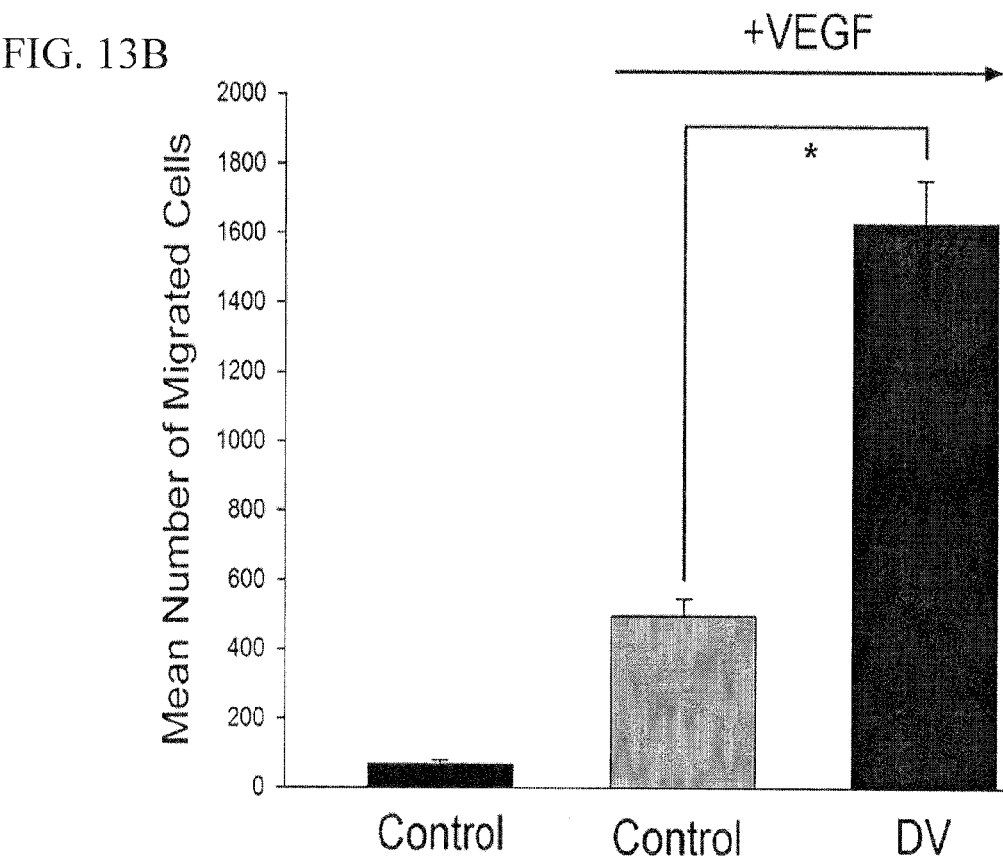
Figure 15B:
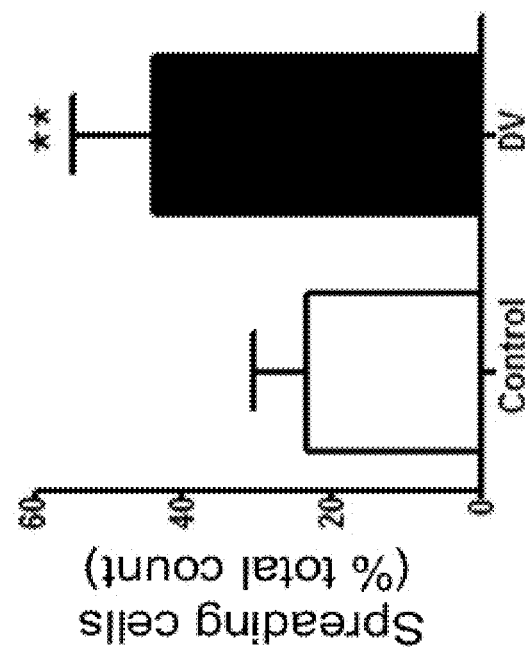
FIGS. 15A-15B. DV does not cause brain endothelial cell actin collapse.
Figure 15A:
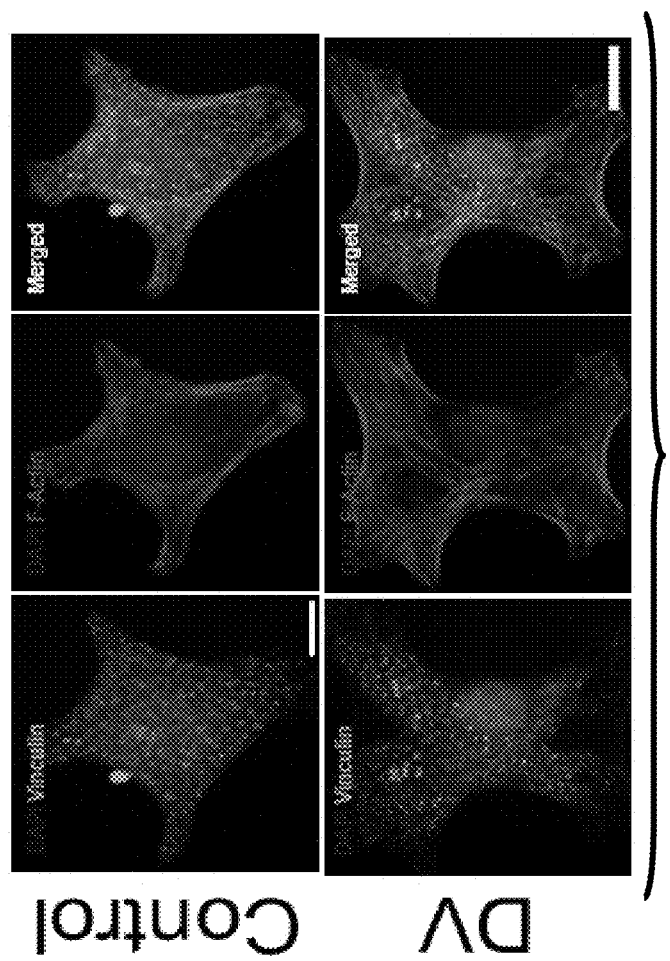

To begin to dissect DV's mechanistic post-stroke effects in the brain, DV's pro-angiogenic effects were examined in several stages of angiogenesis (including capillary-like tube formation, migration, and proliferation) on isolated microvascular brain endothelial cells from mouse, rat and human (FIG. 12). These results were directly compared to those on mouse dermal microvascular endothelial cells where DV has been previously shown to inhibit angiogenesis[25]. DV significantly increased (n=15, $p=0.0009$) brain endothelial cell capillary tube-like structure formation, whereas DV significantly inhibited dermal endothelial cell tube formation (n=15, $p=0.001$, FIGS. 3A, 3B). DV similarly stimulated brain endothelial cell migration towards VEGF (FIG. 3C), stimulating a 450%±25% increase in migration compared to control (n=15, $p=0.00006$). Proliferation rates also increased 50%±3% with DV treatment compared to control (n=15, $p=0.00005$) (FIG. 3D). Similar results were obtained with rat and human brain endothelial cells (FIG. 13). Additionally, as further evidence that these pro-angiogenic effects were not due to any potential fibronectin contamination, anti-fibronectin antibodies (10 and 20 µg/ml) had no effect on DV-induced increases in brain endothelial cell proliferation or tube-like structure formation, but did inhibit fibronectin effects (FIGS. 8C, 8D). Intriguingly, when mouse brain endothelial cells were made to express α2β1 integrin (FIG. 14), DV inhibited ($p=0.00009$) rather than enhanced their proliferation (FIG. 3D), thereby suggesting that the absence of α2β1 integrin from brain microvascular endothelial cells is essential to DV's pro-angiogenic effects in the brain. Finally, as DV has been shown to cause the collapse of the actin cytoskeleton and focal adhesions, as well as inhibit cell spreading[25] in non-brain endothelial cells. FIGS. 15A and 15B demonstrate that DV treatment had no effects on the actin cytoskeleton and focal adhesions, which remained intact, and significantly enhanced ($p=0.0001$) rather than inhibited cell spreading. Collectively, these results demonstrate that DV's pro-angiogenic effects on brain endothelial cells are distinct from DV's effects on non-brain endothelial cells.

Figure 4A:
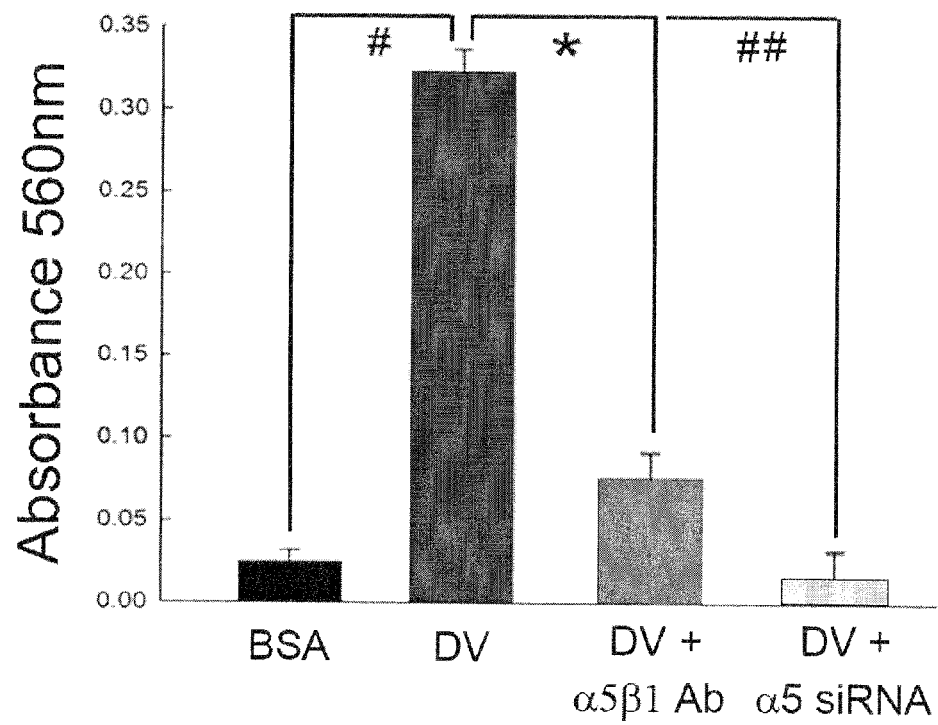
Figure 4B:
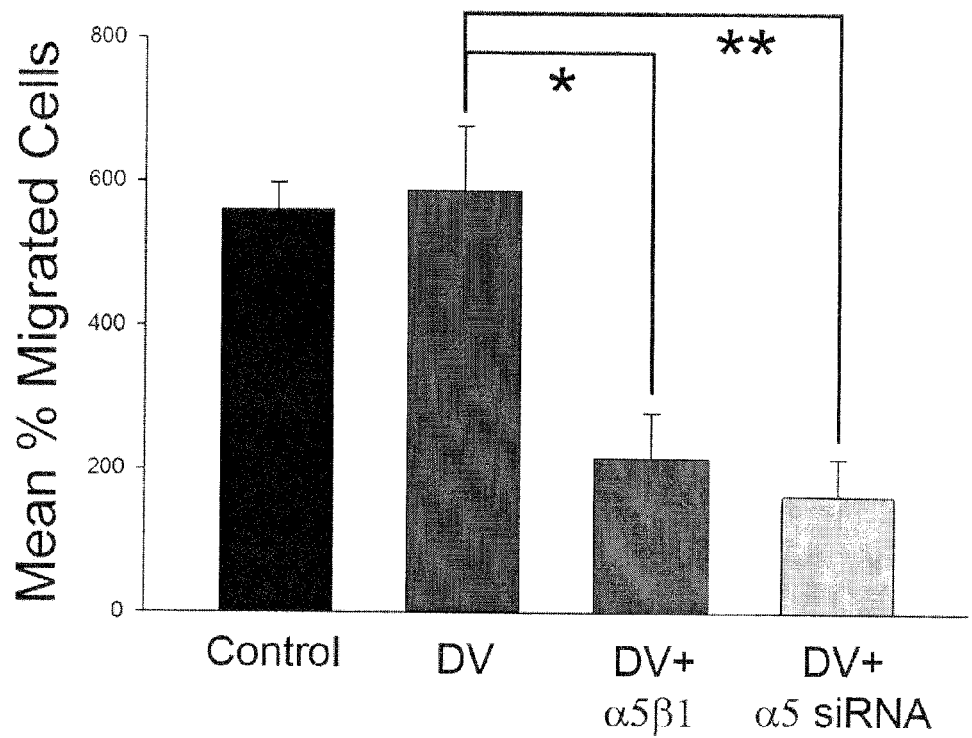
Figure 4F:
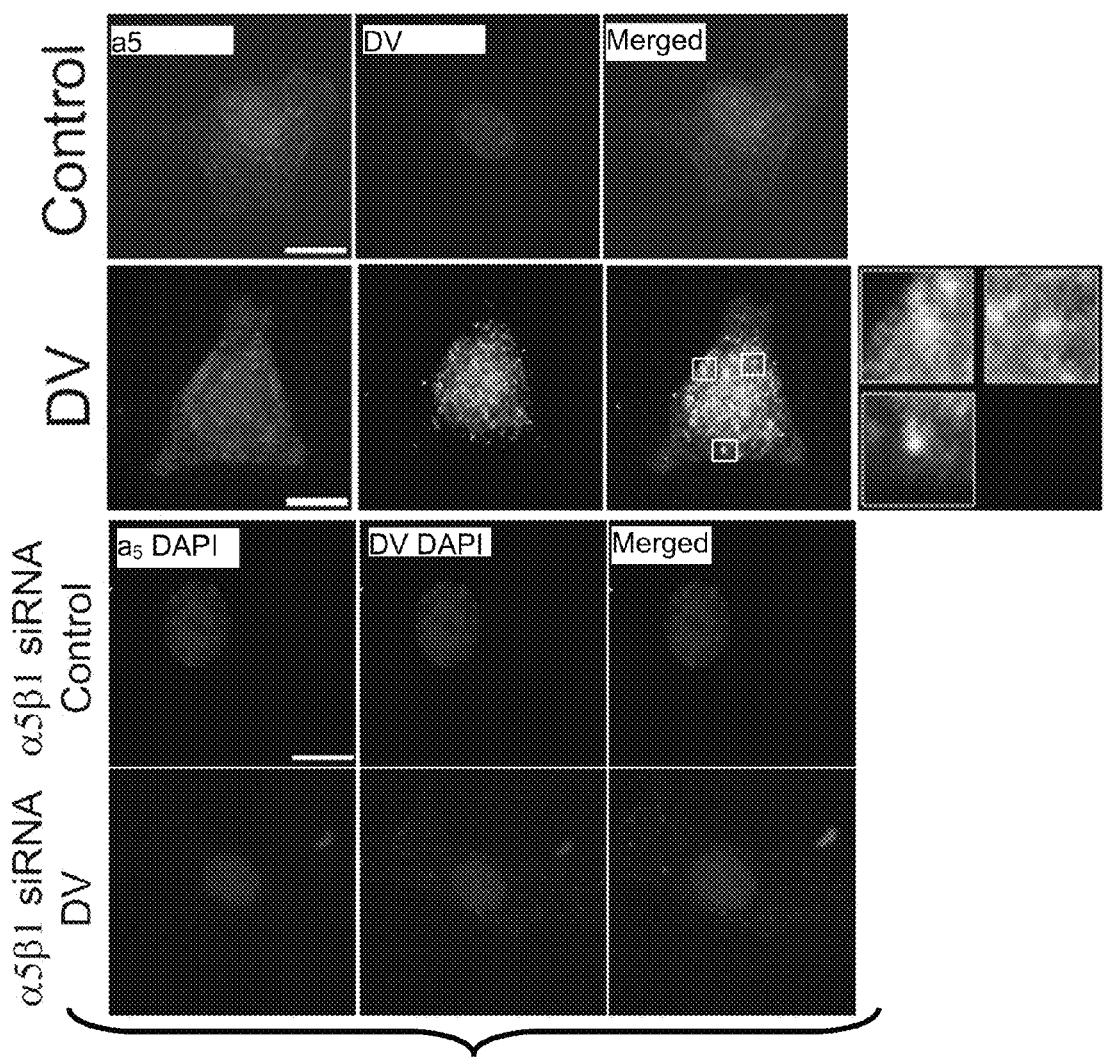
Figure 4H:
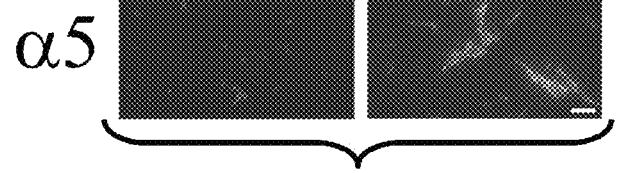
Figure 4I:
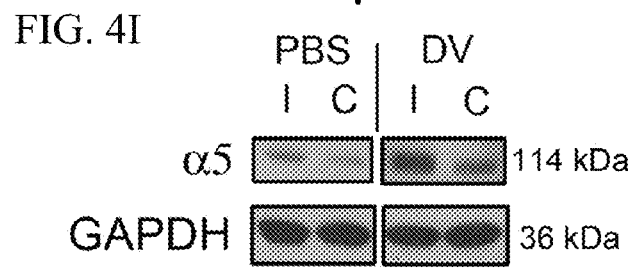
Figure 4G:
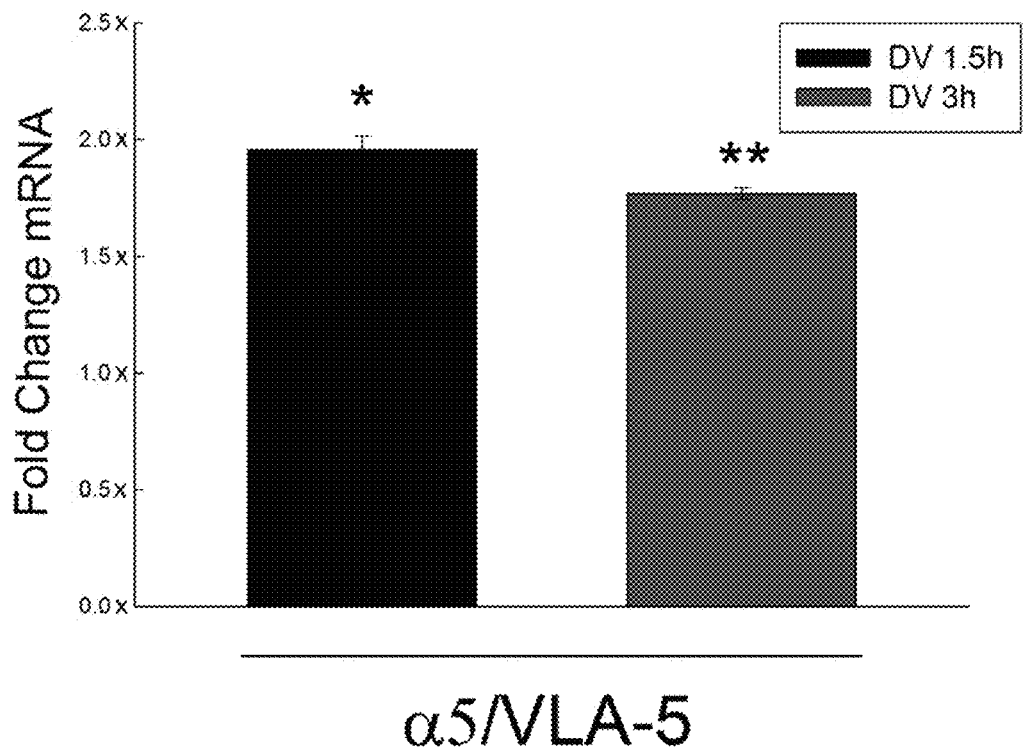

Domain V Interacts with and Exerts its Pro-Angiogenic Effects Via the α5β1 Integrin It was determined that brain microvascular endothelial cell adhesion to immobilized, DV (coating the bottom of cell culture wells) depended on α5β1 by demonstrating that either α5β1 antibody directed against the α5 ligand binding domain or α5 integrin subunit knockdown with α5 siRNA (75% knockdown achieved, FIG. 16) could prevent brain endothelial cell adhesion to immobilized DV (FIG. 4A). Importantly, brain microvascular endothelial cells treated with α5 siRNA remained healthy and intact and no significant differences in cell viability via trypan blue cell exclusion assays were noted (data not shown). Next, it was demonstrated that brain endothelial cell migration towards DV could be inhibited by either α5β1 integrin subunit knockdown or soluble α5β1 protein (FIG. 4B). Likewise, DV enhancement of brain endothelial cell capillary tube-like structure formation and proliferation could be suppressed by the addition of the α5β1 specific binding peptide CRRETAWAC[52] or by α5 knockdown, respectively (FIGS. 4C, 4D, FIG. 17). The potential for direct interaction between α5β1 and DV was next investigated and confirmed via optical biosensor analysis (FIG. 4E). This method determined that DV binds to the α5β1 integrin with a $K_{on}$, $K_{off}$ and $K_d$ of $3.8 \times 10^6 \pm 2.7 \times 10^5$/M-s, $7.2 \times 10^4 \pm 1.1 \times 10^{-1}$/s and $1.6 \times 10^{-7} \pm 7.2 \times 10^{-8}$ M, respectively. Finally, it was noted that DV applied to brain endothelial cells in vitro co-localized with α5β1 integrin while DV applied to α5β1 integrin knock down cells exhibited minimal cellular binding (FIG. 4F). DV mediated increase of α5 integrin mRNA transcription in brain endothelial cells in vitro was also investigated. FIG. 4G demonstrates that by qPCR, after 1.5 h and 3 h of DV exposure, α5 mRNA expression increases by approximately 2 fold (*p=0.0001) and 1.8 fold (**p=0.006) respectively, as compared to cells without DV treatment. Collectively, these experiments demonstrate that DV binds to, increases the mRNA transcription of, and exerts its pro-angiogenic effects (in vitro) via the α5β1 integrin.

Figure 18B:
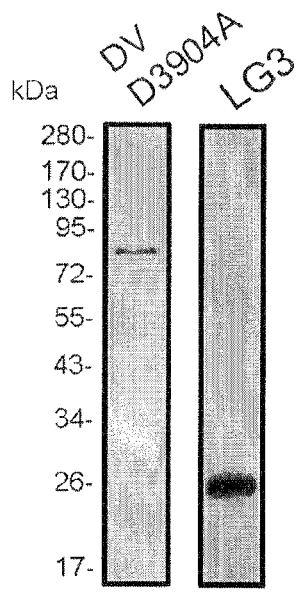
Figure 18C:
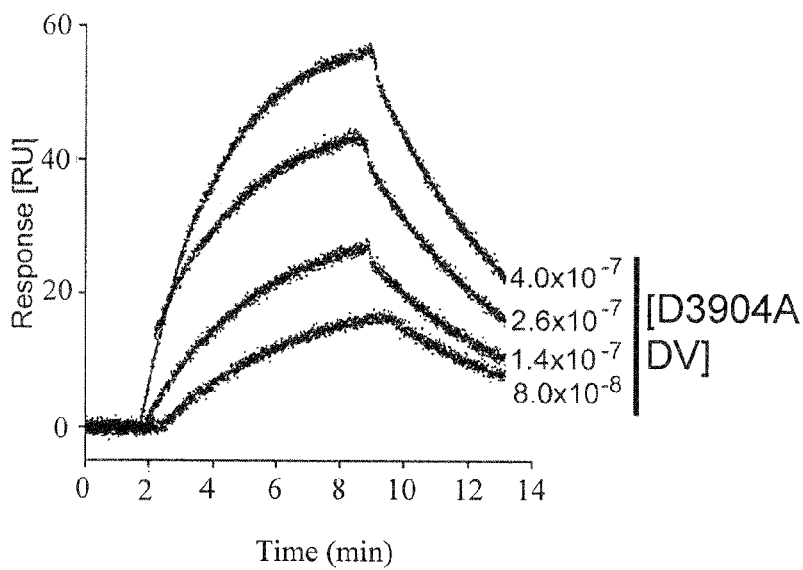
Figure 18D:
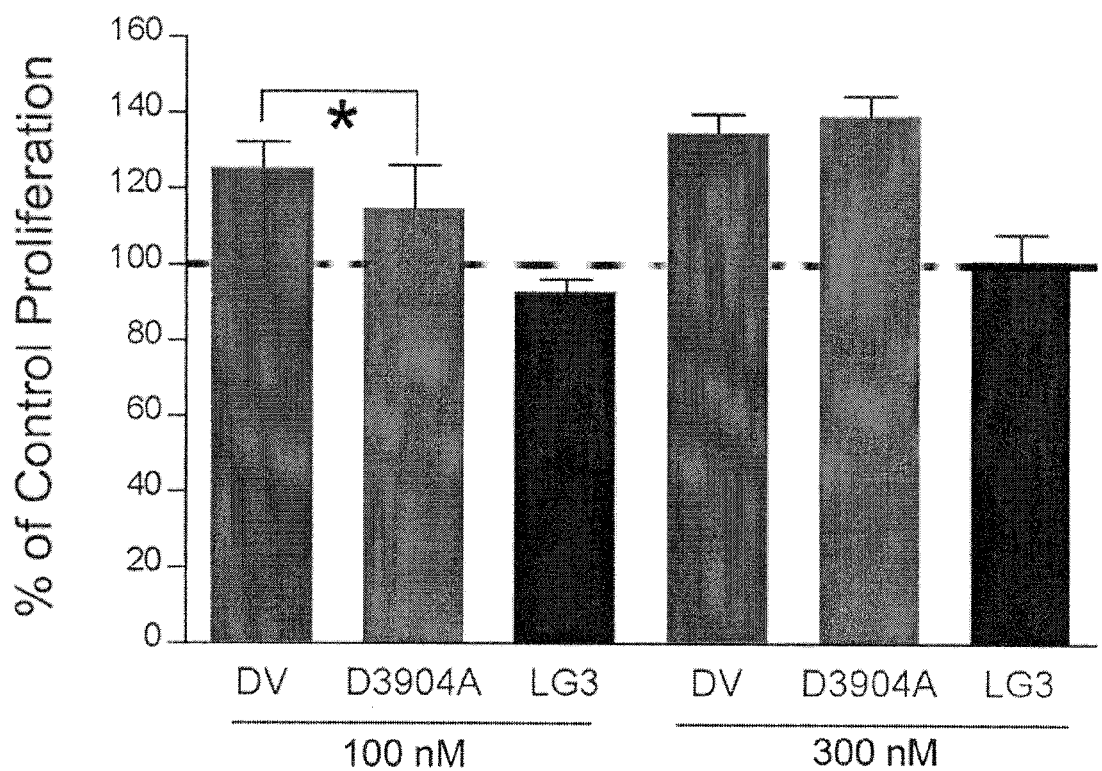
Figure 18E:
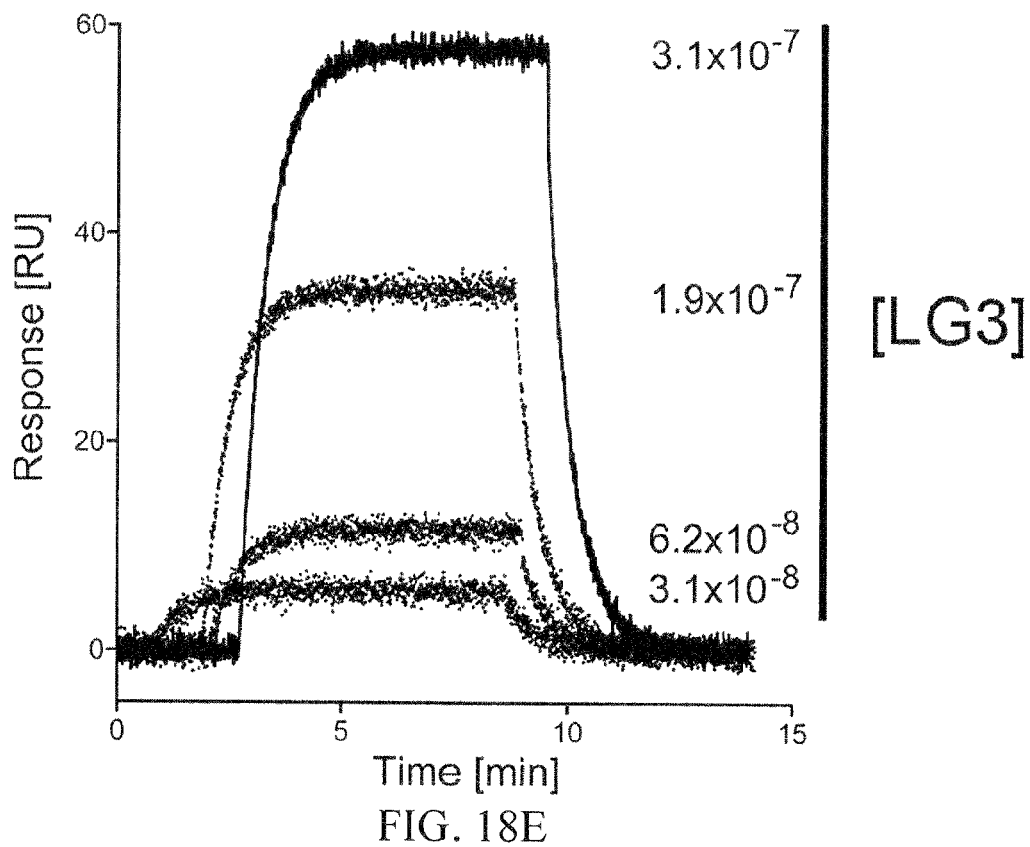
Figure 20:
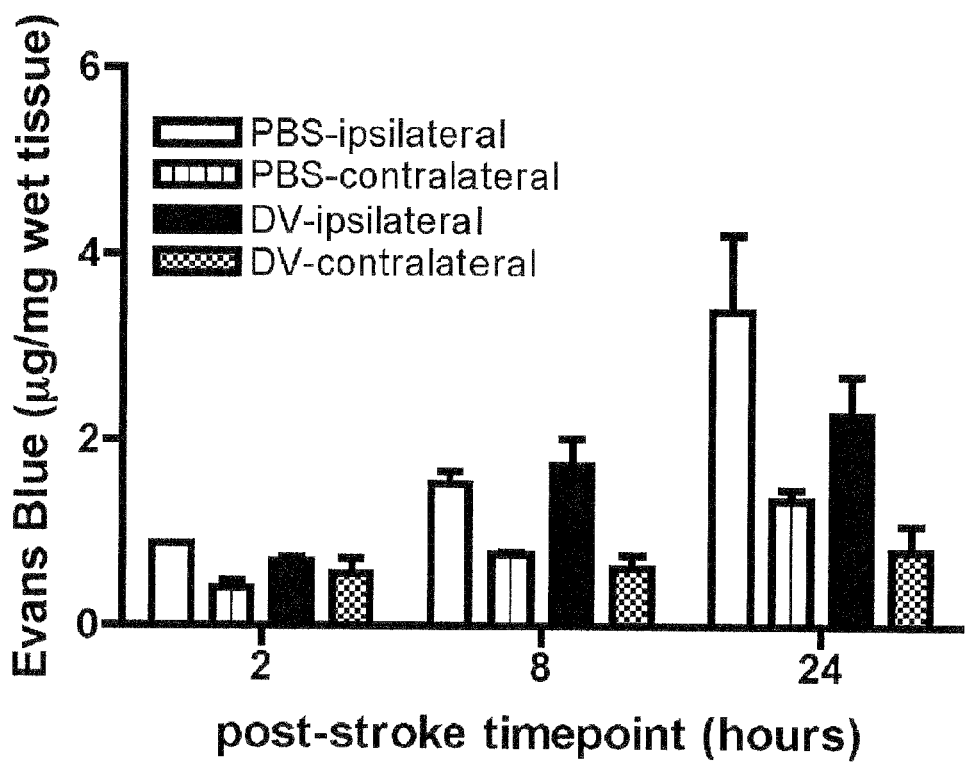
FIG. 20. Post-stroke DV treatment does not significantly affect blood brain barrier permeability. Plot of Evan's blue dye extravasated quantity (µg/mg of wet brain tissue) in ipsilateral (stroked) or corresponding contralateral stroked hemisphere tissue at different post-stroke times (as indicated) with I.P. PBS or DV administration. No significant differences were noted between PBS and DV treatment in the ipsi- or contralateral hemisphere.

The binding of DV to α5β1 was also investigated. DV's DGR sequence was mutated to AGR (D3904A) to determine whether this could disrupt DV binding to α5β1 as measured with optical biosensor (FIG. 18A). Of note, after the D3904A mutation was introduced, and the mutant protein was purified and assessed for purity (via the same methods as unmutated DV); D3904A, DV, like non-mutated DV, did not contain fibronectin (data not shown) and yielded a single 85 kDa band by western blot (FIG. 18B). Optical biosensor analysis demonstrated that D3904A DV bound to α5β1 integrin with a $K_d$ of $3.7 \times 10^{-7} \pm 3.5 \times 10^{-9}$ M, $K_{on}$ of $6.0 \times 10^5 \pm 4.5 \times 10^4$/M-s and $K_{off}$ of $2.2 \times 10^{-1} \pm 1.9 \times 10^{-2}$/s, values that are each significantly different than those obtained for non-mutated DV ($K_d$ of $1.6 \times 10^{-7} \pm 7.2 \times 10^{-8}$ M, $K_{on}$ of $3.8 \times 10^6 \pm 2.7 \times 10^5$/M-s, and $K_{off}$ of $7.2 \times 10^{-1} \pm 1.1 \times 10^{-1}$/s) (FIG. 18C). These results demonstrate that D3904A DV binds to α5β1 integrin with less than half of the affinity than non-mutated DV has for α5β1 integrin and suggests that DV does, at least in part, bind to α5β1 via its DGR sequence. In seeming agreement with these results, D3904A DV was significantly less active in stimulating brain endothelial cell proliferation compared to non-mutated DV at 100 nM concentrations (FIG. 18D, *p=0.02) and almost significantly less when 300 nM concentrations were used (p=0.06). This trend suggests that higher concentrations of DV and D3904A DV could be at saturating levels for the stimulation of brain endothelial cell proliferation To further demonstrate whether the DGR region of DV was necessary for DV binding to α5β1 and DV stimulating of brain endothelial cell proliferation, we cloned and purified the C-terminal LG3 subunit of perlecan DV (purified and assessed to be fibronectin-free in the exact same fashion as full length DV, FIG. 18B), which has been previously suggested to be the portion of DV responsible for its anti-angiogenic activity outside the brain[25, 46, 58]. Biosensor analysis between LG3 and α5β1 integrin (FIG. 18E) demonstrated that LG3 bound with extremely low affinity to α5β1 integrin with a $K_d$ of $1.0 \times 10^{-3} \pm 7.0 \times 10^{-5}$ M, a $K_{on}$ of $1.6 \times 10^3 \pm 5.8 \times 10^1$/M-s, and a $K_{off}$ of $1.7 \pm 4.3 \times 10^{-2}$/s. In agreement with its very low affinity for α5β1, LG3 had no effect on brain endothelial cell proliferation (FIG. 18D) demonstrating that a portion of DV that does not contain the DGR sequence does not bind to α5β1 integrin and does not stimulate brain endothelial cell proliferation. Collectively, these results suggest that DV binds to α5β1 integrin, at least partially, via its DGR motif and that the C-terminal LG3 subdomain of DV binds anti with extremely low affinity, correlating with its lack of proliferative activity in brain endothelial cells.

Figure 4J:
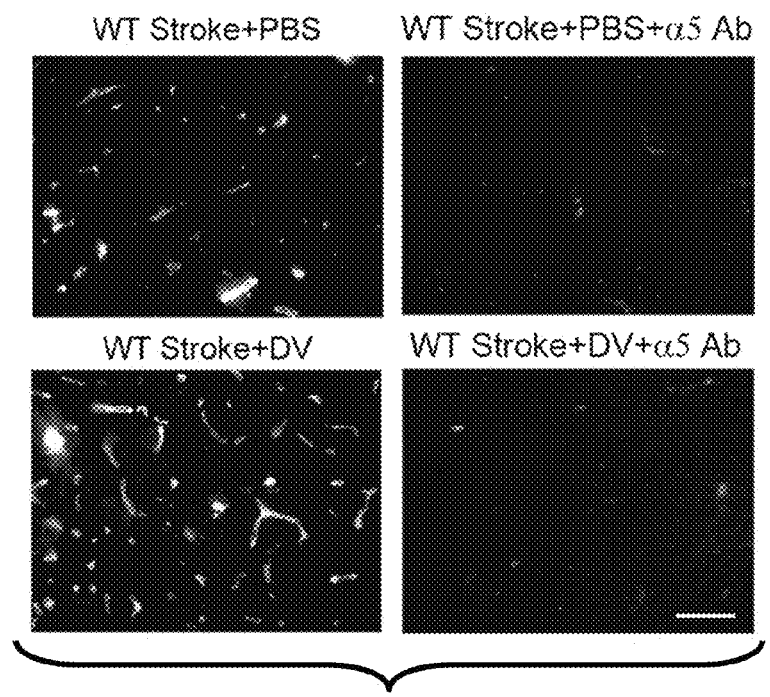
Figure 4K:
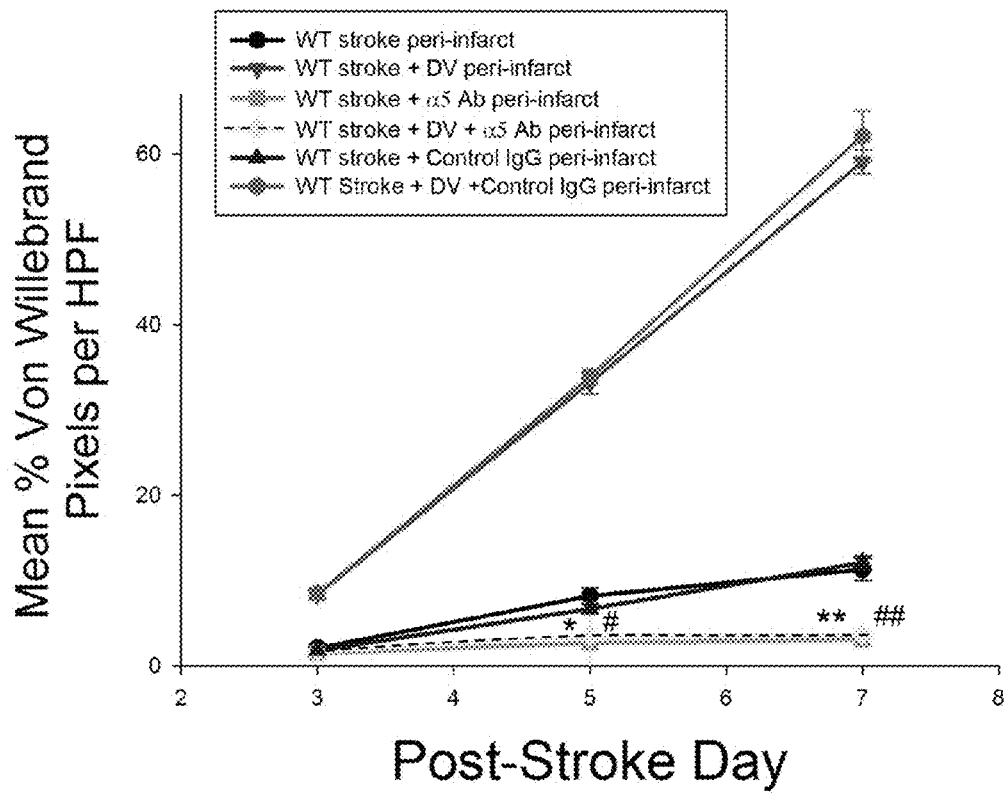
Figure 4L:
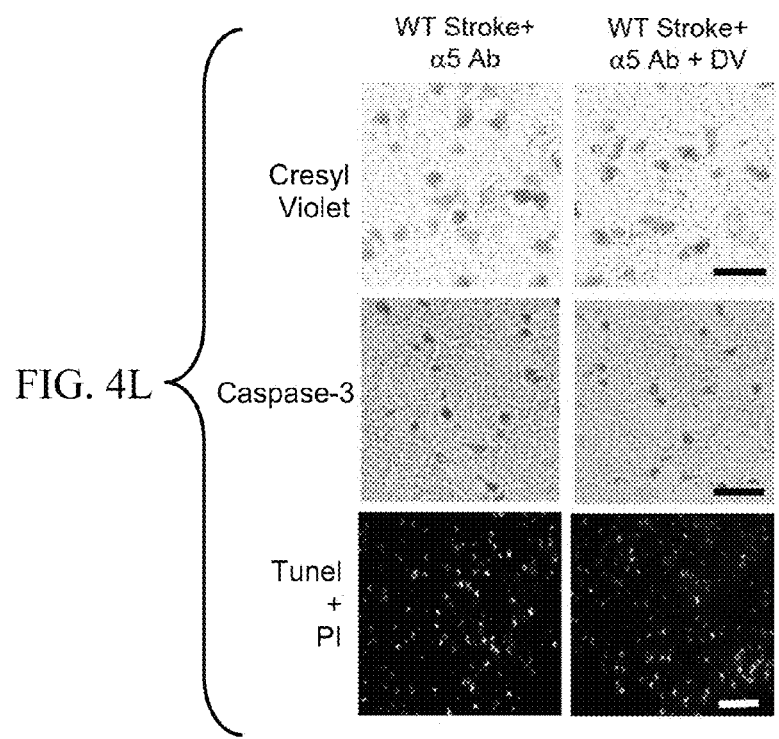

The relevance of α5β1 integrin to DV in vivo effects following stroke was also assessed to determine if DV treatment might increase vascular peri-infarct expression of α5β1 integrin. FIG. 4H demonstrates that on post-stroke day 3, peri-infarct blood vessels (identified morphologically) in DV treated animals expressed more α5β1 integrin than control peri-infarct blood vessels, as measured by α5β1 immunohistochemistry. Furthermore, western blot analysis of brain lysate from the stroked and contralateral hemispheres of post-stroke day 3 animals±DV treatment (FIG. 4I) demonstrated significantly more total α5β1 integrin in the stroked brain tissue treated with DV (p=0.00004, quantification not shown). To further demonstrate the necessity of the α5β1 integrin to DV's in vivo pro-angiogenic effect, experiments in which DV treatment was preceded by tail vein injections of α5β1 function blocking antibody (4 mg/kg) or isotype control IgG (4 mg/kg) were performed. Importantly, this antibody will not discriminate between α5β1 expressed by brain endothelial cells, and α5β1 expressed by other cell types such as astrocytes and neurons. In these experiments a significant decrease (as compared to control animals) in peri-infarct vasculature in animals treated with only α5β1-function blocking antibody on post-stroke days 5 and 7 (FIGS. 4J, 4K) that could not be improved with DV treatment was noted. I.P. injection of control Ig had no effect on peri-infarct vasculature (FIGS. 4J, 4K). Likewise, α5β1-function blocking antibody prevented DV neuroprotection (FIG. 4L) resulting in visibly more apoptotic appearing neurons in the peri-infarct region compared to PBS treated controls as detected by cresyl violet caspase-3 and TUNEL staining (control IgG had no visible effect on neuronal apoptosis, data not shown). The latter result underscores the importance of α5β1 integrin in the post-stroke period. Furthermore, treatment with the α5β1 function blocking antibody completely blocked DV-induced functional recovery as measured by the vibrissae-elicited forelimb placement; Mice treated with α5β1 function blocking antibody and DV, as well as those treated with just the α5β1 function blocking antibody used the affected paw 0% of the time on all post-stroke days measured and neither these group was significantly different than stroked animals treated with PBS (p=0.3, p=0.4, respectively). Again, control IgG had no effect. Collectively, these experiments demonstrate in vivo that DV binds to, affects the expression of, and exerts its post-stroke pro-angiogenic and functional effects, at least in part, via the α5β1 integrin.

Domain V Induces VEGF Release In Vitro and In Vivo

Figure 5A:
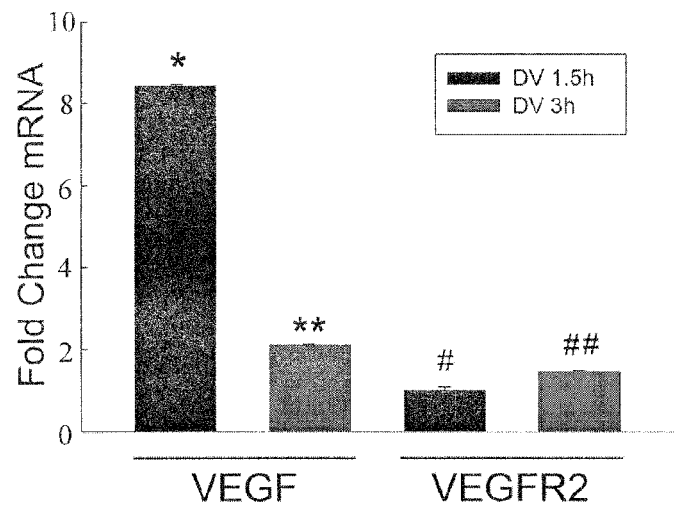
FIGS. 5A-5Z. Domain V induces VEGF release via the α5β1 integrin.
Figure 5B:
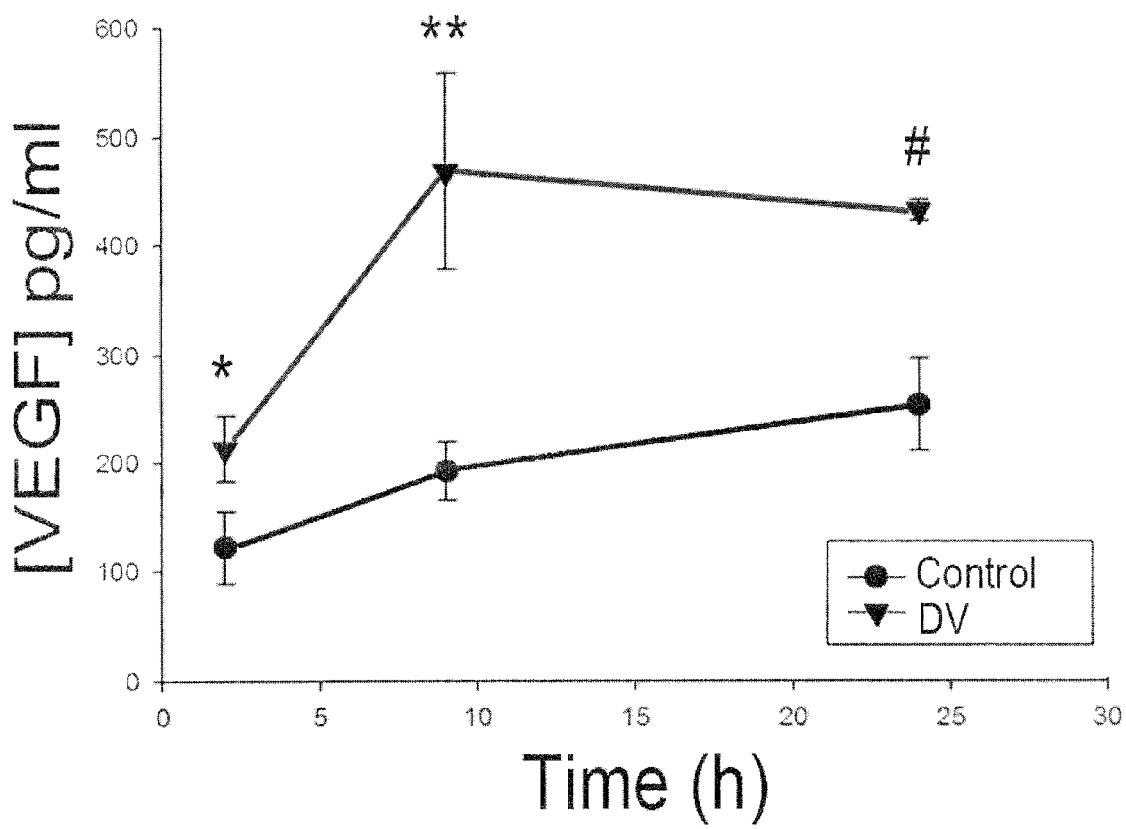
(FIG. 5B) VEGF ELISA of conditioned media from cells treated with DV at times indicated. n=3 for each point. Values are mean±standard deviation. DV caused a significant increase in measured VEGF levels at all time points measured (*p=0.01, **p=0.002, #p=0.006). n=3 for each point.
Figure 5C:
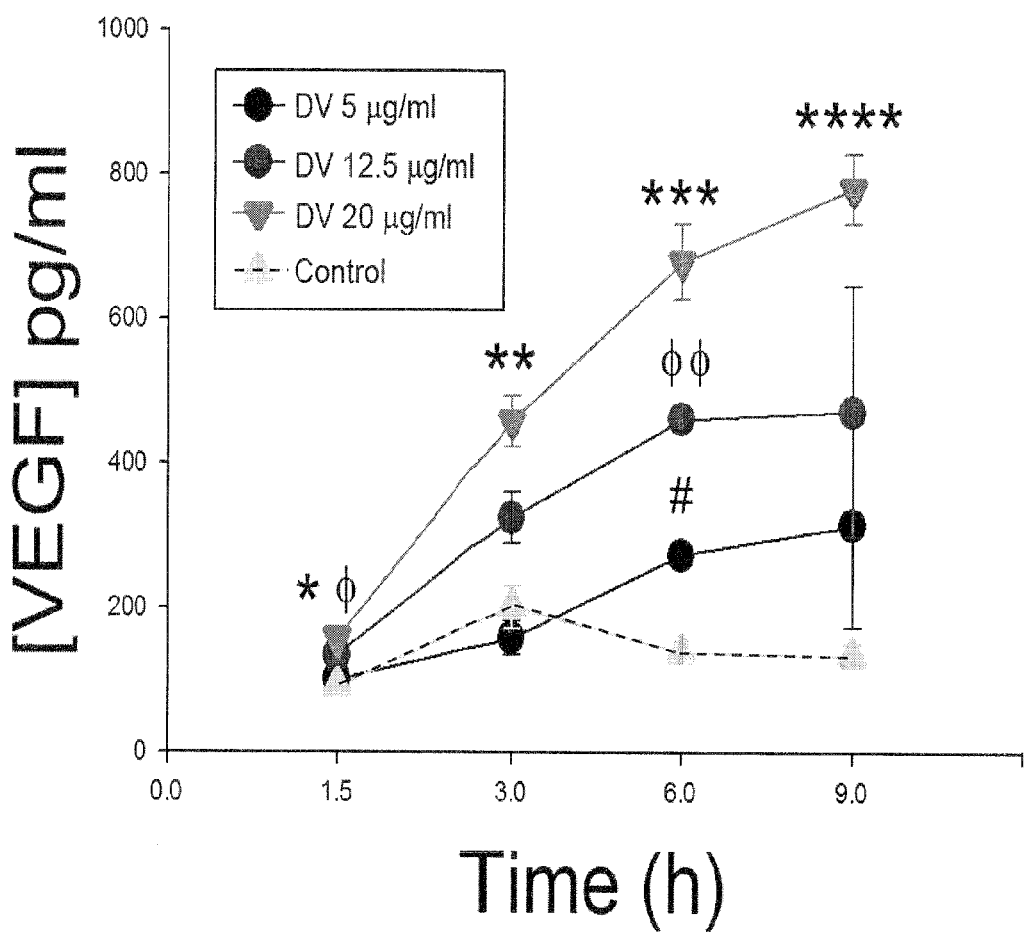
(FIG. 5C) VEGF ELISA of mouse brain endothelial cells conditioned with different treatment concentrations of DV at different times points as indicated demonstrating a DV dose dependent VEGF response. (*p=0.04, p=0.001, *p=0.005, **p=0.00004; Φp=0.03, ΦΦp=0.002; #p=0.003). Values are mean±standard deviation.
Figure 5D:
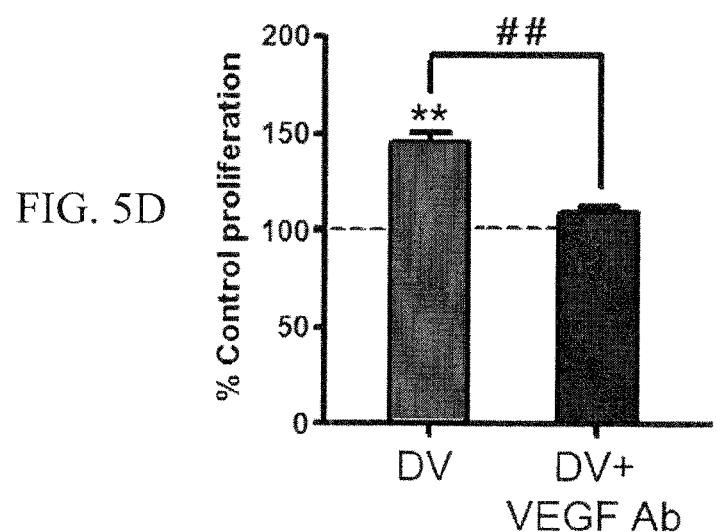
(FIG. 5D) Quantification of brain endothelial cells proliferation±addition of VEGF neutralizing antibody after 48 hours±DV in serum free media as measured via MTS assay. Values shown (n=15, mean±standard deviation normalized to control proliferation arbitrarily set to 100%) demonstrate significant inhibition of DV enhanced proliferation (p=0.00009) by VEGF antibody (##p=0.0004).

FIG. 5A demonstrates that 1.5 and 3 h DV treatment significantly increased VEGF (8.2 fold and 2 fold, p=0.001 and p=0.003, respectively) and VEGFR2 (1.5 and 1.8 fold, p=0.02 and p=0.007, respectively) mRNA expression. VEGF release from brain endothelial cells was also significantly increased from 3 to 24 hours of DV exposure, as measured by VEGF ELISA, (FIG. 5B) in a DV dose-dependent fashion (FIG. 5C, see figure legend for p values). DV's proliferative effect on brain microvascular endothelial cells by co-treatment with a VEGF-neutralizing antibody was significantly inhibited ((p=0.00009; FIG. 5D).

Figure 5G:
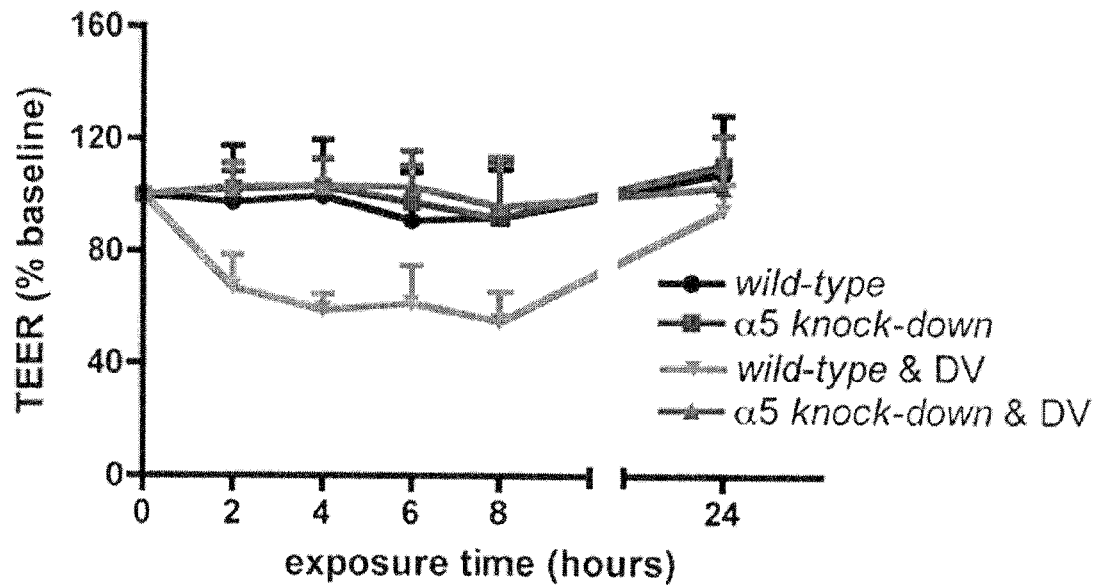
(FIG. 5G) TEER measurements in α5β1 integrin deficient cells are unaffected by DV (p=0.9 between WT and α5 knock-down treated with DV groups).
Figure 5H:
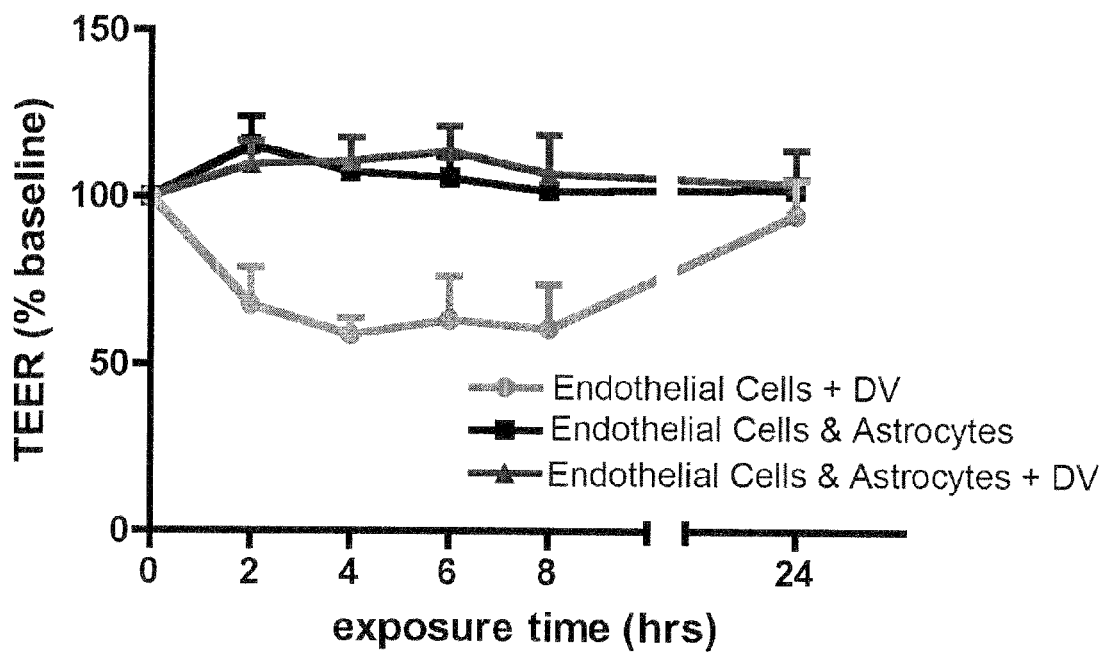
(FIG. 5H) Astrocytes co-cultured on the underside of the membrane insert (to more closely approximate the cellular make-up of the blood brain barrier in vivo[62]) inhibited DV effects on TEER (p=0.8 between brain endothelial cells and astrocytes and brain endothelial cells and astrocytes treated with DV).
Figure 5K:
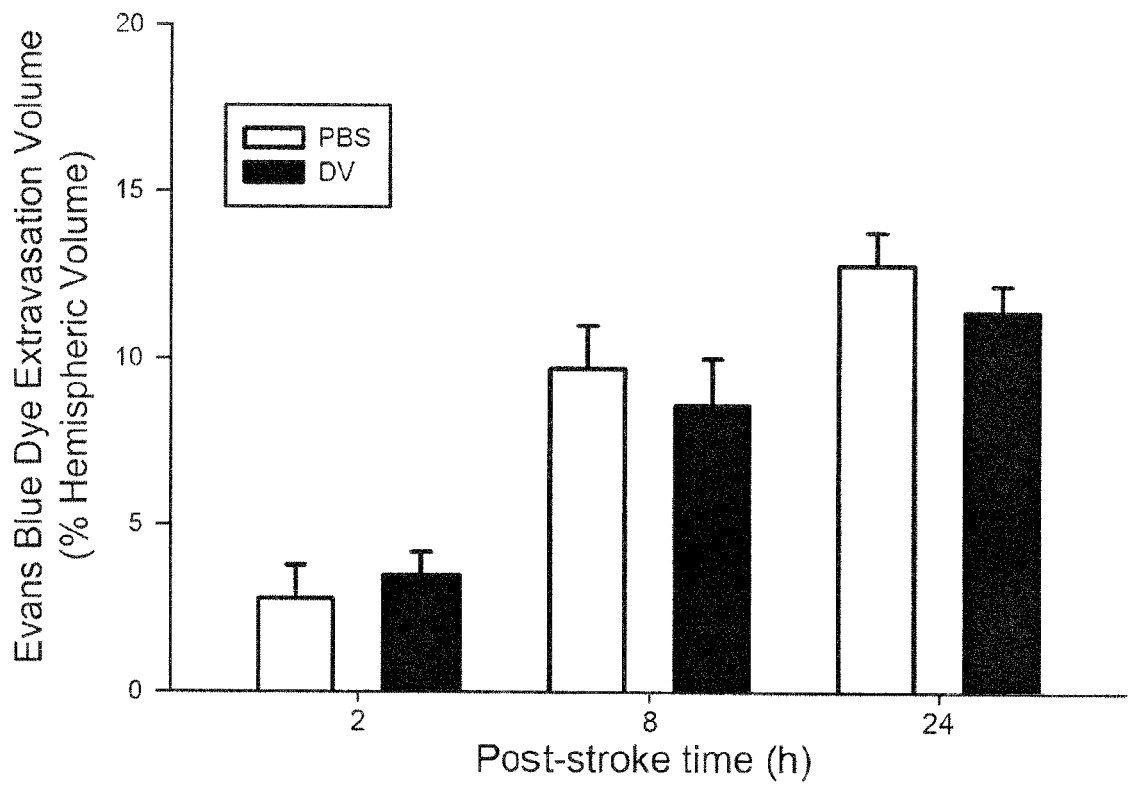
(FIG. 5K) plot of Evan's blue dye extravasation volume as a percentage of the total brain hemisphere volume for the conditions and times of treatment as in FIG. 5J demonstrating no statistically significant difference between PBS and DV treatment at any of the times indicated.

DV-induced VEGF Hyperpermeability In Vitro is Compensated by Astrocyte Co-Culture The effects of DV on mouse brain endothelial monolayer integrity by measuring trans-endothelial electrical resistance (TEER) and permeability were investigated. A significant decrease was noted in TEER by two hours of DV treatment (as compared to control cells) which persisted for 8 hours, but then returned to baseline by 24 hours (FIG. 5E, see figure legend for p values). Importantly, the DV-induced decrease in TEER was absent from α5β1 integrin knockdown cells (FIG. 5G) and could be inhibited with VEGF-neutralizing antibody whereas control antibody had no effect on TEER (FIG. 5E). Furthermore, the DV-induced decrease in TEER correlated with a disruption of continuous staining of the tight junction protein ZO-1 in select regions of cell-cell borders (which could also be prevented with VEGF-neutralizing antibody, FIG. 19) and with a significant increase in permeability in vitro after 8 hour DV exposure (p=0.00001, FIG. 5F). Importantly, however, when astrocytes were co-cultured on the underside of the membrane insert to more closely approximate the cellular make-up of the blood brain barrier in vivo[62], DV treatment had no significant effect on TEER (FIG. 5H).

DV does not Increase Blood Brain Barrier Permeability In Vivo

Figure 5L:
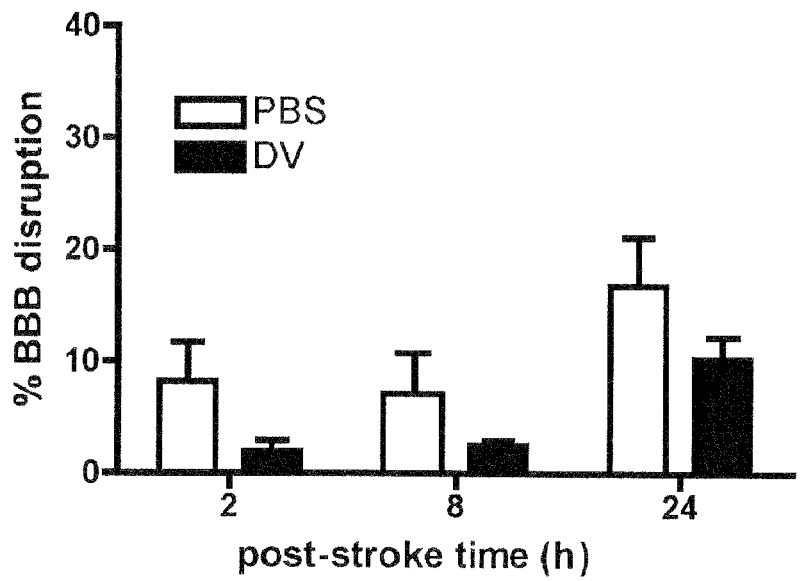
(FIG. 5L) Plot of the % of blood brain barrier (BBB) disruption calculated as in FIG. 5J also demonstrating no statistically significant difference between PBS and DV treatment at any times indicated.

Furthermore, no significant change in blood brain barrier permeability was seen with DV treatment of both non-stroked and stroked mice in vivo (FIGS. 5I, 5J, 5K, 5L, FIG. 20) as measured by radio-labeled sucrose or Evan's blue dye extravasation, respectively. This was the case even when DV was administered as soon as 2 or 8 hours post-stroke, a time when the administration of VEGF may worsen the already disrupted blood brain barrier permeability[18]. Of note, a non-significant trend of increased permeability was noted in the frontal cortex and hippocampus with sucrose suggesting region selective minimal blood brain barrier permeability changes with DV administration in normal, unstroked animals. However, a non-significant trend of decreased % blood brain barrier disruption was noted with post-stroke DV administration (FIG. 5L) underscoring our observation that DV does not appear to increase post-stroke blood brain barrier permeability.

DV Treatment Increases Post-Stroke Brain VEGF Levels

Figure 5M:
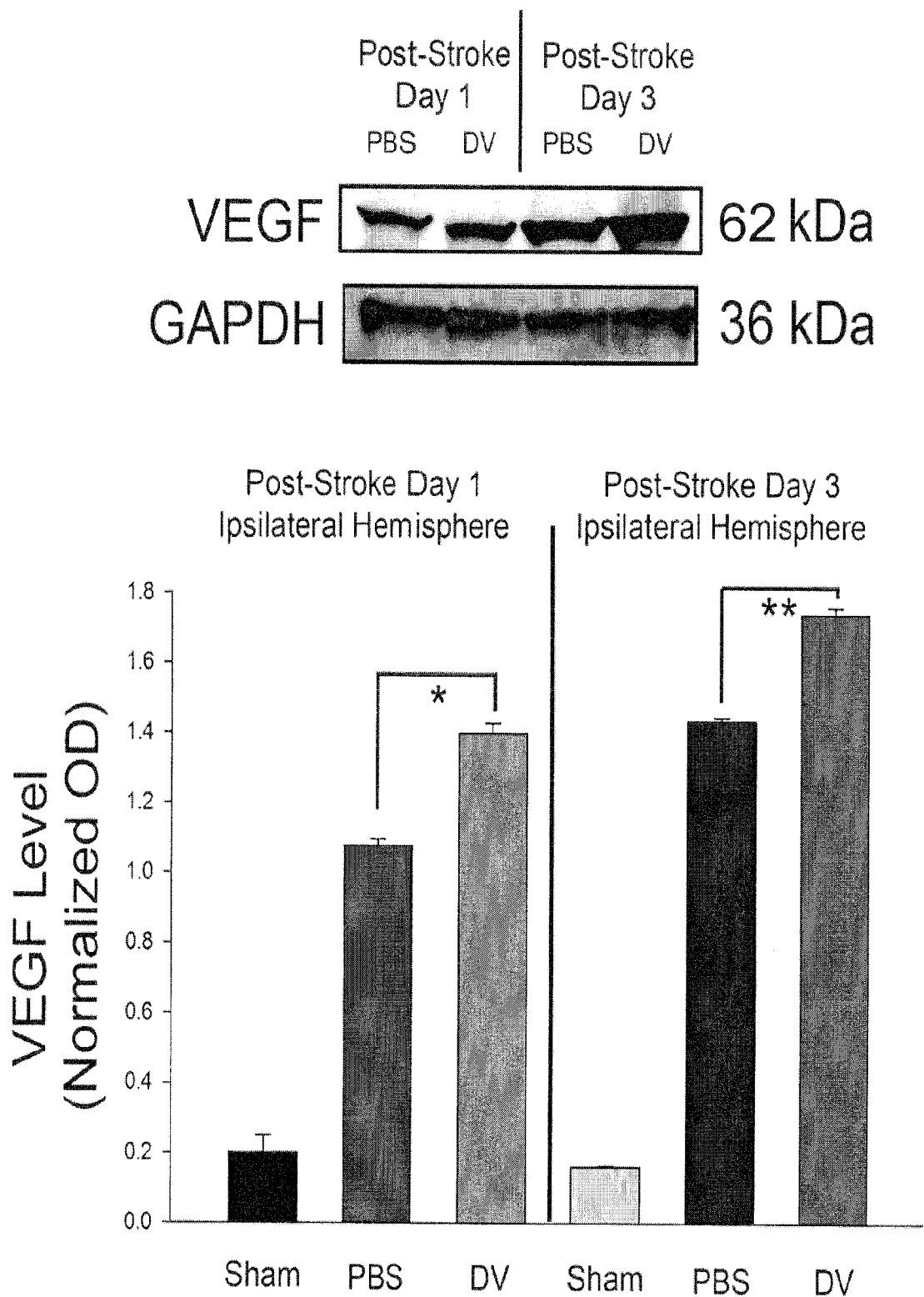
(FIG. 5M) Representative VEGF western blot and GAPDH loading control of ipsilateral stroked hemispheres (or sham surgery control) on post-stroke day 1 and 3 mouse brains demonstrating a significant increase in stroked brain VEGF levels with DV treatment on both post-stroke days ($*p=0.008$ and $p=0.009$, respectively).

DV treatment resulted in a significant increase in total VEGF levels as early as 8 hours after DV administration on post-stroke day 1 (corresponding to the 24 h post-stroke time point in FIGS. 5J, 5K, 5L) in the ipsilateral stroked brain hemisphere as compared to the PBS treated stroked animal and on post-stroke day 3 (FIG. 5M, *p=0.008 and **p=0.009, respectively). Finally, the brain water content at 0 hours (73.3±1.3%) was not significantly affected at 8 (64.6±3.4%), 24 (72.8±2.9%) or 48 (77.1±1.4) hours by the intraperitoneal injection of DV (1 mg/kg). These results collectively suggest that DV does not significantly alter blood brain barrier permeability in vivo despite its enhancement of in vivo post-stroke VEGF levels.

DV Post-Stroke In Vivo Effects are VEGF Dependent

Figure 5N:
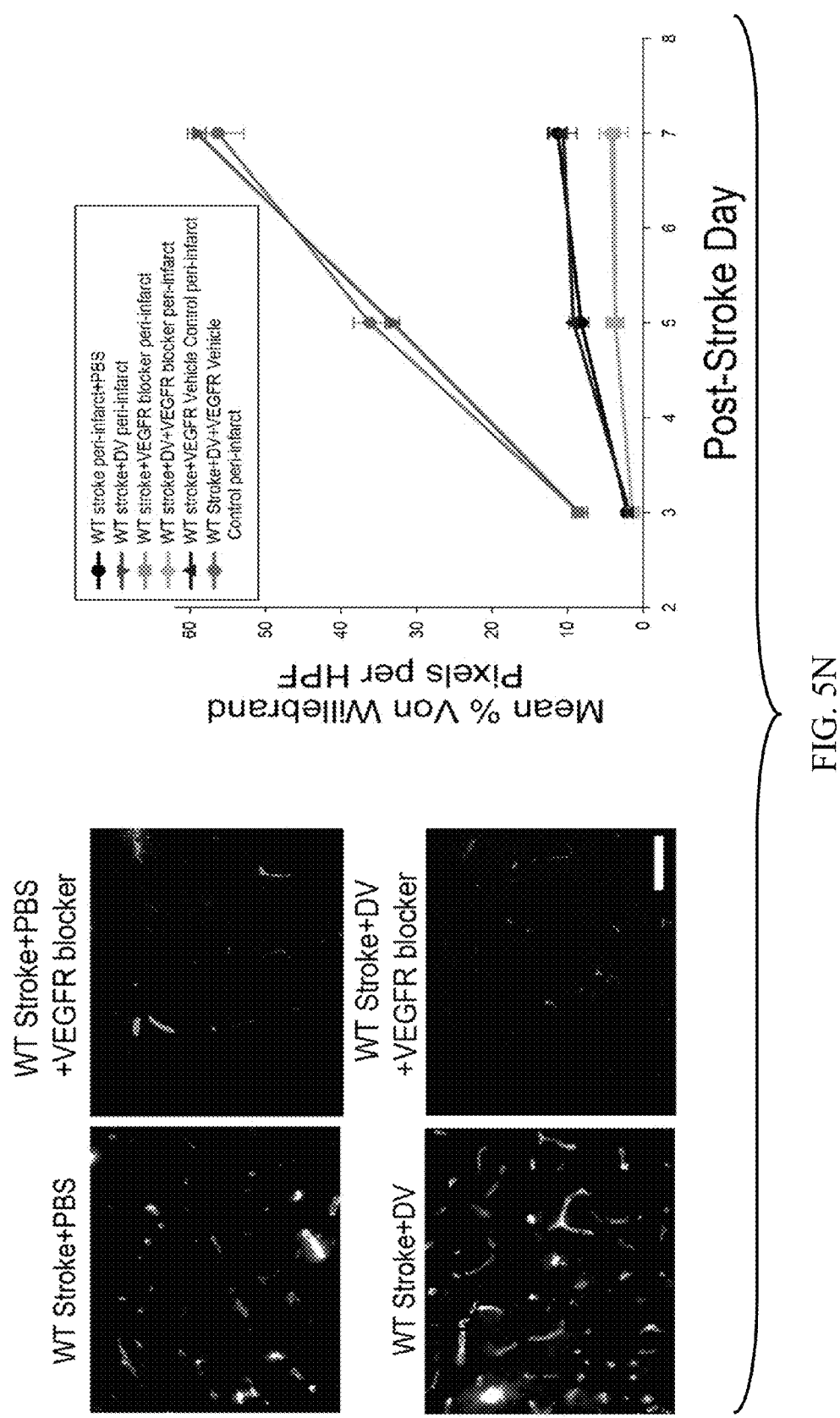
(FIG. 5N) Representative images of von-Willebrand immunohistochemistry (green) on post-stroke day 5 to analyze peri-infarct vasculature in WT animals+/−PBS or DV treatment (as in FIG. 2D) or +the VEGFR blocker PTK787/ZK 222584+/−PBS or DV (1 mg/kg) as labeled. Bar is 10 μm. Graph: Quantification of mean % von Willebrand pixels per high power field (HPF) ±standard deviation as done in FIG. 2E for each treatment group on post-stroke days 3, 5 and 7 (n=20 images analyzed per animal, 10 animals per experimental condition). WT animals treated with the VEGFR blocker PTK787/ZK 222584+ DV (1 mg/kg) were not significantly different than the group just treated with PTK787/ZK 222584 (p=0.6). Likewise, oral gavage with vehicle control for PTK787/ZK 222584 had no effect.
Figure 5O:
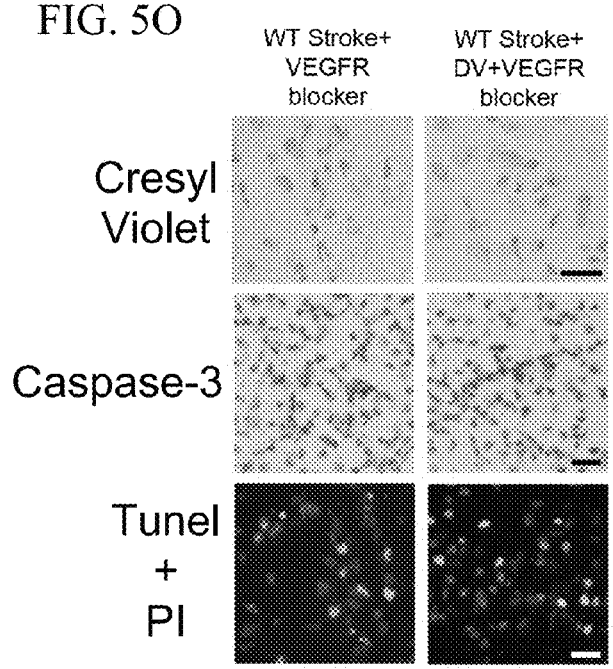
(FIG. 5O) Representative cresyl violet stain, caspase-3 17-to 20-kDa cleavage product stain, and TUNEL stain (nuclei counterstained with propidium iodide (PI) of WT stroked brain tissue (in the peri-infarct region) treated with VEGFR function blocker+/−DV demonstrating that VEGFR blocker treatment resulted in many neurons with abnormal morphology, i.e. shrunken and misshapen, increased staining of the cleaved Caspase-3 product, and increased TUNEL positive cells (all as compared to WT stroke treated with PBS as seen in FIG. 2E). This extensive peri-infarct neuronal apoptosis could not be blocked with DV treatment. Bars are 10 μm.
Figure 5P:
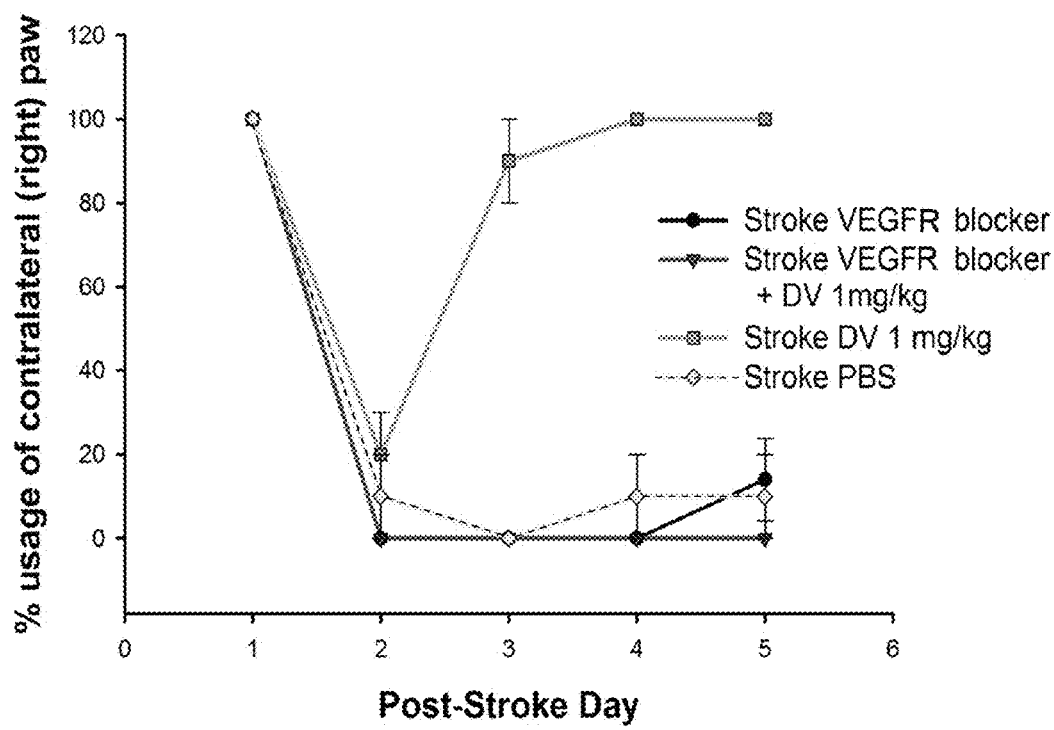
(FIG. 5P) Vibrissae-elicited forelimb placement test on WT (as in FIG. 2L) with WT mice treat with PBS or DV (1 mg/kg)+/−PTK787/ZK 222584 demonstrating that PTK787/ZK 222584 significantly inhibited DV's positive effects on contralateral paw placement (p=0.0001). Oral gavage with PTK787/ZK 222584 vehicle control had no effect (not shown).
Figure 5Q:
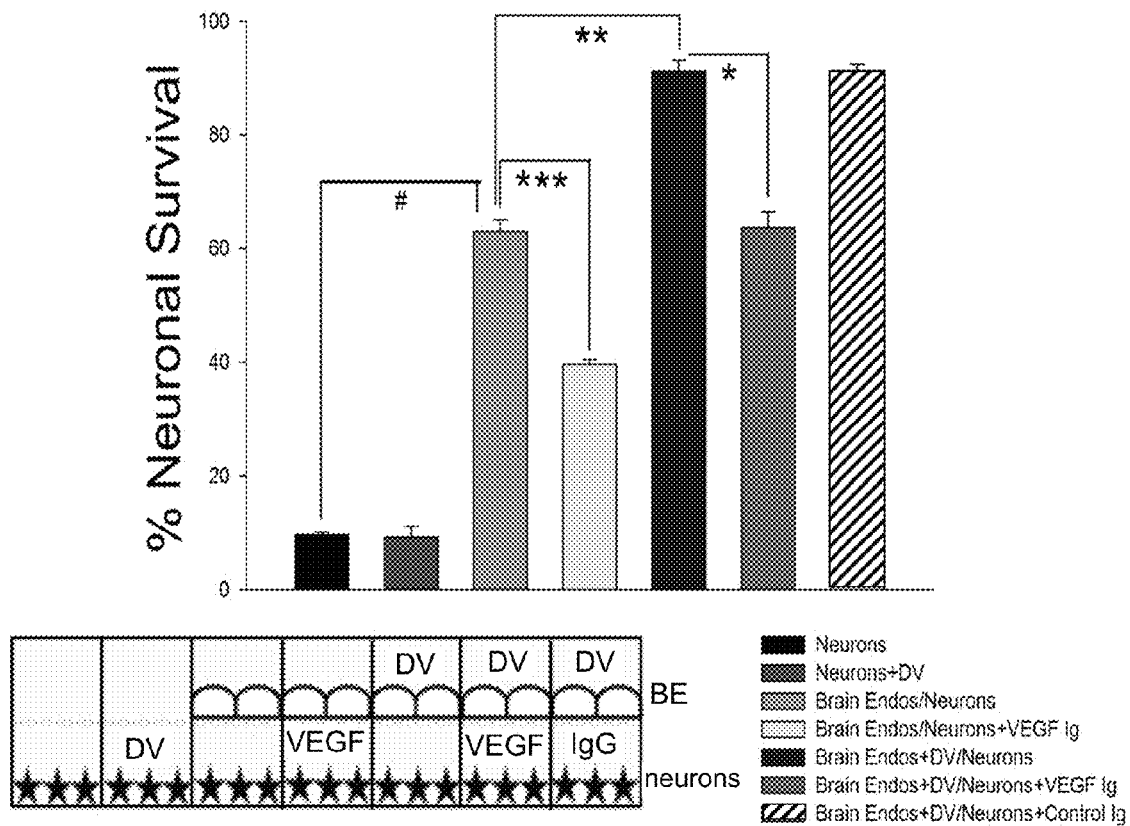
(FIG. 5Q) Quantification (% neuronal survival as normalized to equivalent neuronal numbers in normoxic and normoglycemic conditions) of oxygen/glucose deprivation mouse fetal cortical neuron experiments demonstrating that DV by itself had no direct effect on neuronal survival, but that DV was added to brain endothelial cells grown on a Transwell insert above the neurons, DV significantly enhanced neuronal survival beyond the enhanced survival provided by the endothelial cells alone ($\#p=0.0001, p=0.003$). DV's effect could be completely blocked by the addition of VEGF neutralizing antibody ($*p=0.001$) as could a significant extent of the endothelial cell alone effect on neuronal survival ($***p=0.002$). These results demonstrate that DV neuroprotection is indirect and mediated by its induction of VEGF release from endothelial cells rather than direct effects on the neurons. Mean+/−SD shown, N=9 per condition. Schematic below graph visually demonstrates the various experimental conditions quantified in the above graph.

Experiments were performed in which prior to PBS or DV treatment, mice were treated with the VEGF Receptor (VEGFR) tyrosine kinase inhibitor PTK787/ZK 222584 (inhibits both the VEGFR-1 and VEGFR-2[63]) or PBS vehicle control by oral gavage. As expected, PTK787/ZK 222584 by itself inhibited post-stroke angiogenesis and resulted in more apoptotic neurons in the peri-infarct region (FIGS. 5N, 5O, PBS oral gavage vehicle control had no effect). Furthermore, PTK787/ZK 222584 prevented DV (1 mg/kg) from increasing post-stroke angiogenesis, protecting neurons, and restoring post-stroke motor function (FIGS. 5N, 5O, 5P, PBS vehicle control had no effect, not shown in p). Collectively, these results demonstrate that post-stroke DV administration could not exert its beneficial effects due to inhibition of brain VEGF receptors and thus further implicating VEGF in DV's post-stroke mechanism of action.

Domain V is Neuroprotective Via Stimulation of VEGF Production and Release from Brain Endothelial Cells Experiments with mouse cortical neurons oxygen and glucose deprivation stress (OGD, FIG. 5Q) were performed. It was noted that DV by itself had no direct effect (i.e. when DV was added directly to the neurons) on neuronal survival, but that when added to brain endothelial cells grown on a Transwells insert above the neurons (i.e. neurons and endothelial cells sharing secreted factors but devoid of cell-cell contact), DV significantly enhanced neuronal survival beyond the enhanced survival provided by the endothelial cells alone (#p=0.0001,**p=0.003). Additionally, this enhanced neuronal survival was completely blocked by the addition of VEGF neutralizing antibody (*p=0.001, but was unaffected by the addition of control IgG, data not shown), which could also block a significant extent of the endothelial cell alone effect on neuronal survival (***p=0.002), thereby demonstrating that DV neuroprotection is indirect, i.e. mediated by its enhancement of VEGF release from endothelial cells rather than direct effects on the neurons.

Domain V Induces VEGF Release Via the α5β1 Integrin and Activation of Erk

Figure 5R:
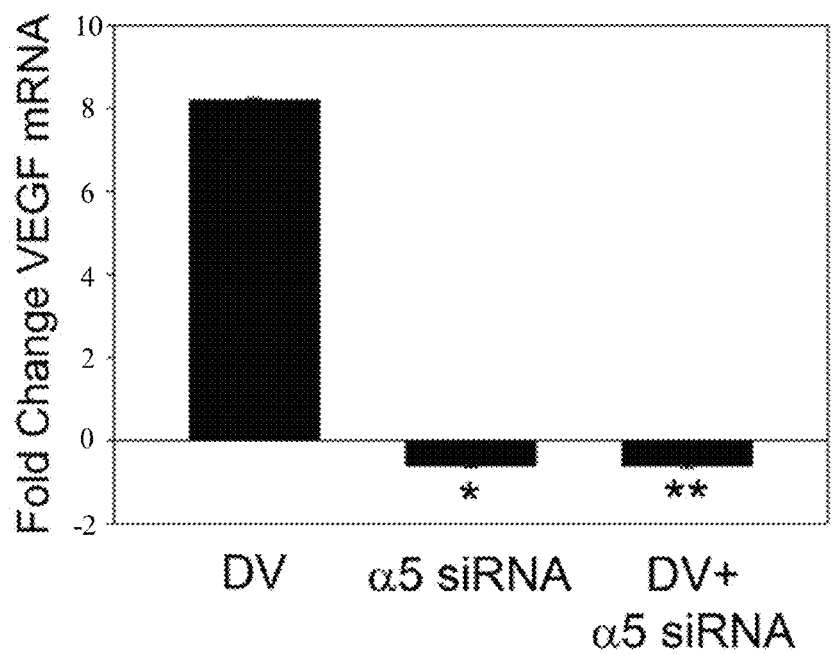
(FIG. 5R) Graph demonstrating that knockdown of α5 integrin with α5 siRNA in brain microvascular endothelial cells significantly inhibits VEGF mRNA generation ($*p=0.008$ compared to control levels, here arbitrarily set to zero, 1.5 h incubation time) and significantly inhibits DV-induced increase in VEGF mRNA ($**p=0.00002$). mean values+/−standard error shown.

FIG. 5R demonstrates that α5β1 integrin knockdown in brain microvascular endothelial cells significantly inhibited VEGF mRNA production (*p=0.008, compared to control arbitrarily set to zero) that was unchanged by the addition of DV (p=0.00002 compared to the addition of DV to wild type cells). Conversely, the α5β1 specific activating antibody SNAKA51, which activates α5β1 by binding outside of the ligand binding domain[64], could significantly increase VEGF secretion from brain endothelial cells (p=0.003) (FIG. 5S). Importantly, when SNAKA51 was added in combination with DV, even more VEGF was secreted from brain endothelial cells (***p=0.000001 compared to control, p=0.002 compared to DV alone) suggesting that activation of α5β1 with SNAKA51 enhances DV-induced VEGF release. Furthermore, DV-induced increases in α5β1 mRNA were inhibited with VEGF neutralizing antibody (data not shown) suggesting that DV-induced VEGF release could result in a positive feedback loop that increases α5β1 integrin levels.

FIG. 5T demonstrates that by western blot, DV addition to brain microvascular endothelial cells results in Akt phosphorylation/activation from 5 to 30 min exposure (*p=0.001) which remained elevated for at least 30 minutes (**p=0.02) as normalized to total Akt. Furthermore, this DV-induced Akt activation could be completely inhibited by the addition of the PI3K inhibitor LY-294002. Next, we demonstrated that DV phosphorylates/activates ERK in brain microvascular endothelial cells after 5 minutes (*p=0.001), which remained elevated for at least 30 minutes (**p=0.02) as normalized to total ERK signal (FIG. 5U). This phosphorylation could be inhibited with the PI3K inhibitor LY-294002 (#p=0.003, ##p=0.009 as compared to DV changes). The inhibitor by itself had no significant effect on ERK phosphorylation.

Figure 5W:
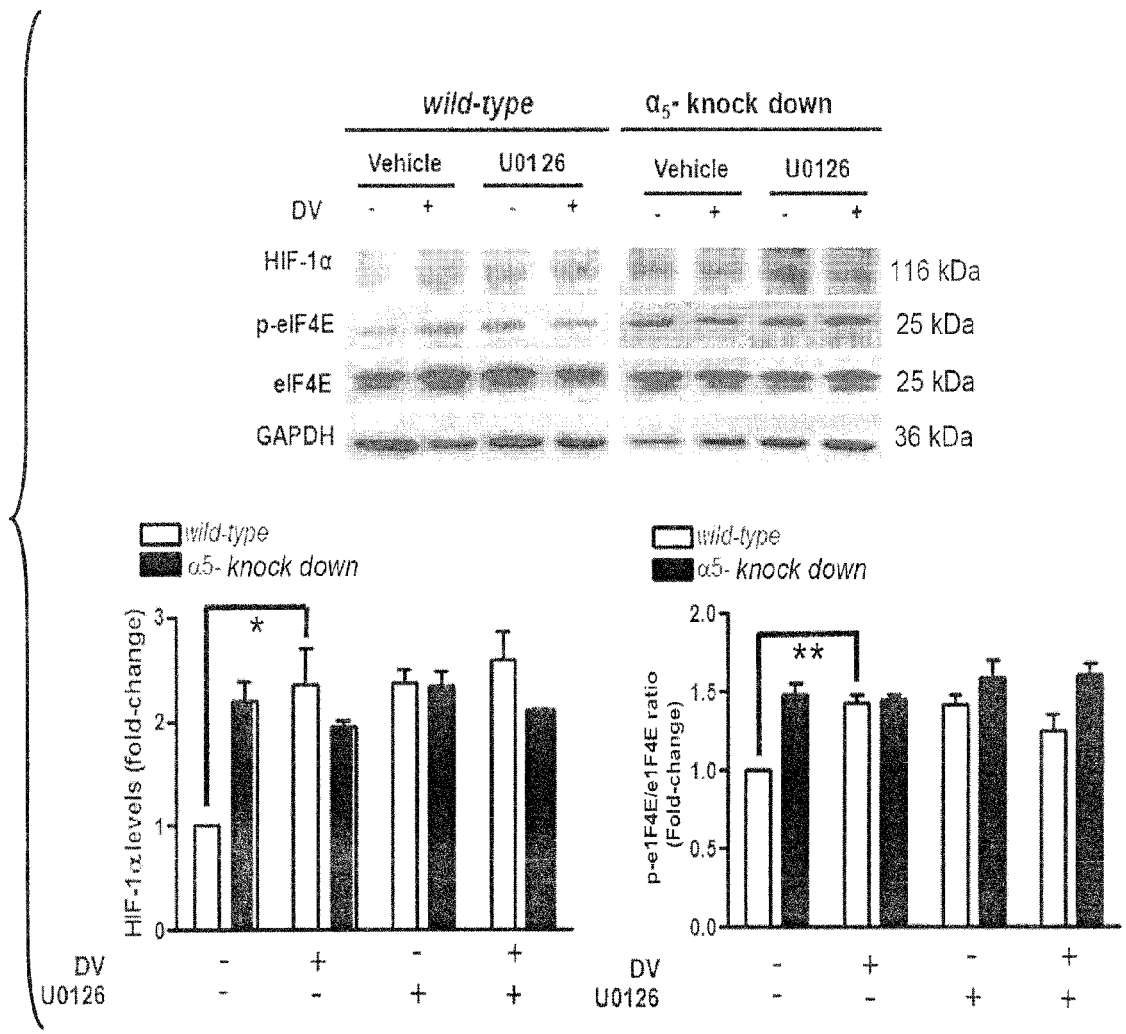
(FIG. 5W) DV increases HIF-1 a levels and phosphorylation/activation of eIF4E in an α5β1 integrin dependent fashion as demonstrated by representative western blots and respective plots (for HIF-1a, $*p=0.02$, plotted as mean fold change+/−standard deviation) for eIF4E, $**p=0.004$, plotted a fold change in the ratio of phosphorylated eIF4E to total eIF4E. In both cases, DV-induced changes were absent in α5β1 knocked down cells and were blocked in wild type cells by the MEK inhibitor U0126.
Figure 5Y:
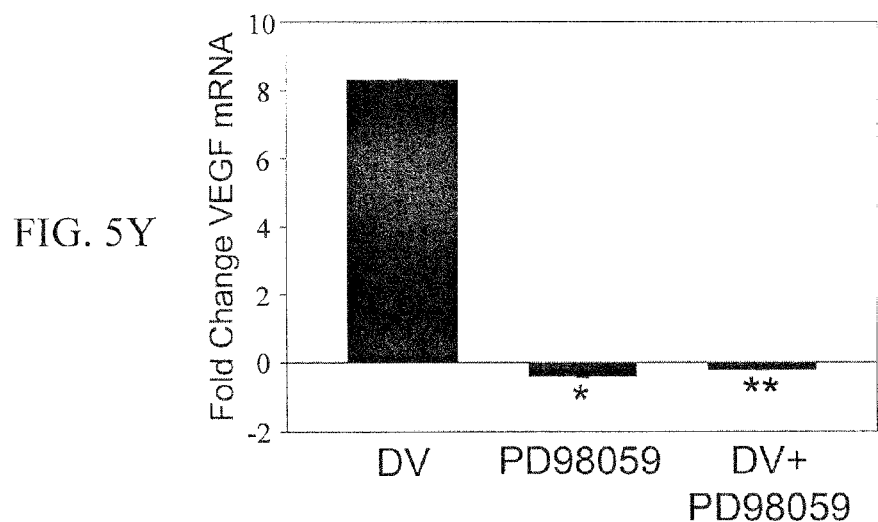
(FIG. 5Y) Inhibition of ERK with PD98059 inhibits VEGF mRNA production in brain microvascular endothelial cells ($*p=0.000002$) which could not be prevented with the addition of DV ($**p=0.000006$). Mean values+/−standard deviation shown.
Figure 5X:
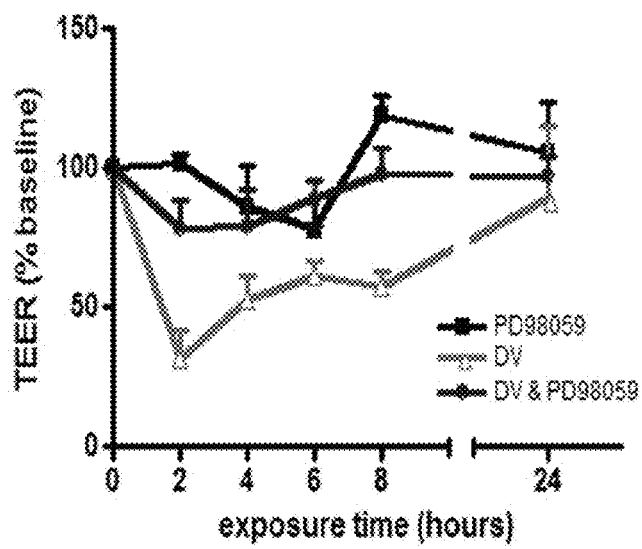
(FIG. 5X) DV induced decreases in TEER are inhibited by the ERK inhibitor PD98059 ($*p=0.008, p=0.01, *p=0.003, ****p=0.0004$) while PD98059 by itself has no significant effect on TEER.

As VEGF constitutes one of the major targets for the hypoxia-induced factor-1α (HIF-1α), changes in HIF-1α levels in brain endothelial cells following DV application (FIG. 5V) were investigated. Under normal conditions, HIF-1α is constantly degraded and almost nonexistent. Application of 0.1% DMSO (vehicle) transiently stabilized HIF-1α which then rapidly became undetectable. Interestingly, DV induced rapid stabilization of HIF-1α which remained stable for up to 15 minutes, followed by a rapid decrease to barely detectable levels after 30 minutes. Among the different protein involved in oxygen-independent stabilization of HIF-1α, changes in elongation factor-4E (eIF4e) phosphorylation (FIG. 5W) were examined. Interestingly, HIF-1α stabilization correlated with increased phosphorylation of eIF4E. In addition, usage of U0126, a potent MEK inhibitor, abrogated any further eIF4E increase. Surprisingly, $\alpha_5$-knockdown by siRNA (FIG. 5W) constitutively induced HIF-1α stabilization. However, the presence of DV did not further enhance HIF-1α levels suggesting that HIF-1α stabilization by DV is strictly regulated by $\alpha_5\beta_1$ upstream signaling. Finally, DV-induced decreases in brain endothelial cell TEER could be prevented with the ERK inhibitor PD98059 (FIG. 5X) which could also inhibit VEGF mRNA production regardless of the presence (**p=0.000006) or absence (*p=0.000002) of added DV (FIG. 5Y). Taken together, these data highlight the involvement of Akt and ERK in DV-induced VEGF secretion via α5b1 as schematically summarized in FIG. 5A.

Discussion

These studies demonstrate that the extracellular matrix-derived non-brain inhibitor of angiogenesis, perlecan DV, is generated in human, rat and mouse stroke injured brain. Administered DV is neuroprotective and quite unexpectedly enhances rather than inhibits brain angiogenesis in vitro and in vivo. We further showed that administered DV homes to stroke and peri-infarct brain tissue, enhances neurovascular niche formation, due at least in part to a previously unreported interaction with the α5β1 integrin and resultant enhanced VEGF release. This ultimately results in the complete restoration of motor deficit to baseline pre-stroke levels in endothelin-1 and tandem ipsilateral CCA & MCA stroke models in rats and mice, respectively.

Perlecan, synthesized and secreted by neurons, astrocytes, and endothelial cells[60], induced in the latter by $VEGF_{165}$[66], has the distinction of being the most sensitive and rapidly processed matrix component after stroke[23]. Perlecan proteolysis by cathepsin L occurs within two hours of the occlusion of the middle cerebral artery in nonhuman primates and persists for several days[23]. The sustained processing of perlecan for days after stroke is consistent with studies demonstrating an increase in perlecan production in neurons and astrocytes after brain injury[66]. In the present study, we have detected a rapid increase in perlecan DV levels that gradually plateaus at an elevated level over the course of seven days post-stroke, a temporal pattern that correlates well with the nonhuman primate post-stroke perlecan proteolysis profile[23]. The significance of perlecan to ischemic stroke is further underscored by the larger ischemic lesion size and diminished angiogenic response observed here in perlecan hypomorph animals (that express 10% of normal perlecan DV levels).

In this study, a rapid functional improvement to pre-stroke levels on post-stroke day 3, after 2 doses of DV was noted (the first dose given 24 hours after stroke onset). This rapid improvement correlated with significant, if modest, post-stroke day 3 increased peri-infarct angiogenesis (FIG. 2E), decreased hemispheric lesion volume (FIGS. 2A, 2B), decreased peri-infarct neuronal apoptosis (FIG. 2C) and increased doublecortin/nestin positive immature neurons in the peri-infarct, angiogenic region. Therefore, it would appear unlikely that the post-stroke day 3 functional restoration is directly due to any single one of these events, but rather is likely to be a consequence of their collective, beneficial influences and cross-talk. For example, the observed modest post-stroke day 3 increase in angiogenesis is by itself unlikely to explain the post-stroke day 3 functional recovery, but when coupled with these other beneficial effects of endothelial cell induced VEGF release (enhanced neuroprotection and neuronal migration) which are also positively reinforced by angiogenic endothelial cells, could explain why the DV treated stroked animals recover better than the controls.

The ability of an anti-angiogenic extracellular matrix fragment to promote brain angiogenesis may be due to the concept of endothelial heterogeneity, whereby endothelial cells in different vascular beds, in this case brain versus nonbrain, respond differently to angiomodulatory factors. This differential response may be due to differences in respective microenvironments, differences in expressed receptors, such as the presence or absence of α2β1 integrin, or differences in signal transduction components. Indeed, angiogenic differences between brain and nonbrain endothelial cells have been reported; Wnt/β-catenin signaling is required for CNS, but not non-CNS angiogenesis[67], platelet-derived pro-angiogenic sphingosine-1-phosphate (S1P) is anti-angiogenic in brain endothelial cells due to their lack of MT1-MMP expression[68]. Additionally, the type XVIII collagen-derived inhibitor of angiogenesis, Endostatin, promotes angiogenesis in immature endothelial cells derived from differentiated embryonic stem cells[69] raising the possibility that angiogenic brain endothelia function or behave like immature endothelia. Indeed, newly angiogenic brain endothelia undergo an integrin receptor switch after brain hypoxia from mature integrin receptors back to developmental integrin expression[70], particularly, the α5β1 integrin. The enhanced post-stroke expression of α5β1 integrin might also explain DV's ability to home to the stroke and peri-infarct cortex vasculature just as α2β1 expression in tumor vasculature supported DV targeting in vivo[26]. Additionally, the near immediate post-stroke proteolysis of perlecan and generation of DV could serve as part of the trigger of the integrin receptor switch. This possibility is supported by our observation that DV increased α5β1 integrin mRNA levels in brain endothelial cells in vitro and α5β1 integrin levels in post-stroke brain tissue.

A number of animal studies within the past few years demonstrate that improving neuroprotection and enhancing post-stroke angiogenesis and/or neurogenesis can improve stroke outcome. These experimental therapies seemingly fit into one of three general categories; pharmacological agents[13-16], growth factors[95], and stem cell therapies[96,97]. We now propose a fourth type of stroke therapy, the bioactive extracellular matrix fragment perlecan DV, that may be native to the brain's post-stroke repair mechanisms, homes specifically to the area of injury when exogenously administered, is seemingly well tolerated, and via newly determined cell receptor interactions and growth factor release has unexpected neurovascular effects that both provide new insights to post-stroke brain pathophysiology and result in normalization of stroke-affected motor function.

Example 2

In Vitro Effects of DV in a MS System

Figure 22A:
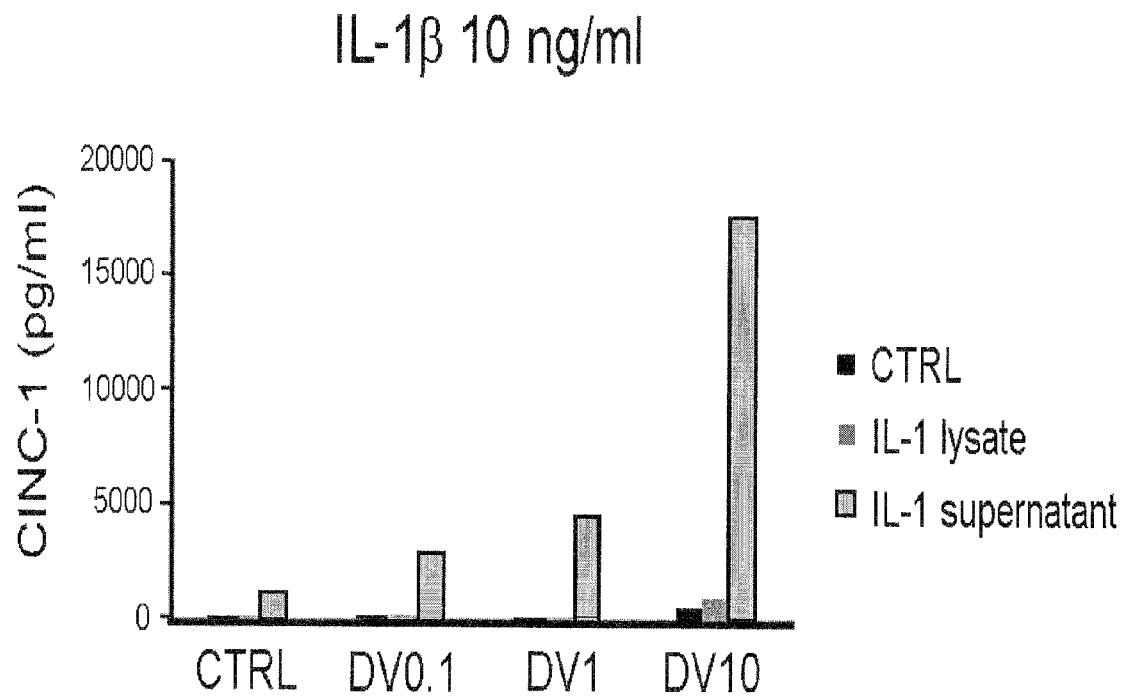
FIGS. 22A-22B. Primary rat astrocytes were seeded onto plastic at $1 \times 10^5$ cells/ml and maintained for 7 days. Cells were treated with domain V (DV) at 0.1, 1 and 10 ng/ml. On top of that, IL-1β (10 ng/ml.
Figure 22B:
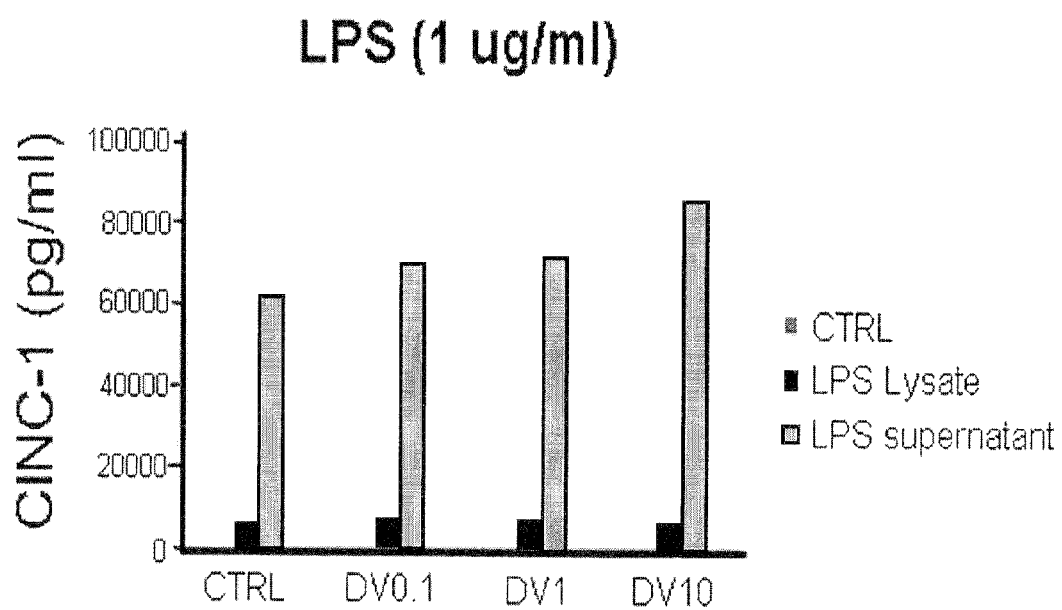

To determine whether perlecan domain V could play a therapeutic role in multiple sclerosis, we treated primary rat astrocytes with domain V (at different doses)+/−LPS or +/−IL-1b and measured CINC-1 levels in the cells and cell supernatant by ELISA. While domain V by itself did not cause any change in CINC-1 production or release as compared to control (no added compound), it very significantly potentiated the release of CINC-1 induced by IL-1β and LPS (FIGS. 22A, 22B). This data strongly suggests that domain V can modulate chemokine release in activated astrocytes, a potentially important therapeutic effect in stimulating oligodendrocytes to remyelinate plaques in multiple sclerosis.

Example 3

Materials and Methods

Human LG3 Production/Purification

Human Perlecan LG3 was produced and purified as described previously (Wright, Parham et al. 2010). Briefly, LG3 DNA was used to transfect 293-ENBA cells. LG3 was purified from the culture supernatant using 6×His-tags and Ni-ATA agarose beads (Qiagen). Eluted fractions containing LG3 were combined and dialyzed against Phosphate Buffered Saline (PBS) and the purity of LG3 was confirmed using Sodium Dodecyl Sulphate (SDS) gel electrophoresis (SDS-PAGE) under denatured conditions. LG3 was visualized by staining with Coomassie Brilliant Blue (Sigma Aldrich) and western blot (data not shown).

Experimental In Vivo Stroke Model

Middle cerebral artery occlusion (MCAo) was performed on adult 3-month old Sprague Dawley rats, as approved by Texas A&M College of Medicine IACUC, as described previously (Lee, et al. 2011). Briefly, ischemic injury was performed by tandem common carotid artery and middle cerebral artery occlusion. Animals with diminished perfusion reading (12% to 15% of the initial value), which was confirmed using laser Doppler flow meter (Perimed, Dickinson, Tex.), were included in further experiments. Occlusions were removed after 60 min and animals were sacrificed 1 day and 3 days post MCAo. Brains were extracted, contralateral and ipsilateral (ischemic) hemispheres were separated, and total homogenates were prepared. Lysates were prepared in RIPA lysis buffer complemented with protease inhibitor cocktail (Calbiochem, EMD Chemicals).

Cell Cultures

All primary cells were extracted from rats or mice as approved by Texas A&M College of Medicine IACUC. All cells were routinely cultured in conditioned incubators (37° C./5% $CO_2$).

Primary fetal cortical neurons were extracted from C57BL6 embryonic day 17-18 mice as previously described (Harris, Lee et al. 2007). Briefly, pregnant females were euthanized using cervical dislocation and embryos were dissected in order to obtain cerebral cortices. After mechanical dissociation and treatment with trypsin, neurons were seeded on Poly-D-Lysine (Sigma Aldrich) coated plates in Dulbecco's modified Eagle Medium (DMEM) high glucose (Invitrogen) containing 2% B27 supplement and 1% penicillin/streptomycin. Experiments were performed after 3-4 days in vitro (DIV).

Primary astrocytes were prepared from 1 day old Sprague-Dawley rat pups as described previously (Chow, Ogunshola et al. 2001) (Cole and DeVries, 2001). Briefly, pups were anesthetized using hypothermia and brains were extracted and dissociated by mechanical tituration and trypsin/DNAse I treatment. Cells were seeded on Poly-D-lysine (Sigma Aldrich) coated flasks in DMEM/F12 (Invitrogen) containing 10% Fetal Bovine Serum (FBS; Denville Scientific Inc.) and 1% penicillin-streptomycin. After 7-9 DIV, the cultures were shaken at 37° C. and 180 rpm for 24 h to remove contaminating microglia and precursor oligodendrocyte cells. Cultures were then trypsinised and cells were seeded into fish gelatin (Sigma Alderich) coated flasks. Cultures contained 95% of astrocytes as assessed by glial fibrillary acid protein (GFAP) immunocytochemistry.

Primary mouse brain endothelial cell (MBEC) cultures were established as described previously (Song and Yachter 2003). Briefly, 4-12 weeks old C57BL6 mice were euthanized using $CO_2$ inhalation. Brains were extracted and homogenized. Microvessels were separated after density centrifugation in 18% (wt/vol) Dextran. Microvessels were digested using colegenase/dispase (Roche) solution containing DNAse (Invitrogen) and then suspended in DMEM-F-12 containing 10% plasma-derived serum (FirstLink, UK), 10% FCS, 100 µg/mL endothelial cell growth supplement (BD Biosciences, UK), 100 µg/mL heparin, 2 mM glutamine, 1% penicillin-streptomycin. Cells were then seeded on murine collagen-IV coated (50 µg/mL, BD Biosciences) plates, and cultures were used after 14 DIV.

Primary brain pericytes cultures were established as described previously (Dore-Duffy 2003; Al Ahmad, Gassmann et al. 2009). Briefly, adult Sprague-Dawley rats were euthanized using $CO_2$ inhalation. Brains were extracted and homogenized. Microvessels were separated after centrifugation in 20% (wt/vol) Dextran. Microvessels were digested in collegenase/dispase (Roche) and seeded on tissue culture plates coated with 250 µg/mL collagen I (BD Biosciences) in DMEM high glucose (Invitrogen) with 20% FBS and 1% penicillin-streptomycin-amphotericin. After cultures became confluent, cells were trypsinised and seeded on uncoated tissue culture plates and were cultured in media containing 10% FBS and were used at passage 2 (P2). Cultures contained 95% of pericytes as assessed by vimentin-positive, Von Willenbrand factor-negative and GFAP-negative immunostaining as described previously (Kim, Tran et al. 2006).

Human brain vascular endothelial cells (hCMEC/D3, kindly provided by Pierre-Olivier Couraud, Institute Cochin Institute, University of Paris, Paris, France) were used as a model for human brain endothelial cells (Weksler, Subileau et al. 2005). hCMEC/D3 were cultured on fish gelatin coated plates in EBM-2 (Lonza) containing 10% FBS, 1% Penicillin-streptomycin, 1.4 µM hydrocortisone, 5 µg/ml ascorbic acid, 1:100 chemically defined lipid concentrate, 1 ng/ml basic fibroblast growth factor (bFGF) and 10 mM HEPES. They were used from passages 29-38. The rat brain endothelial cell line, RBE4, was used as a model for rat brain endothelial cells in some experiments (Roux, Durieu-Trautmann et al. 1994), and were cultured on fish gelatin (Sigma) coated plates from passages 28-35 in Minimum Essential Media alpha (MEM-α) containing nucleosides and ribonucleosides (Invitrogen) and F10 media (Invitrogen) in the ratio of 1:1, and containing 1% penicillin-streptomycin.

In Vitro Oxygen Glucose Deprivation (OGD)

Non-neuronal cells were serum-starved overnight by changing culture media with DMEM high glucose (Invitrogen) with 1% FBS and 1% penicillin-streptomycin. For OGD, both neuronal and non-neuronal cultures were washed twice with OGD media, composed of DMEM no glucose (Invitrogen) containing 1% FBS and 1% penicillin-strepromycin, with the addition of B27 for neuronal cultures. Cultures were then incubated with OGD media and transferred into hypoxic chamber (Billups-Rothenberg) which was flushed with anoxic gas (90% $N_2$, 5% $CO_2$ and 5% $H_2$) for 5 min, according to the manufacturer's instructions. After OGD, the media was collected for western blot analysis and cultures were incubated with oxygenated DMEM high glucose with 1% FBS and 1% penicillin-streptomycin (and B27 for neuronal cultures). After 24 h, reperfusion media was collected for western blot analysis.

IL-1α and IL-1β Treatment

Stocks of IL-1α and IL-1β (R&D Systems) were diluted in 0.1% BSA/0.9% NaCl. For non-neuronal cells, 100 ng/ml IL1-α and IL1-β were prepared in normal culture media of the cells (described above) and lower treatment concentrations were prepared by serial dilution. The media used for neurons contained 5% FBS in addition to their normal culture media. Cells were washed once with their normal culture media before being treated with IL-1α or IL-1β. Treatment was carried out for 24 hours and supernatants were collected for western blot analysis.

Western Blot Analysis

Western blots analyses were performed on brain lysates, which were prepared in RIPA lysis buffer complemented with protease inhibitor cocktail (Calbiochem, EMD chemicals), or were performed on culture supernatants. Cell culture supernatants were concentrated 5-10 fold using vacuum centrifuge (Speedvac, Savant, Thermo Scientific). Bradford assay (Bio-Rad) was used to determine protein concentration, and equal amounts of protein were separated on SDS-PAGE and transferred to nitrocellulose membrane. Non-specific binding sites were blocked in 5% non-fat milk in Tris buffer saline containing 1:1000 Tween20 (TBS-T). Membranes were then incubated overnight with anti-endorepellin (1:1000, R&D Systems), hereby referred to as anti-LG3, followed by incubation with horseradish peroxidase-conjugated secondary antibody (1:5000, Genetex) for 2 h. Membranes were then developed using ECL kit (Thermo Scientific). Bands were quantified using Image J (NIH) as described by Luke Miller (http://lukemiller.org/journal/2007/08/quantifying-western-blots-without.html). Ponceau staining (Sigma Aldrich) was carried out using 0.1% Ponceau S. solution and was used to normalize the blots obtained from supernatants (Romero-Calvo, Ocon et al. 2010). GAPDH was used to normalize the blots from brain lysates.

Viability Assay

Fetal cortical neurons were seeded on Poly-D-Lysine (Sigma) coated 96 well plates and used at 3-4 DIV. Cultures were washed twice with DMEM no glucose (Invitrogen) containing 1% penicillin-streptomycin (OGD media). They were then incubated with OGD media in a hypoxic chamber for 2 h as described above to expose them to OGD. Media was then changed to DMEM high glucose (Invitrogen) containing 1% L-glutamine and 1% penicillin-streptomycin. Cultures were left untreated or were treated with 150 nM LG3, a dose that has previously been demonstrated to be biologically active (Wright, Parham et al, 2010) (Bix, Fu et al, 2004). After 2 days, Alamar blue (AbD Serotec) was added to the wells and fluorescence readings were taken after 24 h with excitation at 560 nm and emission at 590 nm using a florescent plate reader (Victor X3, Perkin Elmer), according to manufacturer's instructions.

Proliferation Assay hCEMC/D3 cells were seeded on uncoated wells at a density of 5000 cells/well in 96-well plates in hCEMC/D3 cell media (see above) containing 10% serum. After 24 h, the media was changed to hCEMC/D3 media containing 1% serum with 150 nM LG3 (treated cells) or no LG3 (untreated). After 48 h, MTS (Cell titer[96], Promega) was added to the cultures and the absorbance was read after 4 h at 590 nm using a spectrophotometer (Phoenix sunrise, Tecan).

Statistical Analysis

All experiments were performed at least 3 independent times, each time in duplicate or more unless otherwise stated. The data is presented as mean±standard error of the mean (SEM). Comparison between groups was performed using Student's t-test, one-way ANOVA with Tukey as a post test, or two-way ANOVA as appropriate using GraphPad Prism 4.0. Significance was defined as $P<0.05$.

Results

Focal Ischemia Induces the Release of LG3

Figure 23:
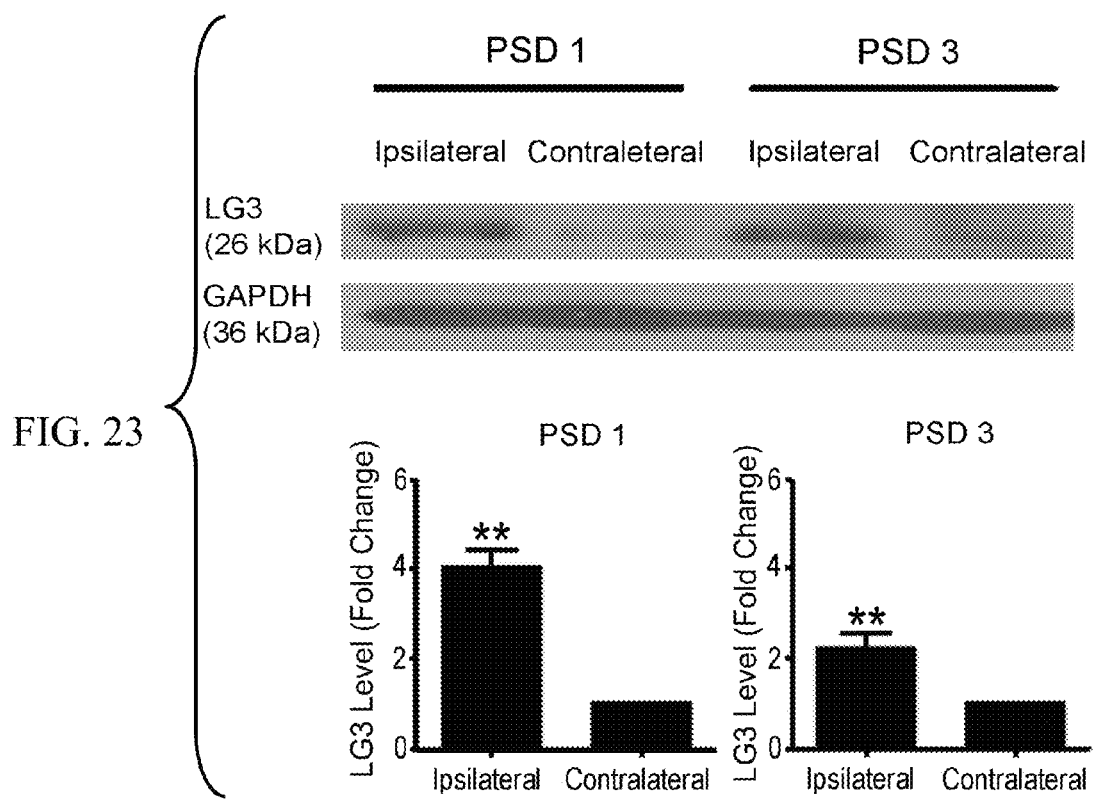
FIG. 23. Perlecan LG3 levels are elevated after stroke. Representative anti-LG3 western blots were normalized to their respective GAPDH blots and show that LG3 levels are elevated in ipsilateral hemisphere (stroked) when compared to contralateral hemisphere at post stroke day (PSD) 1 and PSD 3. Data was analyzed using student's t-test and is significant at **p<0.015.

Since our group recently demonstrated the active generation of perlecan DV following stroke injury (Lee et al., 2011), we wanted to investigate if perlecan LG3 is similarly increased after MCAo. We detected increased LG3 levels in the ipsilateral, ischemic hemisphere compared to the contralateral hemisphere at post stroke day (PSD) 1 (FIG. 23a). No LG3 was detected in sham surgical controls (data not shown). This increase was sustained, although slightly diminished at PSD 3.

Oxygen-Glucose Deprivation (OGD) Causes Neurons and Pericytes, but not Astrocytes, to Release More LG3

Figure 24A:
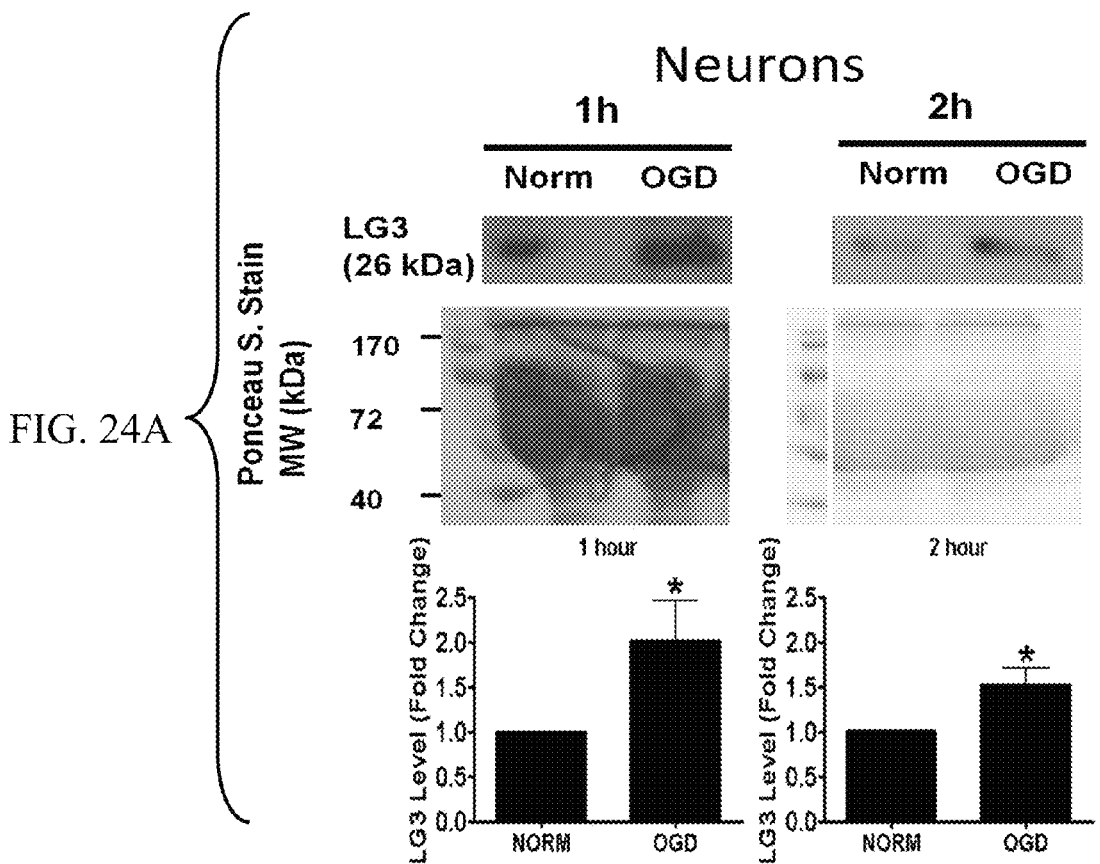
FIGS. 24A-24D. Analysis of perlecan LG3 levels in OGD media of the cells of the NVU. Representative anti-LG3 western blots were normalized to their respective Ponceau S. stains and represent the fold change in LG3 released by a) Neurons b) Astrocytes c) RBE4 brain endothelial cells and d) Brain pericytes during various durations of OGD when compared to LG3 released by control cultures (Norm). Data was analyzed by student's t-test and is significant at *p<0.05 and **p<0.01 when compared to respective control culture LG3 levels.
Figure 24B:
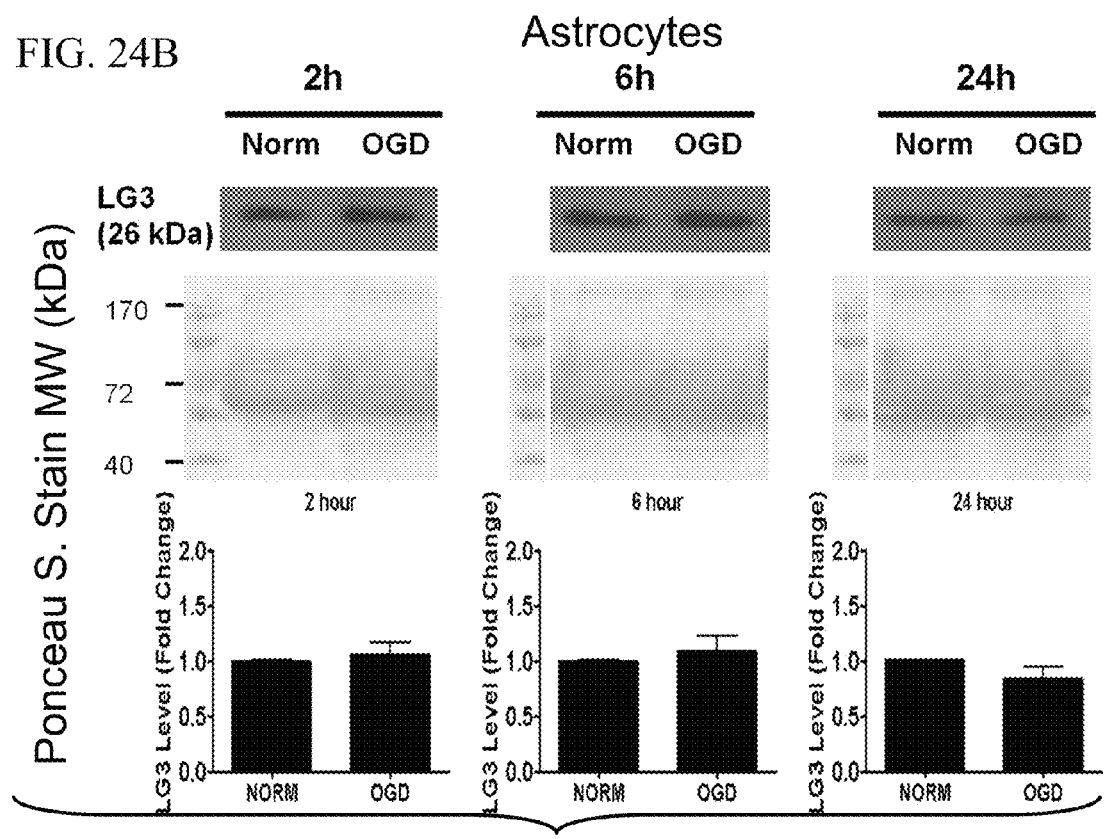
Figure 24C:
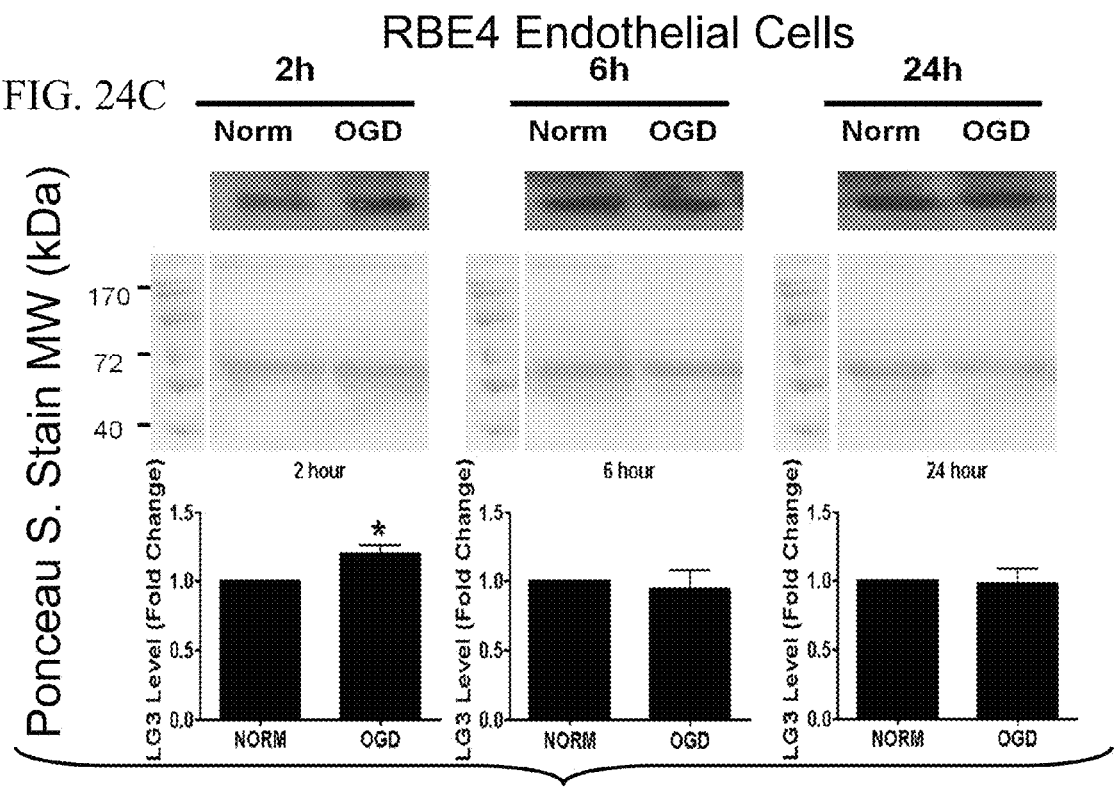
Figure 24D:
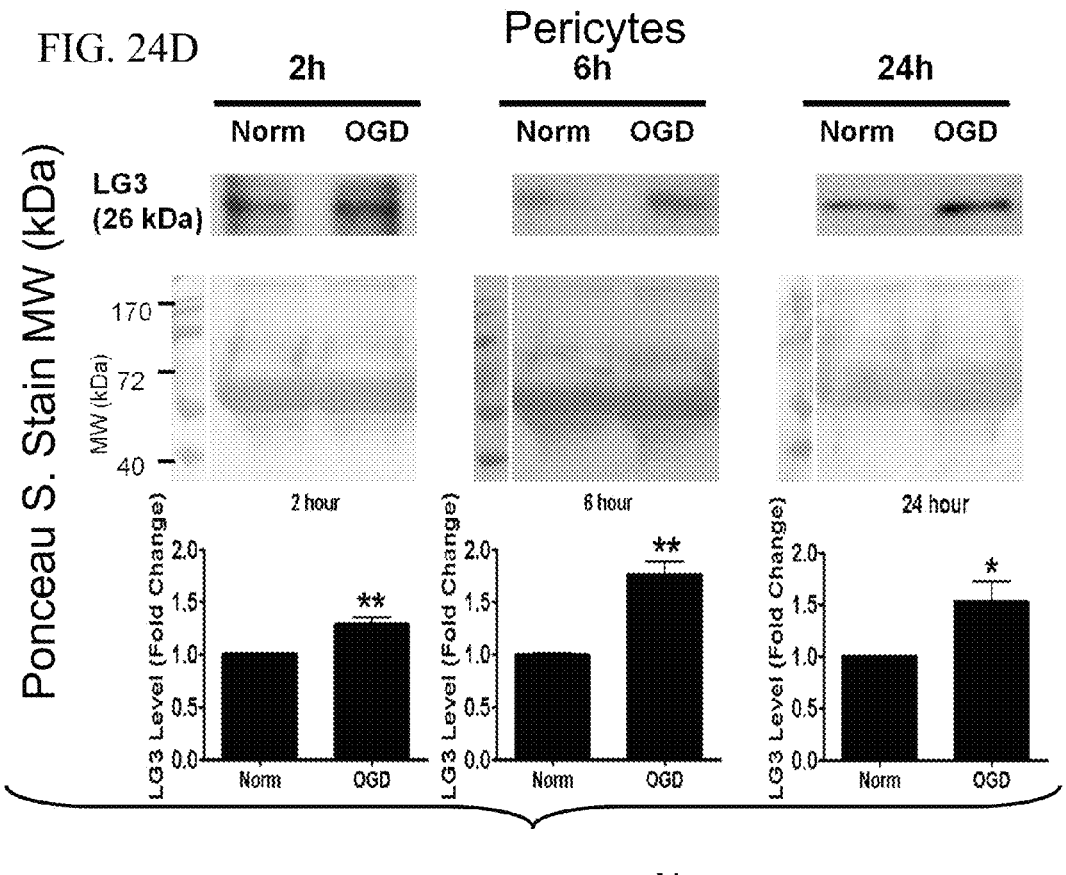

Next, we investigated the possible source of increased LG3 levels seen after MCAo in vivo. Since OGD is the primary stimulus injuring cells during cerebral ischemia, we assessed LG3 levels in the media of neurons, astrocytes, brain endothelial cells and pericytes exposed to OGD. The cells were changed to OGD media and were incubated in hypoxic conditions for various durations, after which the OGD media was collected and analyzed for LG3 levels. These were compared to the LG3 levels present in the media collected from control cultures (normoxic-high glucose) after the same durations. LG3 levels strongly increased in the media of neurons exposed to 1 h and 2 h OGD, although a significant increase was detected during 2 h OGD (FIG. 24a). Exposure of primary astrocyte cultures to OGD for 2 h, 6 h or 24 h had no effect on LG3 release (FIG. 24b), while 2 h OGD, but not 6 or 24 h, induced a slight increase in LG3 levels in the media of RBE4 endothelial cells (FIG. 24c). In contrast, significantly increased levels of LG3 were detected in the media of pericyte cultures exposed to OGD for 2 h, 6 h or 24 h, with maximum release observed during 6 h OGD (FIG. 2d).

Reperfusion Stress Causes Neurons, Astrocytes and Pericytes to Generate More LG3 Only after Brief Durations of OGD Following OGD, another stress which the cells of the NVU face is reperfusion, which results in the generation of reactive oxygen species (ROS) (Chan 2001). Therefore, we were interested to see how reperfusion media of cultures treated with OGD would differ in LG3 levels when compared to that of control cultures. Apart from the reoxygenation induced stress, we were also interested in examining the amounts of LG3 released by OGD-damaged cells when they return to normal conditions.

Figure 25A:
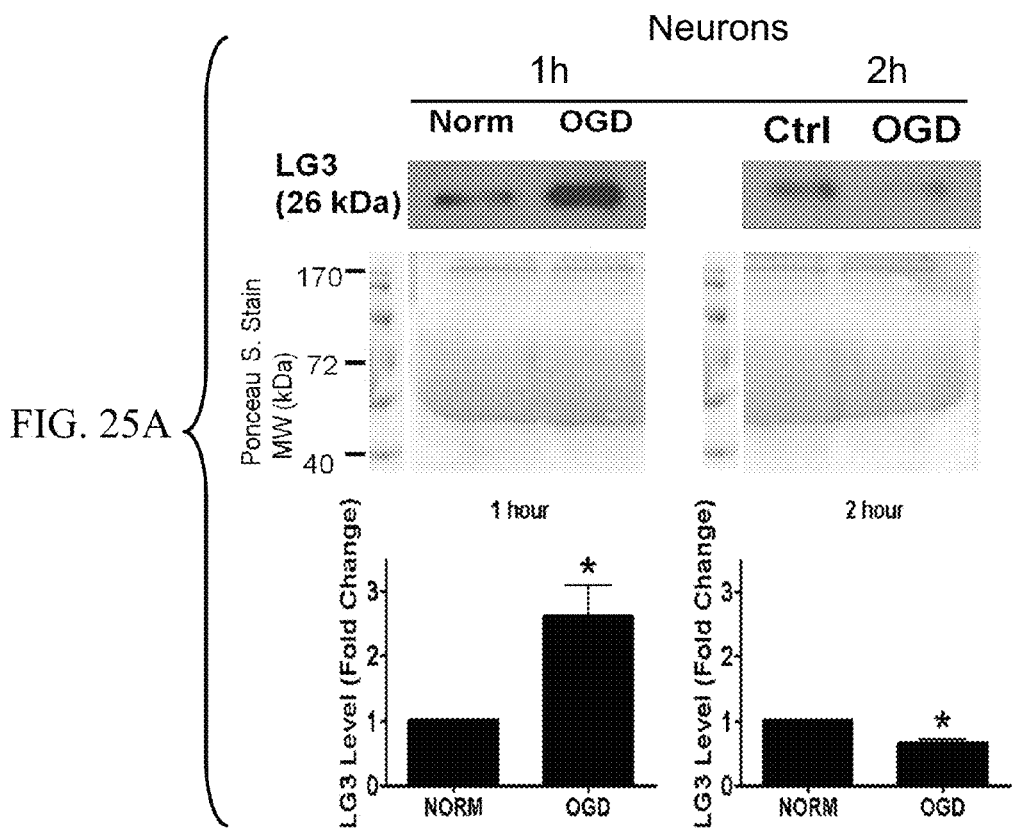
FIGS. 25A-25D. Analysis of perlecan LG3 levels in the reperfusion media of the cells of the NVU. Representative anti-LG3 western blots were normalized to their respective Ponceau S. stains and represent the fold change in LG3 released by a) Neurons b) Astrocytes c) RBE4 brain endothelial cells and d) Brain pericytes after various durations of OGD (during 24 hours of reperfusion) when compared to LG3 released by control cultures (Norm). Data was analyzed by student's t-test and is significant at *p<0.05 and **p<0.01 when compared to respective control culture LG3 levels.
Figure 25B:
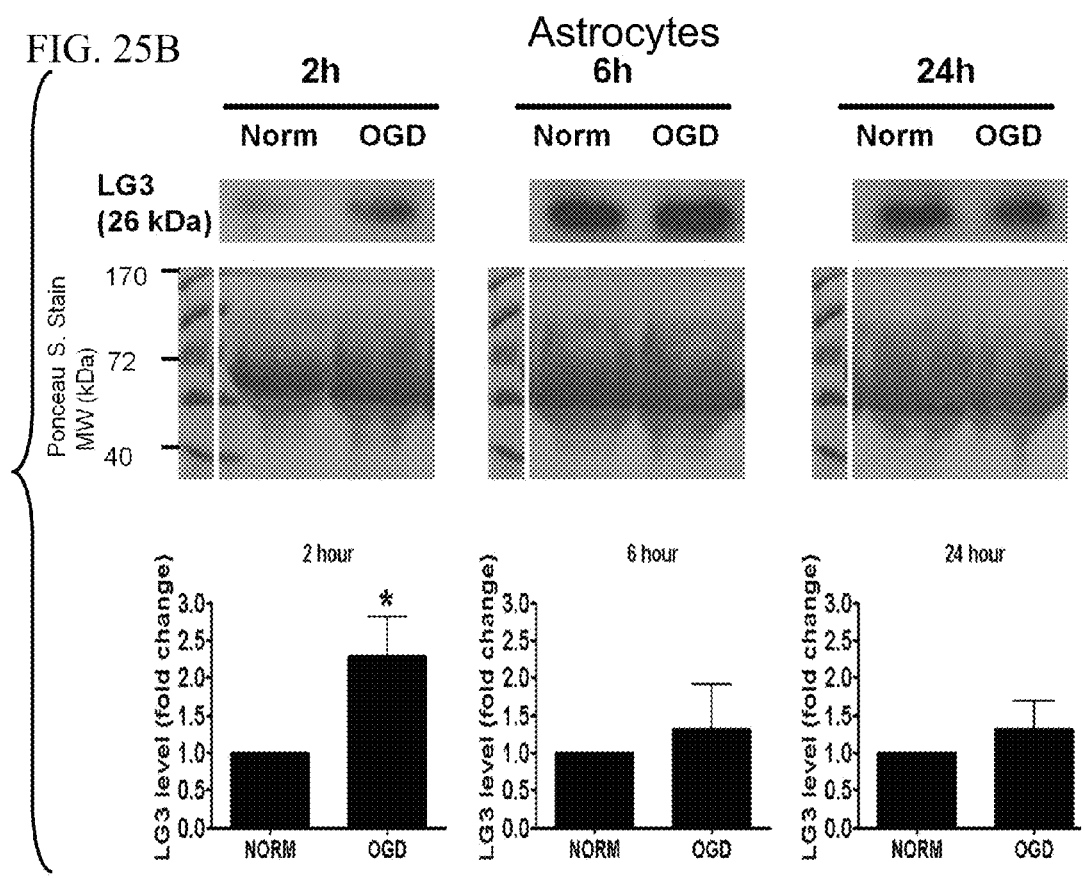
Figure 25C:
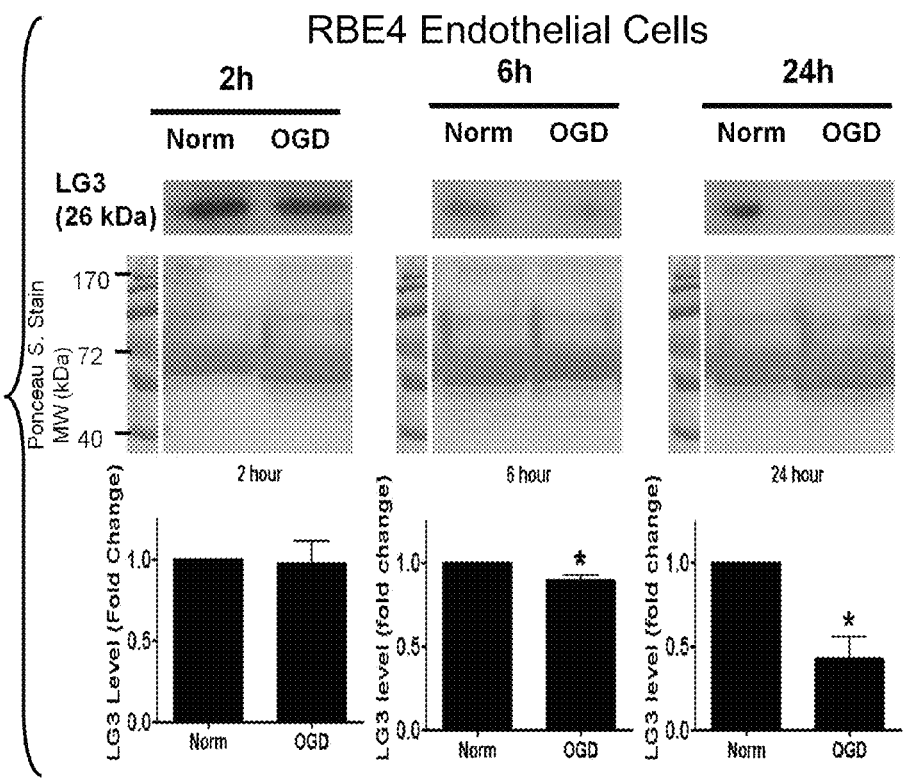
Figure 25D:
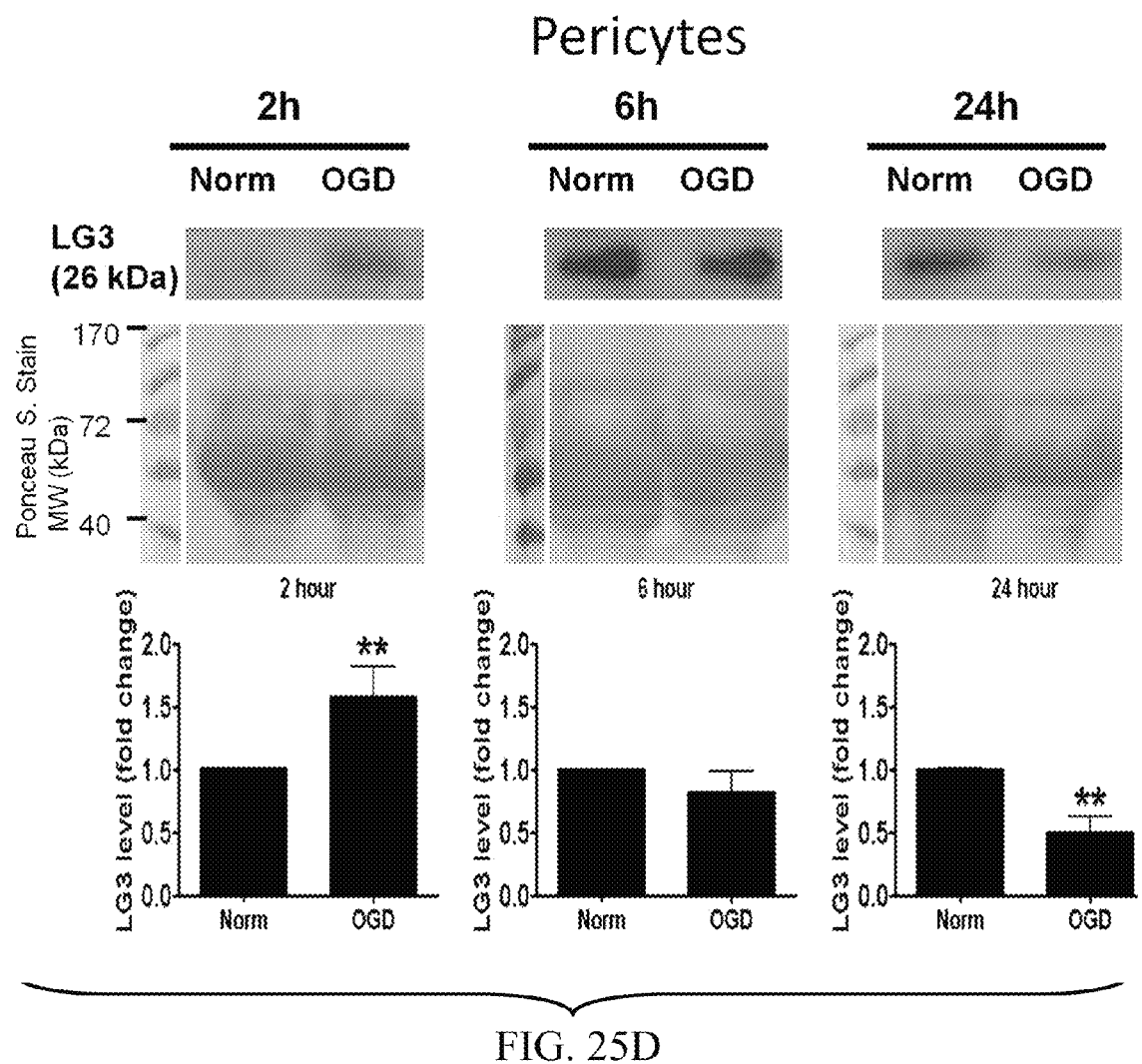

For cultures exposed to OGD, media was changed to normoxic-high glucose media, which was collected after 24 h and termed reperfusion media, as this can be considered to be an in vitro model for in vivo reperfusion. This was analyzed for LG3 levels and compared to LG3 levels in the media from control cultures which were also given a similar change of media. Neurons, astrocytes and pericytes showed an increase in LG3 levels only when OGD was of shorter durations (FIGS. 25a, 25b and 25d). A decrease in the release of LG3 was observed after longer durations of OGD exposure to neurons, brain endothelial cells and pericytes (FIGS. 25a, 25c and 25d).

Neurons reperfused after 1 h OGD, showed the strongest significant increase in LG3 levels (FIG. 25a). This increase was lost when neurons were reperfused after a 2 h OGD/reoxygenation, with LG3 levels being significantly lower than control values. LG3 levels were significantly increased in reperfusion media of astrocyte cultures exposed to 2 h OGD/reoxygenation, but this increase was lost in media of astrocytes exposed to 6 or 24 h OGD/reoxygenation (FIG. 25b). Although RBE4 endothelial cells showed no change in LG3 levels in their reperfusion media after a 2 h OGD/reoxygenation, LG3 levels progressively and significantly decreased after 6 h and 24 h OGD/reoxygenation (FIG. 25c). Pericytes, on the other hand, accumulated significantly more LG3 in their reperfusion media after a 2 h OGD/reoxygenation, when compared to control cultures (FIG. 25d). However, longer durations of OGD induced progressive decrease in the LG3 levels in the media of pericytes, which became significantly lower after 24 h OGD/reoxygenation.

Interleukin-1α and -1β Differentially Regulate LG3 Released by Neurons, Astrocytes, Endothelial Cells and Pericytes The central neuroinflammatory response driven by IL-1 plays a key role in the pathogenesis of cerebral ischemia and is a key regulator of ECM degradation and remodeling in the brain. The effect of IL-1 on LG3 production by brain cells is unknown, and we therefore investigated whether IL-1α and IL-1β could induce changes in LG3 produced by neuron, astrocyte, endothelia and pericyte cultures.

Figure 26A:
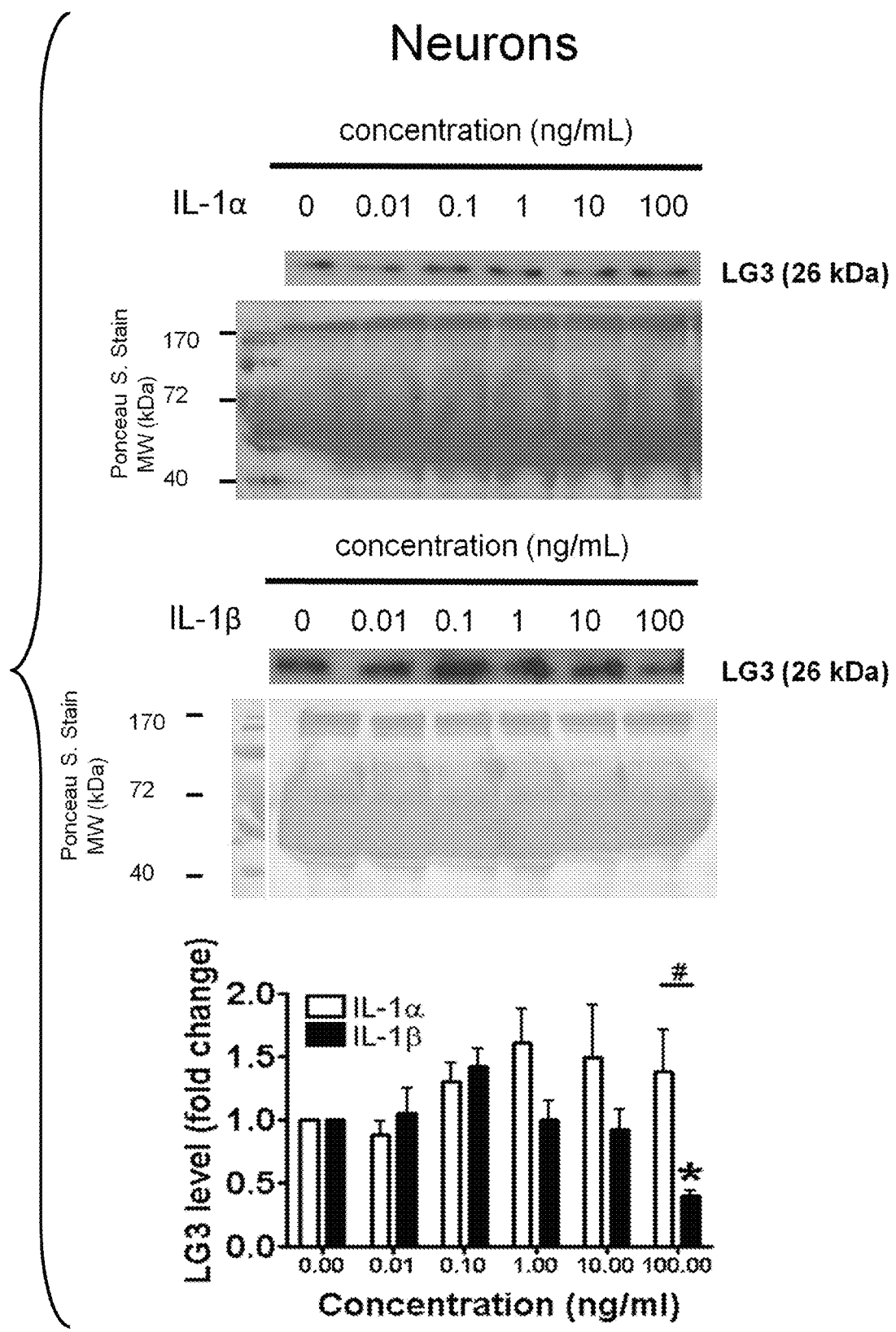
FIGS. 26A-26D. Effect of IL1-α and IL1-β treatment on the LG3 released by cells of NVU. Representative anti-LG3 westerns blots were normalized to their respective Ponceau S. Stains and depict the LG3 released by a) Neurons b) Astrocytes c) primary mouse brain endothelial cells and d) brain pericytes after treatment with various concentrations of IL1-α and IL1-β. The data was analyzed by one-way ANOVA and was found to be significant at *p<0.05 and **p<0.01. For each cell, the dose response to IL1-α treatment was compared to the dose response generated to IL1-β treatment by two-way ANOVA and significance was found at #p<0.05 and ##p<0.001.

In neurons, IL-1α (0.1-100 ng/mL) induced an increase in LG3 levels in the culture media, although this was not found to be statistically significant (FIG. 26a). On the other hand, IL1-β at 0.1 ng/ml caused an increase in the amount of LG3 released, but, higher concentrations progressively caused a decrease in the amount of LG3 released in culture media, which became significant at 100 ng/ml of IL1-β (FIG. 26a). As a result, a statistically significant difference was found between the effects of IL-1α and IL-1β at 100 ng/mL treatment.

Figure 26B:
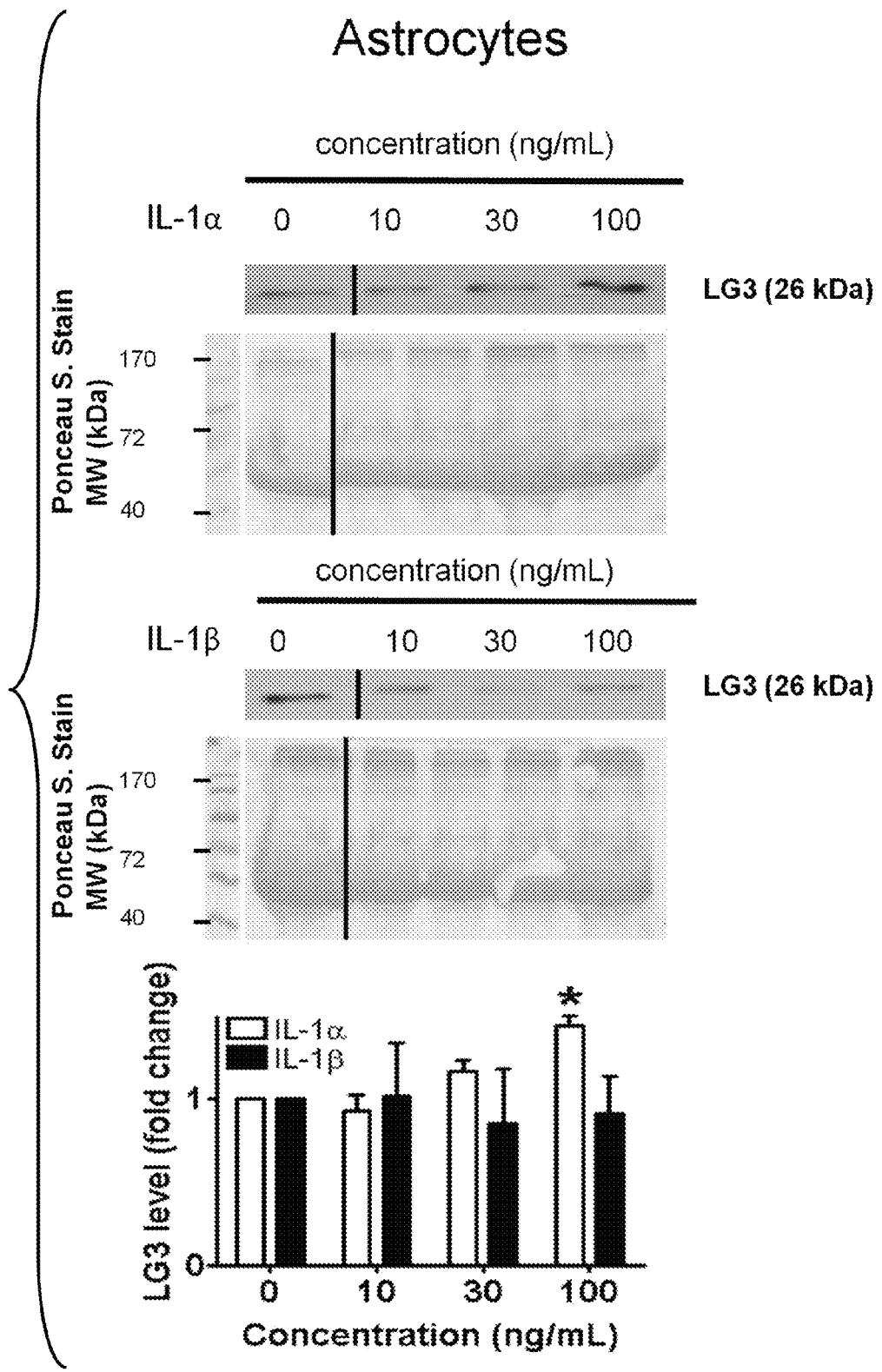

In astrocytes, IL-1β failed to induce changes in LG3 levels at all the concentrations tested (FIG. 26b). By contrast, adding increasing concentrations of IL-1α induced a concentration dependent increase in LG3 release, which was significantly higher after a 100 ng/mL treatment.

Figure 26C:
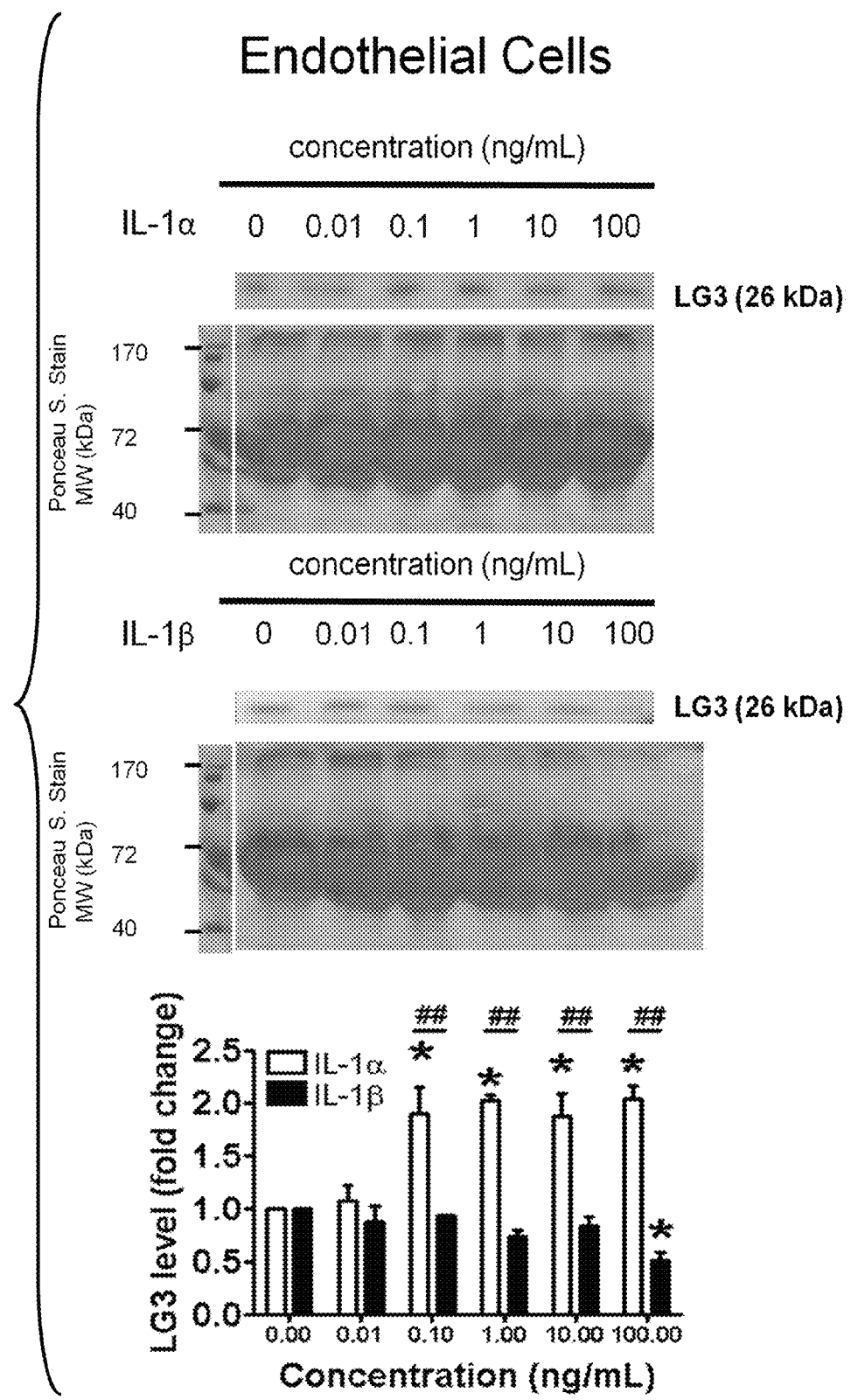
Figure 26D:
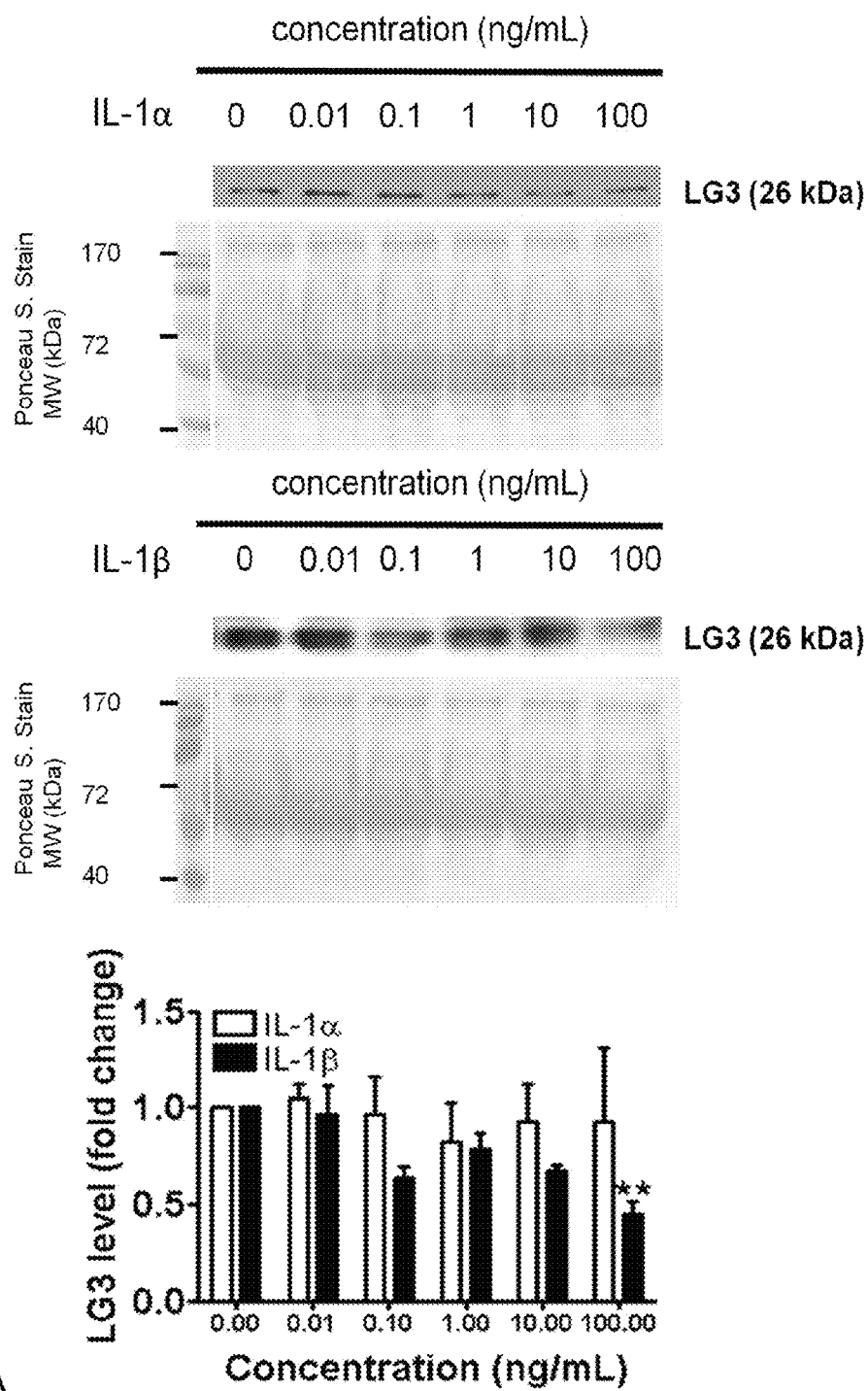

In mouse brain endothelial cells (MBECs) significant differences were found between the effects of IL-1α and IL-1β at concentrations of 0.1-100 ng/ml (FIG. 26c). IL-1α (0.1-100 ng/mL) strongly and significantly induced LG3 release from MBECs (FIG. 26c); IL-1β however failed to induce changes in LG3 levels at 0.01-10 ng/ml (FIG. 26c) but caused a slight, but significant decrease at high concentration (100 ng/mL). Finally, IL-1α had no effect on LG3 levels released by pericyte cultures, but, IL-1β reduced LG3 release at the higher concentration (100 ng/ml).

LG3 Increases Neuronal Survival after OGD and Decreases Brain Endothelial Cell Proliferation In Vitro After investigating the cellular source of increased LG3 levels as a result of ischemic/inflammatory stimuli, we investigated whether increased LG3 levels could have biological activity in the brain after ischemia. Since perlecan Domain V, which is elevated after cerebral ischemia, has been found to be neuroprotective and pro-angiogenic (Lee et al. 2011), we tested the hypothesis that LG3 could regulate cell survival and/or proliferation.

The effect of LG3 on neuronal viability was studied because of their susceptibility to damage due to ischemia/reperfusion (1/R). Fetal cortical neurons were exposed to OGD and then were treated with LG3 or PBS vehicle control. Their viability was measured 72 h later using Alamar blue assays. We found that LG3 treatment resulted in about a 300% increase in neuronal viability compared to PBS treated cells (FIG. 27a). We also studied the effect of LG3 on the proliferation of the hCEMC/D3 brain endothelial cell line. hCEMC/D3 cells treated with LG3 proliferated significantly less than untreated cells (FIG. 27b). In addition to a decrease in proliferation, the brain endothelial cells also showed a "shriveled" morphology in response to LG3 treatment (FIG. 27c).

Discussion

In this study, we observed a significant increase in the generation of the perlecan c-terminal fragment, LG3, in the brain after transient MCAo. The elevation of LG3 levels in the ipsilateral hemisphere occurred within 24 h after ischemia suggesting that events taking place during or immediately after cerebral ischemia cause increased perlecan synthesis/proteolysis. We therefore investigated the effects of ischemia/reperfusion stress and the effect of elevation of cytokines, which takes place within hours of cerebral ischemia (Hill, Gunion-Rinker et al. 1999), on LG3 generation from neurons, astrocytes, brain endothelial cells and pericytes.

OGD May Stimulate the Release of Cysteine Proteases and Degradation of Perlecan Causing Release of LG3

A key factor in cerebral ischemia-induced brain injury and inflammation is reduction in oxygen and glucose supply. Hence, we hypothesized that OGD could be a direct inducer of perlecan proteolysis. Neurons and pericytes were highly responsive during OGD in terms of LG3 release. Brain endothelial cells showed a small increase only during 2 h OGD and astrocytes showed no changes. The increase seen during lower durations of OGD might be due to release of lysosomal proteases and breakdown of already established matrix instead of de novo protein synthesis of perlecan. These results are also in agreement with a previous in vivo study which showed a significant decrease in perlecan positive microvessels 2 h after MCAo which was caused by an increase in the levels of cysteine proteases and hence, proteolysis of perlecan (Fukuda, Fini et al. 2004). Our study shows that neurons (primarily), pericytes and brain endothelial cells may be responsible for such an increase in proteolysis and that merely OGD may initiate the release of proteases.

Cells Release Decreased Levels of LG3 after Longer Exposures to OGD

We also assessed the effects of reperfusion/reoxygenation induced oxidative stress on the generation of LG3. Based on the LG3 levels observed after reperfusion, we could also assess the damage caused to the cells by OGD. Reoxygenation of neurons and astrocyte cultures after 1-2 h of OGD caused substantial increases in LG3 release. This increase in LG3 release during reperfusion after short durations of OGD, by cells present in large numbers in the brain, may partially account for the increased LG3 levels detected in vivo, 1 day after MCAo. Brain pericytes also showed a significant increase in LG3 release during reperfusion after 2 h of OGD.

Interestingly, it appears that longer durations of OGD induce a decrease in LG3 release, as detected in neurons (after 2 h OGD), brain endothelial cells (after 6 and 24 h OGD) and pericytes (after 24 h OGD). Astrocytes, on the other hand, show no such decrease even after exposure to 24 h of OGD. This data for RBE4 endothelial cells and astrocytes is corroborated by the changes in viability seen in these cell types after exposure to various durations of OGD, where astrocytes show no significant decrease in viability even after 24 h of hypoxic OGD (Schmid-Brunclik, Burgi-Taboada et al. 2008; Lee, Chang et al. 2009). For RBE4 endothelial cells, in our OGD model, the decrease in viability after longer durations of OGD/reperfusion was confirmed by lower metabolism of cell medium, as confirmed by lack of change in color of the phenol red ph indicator in the cell medium (data not shown). For neurons, a decrease in viability 24 h after 1 h of OGD has previously been reported (Jones, May et al. 2004). On the other hand, we did not see any significant decrease in neuronal viability 24 h after a 1 hour OGD (data not shown). Given the very short duration of OGD involved, this may represent a difference in experimental setup. Much of cell death caused by OGD is triggered and occurs after the cells are returned to normal conditions (Nakajima, Wakasa et al. 2006). Since we show that dying cells generate lesser amounts of LG3 than healthy cells, our results would seemingly be in contrast with a previous study which showed that apoptotic human umbilical vein endothelial cells (HUVECs) generate greater amounts of LG3(Laplante, Raymond et al. 2006). This discrepancy may be due to the fact that necrosis, rather than apoptosis, forms a major portion of the OGD induced cell death (Gwag, Lobner et al. 1995; Dvoriantchikova, Barakat et al. 2010). Thus, we can collectively conclude that shorter durations of OGD that stress, but do not kill cells of the NVU, lead to an increase in LG3 production, while longer periods of OGD that result in cell death lead to decreased LG3 generation.

An Increase in Levels of LG3 May Partially be Maintained by IL1-α Even 3 Days after Stroke Given that IL-1 is established as a key mediator of inflammation and neuronal injury, we next investigated whether IL-1 could regulate LG3 production by cells associated with the NVU. Both IL-1α and IL-1β induce similar biological actions by binding to the same signaling receptors (Allan, Tyrrell et al. 2005), and have therefore redundant functions (Boutin, LeFeuvre et al. 2001). However, IL-1α and IL-1β have also been found to have clear differential effects (Trebec-Reynolds, Voronov et al. 2010). In agreement with this, we found here that IL-1α and IL-1β have generally opposite effects in neurons and endothelial cells, in that, IL-1α induced strong release of LG3 while IL-1β induced a decrease in LG3 release. Our data strongly correlates with a previous studies which reported that IL-1α increases global perlecan mRNA in the hippocampus and in astrocytes (Garcia de Yebenes, Ho et al. 1999), and we can speculate that IL1-α may cause an increase in LG3 release via an increase in perlecan synthesis.

Both IL-1α and IL-1β are elevated within hours of cerebral ischemia and IL-1α may stay elevated up to 4 days after stroke (Hill, Gunion-Rinker et al. 1999). But, unlike IL-1β, IL-1α is constitutively expressed in the brain (Boutin, LeFeuvre et al. 2001).

Furthermore, IL-1α (but not IL-1β) has been recently shown to be released by blood platelets and induce brain endothelium activation in the ischemic core within 24 h after stroke (Thornton, McColl et al. 2010). Since IL-1α has also previously been shown to be transported across blood-brain barrier (Banks, Kastin et al. 1994), IL1-α is more likely to be present at a higher concentration than IL1-β in the brain. Thus, even though IL-1β is elevated after cerebral ischemia (Hill, Gunion-Rinker et al. 1999), high enough concentrations may not be reached for it to produce an effect since it only decreases LG3 release at high concentrations. IL-1α may, on the other hand, contribute towards maintaining the levels of LG3 released by brain cells, given the sensitivity of cells such as brain endothelial cells to low concentrations of IL-1α, and the possibility of its higher concentrations in the brain, even 3 days after stroke. Additionally, we conclude that pericytes express an IL-1 receptor since they respond to IL-1β.

Increased LG3 Levels have Functional Significance

We observed a beneficial effect of LG3 on neuronal survival. Our group previously showed that LG3 blocks neuronal toxicity induced by amyloid beta through α2β1 integrin binding (Wright, Parham et al. 2010). Here we demonstrate that LG3 may act as an agonist to promote neuronal survival after OGD induced damage. LG3 also causes a small decrease in the proliferation of hCEMC/D3 brain endothelial cells. This is in direct contrast to perlecan DV's enhancement of brain endothelial cell proliferation (Lee, Clark et al, 2011) and may reflect relative differences in their affinities for the perlecan DV pro-angiogenic receptor α5β1 integrin (Clark, Lee et al, submitted manuscript). Furthermore, it is possible that the post-stroke pro-angiogenic activity of DV is regulated by its further proteolytic cleavage yielding the anti-angiogenic LG3.

In summary, we have demonstrated that perlecan LG3 is persistently generated after focal cortical ischemia, provided evidence that specific cells types of the NVU are responsible for the generation of LG3 after OGD or reperfusion, respectively, and demonstrated that IL1a and IL1b differentially affect LG3 production. Finally, we provide evidence that this post ischemia generated LG3 is neuroprotective, suggesting its potential relevance to stroke pathophysiology and hinting at its therapeutic potential.

TABLE 1

Table 1. Measurements of mice (n = 10 per treatment group) taken on post stroke day 1, 2 hours after I.P. injection of PBS (Baseline) or DV (total of 26 hours post-stroke).

| Measured Physiologic Parameters | PBS treated (Mean +/− Standard Deviation) | DV treated (Mean +/− Standard Deviation) |
| --- | --- | --- |
| Systolic blood Pressure (mmHg) | 114.1 +/− 2.4 | 113.9 +/− 3.0 |
| Heart Rate (BPM) | 300 +/− 27.75 | 299.71 +/− 27.17 |
| Breathe Rate (BrPM) | 105.58 +/− 12.85 | 108.62 +/− 13.83 |
| Partial pressure $O_2$ (mmHg) | 165.1 +/− 35.5 | 171.1 +/− 16.1 |
| Partial pressure $CO_2$ (mmHg) | 54.9 +/− 10.9 | 51.1 +/− 1.4 |
| Hematocrit (%) | 34.7 +/− 3.9 | 33.2 +/− 6.5 |
| Sodium (mEq/L) | 150.3 +/− 3.3 | 152.8 +/− 1.5 |
| Potassium (mEq/L) | 6.4 +/− 0.9 | 6.4 +/− 0.8 |
| Ionized Calcium (mg/dL) | 5.2 +/− 0.3 | 5.2 +/− 0.04 |
| Oxygen Saturation % | 98.6 +/− 0.8 | 98.8 +/− 0.4 |
| pH | 7.3 +/− 0.02 | 7.3 +/− 0.1 |
| Partial pressure $O_2$ (mmHg) | 165.1 +/− 35.5 | 171.1 +/− 16.1 |
| Partial pressure $CO_2$ (mmHg) | 54.9 +/− 10.9 | 51.1 +/− 1.4 |
| Hematocrit (%) | 34.7 +/− 3.9 | 33.2 +/− 6.5 |
| Partial pressure $O_2$ (mmHg) | 165.1 +/− 35.5 | 171.1 +/− 16.1 |

No significant differences in any of these parameters was noted between PBS and DV treatment.
Abbreviations: mmHg = millimeters of mercury, BPM = beats per minute, BrPM = breath's per minute, mEq/L = milli-equivalents per liter, mg/dL = milligrams per deciliter.

REFERENCES

1. Lo, E., Dalkara, T., & Moskowitz, M. Mechanisms, challenges and opportunities in stroke. *Nat Rev Neurosci* 4, 399-415 (2003).
2. Lo, E. H. A new penumbra: transitioning from injury into repair after stroke. *Nat Med* 14, 497-500 (2008).
3. Castellanos, M. & Sobrino, T. C. J. Evolving paradigms for neuroprotection: molecular identification of ischemic penumbra. *Cerebrovasc Dis* 21, 71-79 (2006).
4. Zheng, Z., Zhai, H., Steinberg, G., & Yenari, M. Cellular and molecular events underlying ischemia induced neuronal apoptosis. *Drug News Perspect* 16, 497-503 (2003).
5. Ohab, J. J., Fleming, S., Blesch, A., & Carmichael, S. T. A Neurovascular Niche for Neurogenesis after Stroke. *J. Neurosci.* 26, 13007-13016 (2006).
6. Krupinski, J., Kaluza, J., Kumar, P., Kumar, S., & Wang, J. Some remarks on the growth-rate and angiogenesis of microvessels in ischemic stroke. Morphometric and immunocytochemical studies. *Patol Pol* 44, 203-209 (1993).

7. Krupinski, J., Kaluza, J., Kumar, P., Kumar, S., & Wang, J. M. Role of angiogenesis in patients with cerebral ischemic stroke. *Stroke* 25, 1794-1798 (1994).
8. Jones, N., Iljin, K., Dumont, D., & Alitalo, K. Tie receptors: new modulators of angiogenic and lymphangiogenic responses. *Nat Rev Mol Cell Biol* 2, 257-267 (2001).
9. Stumm, R. et al. A dual role for the SDF-1/CXCR4 chemokine receptor system in adult brain: isoform-selective regulation of SDF-1 expression modulates CXCR4-dependent neuronal plasticity and cerebral leukocyte recruitment after focal ischemia. *J Neurosci* 22, 5865-5878 (2002).
10. Guo, S. et al. Neuroprotection via matrix-trophic coupling between cerebral endothelial cells and neurons. *PNAS* 105, 7582-7587 (2008).
11. Li, Q., Ford, M. C., Lavik, E. B., & Madri, J. A. Modeling the neurovascular niche: VEGF- and BDNF-mediated cross-talk between neural stem cells and endothelial cells: an in vitro study. *J Neurosci Res.* 84, 1656-1668 (2006).
12. Arai, K., Guang, J., Navaratna, D., & Lo, E. Brain angiogenesis in developmental and pathological processes: neurovascular injury and angiogenic recovery after stroke. *FEBS Journal* 276, 4644-4652 (2009).
13. Chen, J., Cui, X., Zacharek, A., & Chopp, M. Increasing Ang1/Tie2 expression by simvastatin treatment induces vascular stabilization and neuroblast migration after stroke. *J Cell Mol Med* 13, 1348-1357 (2008).
14. Kozak, A. et al. Candesartan augments ischemia-induced proangiogenic state and results in sustained improvement after stroke. *Stroke* 40, 1870-1876 (2009).
15. Yao, R., Zhang, L., Wang, W., & Li, L. Cornel iridoid glycoside promotes neurogenesis and angiogenesis and improves neurological function after focal cerebral ischemia. *Brain Res Bull* 79, 69-76 (2009).
16. Chen, J. et al. Atorvastatin induction of VEGF and BDNF promotes brain plasticity after stroke in mice. *J Cereb Blood Flow Metab* 25, 281-290 (2005).
17. The STEPS Participants Stem cell therapies as an emerging paradigm in stroke: Bridging basic and clinical science for cellular and neurogenic factor therapy in treating stroke. *Stroke* 40, 510-515 (2009).
18. Zhang, Z. G. et al. VEGF enhances angiogenesis and promotes blood-brain barrier leakage in the ischemic brain. *J Clin Invest* 106, 829-838. 2000.
19. Hansen, T., Moss, A., & Brindle, N. Vascular endothelial growth factor and angiopoietins in neurovascular regeneration and protection following stroke. *Curr Neurovasc Res* 5, 235-244 (2008).
20. Fagan, S., Hess, D., Hohnadel, E., Pollock, D., & Ergul, A. Targets for vascular protection after acute ischemic stroke. *Stroke* 35, 2220-2225 (2004).
21. Sun, Y. et al. VEGF-induced neuroprotection, neurogenesis, and angiogenesis after focal cerebral ischemia. *J Clin Invest* 111, 1843-1851. 2010.
22. Bix, G. & Iozzo, R. V. Matrix revolutions: "tails" of basement-membrane components with angiostatic functions. *Trends Cell Biol.* 15, 52-60 (2005).
23. Fukuda, S. et al. Focal Cerebral Ischemia Induces Active Proteases That Degrade Microvascular Matrix. *Stroke* 35, 998-1004 (2004).
24. Giros, A., Morante, J., Gil-Sanz, C., Fairen, A., & Costell, M. Perlecan controls neurogenesis in the developing telencephalon. *BMC Developmental Biology* 7, 29 (2007).
25. Bix, G. et al. Endorepellin causes endothelial cell disassembly of actin cytoskeleton and focal adhesions through the $\alpha 2\beta 1$ integrin. *J. Cell Biol.* 166, 97-109 (2004).
26. Bix, G. et al. Endorepellin in vivo: targeting the tumor vasculature and retarding cancer growth and metabolism. *J. Natl. Cancer Inst.* 98, 1634-1646 (2006).
27. McGeer, P. L., Zhu, S. G., & Dedhar, S. Immunostaining of human brain capillaries by antibodies to very late antigens. *Journal of Neuroimmunology* 26, 213-218 (1990).
28. Sharkey, J., Richie, I., & Kelley, P. Perivascular microapplication of endothelin-1: a new model of focal cerebral ischaemia in the rat. *J. Cereb. Blood Flow Metab.* 13, 865-871 (1993).
29. Moyanova, S., Kortenska, L., & Mitreva, R. Endothelin-1-induced cerebral ischemia: Effects of ketanserin and MK-801 on limb placing in rats. *International Journal of Neuroscience* 117, 1361-1381 (2007).
30. Macrae, C., Robinson, M., Graham, D., Reid, J., & McCulloch, J. Endothelin-1-induced reductions in cerebral blood flow: dose dependency, time course, and neuropathological consequences. *J. Cereb. Blood Flow Metab.* 13, 276-284 (1993).
31. Shimoda, M., Oda, S., Mamata, Y., Ryuichi, T., & Sata, O, Surgical indications in patients with an intracerebral hemorrhage due to ruptured middle cerebral artery aneurysm. *J Neurosurg* 87, 170-175. 1997.
32. Shen, J. et al. Neurogenesis after primary intracerebral hemorrhage in adult human brain. *J Cereb Blood Flow Metab* 28, 1460-1468. 2008.
33. Waxham, M. N., Grotta, J. C., Silva, A. J., Roger, S., & Jaroslaw, A. Ischemia-Induced Neuronal Damage: A Role for Calcium/Calmodulin-Dependent Protein Kinase II. *J Cereb Blood Flow Metab* 16, 1-6 (1996).
34. Aronowski, J., Grotta, J. C., Strong, R., & Waxham, M. N. Interplay Between the Gamma Isoform of PKC and Calcineurin in Regulation of Vulnerability to Focal Cerebral Ischemia. *J Cereb Blood Flow Metab* 20, 343-349 (2000).
35. Bix, G. & Iozzo, R. Novel interactions of perlecan: unraveling perlecan's role in angiogenesis. *Micro. Res. Techniq.* 71, 339-348 (2008).
36. Iozzo, R. V. Basement membrane proteoglycans: from cellar to ceiling. *Nature Reviews Mol Cell Biol.* 6, 646-656 (2005).
37. Bix, G. et al. Endorepellin, the C-terminal angiostatic module of perlecan, enhances collagen-platelet responses via the $\alpha 2\beta 1$ integrin receptor. *Blood,* 109, 3745-3748 (2007).
38. Sakai, T. et al. Plasma fibronectin supports neuronal survival and reduces brain injury following transient focal cerebral ischemia but is not essential for skin-wound healing and hemostasis. *Nature Medicine* 7, 324-330 (2001).
39. Rodgers, K. D., Sasaki, T., Aszodi, A., & Jacenko, O. Reduced perlecan in mice results in chondrodysplasia resembling Schwartz-Jampel syndrome. *Hum. Mol. Genet.* 16, 515-528 (2007).
40. Stum, M., Davoine, C. S., Fontaine, B., & Nicole, S. Schwartz-Jampel syndrome and perlecan deficiency. *Acta Myol.* 22, 89-92 (2005).
41. Arikawa-Hirasawa, E. et al. Dyssegmental dysplasia, Silverman-Handmaker type, is caused by functional null mutations of the perlecan gene. *Nature Genet.* 27, 431-434 (2001).
42. Schallert, T., Fleming, S., Leasure, J. L., Tillerson, J. L., & Bland, S. T. CNS plasticity and assessment of forelimb sensorimotor outcome in unilateral rat models of stroke, cortical ablation, parkinsonism and spinal cord injury. *Neuropharmicology* 39, 777-787. 2000.
43. Woodlee, M. et al. Testing forelimb placing "across the midline" reveals distinct, lesion-dependent patterns of recovery in rats. *Exp. Neurol.* 191, 310-317 (2005).

44. Milner, R. et al. Responses of Endothelial Cell and Astrocyte Matrix-Integrin Receptors to Ischemia Mimic Those Observed in the Neurovascular Unit. *Stroke* 39, 191-197 (2008).
45. Brown, J. C., Sasaki, T., Gohring, W., Yamada, E., & Timpl, R. The C-terminal domain V of perlecan promotes β1 integrin-mediated cell adhesion, binds heparin, nidogen and fibulin-2 and can be modified by glycosaminoglycans. *Eur. J. Biochem.* 250, 39-46 (1997).
46. Mongiat, M., Sweeney, S., San Antonio, J. D., Fu, J., & Iozzo, R. V. Endorepellin, a novel inhibitor of angiogenesis derived from the C terminus of perlecan. *J. Biol. Chem.* 278, 4238-4249 (2003).
47. Iozzo, R. V. Perlecan: a gem of a proteoglycan. *Matrix Biol.* 14, 203-208 (1994).
48. Corti, A., Curnis, F., Arap, W., & Pasqualini, R. The neovasculature homing motif NGR: more than meets the eye. *Blood,* 112, 2628-35 (2008).
49. Francis, S. E. et al. Central Roles of {alpha}5{beta}1 Integrin and Fibronectin in Vascular Development in Mouse Embryos and Embryoid Bodies. *Arterioscler Thromb Vasc Biol* 22, 927-933 (2002).
50. Milner, R. et al. Increased expression of fibronectin and the [alpha]5[beta]1 integrin in angiogenic cerebral blood vessels of mice subject to hypobaric hypoxia. *Molecular and Cellular Neuroscience,* 38, 43-52 (2008)
51. Weber, C. C. et al. Effects of Protein and Gene Transfer of the Angiopoietin-1 Fibrinogen-like Receptor-binding Domain on Endothelial and Vessel Organization. *Journal of Biological Chemistry* 280, 22445-22453 (2005).
52. Koivunen, E., Wang, B., & Ruoslahti, E. Isolation of a highly specific ligand for the alpha5 beta 1 integrin from a phage display library. *J. Cell Biol.* 124, 373-380 (1994).
53. Noonan, D. M. et al. The complete sequence of perlecan, a basement membrane heparan sulfate proteoglycan, reveals extensive similarity with laminin A chain, low density lipoprotein-receptor, and the neural cell adhesion molecule. *J. Biol. Chem.* 266, 22939-22947 (1991).
54. Murdoch, A. D., Dodge, G. R., Cohen, I., Tuan, R. S., & Iozzo, R. V. Primary structure of the human heparan sulfate proteoglycan from basement membrane (HSPG2/perlecan). A chimeric molecule with multiple domains homologous to the low density lipoprotein receptor, laminin, neural cell adhesion molecules, and epidermal growth factor. *J. Biol. Chem.* 267, 8544-8557 (1992).
55. Curnis, F. et al. Isoaspartate-Glycine-Arginine: A New Tumor Vasculature-Targeting Motif. *Cancer Res* 68, 7073-7082 (2008).
56. Curnis, F. et al. Spontaneous Formation of L-Isoaspartate and Gain of Function in Fibronectin. *Journal of Biological Chemistry* 281, 36466-36476 (2006).
57. Xu, J., Maurer, L., Hoffman, B., Annis, D., & Mosher, D. F. IsoDGR sequences do not mediate binding of fibronectin N-terminal modules to adherent fibronectin-null fibroblasts. *J Biol Chem*, in press. (2010).
58. Gonzalez, E. M. et al. BMP-1/Tolloid-like metalloproteases process endorepellin, the angiostatic C-terminal fragment of perlecan. *J. Biol. Chem.* 280, 7080-7087 (2005).
59. Nystrom, A. et al. Role of tyrosine phosphatase SHP-1 in the mechanism of endorepellin angiostatic activity. *Blood* 114, 4897-4906 (2009).
60. Kaji, T. et al. The vascular endothelial growth factor VEGF165 induces perlecan synthesis via VEGF receptor-2 in cultured human brain microvascular endothelial cells. *Biochimica et Biophysica Acta (BBA)—General Subjects* 1760, 1465-1474 (2006).
61. Kim, S., Bell, K., Mousa, S. A., & Varner, J. A. Regulation of Angiogenesis in Vivo by Ligation of Integrin {alpha}5{beta}1 with the Central Cell-Binding Domain of Fibronectin. *American Journal of Pathology* 156, 1345-1362 (2000).
62. Al Ahmad, A., Gassman, M., & Ogunshola, O. O. Maintaining blood-brain barrier integrity: pericytes perform better than astrocytes during prolonged oxygen deprivation. *J Cell Physiol* 218, 612-622. 2009.
63. Drevs, J. et al. PTK787/ZK 222584, a Specific Vascular Endothelial Growth Factor-Receptor Tyrosine Kinase Inhibitor, Affects the Anatomy of the Tumor Vascular Bed and the Functional Vascular Properties as Detected by Dynamic Enhanced Magnetic Resonance Imaging. *Cancer Res* 62, 4015-4022 (2002).
64. Clark, K. et al. A specific {alpha}5 {beta}1-integrin conformation promotes directional integrin translocation and fibronectin matrix formation. *J Cell Sci* 118, 291-300 (2005).
65. Berra, E. et al. Signaling angiogenesis via p42/p44 MAP kinase and hypoxia. *Biochemical Pharmacology* 60, 1171-1178. 2000.
66. Shee, W. L., Ong, W. Y., & Lim, T. M. Distribution of perlecan in mouse hippocampus following intracerebroventricular kainate injections. *Brain Research* 799, 292-300 (1998).
67. Daneman, R. et al. Wnt/beta-catenin signaling is required for CNS, but not non-CNS angiogenesis. *PNAS* 102, 641-646 (2009).
68. Pilorget, A. et al. Inhibition of angiogenic properties of brain endothelial cells by platelet-derived sphingosine-1-phosphate. *Journal of Cerebral blood Flow & Metabolism* 25, 1171-1182 (2005).
69. Schmidt, A., Addicks, K., & Bloch, W. Opposite effects of endostatin on different endothelial cells. *Cancer Biology and Therapy* 3, 1162-1166 (2004).
70. Milner, R. & Campbell, I. Developmental regulation of beta1 integrins during angiogenesis in the central nervous system. *Molecular and Cellular Neuroscience* 20, 616-626 (2002).
71. Mould, A. P., Burrows, L., & Humphries, M. J. Identification of Amino Acid Residues That Form Part of the Ligand-binding Pocket of Integrin alpha5beta 1. *Journal of Biological Chemistry* 273, 25664-25672 (1998).
72. Appella, E., Weber, I. T., & Blasi, F. Structure and function of epidermal growth factor-like regions in proteins. *FEBS (Lett)* 231, 1-4 (1988).
73. Wouters, M. et al. Evolution of distinct EGF domains with specific functions. *Protein Sci.* 14, 1091-1103 (2005).
74. Troup, S. et al. Reduced expression of the small leucine-rich proteoglycans, lumican, and decorin is associated with poor outcome in node-negative invasive breast cancer. *Clin. Cancer Res,* 9, 207-214 (2003).
75. Woodall, B. P. et al. Integrin alpha2beta1 Is the Required Receptor for Endorepellin Angiostatic Activity. *Journal of Biological Chemistry* 283, 2335-2343 (2008).
76. Suzuki, S., Brown, C., & Wise, P. Neuroprotective effects of estrogens following ischemic stroke. *Front Neuroendocrinol* 30, 201-211 (2009).
77. Hermann, D. M. & Zechariah, A. Implications of vascular endothelial growth factor for postischemic neurovascular remodeling. *J Cereb Blood Flow Metab* 29, 1620-1643. 2009.
78. Ferraran, N., Gerber, H. P., & LeCouter, J. The biology of VEGF and its receptors. *Nat Med* 9, 669-676. 2003.
79. Fischer, S., Wobben, M., Marti, H. H., Renz, D., & Schaper, W. Hypoxia-induced hyperpermeability in brain 79. microvessel endothelial cells involves VEGF-mediated changes in the expression of zonula occludens-1. *Microvasc Res.* 63, 70-80 (2002).
80. Al Ahmad, A., Gassman, M., & Ogunshola, O. Maintaining blood-brain barrier integrity: pericytes perform better than astrocytes during prolonged oxygen deprivation. *J Cell Physiol.* 218, 612-622 (2009).
81. Snapyan, M. et al. Vasculature Guides Migrating Neuronal Precursors in the Adult Mammalian Forebrain via Brain-Derived Neurotrophic Factor Signaling. *J. Neurosci.* 29, 4172-4188 (2009).
82. Li, Q., Ford, M., Lavik, E., & Madri, J. Modeling the neurovascular niche:VEGF- and BDNF-mediated crosstalk between neural stem cells and endothelial cells: an in vitro study. *J Neurosci Res* 84, 1656-1668 (2006).
83. Sharma, H. Neurotrophic factors attenuate microvascular permeability disturbances and axonal injury following trauma to rat spinal cord. *Acta Neurochir Suppl* 86, 383-388 (2003).
84. Yang, R. et al. Substantially Attenuated Hemodynamic Responses to *Escherichia coli*-Derived Vascular Endothelial Growth Factor Given by Intravenous Infusion Compared with Bolus Injection. *Journal of Pharmacology and Experimental Therapeutics* 284, 103-110 (1998).
85. Yang, R. et al. Effects of vascular endothelial growth factor on hemodynamics and cardiac performance. *Cardiovasc Pharmacol* 27, 838-844. 1996.
86. Mousa, S. A., Lorelli, W., & Campochiaro, P. A. Role of hypoxia and extracellular matrix-integrin binding in the modulation of angiogenic growth factors secretion by retinal pigmented epithelial cells. *J Cellular Biochemistry* 74, 135-143. 1999.
87. Alghisi, G. C. & Ruegg, C. Vascular integrins in tumor angiogenesis: mediators and therapeutic targets. *Endothelium.* 13, 113-135 (2006).
88. Chetty, C., Lakka, S. S., Bhoopathi, P., & Rao, J. S. MMP-2 alters VEGF expression via alphaVbeta3 integrin-mediated PI3K/AKT signaling in A549 lung cancer cells. *Int J. Cancer.* Epub ahead of print, (2009).
89. Forsythe, J. A. et al. Activation of vascular endothelial growth factor gene transcription by hypoxia-inducible factor 1. *Mol Cell Biol.* 16, 4604-4613 (1996).
90. Hudson, C. C. et al. Regulation of hypoxia-inducible factor 1alpha expression and function by the mammalian target of rapamycin. *Mol Cell Biol.* 22, 7004-7014 (2002).
91. Zhong, H. et al. Modulation of hypoxia-inducible factor 1 alpha expression by the epidermal growth factor/phosphatidylinositol 3-kinase/PTEN/AKT/FRAP pathway in human prostate cancer cells: implications for tumor angiogenesis and therapeutics. *Cancer Res.* 60, 1541-1545 (2000).
92. Ye, X. et al. ERK1/2 signaling pathways involved in VEGF release in diabetic rat retina. *Investigative Ophthalmology & Visual Science*, in press online. (2010).
93. Berra, E., Pages, G., & Pouyssegur, J. MAP kinases and hypoxia in the control of VEGF expression. *Cancer and Metastasis Reviews* 19, 139-146. (2000).
94. Ryu, M. H., Park, H. M., Chung, J., Lee, C. H., & Park, H. R. Hypoxia-inducible factor-1alpha mediates oral squamous cell carcinoma invasion via upregulation of alpha5 integrin and fibronectin. *Biochem Biophys Res Commun* 393, 11-15 (2010).
95. Wang, L., Zhang, Z., Wang, Y., Zhang, R., & Chopp, M. Treatment of Stroke With Erythropoietin Enhances Neurogenesis and Angiogenesis and Improves Neurological Function in Rats. *Stroke* 35, 1732-1737 (2004).
96. Deng, Y. et al. Intravenously administered BMSCs reduce neuronal apoptosis and promote neuronal proliferation through the release of VEGF after stroke in rats. *Neurol Res* epub ahead of print, (2009).
97. Hicks, A. & Jolkkonen, J. Challenges and possibilities of intravascular cell therapy in stroke. *Acta Neurobiol* 69, 1-10 (2009).
98. Bayless, K. J., Kwak, H. I., & Su, S. C. Investigating endothelial invasion and sprouting behavior in three-dimensional collagen matrices. *Nat. Protocols* 4, 1888-1898 (2009).
99. Aronowski, J., Cho, K., Strong, R., & Grotta, J. Neurofilament proteolysis after focal ischemia; when do cells die after experimental stroke? *J Cereb Blood Flow Metab* 19, 652-660 (1999).
100. Lundy, E., Solik, B., & Frank, R. Morphometric evaluation of brain infarcts in rats and gerbils. *J Pharmacol Methods* 16, 201-214 (1986).
101. Li, J., Henman, M., Tatlisumak, T., Shaw, G., & Doyle, K. The pre-ischaemic neuroprotective effects of N1-dansyl-spermine in a transient focal cerebral ischaemia model in mice. *Brain Research* 1055, 180-185 (2005).
102. O'Reilly, M. S. et al. Endostatin: an endogenous inhibitor of angiogenesis and tumor growth. *Cell* 88, 277-285 (1997).
103. Roux, F. et al. Regulation of gamma-glutamyl transpeptidase and alkaline phosphatase activities in immortalized rat brain microvessel endothelial cells. *Journal of Cell Physiology* 159, 101-113 (1994).
104. Sanderson, L., Khan, A., & Thomas, S. Distribution of suramin, an antitrypanosomal drug, across the blood-brain and blood-cerebrospinal fluid interfaces in wild-type and P-glycoprotein transporter-deficient mice. *Antimicrob. Agents Chem.* 51, 3136-3146. (2007).
105. Kumai, Y. et al. Postischemic gene transfer of soluble Flt-1 protects against brain ischemia with marked attenuation of blood-brain barrier permeability. *J Cereb Blood Flow Metab* 27, 1152-1160 (2006).
106. Ogunshola, O. O., Djonov, V., Staudt, R., Vogel, J., & Gassmann, M. Chronic excessive erythrocytosis induces endothelial activation and damage in mouse brain. *Am J Physiol Regul Integr Comp Physiol* 290, R678-R684 (2006),
107. Strbian, D. et al. The blood-brain barrier is continuously open for several weeks following transient focal cerebral ischemia. *Neuroscience* 153, 175-181 (2008).
108. Brittingham, R. et al. Single amino acid substitutions in procollagen VII affect early stages of assembly of anchoring fibrils. *J Biol Chem* 280, 191-198. (2005).
109. Myszka, D. G. & Morton, T. A. CLAMP: a biosensor kinetic data analysis program. *Trends Biochem Sci* 23, 149-190. (1998).
110. Shehadah, A., Chen, J., Zacharek, A., Yisheng, C., Ion, M., Roberts, C., Kapke, A., Chopp, M. Niaspan treatment induces neuroprotection after stroke. *Neurobiol. Dis.*, in press (2010).
111. Allan, S. M., P. J. Tyrrell, et al. (2005). "Interleukin-1 and neuronal injury." *Nat Rev Immunol* 5(8): 629-640.
112. Banks, W. A., A. J. Kastin, et al. (1994). "Blood-borne interleukin-1 alpha is transported across the endothelial blood-spinal cord barrier of mice." *J Physiol* 479 (Pt 2): 257-264.
113. Bix, G., J. Fu, et al. (2004). "Endorepellin causes endothelial cell disassembly of actin cytoskeleton and focal adhesions through alpha2beta1 integrin." *J Cell Biol* 166 (1): 97-109.

114. Boutin, H., R. A. LeFeuvre, et al. (2001). "Role of IL-1 alpha and IL-1beta in ischemic brain damage." *J Neurosci* 21(15): 5528-5534.
115. Chow, J., O. Ogunshola, et al. (2001). "Astrocyte-derived VEGF mediates survival and tube stabilization of hypoxic brain microvascular endothelial cells in vitro." *Brain Res Dev Brain Res* 130(1): 123-132.
116. Dore-Duffy, P. (2003). "Isolation and characterization of cerebral microvascular pericytes." *Methods Mol Med* 89: 375-382.
117. Dvoriantchikova, G., D. J. Barakat, et al. (2010). "Liposome-delivered ATP effectively protects the retina against ischemia-reperfusion injury." *Mol Vis* 16: 2882-2890.
118. Garcia de Yebenes, E., A. Ho, et al. (1999). "Regulation of the heparan sulfate proteoglycan, perlecan, by injury and interleukin-1alpha." *J Neurochem* 73(2): 812-820.
119. Gwag, B. J., D. Lobner, et al. (1995). "Blockade of glutamate receptors unmasks neuronal apoptosis after oxygen-glucose deprivation in vitro." *Neuroscience* 68(3): 615-619.
120. Harris, J., H. Lee, et al. (2007). "Preparing e18 cortical rat neurons for compartmentalization in a microfluidic device." *J Vis Exp*(8): 305.
121. Hill, J. K., L. Gunion-Rinker, et al. (1999). "Temporal modulation of cytokine expression following focal cerebral ischemia in mice." *Brain Res* 820(1-2): 45-54.
122. Jones, P. A., G. R. May, et al. (2004). "Apoptosis is not an invariable component of in vitro models of cortical cerebral ischaemia." *Cell Res* 14(3): 241-250.
123. Kim, J. A., N. D. Tran, et al. (2006). "Brain endothelial hemostasis regulation by pericytes." *J Cereb Blood Flow Metab* 26(2): 209-217.
124. Laplante, P., M. A. Raymond, et al. (2006). "Perlecan proteolysis induces an alpha2beta1 integrin- and Src family kinase-dependent anti-apoptotic pathway in fibroblasts in the absence of focal adhesion kinase activation." *J Biol Chem* 281(41): 30383-30392.
125. Lee, H. T., Y. C. Chang, et al. (2009). "VEGF-A/VEGFR-2 signaling leading to cAMP response element-binding protein phosphorylation is a shared pathway underlying the protective effect of preconditioning on neurons and endothelial cells." *J Neurosci* 29(14): 4356-4368.
126. Lee, B., Clarke, D., Ahmad, A., Kahle, M., Parham, C., Auckland, L., Shaw, C., Fidanboylu, M., Orr, A., Ogunshola, O., Fertala, A., Thomas, S., Bix, G. (2011) Perlecan domain V is neuroprotective and proangiogenic following ischemic stroke in rodents, JCL in press.
127. Nakajima, T., T. Wakasa, et al. (2006). "Dual inhibition of protein phosphatase-1/2A and calpain rescues nerve growth factor-differentiated PC 12 cells from oxygen-glucose deprivation-induced cell death." J Neurosci Res 83(3): 459-468.
128. Romero-Calvo, I., B. Ocon, et al. (2010). "Reversible Ponceau staining as a loading control alternative to actin in Western blots." Anal Biochem 401(2): 318-320.
129. Schmid-Brunclik, N., C. Burgi-Taboada, et al. (2008). "Astrocyte responses to injury: VEGF simultaneously modulates cell death and proliferation." Am J Physiol Regul Integr Comp Physiol 295(3): R864-873.
130. Song, L. and J. S. Pachter (2003). "Culture of murine brain microvascular endothelial cells that maintain expression and cytoskeletal association of tight junction-associated proteins." In Vitro Cell Dev Biol Anim 39(7): 313-320.
131. Thornton, P., B. W. McColl, et al. (2010). "Platelet interleukin-1 alpha drives cerebrovascular inflammation." Blood 115(17): 3632-3639.
132. Trebec-Reynolds, D. P., I. Voronov, et al. (2010). "IL-1alpha and IL-1 beta have different effects on formation and activity of large osteoclasts." J Cell Biochem 109(5): 975-982.
133. Weksler, B. B., E. A. Subileau, et al. (2005). "Blood-brain barrier-specific properties of a human adult brain endothelial cell line." FASEB J 19(13): 1872-1874.
134. Wright, S., C. Parham, et al. (2010). "Perlecan domain V inhibits alpha2 integrin-mediated amyloid-beta neurotoxicity." Neurobiol Aging.

I claim:

1. A method of treating stroke, traumatic brain injury (TBI) or spinal cord injury (SCI) comprising administering to a subject having had a stroke, TBI or SCI a first composition comprising a pharmaceutically acceptable excipient and:
   a) perlecan domain V (SEQ ID NO: 1; DV);
   b) a fusion protein comprising DV;
   c) a fragment of SEQ ID NO: 1, said fragment:
      (i) consisting of SEQ ID NO: 2; or
      (ii) consisting essentially of SEQ ID NO: 2; or
   d) a fusion protein comprising a heterologous sequence operably fused to a fragment of SEQ ID NO: 1, said fragment:
      (i) consisting of SEQ ID NO: 2; or
      (ii) consisting essentially of SEQ ID NO: 2; wherein said subject is administered the first composition alone or in combination with a second composition.

2. The method according to claim 1, wherein said first composition is administered to the subject within 168, 144, 120, 96, 72, 48, 24, 12, 6, 2, 1 hour or 15 minutes of a stroke, TBI or SCI.

3. The method according to claim 1, wherein said first composition comprises a pharmaceutically acceptable excipient and a polypeptide consisting of SEQ ID NO: 1.

4. The method according to claim 3, wherein said first composition is administered to a subject having had a stroke.

5. The method according to claim 3, wherein said first composition is administered to a subject having had a TBI.

6. The method according to claim 3, wherein said first composition is administered to a subject having had an SCI.

7. The method according to claim 1, wherein said first composition comprises a pharmaceutically acceptable excipient and a fusion protein comprising a heterologous sequence operably linked to SEQ ID NO: 1.

8. The method according to claim 7, wherein said first composition is administered to a subject having had a stroke.

9. The method according to claim 7, wherein said first composition is administered to a subject having had a TBI.

10. The method according to claim 7, wherein said first composition is administered to a subject having had an SCI.

11. The method according to claim 1, wherein said first composition comprises a fragment of SEQ ID NO: 1, said fragment consisting of SEQ ID NO: 2.

12. The method according to claim 11, wherein said first composition is administered to a subject having had a stroke.

13. The method according to claim 11, wherein said first composition is administered to a subject having had a TBI.

14. The method according to claim 11, wherein said first composition is administered to a subject having had an SCI.

15. The method according to claim 1, wherein said first composition comprises a pharmaceutically acceptable excipient and a polypeptide consisting essentially of SEQ ID NO: 2.

16. The method according to claim 15, wherein said first composition is administered to a subject having had a stroke.

17. The method according to claim 15, wherein said first composition is administered to a subject having had a TBI.

18. The method according to claim 15, wherein said first composition is administered to a subject having had an SCI.

19. The method according to claim 1, wherein said subject has a stroke and said subject is treated with a first composition according to claim 1 alone or in combination with a second composition comprising a pharmaceutically acceptable excipient and an agent selected from a thrombolytic agent, an anti-inflammatory agent, a thrombin-like enzyme, a thrombin inhibitor, an anticoagulant; an anti-platelet drug, a glycoprotein IIb/IIIa inhibitor, a glycosaminoglycan; a caspase inhibitor; an anti-oxidant, niacin, extended release forms of niacin, a corticosteroid, a neuroprotectant, an anti-CD 18 antibody, IL-1 a; an anti-CD11a antibody, an anti-ICAM-1 antibody; an anti-VLA-4 antibody, an anti-TWEAK antibody, or an anti-TWEAK-R antibody.

20. The method according to claim 19, wherein said subject is treated with a first composition according to claim 1, alone.

21. The method according to claim 19, wherein said subject is treated with a combination of said first and said second compositions.

22. The method according to claim 21, wherein said first and second compositions are administered separately, sequentially or contemporaneously.

23. The method according to claim 21, wherein said first and second compositions are administered as a combined composition.

24. The method according to claim 1, wherein said subject has suffered a TBI or SCI and is treated with a first composition according to claim 1 alone or in combination with a second composition comprising a pharmaceutically acceptable excipient and a corticosteroid.

25. The method according to claim 1, wherein said subject is a human.

26. The method according to claim 1, wherein said treatment restores motor function.

27. The method according to claim 1, wherein said first composition comprises a fusion protein comprising a heterologous sequence operably fused to the fragment consisting of SEQ ID NO: 2.

28. The method according to claim 27, wherein said first composition is administered to a subject having had a stroke.

29. The method according to claim 27, wherein said first composition is administered to a subject having had a TBI.

30. The method according to claim 27, wherein said first composition is administered to a subject having had an SCI.

31. The method according to claim 1, wherein said first composition comprises a fusion protein comprising a heterologous sequence operably fused to a polypeptide consisting essentially of SEQ ID NO: 2.

32. The method according to claim 1, wherein said first composition is administered to a subject having had a stroke.

33. The method according to claim 1, wherein said first composition is administered to a subject having had a TBI.

34. The method according to claim 1, wherein said first composition is administered to a subject having had an SCI.

* * * * *

UNITED STATES PATENT AND TRADEMARK OFFICE
CERTIFICATE OF CORRECTION

PATENT NO. : 9,072,713 B2
APPLICATION NO. : 13/175518
DATED : July 7, 2015
INVENTOR(S) : Bix It is certified that error appears in the above-identified patent and that said Letters Patent is hereby corrected as shown below:

In the specification

Column 3,
Line 27, "(TIC negative)." should read --(TTC negative).--.

Column 4,
Line 7, "5 p.m." should read --5 μm.--.
Line 29, "for pin" should read --for pln--.
Line 31, "WI DV" should read --WT DV--.

Column 5,
Line 8, "after hours" should read --after 48 hours--.

Column 8,
Line 36, "HIF-1 a" should read --HIF-1α--.

Column 24,
Line 40, "Asci" should read --Asc1--.
Line 65, "(Abeam)" should read --(Abcam)--.

Column 26,
Line 28, "(Abeam," should read --(Abcam,--.
Line 32, "(Abeam)," should read --(Abcam),--.
Line 34, "(Abeam)," should read --(Abcam),--.
Line 47, "Cary II" should read --Carv II--.
Line 53, "(TIC)" should read --(TTC)--.

Column 30,
Line 5, "central gyms)" should read --central gyrus)--.

Signed and Sealed this
Ninth Day of February, 2016

Michelle K. Lee
*Director of the United States Patent and Trademark Office*

CERTIFICATE OF CORRECTION (continued)
U.S. Pat. No. 9,072,713 B2

In the specification

Column 31,
Line 27, "(KO values" should read --($K_d$) values--.

Column 38,
Line 15, "binds anti" should read --binds α5β1--.

Column 42,
Line 27, "ML 1-MMP" should read --MT1-MMP--.

Column 68,
Line 22, "1L-1 a;" should read --IL-1α;--.